(12) United States Patent
Kharul et al.

(10) Patent No.: US 9,682,953 B2
(45) Date of Patent: Jun. 20, 2017

(54) AMIDE COMPOUNDS, COMPOSITIONS AND APPLICATIONS THEREOF

(71) Applicant: Advinus Therapeutics Limited, Karnataka (IN)

(72) Inventors: Rajendra Kharul, Pune (IN); Debnath Bhuniya, Pune (IN); Kasim A. Mookhtiar, Pune (IN); Umesh Singh, Pune (IN); Atul Hazare, Pune (IN); Satish Patil, Pune (IN); Laxmikant Datrange, Pune (IN); Mahesh Thakkar, Pune (IN)

(73) Assignee: ADVINUS THERAPEUTICS LIMITED, Bangalore (IN)

( * ) Notice: Subject to any disclaimer, the term of this patent is extended or adjusted under 35 U.S.C. 154(b) by 367 days.

(21) Appl. No.: 14/344,661

(22) PCT Filed: Sep. 21, 2012

(86) PCT No.: PCT/IN2012/000633
§ 371 (c)(1),
(2) Date: Mar. 13, 2014

(87) PCT Pub. No.: WO2013/042139
PCT Pub. Date: Mar. 28, 2013

(65) Prior Publication Data
US 2015/0065464 A1    Mar. 5, 2015

(30) Foreign Application Priority Data
Sep. 23, 2011  (IN) .......................... 3308/CHE/2011

(51) Int. Cl.
| | | |
|---|---|---|
| *C07D 401/12* | (2006.01) | |
| *A61K 31/4439* | (2006.01) | |
| *A61K 31/444* | (2006.01) | |
| *A61K 31/497* | (2006.01) | |
| *C07D 413/12* | (2006.01) | |
| *C07D 213/75* | (2006.01) | |
| *C07D 409/12* | (2006.01) | |
| *C07D 417/12* | (2006.01) | |
| *C07D 471/04* | (2006.01) | |
| *A61K 31/675* | (2006.01) | |
| *A61K 45/06* | (2006.01) | |

(Continued)

(52) U.S. Cl.
CPC .......... *C07D 401/12* (2013.01); *A61K 31/444* (2013.01); *A61K 31/4439* (2013.01); *A61K 31/497* (2013.01); *A61K 31/675* (2013.01); *A61K 45/06* (2013.01); *C07D 213/75* (2013.01); *C07D 401/14* (2013.01); *C07D 409/12* (2013.01); *C07D 413/12* (2013.01); *C07D 417/12* (2013.01); *C07D 471/04* (2013.01); *C07F 9/65616* (2013.01)

(58) Field of Classification Search
None
See application file for complete search history.

(56) References Cited

FOREIGN PATENT DOCUMENTS

| WO | WO2006/054652 | 5/2006 |
| WO | WO2006/074025 | 7/2006 |
| WO | WO2008/011131 | 1/2008 |

(Continued)

OTHER PUBLICATIONS

Ahn, K. et. al. "Novel mechanistic class of fatty acid amide hydrolase inhibitors with remarkable selectivity," Biochemistry, 46(45), 13019-13030 (2007).

(Continued)

*Primary Examiner* — Kortney L Klinkel
*Assistant Examiner* — Tori M Strong
(74) *Attorney, Agent, or Firm* — Perkins Coie LLP

(57) ABSTRACT

The present disclosure relates to substituted amide compounds that are inhibitors of Fatty Acid Amide Hydrolase (FAAH), their stereoisomers, tautomers, prodrugs, polymorphs, solvates, pharmaceutically acceptable salts, and pharmaceutical compositions containing them. These compounds are useful in the treatment, prevention, prophylaxis, management, or adjunct treatment of all medical conditions related to inhibition of Fatty Acid Amide Hydrolase (FAAH), such as pain including acute and post operative pain, chronic pain, cancer pain, cancer chemotherapy induced pain, neuropathic pain, nociceptive pain, inflammatory pain, back pain, pain due to disease of various origin such as: diabetic neuropathy, neurotropic viral disease including human immunodeficient virus (HIV), herpes zoster such as post herpetic neuralgia; polyneuropathy, neurotoxicity, mechanical nerve injury, carpal tunnel syndrome, immunologic mechanisms like multiple sclerosis; sleep disorders, anxiety and depression disorders, inflammatory disorders, weight and eating disorders, Parkinson's disease, addiction, spasticity, hypertension or other disorders. The disclosure also relates to the process of preparation of the amide compounds.

(I)

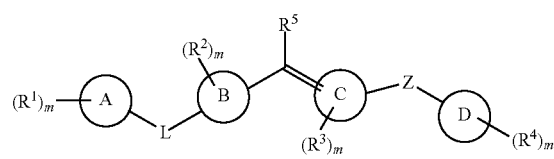

The present disclosure also relates to methods for the preparation of such compounds, and to pharmaceutical compositions containing them.

11 Claims, No Drawings

(51) Int. Cl.
C07D 401/14 (2006.01)
C07F 9/6561 (2006.01)

(56) References Cited

FOREIGN PATENT DOCUMENTS

| WO | WO2009/013211 | 1/2009 |
| WO | WO2009/127943 | 10/2009 |
| WO | WO2011/149950 | 12/2011 |

OTHER PUBLICATIONS

Ahn, K. et. al., "Discovery and characterization of a highly selective FAAH inhibitor that reduces inflammatory pain," Chem. Biol., 16(4), 411-420 (2009).
Boger, D. L., et. al. "Exceptionally potent inhibitors of fatty acid amide hydrolase: the enzyme responsible for degradation of endogenous oleamide and anandamide," Proc. Natl. Acad. Sci. USA 97(10), 5044-5049 (2000).
Chan et al., "New N- and O-arylations with phenylboronic acids and cupric acetate," Tet. Lett.,39(19), 2933-2936 (1998).
Chebrou, H. et. al., "Study of the amidase signature group," Biochim. Biophys. Acta., 1298(2), 285-293 (1996).
Cravatt, B. F. et. al., "Molecular characterization of an enzyme that degrades neuromodulatory fatty-acid amides," Nature, 384(6604), 83 (1996).
Cristau et al., "A general and mild Ullmann-type synthesis of diaryl ethers," Org. Lett. 6(8), 913-916 (2004).
Deng, "Recent advances in the discovery and evaluation of fatty acid amide hydrolase inhibitors," Expert. Opin. Drug Discv., 5(10), 961-993 (2010).
Fowler, "The cannabinoid system and its pharmacological manipulation—a review, with emphasis upon the uptake and hydrolysis of anandamide," Pharmacol, 20(6), 549-562 (2006).
Gobbi et. al., "Antidepressant-like activity and modulation of brain monoaminergic transmission by blockade of anandamide hydrolysis," Proc. Natl. Acad. Sci., 102(51), 18620-18625 (2005).
Jayamanne et. al., "Actions of the FAAH inhibitor URB597 in neuropathic and inflammatory chronic pain models," Br. J. Pharmacol., 147(3), 281-288 (2006).
Johnson et al., "Discovery of PF-04457845: a Highly Potent, Orally Bioavailable, and Selective Urea FAAH Inhibitor," ACS Medicinal Chem Letters, Amer. Chem Society, vol. 2, No. 2, pp. 91-96 (2011).
Johnson, D. S., et. al., Benzothiophene piperazine and piperidine urea inhibitors of fatty acid amide hydrolase (FAAH).Bioorg. Med. Chem. Lett., 19(10), 2865-2869 (2009).
Kathuria, S. et. al., "Modulation of anxiety through blockade of anandamide hydrolysism," Nat. Med., 9(1), 76-81 (2003).
Keith, J. M. et. al., Thiadiazolopiperazinyl ureas as inhibitors of fatty acid amide hydrolase, Bioorg. Med. Chem. Lett., 2008, 18, 4838-4843.
Leung, D. et. al., "Discovering potent and selective reversible inhibitors of enzymes in complex proteomes," Nat. Biotechnol., 21(6), 687-691 (2003).
Lichtman, A. H., et. al., "Reversible inhibitors of fatty acid amide hydrolase that promote analgesia: evidence for an unprecedented combination of potency and selectivity," J. Pharmacol. Exp. Ther., 311(2), 441-448 (2004).
Ma et al., "N,N-dimethyl glycine-promoted Ullmann coupling reaction of phenols and aryl halides," Org. Lett., 5(21), 3799-3802 (2003).
Meyers et al., "Discovery of novel spirocyclic inhibitors of fatty acid amide hydrolase (FAAH), Part 1: Identification of 7-azaspiro [3.5] nonane and 1-oxa-8-azasprio [4.5] decane as lead scaffolds," Bioorg. & Med. Chem. Letters, VO. 21, No. 21, pp. 6538-6544 (2011).
Mileni et al., "Structure-guided inhibitor design for human FAAH by interspecies active site conversion," Proc Natl Acad Sci, 105(35),12820-4 (2008).
Min, X. et. al., "Discovery and molecular basis of potent noncovalent inhibitors of fatty acid amide hydrolase (FAAH)," Proc. Natl. Acad. Sci. USA, 108(18), 7379-7384 (2011).
Miyaura et al., "Palladium-Catalyzed Cross-Coupling Reactions to Organoboron Compounds," Chemical Reviews 95 (7): 2457-2483 (1995).
Mor, M. et. al., "Cyclohexylcarbamic acid 3'- or 4'-substituted biphenyl-3-yl esters as fatty acid amide hydrolase inhibitors: synthesis, quantitative structure-activity relationships, and molecular modeling studies," J. Med. Chem., 2004, 47(21), 4998-5008 (2004).
Muci et al., "Practical Palladium Catalysts for C—N and C—O Bond Formation," Topics in Curr. Chem. 219, 131-209 (2002).
Pacher, P., et. al., "The endocannabinoid system as an emerging target of pharmacotherapy," Pharmacol. Rev., 58(3), 389-462 (2006).
Patricelli et al., "Comparative characterization of a wild type and transmembrane domain-deleted fatty acid amide hydrolase: identification of the transmembrane domain as a site for oligomerization." Biochemistry. 37(43), 15177-87 (1998).
Ramaro et al., "A fluorescence-based assay for fatty acid amide hydrolase compatible with high-throughput screening," Anal Biochem., 343(1):143-51 (2005).
Shaikh et al., "A mild procedure for the clay catalyzed selective removal of the tert-butoxycarbonyl protecting group from aromatic amines," Tetr. Letters 41: 385-387 (2000).
Sun et al., "Highly efficient chemoselective deprotection of O,O-acetals and O,O-ketals catalyzed by molecular iodine in acetone," J. Org. Chem., 69(25), 8932-8934 (2004).
Tarzia, G. et. al., "Design, synthesis, and structure-activity relationships of alkylcarbamic acid aryl esters, a new class of fatty acid amide hydrolase inhibitors," J. Med. Chem., 46(12), 2352-2360 (2003).
Timmons, A., et. al., Novel ketooxazole based inhibitors of fatty acid amide hydrolase (FAAH), Bioorg. Med. Chem. Lett., 2008, 18, 2109-13.
Wang et al., "Structure based design of novel irreversible FAAH inhibitors," Bioorg. & Med. Chem Letters, vol. 19, No. 20, pp. 5970-5974 (2009).
Zinelaabidine et al., "A simple and efficient green method for the deprotection of N-Boc in various structurally diverse amines under water-mediated catalyst-free conditions," Inter. Journal of Chem.; 2012, 4, 73-79.

AMIDE COMPOUNDS, COMPOSITIONS AND APPLICATIONS THEREOF

CROSS REFERENCE TO RELATED APPLICATIONS

This application is a 35 USC §371 National Stage application of International Application No. PCT/IN2012/000633 filed Sep. 21, 2012, entitled "AMIDE COMPOUNDS, COMPOSITIONS AND APPLICATIONS THEREOF" which claims the benefit of priority to Indian Application No. 3308/CHE/2011 filed Sep. 23, 2011; the entirety of each of which is incorporated herein by reference.

TECHNICAL FIELD

The present disclosure relates to substituted amide compounds that are inhibitors of Fatty Acid Amide Hydrolase (FAAH), their stereoisomers, tautomers, prodrugs, polymorphs, solvates, pharmaceutically acceptable salts, and pharmaceutical compositions containing them. These compounds, pharmaceutical compositions and methods provided are useful in the treatment, prevention, prophylaxis, management, or adjunct treatment of all medical conditions related to inhibition of Fatty Acid Amide Hydrolase (FAAH)

BACKGROUND

The endocannabinoid system consists of two G-protein coupled receptors, CB1 and CB2; their endogenous ligands like N-arachidonoyl ethanolamine (Anandamide, AEA) and 2-Archadanoyl glycerol (2-AG); the enzymes responsible for their biosynthesis and biodegradation (Fowler, C. J. et. al., *Clin. Pharmacol,* 2006, 20, 549-562; Pacher, P., et. al. *Pharmacol. Rev.,* 2006, 58, 389-462). The amplitude and duration of action of fatty acid amides signaling are regulated in vivo mainly by a single degradative enzyme, fatty acid amide hydrolase (FAAH) (Cravatt, B. F. et. al., *Nature,* 1996, 384, 83). Fatty Acid Amide Hydrolase (FAAH) is an integral membrane protein belonging to a large class of enzymes known as amidase signature class (Chebrou, H. et. al. *Biochim. Biophys. Acta.,* 1996, 1298, 285-293). FAAH knock-out data indicates that, selective inhibition of FAAH represents an attractive target for treatment of pain as well as other related indications without side effects caused by direct CB1 agonism.

Beside Anandamide and 2-AG, $\Delta^9$-tetrahydrocannabinol (THC, psychoactive ingredient of Marijuana) also activates CB1 and CB2. (Mechoulam, R. et. al. Boca Raton, Fla.: CRC Press). THC and other CB1 agonists have been recognized to possess beneficial therapeutic properties. However, these reagents also produce side effects including impairments in cognition, motor control that limit their broad clinical utility. Anandamide has been shown to possess cannabinoid-like analgesic properties and it is released by stimulated neurons. Elevated anadamide levels result in pain relief without motor and cognitive side effects. Supporting this, FAAH inhibitors that elevate anadamide levels have demonstrated efficacy in animal models of pain (Litchman, A. H., et. al. *J. Pharmacol. Exp. Ther.* 2004, 311, 441-448), inflammation (Jayamanne et. al., *Br. J. Pharmacol.,* 2006, 147, 281-288), anxiety (Kathuria, S. et. al., *Nat. Med.* 2003, 9, 76-81), and depression (Piomelli, D., et. al., *Proc. Natl. Acad. Sci. USA,* 2005, 102, 18620-18625).

Several classes of Fatty Acid Amide Hydrolase (FAAH) inhibitors are known (Deng, H., et. al., *Expert. Opion. Drug Discv.,* 2010, 5, 961-993). Based on mechanism of action, these inhibitors broadly can be classified as covalent irreversible inhibitors, covalent reversible inhibitors, noncovalent reversible inhibitors. Examples of α-ketoheterocycles (Boger, D. L., et. al. *Proc. Natl. Acad. Sci. USA* 2000, 97, 5044-5049; Leung, D. et. al., *Nat. Biotechnol.* 2003, 21, 687-691) belong to covalent reversible inhibitors. Series of N-Piperidine/N-piperazine carboxamides (Urea derivatives) (Ahn, K. et. al. *Biochem,* 2007, 46, 13019-13030; Ahn, K. et. al., *Chem. Biol.,* 2009, 16, 411-420; Johnson, D. S., et. al., *Bioorg. Med. Chem. Lett.,* 2009, 19, 2865-2869; Keith, J. M. et. al., *Bioorg. Med. Chem. Lett.,* 2008, 18, 4838-4843), carbamates (Timmons, A., et. al. *Bioorg. Med. Chem. Lett.,* 2008, 18, 2109-13; Tarzia, G. et. al., *J. Med. Chem.,* 2003, 46, 2352-2360; Mor, M. et. al. *J. Med. Chem.,* 2004, 47, 4998-5008) belong to covalent irreversible inhibitors. Examples of Ketobenzimidazoles (Min, X. et. al., *Proc. Natl. Acad. Sci. USA,* 2011, 108, 7379-7384) represent noncovalent reversible inhibitors.

International (PCT) publication number WO2009/127943 discloses piperidine based urea derivatives as fatty acid amide hydrolase inhibitors. International (PCT) publication number WO2006/054652 relates piperazine based urea derivatives as fatty acid amide hydrolase inhibitors for the treatment of sleep disorders, cerebrovascular disorders.

International (PCT) publication number WO2006/074025 discloses piperazinyl and piperidinyl ureas as modulators of fatty acid amide hydrolase.

There remains a need to find new compounds that are inhibitors of Fatty Acid Amide Hydrolase (FAAH) useful for the treatment of disease states mediated by Fatty Acid Amide Hydrolase (FAAH) including pain, inflammation.

SUMMARY

The present disclosure provides compounds of formula (I), their tautomers, polymorphs, stereoisomers, prodrugs, solvates, pharmaceutically acceptable salts, pharmaceutical compositions containing them and methods of treating conditions and diseases that are mediated by the inhibition of Fatty Acid Amide Hydrolase (FAAH),

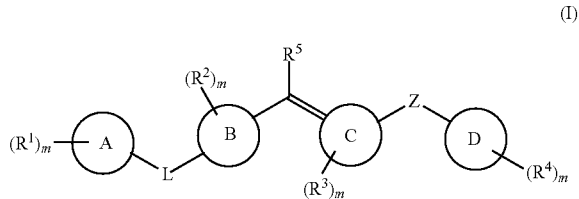

wherein
ring A is selected from aryl, cycloalkyl, heteroaryl or heterocyclyl;
L is absent or is $C_{1-4}$alkylene wherein one or more methylene groups is optionally replaced by hetero atoms or groups such as —O—, —S(O)p—, —N(R)—, —C(O)— or —$(CR^aR^b)$—; alkylene is optionally substituted with hydroxy, amino, aminoalkyl, cyano, halogen, haloalkyl, perhaloalkyl, carboxy, carboxyalkyl, alkylcarboxy, alkoxy, hydroxyalkyl, alkoxyalkyl, alkoxyalkoxy or alkyl;
ring B is selected from aryl, heteroaryl or heterocyclyl;
ring C is cycloalkyl;
Z is selected from —C(Y)NR—$(CR^aR^b)_q$— or —NRC(Y)—C$(R^aR^b)_q$;
Y is selected from O, S or N(R'");

R and R''' are independently selected from hydrogen, cyano, alkyl or haloalkyl;

ring D is selected from aryl, cycloalkyl, heteroaryl or heterocyclyl;

$R^1$, $R^2$, $R^3$ and $R^4$ are independently selected from hydrogen, halo, cyano, nitro, $-(CR^aR^b)_nOR^6$, $-(CR^aR^b)_nC(O)R^6$, $-(CR^aR^b)_nSR^6$, $-(CR^aR^b)_nCOOR^6$, $-(CR^aR^b)_nNR^7R^8$, $-(CR^aR^b)_nC(O)NR^7R^8$, $-(CR^aR^b)_nNR^7C(O)OR^6$, $-(CR^aR^b)_nNR^7C(O)NR^7R^8$, $-NR^7S(O)_2R^6$, $-S(O)_pR^6$, $-SO_3H$, $-S(O)_2NR^7R^8$, azido, oxo, thiocarbonyl, $C_{1-6}$alkyl, $C_{2-6}$alkenyl, $C_{2-6}$alkynyl, cyanoalkyl, cyanoalkylcarbonyl, haloalkyl, perhaloalkyl, haloalkoxy, perhaloalkoxy, alkoxyalkoxy, alkoxyalkoxyalkyl, cycloalkyl, cycloalkenyl, cycloalkylalkyl aryl, arylalkyl, heterocyclyl, heterocyclylalkyl, heteroaryl or heteroarylalkyl;

wherein each substituent is unsubstituted or substituted with 1, 2, or 3 substituents independently selected from alkyl, halogen, haloalkyl, perhaloalkyl, haloalkoxy, perhaloalkoxy, cyano $-(CR^aR^b)_nOR^6$, $-(CR^aR^b)_nCOOR^6$, $-(CR^aR^b)_nNR^7R^8$, $-(CR^aR^b)_nC(O)NR^7R^8$, $-S(O)_pR^6$ or $-SO_3H$.

$R^5$ is selected from hydrogen, halogen, haloalkyl, cyano, $C_{1-6}$alkyl, cycloalkyl, cycloalkylalkyl, aryl, arylalkyl, heterocyclyl, heterocyclylalkyl, heteroaryl or heteroarylalkyl;

wherein alkyl, cycloalkyl, cycloalkylalkyl, aryl, arylalkyl, heterocyclyl, heterocyclylalkyl, heteroaryl and heteroarylalkyl is unsubstituted or substituted with 1, 2, or 3 substituents independently selected from alkyl, halogen, haloalkyl, perhaloalkyl, haloalkoxy, perhaloalkoxy, cyano $-(CR^aR^b)_nOR^6$, $-(CR^aR^b)_nCOOR^6$, $-(CR^aR^b)_nNR^7R^8$, $-(CR^aR^b)_nC(O)NR^7R^8$, $-S(O)_pR^6$ or $-SO_3H$.

$R^6$ is selected from hydrogen, alkyl, haloalkyl, $-(CR^aR^b)_nOR^6$, $-(CR^aR^b)_nCOOR^6$, $-(CR^aR^b)_nC(O)R^6$, aminocarbonyl, cycloalkyl, cycloalkylalkyl, aryl, arylalkyl, heteroaryl, heteroarylalkyl, heterocyclyl or heterocyclylalkyl;

$R^7$ and $R^8$ are independently selected from the group consisting of hydrogen, alkyl, haloalkyl, $-(CR^aR^b)_nOR^6$, $-(CR^aR^b)_nC(O)R^6$, aryl, arylalkyl, heteroaryl, heteroarylalkyl, cycloalkyl, cycloalkylalkyl, heterocyclyl and heterocyclylalkyl, or $R^7$ and $R^8$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, alkenyl, alkynyl, nitro, cyano, $-(CR^aR^b)_nOR^6$, $-(CR^aR^b)_nSR^6$, $-(CR^aR^b)_nNR^7R^8$, oxo, alkylsulfonyl, $-(CR^aR^b)_nCOOR^6$, $-(CR^aR^b)_nC(O)NR^7R^8$, cycloalkyl, cycloalkylalkyl, aryl, arylalkyl, heterocyclyl, heterocyclylalkyl, heteroaryl, or heteroarylalkyl;

$R^a$ and $R^b$ are independently selected from the group consisting of hydrogen, $-OR^6$, halogen, haloalkyl, perhaloalkyl and alkyl; or $R^a$ and $R^b$ taken together form a monocyclic or a bicyclic ring system which is saturated or partially unsaturated and optionally have additional heteroatoms selected from O, N or S m is independently selected from 0, 1, 2, 3 or 4 n is an integer and selected from 0, 1, 2, 3 or 4;

p is an integer selected from 0, 1 or 2; and q is an integer selected from 0, 1, 2, 3 or 4.

These and other features, aspects, and advantages of the present subject matter will become better understood with reference to the following description. This Summary is provided to introduce a selection of concepts in a simplified form. This Summary is not intended to identify key features or essential features of the subject matter, nor is it intended to be used to limit the scope of the disclosed subject matter.

DETAILED DESCRIPTION OF THE INVENTION

Definitions

In the structural formulae given herein and throughout the present disclosure, the following terms have the indicated meaning, unless specifically stated otherwise.

The term "optionally substituted" as used herein means that the group in question is either unsubstituted or substituted with one or more of the substituents specified. When the group in question is substituted with more than one substituent, the substituent may be same or different.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methyl, ethyl, n-propyl, iso-propyl, n-butyl, iso-butyl, t-butyl, neo-pentyl, n-hexyl, n-decyl, tetradecyl, and the like.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methylene ($-CH_2-$), ethylene ($-CH_2CH_2-$), the propylene isomers (e.g., $-CH_2CH_2CH_2-$ and $-CH(CH_3)CH_2-$) and the like.

The term "substituted alkyl" or "substituted alkylene" refers to: (1) an alkyl group or alkylene group as defined above, having 1, 2, 3, 4 or 5 substituents, preferably 1, 2 or 3 substituents, selected from the group consisting of alkenyl, alkynyl, alkoxy, cycloalkyl, cycloalkenyl, acyl, acylamino, acyloxy, amino, monoalkylamino, dialkylamino, arylamino, heteroarylamino, aminocarbonyl, alkoxycarbonylamino, azido, cyano, halogen, hydroxy, hydroxyalkyl, keto, thiocarbonyl, carboxy, carboxyalkyl, $-SO_3H$, aryl, aryloxy, heteroaryl, aminocarbonylamino, heteroaryloxy, heterocyclyl, heterocyclyloxy, hydroxyamino, alkoxyamino, nitro, $-S(O)_2NR^aR^a$, $-NR^aS(O)_2R^a$ and $-S(O)_pR^b$, where each $R^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; heterocyclyloxy where $R^b$ is hydrogen, alkyl, aryl, heteroaryl or heterocyclyl. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, $CF_3$, amino, substituted amino, cyano, and $-S(O)_pR^c$, where $R^c$ is alkyl, aryl, or heteroaryl and p is 0, 1 or 2;

or (2) an alkyl group or alkylene group as defined above that is interrupted by 1, 2, 3, 4, 5, 6, 7, 8, 9 or 10 atoms independently selected from oxygen, sulphur and $NR^d$, where $R^d$ is selected from hydrogen, alkyl, cycloalkyl, cycloalkenyl, aryl, heteroaryl and heterocyclyl, carbonylalkyl, carboxyester, carboxyamide and sulfonyl. All substituents may be optionally further substituted by alkyl, alkoxy, halogen, $CF_3$, amino, substituted amino, cyano, or $-S(O)_pR^c$, in which $R^c$ is alkyl, aryl, or heteroaryl and p is 0, 1, or 2;

or (3) an alkyl or alkylene as defined above that has 1, 2, 3, 4 or 5 substituents as defined above, as well as interrupted by 1, 2, 3, 4, 5, 6, 7, 8, 9 or 10 atoms as defined above.

The term "alkenyl" refers to a monoradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 double bond (vinyl), preferably 1 double bond. Preferred alkenyl groups include ethenyl or vinyl (—CH=CH$_2$), 1-propylene or allyl (—CH$_2$CH=CH$_2$), isopropylene (—C(CH$_3$)=CH$_2$), bicyclo[2.2.1]heptene, and the like.

The term "alkenylene" refers to a diradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 double bond (vinyl), preferably 1 double bond.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, thiocarbonyl, carboxy, carboxyalkyl, SO$_3$H, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$ where each R$^a$ is independently selected from the group consisting of hydrogen, alkyl, cycloalkyl, cycloalkylalkyl, aryl, arylalkyl, heteroaryl heteroarylalkyl, heterocyclyl, heterocyclylalkyl and heterocyclyloxy, where R$^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF$_3$, amino, substituted amino, cyano, and —S(O)$_p$R$^c$, where R$^c$ is alkyl, aryl, or heteroaryl and p is 0, 1 or 2.

The term "alkynyl" refers to a monoradical of an unsaturated hydrocarbon, preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 sites of acetylene (triple bond) unsaturation, preferably 1 triple bond. Preferred alkynyl groups include ethynyl, (—C≡CH), propargyl (or prop-1-yn-3-yl, —CH$_2$C≡CH), homopropargyl (or but-1-yn-4-yl, —CH$_2$CH$_2$C≡CH) and the like.

The term "alkynylene" refers to a diradical of a branched or an unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 sites of acetylene (triple bond) unsaturation, preferably 1 triple bond.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, —SO$_3$H, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$, where each R$^a$ is independently selected from the group consisting of hydrogen, alkyl, cycloalkyl, cycloalkylalkyl, aryl, arylalkyl, heteroaryl heteroarylalkyl, heterocyclyl, heterocyclylalkyl and heterocyclyloxy, where R$^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF$_3$, amino, substituted amino, cyano, and —S(O)$_p$R$^c$ where R$^c$ is alkyl, aryl, or heteroaryl and p is 0, 1 or 2.

The term "cycloalkyl" refers to unless otherwise mentioned, carbocyclic groups of from 3 to 20 carbon atoms having a single cyclic ring or multiple condensed rings or spirocyclic rings which may be saturated or partially unsaturated. Such cycloalkyl groups include, by way of example, single ring structures such as cyclopropyl, cyclobutyl, cyclopentyl, cyclopentenyl, cyclohexyl, cyclohexenyl, cycloheptyl, cyclohetynyl, cyclooctyl, and the like, or multiple ring structures such as adamantanyl, bicyclo[2.2.1]heptane, bicyclo[2.2.2]octane, 1,3,3-trimethylbicyclo[2.2.1]hept-2-yl, (2,3,3-trimethylbicyclo[2.2.1]hept-2-yl), spiro[3,5]nonan-2-yl, spiro[2,5]octan-2-yl, spiro[3,5]nonan-7-yl, spiro[2,5]octan-6-yl, spiro[4,5]decan-3-yl spiro[5,5]undecan-3-yl, spiro[5,5]undecan-4-yl or carbocyclic groups to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, oxo, thiocarbonyl, aryl, aryloxy, heteroaryl, aminosulfonyl, aminocarbonylamino, heteroaryloxy, heterocyclyl, heterocyclyloxy, hydroxyamino, alkoxyamino, nitro, —C(O)R and —S(O)$_p$R$^b$, where R is hydrogen, hydroxyl, alkoxy, alkyl and cyclocalkyl, heterocyclyloxy where R$^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF$_3$, amino, substituted amino, cyano, and —S(O)$_p$R$^c$, where R$^c$ is alkyl, aryl, or heteroaryl and p is 0, 1 or 2.

"Halo" or "Halogen", alone or in combination with any other term means halogens such as chloro (Cl), fluoro (F), bromo (Br) and iodo (I).

"Haloalkyl" refers to a straight chain or branched chain haloalkyl group with 1 to 6 carbon atoms. The alkyl group may be partly or totally halogenated. Representative examples of haloalkyl groups include but are not limited to fluoromethyl, chloromethyl, bromomethyl, difluoromethyl, dichloromethyl, dibromomethyl, trifluoromethyl, trichloromethyl, 2-fluoroethyl, 2-chloroethyl, 2-bromoethyl, 2,2,2-trifluoroethyl, 3-fluoropropyl, 3-chloropropyl, 3-bromopropyl and the like.

The term "alkoxy" refers to the group R'''—O—, where R''' is optionally substituted alkyl or optionally substituted cycloalkyl, or optionally substituted alkenyl or optionally substituted alkynyl; or optionally substituted cycloalkenyl, where alkyl, alkenyl, alkynyl, cycloalkyl and cycloalkenyl are as defined herein. Representative examples of alkoxy groups include but are not limited to methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "aminocarbonyl" refers to the group —C(O)NR'R' where each R' is independently hydrogen, alkyl, aryl, heteroaryl, heterocyclyl or both R' groups are joined to form a heterocyclic group (e.g. morpholino). Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and —S(O)$_p$R$^c$, where R$^c$ is alkyl, aryl, or heteroaryl and p is 0, 1 or 2.

The term "acylamino" refers to the group —NR"C(O)R" where each R" is independently hydrogen, alkyl, aryl, heteroaryl, or heterocyclyl. Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and —S(O)$_p$R$^c$, where R$^c$ is alkyl, aryl, or heteroaryl and p is 0, 1 or 2.

The term "acyloxy" refers to the groups —OC(O)-alkyl, —OC(O)-cycloalkyl, —OC(O)-aryl, —OC(O)-heteroaryl, and —OC(O)-heterocyclyl. Unless otherwise constrained by the definition, all substituents may be optionally further substituted by alkyl, carboxy, carboxyalkyl, aminocarbonyl, hydroxy, alkoxy, halogen, $CF_3$, amino, substituted amino, cyano, or —S(O)$_p$R$^c$, where R$^c$ is alkyl, aryl, or heteroaryl and p is 0, 1 or 2.

"Alkoxyalkyl" refers to alkyl groups as defined above wherein at least one of the hydrogen atoms of the alkyl group is replaced by an alkoxy group as defined above. Representative examples of alkoxyalkyl groups include but are not limited to methoxymethyl, methoxyethyl, ethoxymethyl and the like.

"Aryloxyalkyl" refers to the group -alkyl-O-aryl. Representative examples of aryloxyalkyl include but are not limited to phenoxymethyl, naphthyloxymethyl, phenoxyethyl, naphthyloxyethyl and the like.

"Di alkylamino" refers to an amino group, to which two same or different straight chain or branched chain alkyl groups with 1 to 6 carbon atoms are bound. Representative examples of di alkylamino include but are not limited to dimethylamino, diethylamino, methylethylamino, dipropylamino, dibutylamino and the like.

"Cycloalkylalkyl" refers to an alkyl radical as defined above which is substituted by a cycloalkyl radical as defined above. Representative examples of cycloalkylalkyl include but are not limited to cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

"Aminoalkyl" refers to an amino group that is attached to ($C_{1-6}$)alkylene as defined herein. Representative examples of aminoalkyl include but are not limited to aminomethyl, aminoethyl, 1-aminopropyl, 2-aminopropyl, and the like. The amino moiety of aminoalkyl may be substituted once or twice with alkyl to provide alkylaminoalkyl and dialkylaminoalkyl respectively. Representative examples of alkylaminoalkyl include but are not limited to methylaminomethyl, methylaminoethyl, methylaminopropyl, ethylaminoethyl and the like. Representative examples of dialkylaminoalkyl include but are not limited to dimethylaminomethyl, dimethylaminoethyl, dimethylaminopropyl, N-methyl-N-ethylaminoethyl and the like.

The term "aryl" refers to an aromatic carbocyclic group of 6 to 20 carbon atoms having a single ring (e.g. phenyl) or multiple rings (e.g. biphenyl), or multiple condensed (fused) rings (e.g. naphthyl or anthranyl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained the aryl or arylene groups may optionally be substituted with 1, 2, 3 4 or 5 substituents, preferably 1, 2 or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, carboxy, carboxyalkyl, —SO$_3$H, aryl, aryloxy, heteroaryl, aminosulfonyl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$ where each R$^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl; where R$^b$ is hydrogen, alkyl, aryl, heterocyclyl or heteroaryl and p is 0, 1 or 2. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, $CF_3$, amino, substituted amino, cyano, and —S(O)$_p$R$^c$ where R$^c$ is hydrogen, alkyl, aryl, or heteroaryl and p is 0, 1 or 2.

The term "arylalkyl" refers to an aryl group covalently linked to an alkylene group, where aryl and alkylene are defined herein.

"Optionally substituted arylalkyl" refers to an optionally substituted aryl group covalently linked to an optionally substituted alkylene group. Such arylalkyl groups are exemplified by benzyl, phenethyl, naphthylmethyl, and the like.

The term "aryloxy" refers to the group aryl-O— wherein the aryl group is as defined above, and includes optionally substituted aryl groups as also defined above.

The term "arylthio" refers to the group —S-aryl, where aryl is as defined herein including optionally substituted aryl groups as also defined above.

The term "substituted amino" refers to the group —NR'R' where each R' is independently selected from the group consisting of hydrogen, alkyl, cycloalkyl, carboxyalkyl, alkoxycarbonyl, aryl, heteroaryl and heterocyclyl. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, $CF_3$, amino, substituted amino, cyano, and —S(O)$_p$R$^c$, where R$^c$ is alkyl, aryl, or heteroaryl and p is 0, 1 or 2.

The term "carboxyalkyl" refers to the groups -alkylene-C(O)OH.

The term "alkylcarboxyalkyl" refers to the groups -alkylene-C(O)OR$^d$ where R$^d$ is alkyl, cycloalkyl, where alkyl, cycloalkyl are as defined herein, and may be optionally further substituted by alkyl, halogen, $CF_3$, amino, substituted amino, cyano, or —S(O)$_p$R$^c$, in which R$^c$ is alkyl, aryl, or heteroaryl and p is 0, 1 or 2.

The term "heteroaryl" refers to an aromatic cyclic group having 1, 2, 3, 4, 5, 6, 7, 8, 9, 10, 11, 12, 13, 14, or 15 carbon atoms and 1, 2, 3 or 4 heteroatoms selected from oxygen, nitrogen and sulphur within at least one ring. Such heteroaryl groups can have a single ring (e.g. pyridinyl or furanyl) or multiple condensed rings (e.g. indolizinyl, benzooxazolyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, quinoxaline, quinazoline, cinnoline, pteridine, carbazole, carboline, phenanthridine, acridine, phenanthroline, isothiazole, phenazine, isoxazole, phenoxazine, phenothiazine, furan, thiophene, oxazole, thiazole, triazole, triazine and the like.

The term "heteroarylene" refers to a diradical of a heteroaryl group as defined above.

Unless otherwise constrained the heteroaryl or heterarylene groups can be optionally substituted with 1, 2, 3, 4 or 5 substituents, preferably 1, 2 or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, thiocarbonyl, carboxy, carboxyalkyl, —SO$_3$H, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$, where each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; where R$^b$ is hydrogen, alkyl, aryl, heterocyclyl or heteroaryl, and p is 0, 1 or 2. Unless otherwise constrained by the definition, all substituents may optionally be further substituted by 1-3 substituents selected from alkyl, carboxy, carboxyalkyl, aminocarbonyl, hydroxy, alkoxy, halogen, CF$_3$, amino, substituted amino, cyano, and —S(O)$_n$R$^c$, where R$^c$ is alkyl, aryl, or heteroaryl and n is 0, 1 or 2.

The term "heteroarylalkyl" refers to a heteroaryl group covalently linked to an alkylene group, where heteroaryl and alkylene are defined herein.

"Optionally substituted heteroarylalkyl" refers to an optionally substituted heteroaryl group covalently linked to an optionally substituted alkylene group. Such heteroarylalkyl groups are exemplified by 3-pyridylmethyl, quinolin-8-ylethyl, 4-methoxythiazol-2-ylpropyl, and the like.

The term "heterocyclyl" refers to a saturated or partially unsaturated group having a single ring or multiple condensed rings or spirocyclic rings, unless otherwise mentioned, having from 1 to 40 carbon atoms and from 1 to 10 hetero atoms, preferably 1, 2, 3 or 4 heteroatoms, selected from nitrogen, sulphur, phosphorus, and/or oxygen within the ring. Heterocyclic groups can have a single ring or multiple condensed rings, and include dihydrofuranyl, tetrahydrofuranyl, morpholinyl, pyrrolidinyl, dihydropyrrole, dihydropyranyl, tetrahydropyranyl, pyrazolidinyl, imidazolidinyl, dihydropyridinyl, tetrahydropyridinyl, piperidinyl, dihydropyrazinyl, tetrahydropyrazinyl, piperazinyl, dihydropyridinyl, benzodioxolyl, tetrahydroquinolinyl, tetrahydroisoquinolinyl, tetrahydronaphthyridinyl, tetrahydrothienopyridinyl, 7-azaspiro[3,5]nonan-2-yl, 2,7-diazaspiro[3,5] nonan-2-yl, 9-azaspiro[5.5]undecan-4-yl, and the like. Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, oxo, —C(O)R where R is hydrogen, hydroxyl, alkoxy, alkyl and cyclocalkyl, thiocarbonyl, carboxy, carboxyalkyl, aryl, aryloxy, heteroaryl, aminosulfonyl, aminocarbonylamino, heteroaryloxy, heterocyclyl, heterocyclyloxy, hydroxyamino, alkoxyamino, nitro, and —S(O)$_p$R$^b$, where R$^b$ is hydrogen, alkyl, aryl, heterocyclyl or heteroaryl and p is 0, 1 or 2.

Unless otherwise constrained by the definition, all substituents may optionally be further substituted by 1-3 substituents selected from alkyl, carboxy, carboxyalkyl, aminocarbonyl, hydroxy, alkoxy, halogen, CF$_3$, amino, substituted amino, cyano, and —S(O)R$^c$, where R$^c$ is alkyl, aryl, or heteroaryl and n is 0, 1 or 2.

The term "heterocyclylalkyl" refers to a heterocyclyl group covalently linked to an alkylene group, where heterocyclyl and alkylene are defined herein.

"Optionally substituted heterocyclylalkyl" refers to an optionally substituted heterocyclyl group covalently linked to an optionally substituted alkylene group.

The term "heteroaryloxy" refers to the group heteroaryl-O—.

The term "thiol" refers to the group —SH.

The term "substituted alkylthio" refers to the group —S-substituted alkyl.

The term "heteroarylthio" refers to the group —S-heteroaryl wherein the heteroaryl group is as defined above including optionally substituted heteroaryl groups as also defined above.

The term "sulfoxide" refers to a group —S(O).

"Substituted sulfoxide" refers to a group —S(O)R, in which R is substituted alkyl, substituted aryl, or substituted heteroaryl, as defined herein.

The term "sulfone" or "substituted sulfone" refers to a group —S(O)$_2$R, in which R is alkyl, aryl, or heteroaryl.

The compounds of the present disclosure may have the ability to crystallize in more than one form, a characteristic known as polymorphism, and all such polymorphic forms ("polymorphs") are encompassed within the scope of the present disclosure. Polymorphism generally can occur as a response to changes in temperature or pressure or both, and can also result from variations in the crystallization process. Polymorphs can be distinguished by various physical characteristics, and typically the x-ray diffraction patterns, solubility behavior, and melting point of the compound are used to distinguish polymorphs.

The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof.

Accordingly, the chemical structures depicted herein encompass all possible tautomeric forms of the illustrated or identified compounds.

Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the present disclosure are congeners, analogs, hydrolysis products, metabolites and precursor or prodrugs of the compound. In general, unless otherwise indicated, all physical forms are equivalent for the uses contemplated herein and are intended to be within the scope of the present invention.

"Prodrug" refers to a derivative of a drug molecule as, for example, esters, carbonates, carbamates, ureas, amides or phosphates that requires a transformation within the body to release the active drug. Prodrugs are frequently, although not necessarily, pharmacologically inactive until converted to the parent drug. Prodrugs may be obtained by bonding a promoiety (defined herein) typically via a functional group, to a drug.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach or the agent may be supplied exogenously.

"Pharmaceutically acceptable salt" embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the present disclosure are quaternary ammonium compounds wherein an equivalent of an anion (M–) is associated with the positive charge of the N atom. M– may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. M- is preferably an anion selected from chloride, bromide, iodide, sulphate, nitrate, acetate, maleate, oxalate, succinate or trifluoroacetate. More preferably M- is chloride, bromide, trifluoroacetate or methanesulphonate.

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present disclosure are inert organic solvents. The term "q.s." means adding a quantity sufficient to achieve a stated function, e.g., to bring a solution to the desired volume (i.e., 100%).

The present disclosure provides compounds of formula (I), or their tautomers, polymorphs, stereoisomers, prodrugs, solvates, pharmaceutically acceptable salts, pharmaceutical compositions containing them and methods of treating conditions and diseases that are mediated by the inhibition of Fatty Acid Amide Hydrolase (FAAH),

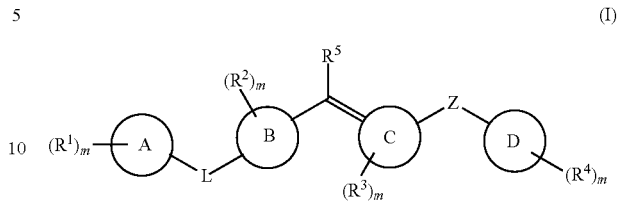

(I)

wherein
ring A is selected from aryl, cycloalkyl, heteroaryl or heterocyclyl;
L is absent or is $C_{1-4}$alkylene wherein one or more methylene groups is optionally replaced by hetero atoms or groups such as —O—, —S(O)p—, —N(R)—, —C(O)— or —(CR$^a$R$^b$)—; alkylene is optionally substituted with hydroxy, amino, aminoalkyl, cyano, halogen, haloalkyl, perhaloalkyl, carboxy, carboxyalkyl, alkylcarboxy, alkoxy, hydroxyalkyl, alkoxyalkyl, alkoxyalkoxy or alkyl;
ring B is selected from aryl, heteroaryl or heterocyclyl;
ring C is cycloalkyl;
Z is selected from —C(Y)NR—(CR$^a$R$^b$)$_q$— or —NRC(Y)—C(R$^a$R$^b$)$_q$;
Y is selected from O, S or N(R''');
R and R''' are independently selected from hydrogen, cyano, alkyl or haloalkyl;
ring D is selected from aryl, cycloalkyl, heteroaryl or heterocyclyl;
$R^1$, $R^2$, $R^3$ and $R^4$ are independently selected from hydrogen, halo, cyano, nitro, —(CR$^a$R$^b$)$_n$OR$^6$, —(CR$^a$R$^b$)$_n$C(O)R$^6$, —(CR$^a$R$^b$)$_n$SR$^6$, —(CR$^a$R$^b$)$_n$COOR$^6$, —(CR$^a$R$^b$)$_n$NR$^7$R$^8$, —(CR$^a$R$^b$)$_n$C(O)NR$^7$R$^8$, —(CR$^a$R$^b$)$_n$NR$^7$C(O)OR$^6$, —(CR$^a$R$^b$)$_n$NR$^7$C(O)NR$^7$R$^8$, —NR$^7$S(O)$_2$R$^6$, —S(O)$_p$R$^6$, —SO$_3$H, —S(O)$_2$NR$^7$R$^8$, azido, oxo, thiocarbonyl, $C_{1-6}$alkyl, $C_{2-6}$alkenyl, $C_{2-6}$alkynyl, cyanoalkyl, cyanoalkylcarbonyl, haloalkyl, perhaloalkyl, haloalkoxy, perhaloalkoxy, alkoxyalkyl, alkoxyalkoxyalkyl, cycloalkyl, cycloalkenyl, cycloalkylalkyl aryl, arylalkyl, heterocyclyl, heterocyclylalkyl, heteroaryl or heteroarylalkyl
wherein each substituent is unsubstituted or substituted with 1, 2, or 3 substituents independently selected from alkyl, halogen, haloalkyl, perhaloalkyl, haloalkoxy, perhaloalkoxy, cyano —(CR$^a$R$^b$)$_n$OR$^6$, —(CR$^a$R$^b$)$_n$COOR$^6$, —(CR$^a$R$^b$)$_n$NR$^7$R$^8$, —(CR$^a$R$^b$)$_n$C(O)NR$^7$R$^8$, —S(O)$_p$R$^6$ or —SO$_3$H.
$R^5$ is selected from hydrogen, halogen, haloalkyl, cyano, $C_{1-6}$alkyl, cycloalkyl, cycloalkylalkyl, aryl, arylalkyl, heterocyclyl, heterocyclylalkyl, heteroaryl or heteroarylalkyl;
wherein alkyl, cycloalkyl, cycloalkylalkyl, aryl, arylalkyl, heterocyclyl, heterocyclylalkyl, heteroaryl and heteroarylalkyl is unsubstituted or substituted with 1, 2, or 3 substituents independently selected from alkyl, halogen, haloalkyl, perhaloalkyl, haloalkoxy, perhaloalkoxy, cyano —(CR$^a$R$^b$)$_n$OR$^6$, —(CR$^a$R$^b$)$_n$COOR$^6$, —(CR$^a$R$^b$)$_n$NR$^7$R$^8$, —(CR$^a$R$^b$)$_n$C(O)NR$^7$R$^8$, —S(O)$_p$R$^6$ or —SO$_3$H.
$R^6$ is selected from hydrogen, alkyl, haloalkyl, —(CR$^a$R$^b$)$_n$OR$^6$, —(CR$^a$R$^b$)$_n$COOR$^6$, —(CR$^a$R$^b$)$_n$C(O)R$^6$, aminocarbonyl, cycloalkyl, cycloalkylalkyl, aryl, arylalkyl, heteroaryl, heteroarylalkyl, heterocyclyl or heterocyclylalkyl;

$R^7$ and $R^8$ are independently selected from the group consisting of hydrogen, alkyl, haloalkyl, —$(CR^aR^b)_nOR^6$, —$(CR^aR^b)_nC(O)R^6$, aryl, arylalkyl, heteroaryl, heteroarylalkyl, cycloalkyl, cycloalkylalkyl, heterocyclyl and heterocyclylalkyl, or $R^7$ and $R^8$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, alkenyl, alkynyl, nitro, cyano, —$(CR^aR^b)_nOR^6$, —$(CR^aR^b)_nSR^6$, —$(CR^aR^b)_nNR^7R^8$, oxo, alkylsulfonyl, —$(CR^aR^b)_nCOOR^6$, —$(CR^aR^b)_nC(O)NR^7R^8$, cycloalkyl, cycloalkylalkyl, aryl, arylalkyl, heterocyclyl, heterocyclylalkyl, heteroaryl, or heteroarylalkyl;

$R^a$ and $R^b$ are independently selected from the group consisting of hydrogen, —$OR^6$, halogen, haloalkyl, perhaloalkyl and alkyl; or $R^a$ and $R^b$ taken together form a monocyclic or a bicyclic ring system which is saturated or partially unsaturated and optionally have additional heteroatoms selected from O, N or S m is independently selected from 0, 1, 2, 3 or 4;
n is an integer and selected from 0, 1, 2, 3 or 4;
p is an integer selected from 0, 1 or 2; and
q is an integer selected from 0, 1, 2, 3 or 4.

According to an embodiment, the present disclosure relates to compounds of formula (I) wherein;
ring A is selected from heteroaryl or heterocyclyl;
L is absent or is $C_{1-4}$alkylene wherein one or more methylene groups is optionally replaced by hetero atoms or groups such as —O—, —S(O)$_p$—, —N(R)—, —C(O)— or —$(CR^aR^b)$—;
ring B is selected from aryl, heteroaryl or heterocyclyl;
ring C is cycloalkyl;
Z is selected from —C(Y)NR—$(CR^aR^b)_q$— or —NRC(Y)—$C(R^aR^b)_q$;
Y is selected from O, S or N(R''');
R and R''' are independently selected from hydrogen, cyano, alkyl or haloalkyl;
ring D is selected from aryl, cycloalkyl, heteroaryl or heterocyclyl;
$R^1$, $R^2$, $R^3$ and $R^4$ are independently selected from hydrogen, halo, cyano, nitro, —$(CR^aR^b)_nOR^6$, —$(CR^aR^b)_nC(O)R^6$, —$(CR^aR^b)_nSR^6$, —$(CR^aR^b)_nCOOR^6$, —$(CR^aR^b)_nNR^7R^8$, —$(CR^aR^b)_nC(O)NR^7R^8$, —$(CR^aR^b)_nNR^7C(O)OR^6$, —$(CR^aR^b)_nNR^7C(O)NR^7R^8$, —$NR^7S(O)_2R^6$, —$S(O)_pR^6$, —$SO_3H$, —$S(O)_2NR^7R^8$, azido, oxo, thiocarbonyl, $C_{1-6}$alkyl, cyanoalkyl, cyanoalkylcarbonyl, haloalkyl, perhaloalkyl, haloalkoxy, perhaloalkoxy, alkoxyalkoxy, alkoxyalkoxyalkyl, cycloalkyl, cycloalkylalkyl aryl, arylalkyl, heterocyclyl, heterocyclylalkyl, heteroaryl or heteroarylalkyl
 wherein each substituent is unsubstituted or substituted with 1, 2, or 3 substituents independently selected from alkyl, halogen, haloalkyl, perhaloalkyl, haloalkoxy, perhaloalkoxy, cyano —$(CR^aR^b)_nOR^6$, —$(CR^aR^b)_nCOOR^6$, —$(CR^aR^b)_nNR^7R^8$, —$(CR^aR^b)_nC(O)NR^7R^8$, —$S(O)_pR^6$ or —$SO_3H$.

$R^5$ is selected from hydrogen, halogen, haloalkyl, cyano, $C_{1-6}$alkyl, cycloalkyl, cycloalkylalkyl, aryl, arylalkyl, heterocyclyl, heterocyclylalkyl, heteroaryl or heteroarylalkyl;

$R^6$ is selected from hydrogen, alkyl, haloalkyl, —$(CR^aR^b)_nOR^6$, —$(CR^aR^b)_nCOOR^6$, —$(CR^aR^b)_nC(O)R^6$, aminocarbonyl, cycloalkyl, cycloalkylalkyl, aryl, arylalkyl, heteroaryl, heteroarylalkyl, heterocyclyl or heterocyclylalkyl;

$R^7$ and $R^8$ are independently selected from the group consisting of hydrogen, alkyl, haloalkyl, —$(CR^aR^b)_nOR^6$, —$(CR^aR^b)_nC(O)R^6$, aryl, arylalkyl, heteroaryl, heteroarylalkyl, cycloalkyl, cycloalkylalkyl, heterocyclyl and heterocyclylalkyl, or $R^7$ and $R^8$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, alkenyl, alkynyl, nitro, cyano, —$(CR^aR^b)_nOR^6$, —$(CR^aR^b)_nSR^6$, —$(CR^aR^b)_nNR^7R^8$, oxo, alkylsulfonyl, —$(CR^aR^b)_nCOOR^6$, —$(CR^aR^b)_nC(O)NR^7R^8$, cycloalkyl, cycloalkylalkyl, aryl, arylalkyl, heterocyclyl, heterocyclylalkyl, heteroaryl, or heteroarylalkyl;

$R^a$ and $R^b$ are independently selected from the group consisting of hydrogen, —$OR^6$, halogen, haloalkyl, perhaloalkyl and alkyl; or $R^a$ and $R^b$ taken together form a monocyclic or a bicyclic ring system which is saturated or partially unsaturated and optionally have additional heteroatoms selected from O, N or S m is independently selected from 0, 1, 2, 3 or 4
n is an integer and selected from 0, 1, 2, 3 or 4;
p is an integer selected from 0, 1 or 2; and
q is an integer selected from 0, 1, 2, 3 or 4.

According to an embodiment, the present disclosure relates to compounds of formula (I) wherein;
ring A is selected from aryl or cycloalkyl;
L is absent or is $C_{1-4}$alkylene wherein one or more methylene groups is optionally replaced by hetero atoms or groups such as —O—, —S(O)$_p$—, —N(R)—, —C(O)— or —$(CR^aR^b)$—;
ring B is selected from aryl, heteroaryl or heterocyclyl;
ring C is cycloalkyl;
Z is selected from —C(Y)NR—$(CR^aR^b)_q$— or —NRC(Y)—$C(R^aR^b)_q$;
Y is selected from O, S or N(R''');
R and R''' are independently selected from hydrogen, cyano, alkyl or haloalkyl;
ring D is selected from aryl, cycloalkyl, heteroaryl or heterocyclyl;
$R^1$, $R^2$, $R^3$ and $R^4$ are independently selected from hydrogen, halo, cyano, nitro, —$(CR^aR^b)_nOR^6$, —$(CR^aR^b)_nC(O)R^6$, —$(CR^aR^b)_nSR^6$, —$(CR^aR^b)_nCOOR^6$, —$(CR^aR^b)_nNR^7R^8$, —$(CR^aR^b)_nC(O)NR^7R^8$, —$(CR^aR^b)_nNR^7C(O)OR^6$, —$(CR^aR^b)_nNR^7C(O)NR^7R^8$, —$NR^7S(O)_2R^6$, —$S(O)_pR^6$, —$SO_3H$, —$S(O)_2NR^7R^8$, azido, oxo, thiocarbonyl, $C_{1-6}$alkyl, cyanoalkyl, cyanoalkylcarbonyl, haloalkyl, perhaloalkyl, haloalkoxy, perhaloalkoxy, alkoxyalkoxy, alkoxyalkoxyalkyl, cycloalkyl, cycloalkylalkyl aryl, arylalkyl, heterocyclyl, heterocyclylalkyl, heteroaryl or heteroarylalkyl;
 wherein each substituent is unsubstituted or substituted with 1, 2, or 3 substituents independently selected from alkyl, halogen, haloalkyl, perhaloalkyl, haloalkoxy, perhaloalkoxy, cyano —$(CR^aR^b)_nOR^6$, —$(CR^aR^b)_nCOOR^6$, —$(CR^aR^b)_nNR^7R^8$, $(CR^aR^b)_nC(O)NR^7R^8$, —$S(O)_pR^6$ or —$SO_3H$.

R$^5$ is selected from hydrogen, halogen, haloalkyl, cyano, C$_{1-6}$alkyl, cycloalkyl, cycloalkylalkyl, aryl, arylalkyl, heterocyclyl, heterocyclylalkyl, heteroaryl or heteroarylalkyl;

R$^6$ is selected from hydrogen, alkyl, haloalkyl, —(CR$^a$R$^b$)$_n$OR$^6$, —(CR$^a$R$^b$)$_n$COOR$^6$, —(CR$^a$R$^b$)$_n$C(O)R$^6$, aminocarbonyl, cycloalkyl, cycloalkylalkyl, aryl, arylalkyl, heteroaryl, heteroarylalkyl, heterocyclyl or heterocyclylalkyl;

R$^7$ and R$^8$ are independently selected from the group consisting of hydrogen, alkyl, haloalkyl, —(CR$^a$R$^b$)$_n$OR$^6$, —(CR$^a$R$^b$)$_n$C(O)R$^6$, aryl, arylalkyl, heteroaryl, heteroarylalkyl, cycloalkyl, cycloalkylalkyl, heterocyclyl and heterocyclylalkyl, or R$^7$ and R$^8$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, alkenyl, alkynyl, nitro, cyano, —(CR$^a$R$^b$)$_n$OR$^6$, —(CR$^a$R$^b$)$_n$SR$^6$, —(CR$^a$R$^b$)$_n$NR$^7$R$^8$, oxo, alkylsulfonyl, —(CR$^a$R$^b$)$_n$COOR$^6$, —(CR$^a$R$^b$)$_n$C(O)NR$^7$R$^8$, cycloalkyl, cycloalkylalkyl, aryl, arylalkyl, heterocyclyl, heterocyclylalkyl, heteroaryl, or heteroarylalkyl;

R$^a$ and R$^b$ are independently selected from the group consisting of hydrogen, —OR$^6$, halogen, haloalkyl, perhaloalkyl and alkyl; or R$^a$ and R$^b$ taken together form a monocyclic or a bicyclic ring system which is saturated or partially unsaturated and optionally have additional heteroatoms selected from O, N or S m is independently selected from 0, 1, 2, 3 or 4;
n is an integer and selected from 0, 1, 2, 3 or 4;
p is an integer selected from 0, 1 or 2; and
q is an integer selected from 0, 1, 2, 3 or 4.

According to an embodiment, the present disclosure relates to compounds of formula (I) wherein;

ring A is selected from aryl, cycloalkyl, heteroaryl or heterocyclyl;

L is C$_{1-4}$alkylene wherein one or more methylene groups is optionally replaced by hetero atoms or groups such as —O—, —N(R)—, —C(O)— or —(CR$^a$R$^b$)—;

ring B is selected from aryl, heteroaryl or heterocyclyl;
ring C is cycloalkyl;
Z is selected from —C(Y)NR—(CR$^a$R$^b$)$_q$— or —NRC(Y)—C(R$^a$R$^b$)$_q$;
Y is selected from O, S or N(R''');
R and R''' are independently selected from hydrogen, cyano, alkyl or haloalkyl;
ring D is selected from aryl, cycloalkyl, heteroaryl or heterocyclyl;
R$^1$, R$^2$, R$^3$ and R$^4$ are independently selected from hydrogen, halo, cyano, nitro, —(CR$^a$R$^b$)$_n$OR$^6$, —(CR$^a$R$^b$)$_n$C(O)R$^6$, —(CR$^a$R$^b$)$_n$SR$^6$, —(CR$^a$R$^b$)$_n$COOR$^6$, —(CR$^a$R$^b$)$_n$NR$^7$R$^8$, —(CR$^a$R$^b$)$_n$C(O)NR$^7$R$^8$, —(CR$^a$R$^b$)$_n$NR$^7$C(O)OR$^6$, —(CR$^a$R$^b$)$_n$NR$^7$C(O)NR$^7$R$^8$, —NR$^7$S(O)$_2$R$^6$, —S(O)$_p$R$^6$, —SO$_3$H, —S(O)$_2$NR$^7$R$^8$, azido, oxo, thiocarbonyl, C$_{1-6}$alkyl, cyanoalkyl, cyanoalkylcarbonyl, haloalkyl, perhaloalkyl, haloalkoxy, perhaloalkoxy, alkoxyalkoxy, alkoxyalkoxyalkyl, cycloalkyl, cycloalkylalkyl aryl, arylalkyl, heterocyclyl, heterocyclylalkyl, heteroaryl or heteroarylalkyl;
wherein each substituent is unsubstituted or substituted with 1, 2, or 3 substituents independently selected from alkyl, halogen, haloalkyl, perhaloalkyl, haloalkoxy, perhaloalkoxy, cyano —(CR$^a$R$^b$)$_n$OR$^6$, —(CR$^a$R$^b$)$_n$COOR$^6$, —(CR$^a$R$^b$)$_n$NR$^7$R$^8$, —(CR$^a$R$^b$)$_n$C(O)NR$^7$R$^8$, —S(O)$_p$R$^6$ or —SO$_3$H.

R$^5$ is selected from hydrogen, halogen, haloalkyl, cyano or C$_{1-6}$alkyl;

R$^6$ is selected from hydrogen, alkyl, haloalkyl, —(CR$^a$R$^b$)$_n$OR$^6$, —(CR$^a$R$^b$)$_n$COOR$^6$, —(CR$^a$R$^b$)$_n$C(O)R$^6$ or aminocarbonyl;

R$^7$ and R$^8$ are independently selected from the group consisting of hydrogen, alkyl, haloalkyl, —(CR$^a$R$^b$)$_n$OR$^6$, —(CR$^a$R$^b$)$_n$C(O)R$^6$, aryl, heteroaryl, cycloalkyl and heterocyclyl;

R$^a$ and R$^b$ are independently selected from the group consisting of hydrogen, —OR$^6$, halogen, haloalkyl, perhaloalkyl and alkyl; or R$^a$ and R$^b$ taken together form a monocyclic or a bicyclic ring system which is saturated or partially unsaturated;
m is independently selected from 0, 1, 2, 3 or 4;
n is an integer and selected from 0, 1, 2, 3 or 4;
p is an integer selected from 0, 1 or 2; and
q is an integer selected from 0, 1, 2, 3 or 4.

According to another embodiment, the present disclosure relates to compounds of formula (I) wherein;
ring A is selected from;

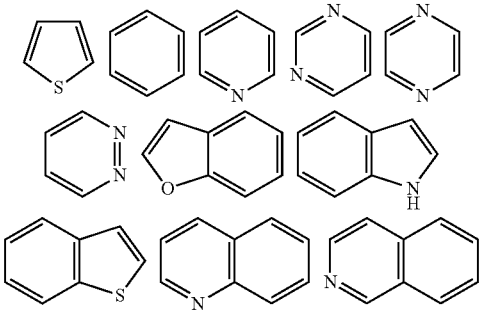

ring B is selected from;

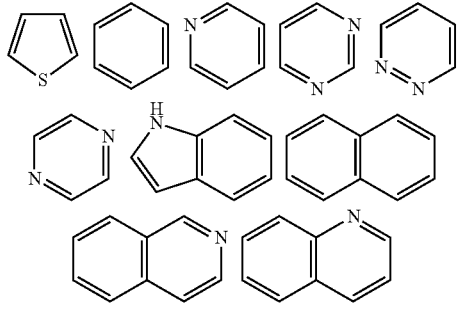

ring C is selected from;

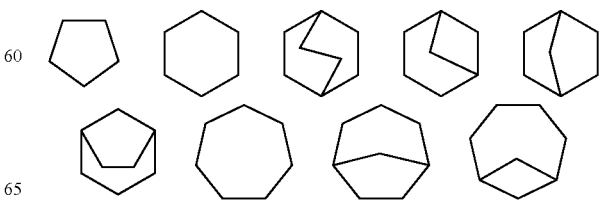

ring D is selected from;

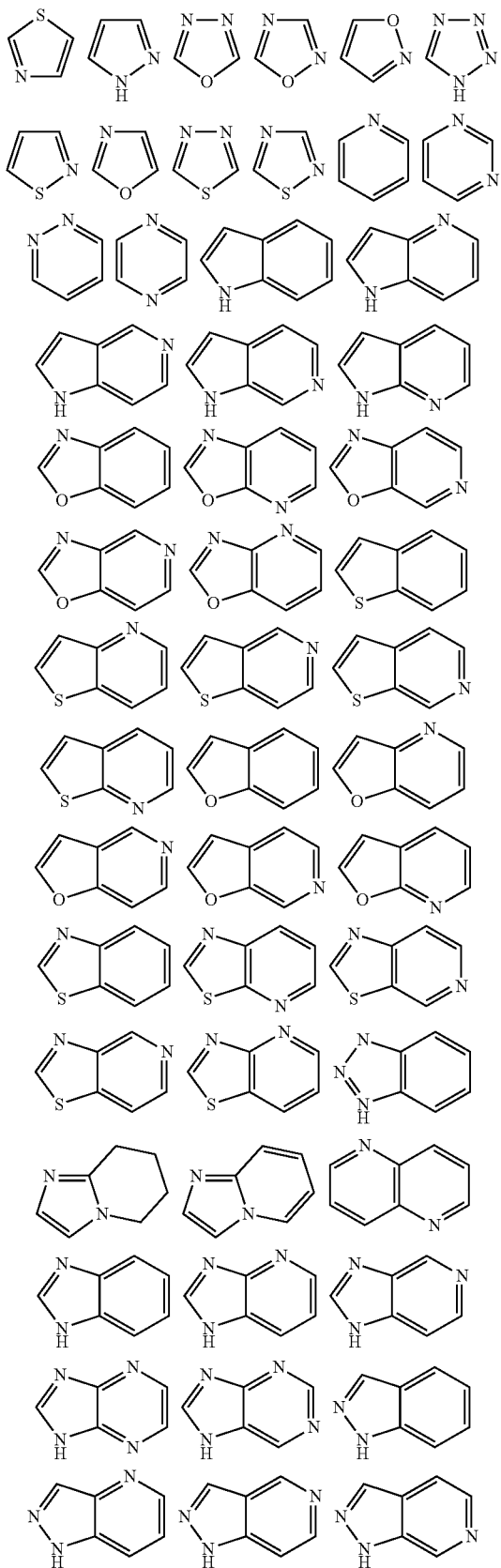

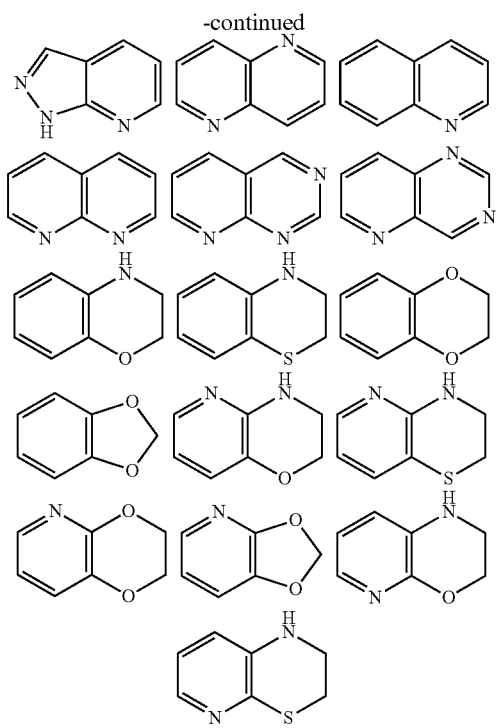

L is $C_{1-4}$alkylene wherein one or more methylene groups is optionally replaced by hetero atoms or groups such as —O—, —N(R)—, —C(O)— or —$(CR^aR^b)$—;

Z is selected from —C(Y)NR—$(CR^aR^b)_q$— or —NRC(Y)—C$(R^aR^b)_q$;

Y is selected from O, S or N(R′′′);

R and R′′′ are independently selected from hydrogen, cyano, alkyl or haloalkyl;

$R^1$, $R^2$, $R^3$ and $R^4$ are independently selected from hydrogen, halo, cyano, nitro, —$(CR^aR^b)_nOR^6$, —$(CR^aR^b)_nC(O)R^6$, —$(CR^aR^b)_nSR^6$, —$(CR^aR^b)_nCOOR^6$, —$(CR^aR^b)NR^7R^8$, —$(CR^aR^b)_nC(O)NR^7R^8$, —$(CR^aR^b)_nNR^7C(O)OR^6$, —$(CR^aR^b)_nNR^7C(O)NR^7R^8$, —$NR^7S(O)_2R^6$, —$S(O)_pR^6$, —$SO_3H$, —$S(O)_2NR^7R^8$, azido, oxo, thiocarbonyl, $C_{1-6}$alkyl, cyanoalkyl, cyanoalkylcarbonyl, haloalkyl, perhaloalkyl, haloalkoxy, perhaloalkoxy, alkoxyalkoxy, alkoxyalkoxyalkyl, cycloalkyl, cycloalkylalkyl aryl, arylalkyl, heterocyclyl, heterocyclylalkyl, heteroaryl or heteroarylalkyl;

wherein each substituent is unsubstituted or substituted with 1, 2, or 3 substituents independently selected from alkyl, halogen, haloalkyl, perhaloalkyl, haloalkoxy, perhaloalkoxy, cyano —$(CR^aR^b)_nOR^6$, —$(CR^aR^b)_n$ COOR$^6$, —$(CR^aR^b)_nNR^7R^8$, $(CR^aR^b)_nC(O)NR^7R^8$, —$S(O)_pR^6$ or —$SO_3H$.

$R^5$ is selected from hydrogen, halogen, haloalkyl, cyano or $C_{1-6}$alkyl;

$R^6$ is selected from hydrogen, alkyl, haloalkyl, —$(CR^aR^b)_nOR^6$, —$(CR^aR^b)_nCOOR^6$, —$(CR^aR^b)_nC(O)R^6$ or aminocarbonyl;

$R^7$ and $R^8$ are independently selected from the group consisting of hydrogen, alkyl, haloalkyl, —$(CR^aR^b)_nOR^6$, —$(CR^aR^b)_nC(O)R^6$, aryl, heteroaryl, cycloalkyl and heterocyclyl; or $R^a$ and $R^b$ are independently selected from the group consisting of hydrogen, —$OR^6$, halogen, haloalkyl, perhaloalkyl and alkyl; or $R^a$ and $R^b$ taken together form a monocyclic or a bicyclic ring system which is saturated or partially unsaturated;

m is independently selected from 0, 1, 2, 3 or 4;

n is an integer and selected from 0, 1, 2, 3 or 4;

p is an integer selected from 0, 1 or 2; and q is an integer selected from 0, 1, 2, 3 or 4.

According to yet another embodiment, the present disclosure relates to compounds of formula (I) wherein;

ring A is selected from;

ring B is selected from;

ring C is selected from;

ring D is selected from;

L is C$_{1-4}$alkylene wherein one or more methylene groups is optionally replaced by hetero atoms or groups such as —O—, —N(R)—, —C(O)— or —(CR$^a$R$^b$)—;

Z is selected from —C(Y)NR—(CR$^a$R$^b$)$_q$— or —NRC(Y)—C(R$^a$R$^b$)$_q$;

Y is selected from O, S or N(R''');

R and R''' are independently selected from hydrogen, cyano, alkyl or haloalkyl;

R$^1$, R$^2$, R$^3$ and R$^4$ are independently selected from hydrogen, halo, cyano, nitro, —(CR$^a$R$^b$)$_n$OR$^6$, —(CR$^a$R$^b$)$_n$C(O)R$^6$, —(CR$^a$R$^b$)$_n$SR$^6$, —(CR$^a$R$^b$)$_n$COOR$^6$, —(CR$^a$R$^b$)NR$^7$R$^8$, —(CR$^a$R$^b$)$_n$C(O)NR$^7$R$^8$, —(CR$^a$R$^b$)$_n$NR$^7$C(O)OR$^6$, —(CR$^a$R$^b$)$_n$NR$^7$C(O)NR$^7$R$^8$, —NR$^7$S(O)$_2$R$^6$, —S(O)$_p$R$^6$, —SO$_3$H, —S(O)$_2$NR$^7$R$^8$, azido, oxo, thiocarbonyl, C$_{1-6}$alkyl, cyanoalkyl, cyanoalkylcarbonyl, haloalkyl, perhaloalkyl, haloalkoxy, perhaloalkoxy, alkoxyalkoxy, alkoxyalkoxyalkyl, cycloalkyl, cycloalkylalkyl aryl, arylalkyl, heterocyclyl, heterocyclylalkyl, heteroaryl or heteroarylalkyl
wherein each substituent is unsubstituted or substituted with 1, 2, or 3 substituents independently selected from alkyl, halogen, haloalkyl, perhaloalkyl, haloalkoxy, perhaloalkoxy, cyano —(CR$^a$R$^b$)$_n$OR$^6$, —(CR$^a$R$^b$)$_n$COOR$^6$, —(CR$^a$R$^b$)$_n$NR$^7$R$^8$, —(CR$^a$R$^b$)$_n$C(O)NR$^7$R$^8$, —S(O)$_p$R$^6$ or —SO$_3$H.

R$^5$ is selected from hydrogen, halogen, haloalkyl, cyano or C$_{1-6}$alkyl;

R$^6$ is selected from hydrogen, alkyl, haloalkyl, —(CR$^a$R$^b$)$_n$OR$^6$, —(CR$^a$R$^b$)$_n$COOR$^6$, —(CR$^a$R$^b$)$_n$C(O)R$^6$ or aminocarbonyl;

R$^7$ and R$^8$ are independently selected from the group consisting of hydrogen, alkyl, haloalkyl, —(CR$^a$R$^b$)$_n$OR$^6$, —(CR$^a$R$^b$)$_n$C(O)R$^6$, aryl, heteroaryl, cycloalkyl and heterocyclyl; or R$^a$ and R$^b$ are independently selected from the group consisting of hydrogen, —OR$^6$, halogen, haloalkyl, perhaloalkyl and alkyl; or R$^a$ and R$^b$ taken together form a monocyclic or a bicyclic ring system which is saturated or partially unsaturated;

m is independently selected from 0, 1, 2, 3 or 4 n is an integer and selected from 0, 1, 2, 3 or 4;

p is an integer selected from 0, 1 or 2; and q is an integer selected from 0, 1, 2, 3 or 4.

According to another embodiment, the present disclosure relates to compounds of formula (I) wherein;

ring A is selected from pyridine, pyrimidine, pyridazine or pyrazine;

ring B is selected from phenyl, thiophene, pyridine, pyrimidine, pyridazine or pyrazine;

ring C is selected from cyclopentyl, cyclohexyl, bicyclo[3.1.1]heptane, bicyclo[2.2.1]heptane or bicyclo[2.2.2]octane;

ring D is selected from phenyl, pyrrole, thiazole, isothiazole, pyrazole, oxazole, isoxazole, oxadiazole, thiadiazole, triazole, tetrazole, pyridine, pyrimidine, pyridazine, pyrazine, indole, thiazolopyridine, thienopyridine or pyrrolopyridine;

L is C$_{1-4}$alkylene wherein one or more methylene groups is optionally replaced by hetero atoms or groups such as —O—, —N(R)—, —C(O)— or —(CR$^a$R$^b$)—;

Z is selected from —C(Y)NR—$(CR^aR^b)_q$— or —NRC(Y)—$C(R^aR^b)_q$;

Y is selected from O, S or N(R''');

R and R''' are independently selected from hydrogen, alkyl or haloalkyl;

$R^1$, $R^2$, $R^3$ and $R^4$ are independently selected from hydrogen, halo, cyano, nitro, —$(CR^aR^b)_nOR^6$, —$(CR^aR^b)_nC(O)R^6$, —$(CR^aR^b)_nSR^6$, —$(CR^aR^b)_nCOOR^6$, —$(CR^aR^b)_nNR^7R^8$, —$(CR^aR^b)_nC(O)NR^7R^8$, —$(CR^aR^b)_nNR^7C(O)OR^6$, —$(CR^aR^b)_nNR^7C(O)NR^7R^8$, —$NR^7S(O)_2R^6$, —$S(O)_pR^6$, —$SO_3H$, —$S(O)_2NR^7R^8$, azido, oxo, thiocarbonyl, $C_{1-6}$alkyl, cyanoalkyl, cyanoalkylcarbonyl, haloalkyl, perhaloalkyl, haloalkoxy, perhaloalkoxy, alkoxyalkoxy, alkoxyalkoxyalkyl, cycloalkyl, cycloalkylalkyl aryl, arylalkyl, heterocyclyl, heterocyclylalkyl, heteroaryl or heteroarylalkyl;

wherein each substituent is unsubstituted or substituted with 1, 2, or 3 substituents independently selected from alkyl, halogen, haloalkyl, perhaloalkyl, haloalkoxy, perhaloalkoxy, cyano —$(CR^aR^b)_nOR^6$, —$(CR^aR^b)_nCOOR^6$, —$(CR^aR^b)_nNR^7R^8$, —$(CR^aR^b)_nC(O)NR^7R^8$, —$S(O)_pR^6$ or —$SO_3H$.

$R^5$ is selected from hydrogen, haloalkyl or $C_{1-6}$ alkyl;

$R^6$ is selected from hydrogen, alkyl or haloalkyl;

$R^7$ and $R^8$ are independently selected from the group consisting of hydrogen, alkyl and haloalkyl;

$R^a$ and $R^b$ are independently selected from the group consisting of hydrogen, —$OR^6$, halogen, haloalkyl, perhaloalkyl and alkyl; or $R^a$ and $R^b$ taken together form a monocyclic or a bicyclic ring system which is saturated or partially unsaturated;

m is independently selected from 0, 1, 2, 3 or 4;

n is an integer and selected from 0, 1, 2, 3 or 4;

p is an integer selected from 0, 1 or 2.

According to an embodiment, the present disclosure relates to an intermediate of formula (IV)

(IV)

wherein;

ring A is selected from;

ring B is selected from;

ring C is selected from;

L is $C_{1-4}$alkylene wherein one or more methylene groups is optionally replaced by hetero atoms or groups such as —O—, —N(R)—, —C(O)— or —$(CR^aR^b)$—;

R is selected from hydrogen, cyano, alkyl or haloalkyl;

$R^1$, $R^2$ and $R^3$ are independently selected from hydrogen, halo, cyano, nitro, —$(CR^aR^b)_nOR^6$, —$(CR^aR^b)_nC(O)R^6$, —$(CR^aR^b)_nSR^6$, —$(CR^aR^b)_nCOOR^6$, —$(CR^aR^b)_nNR^7R^8$, —$(CR^aR^b)_nC(O)NR^7R^8$, —$(CR^aR^b)_nNR^7C(O)OR^6$, —$(CR^aR^b)_nNR^7C(O)NR^7R^8$, —$NR^7S(O)_2R^6$, —$S(O)_pR^6$, —$SO_3H$, —$S(O)_2NR^7R^8$, azido, oxo, thiocarbonyl, $C_{1-6}$alkyl, cyanoalkyl, cyanoalkylcarbonyl, haloalkyl, perhaloalkyl, haloalkoxy, perhaloalkoxy, alkoxyalkoxy, alkoxyalkoxyalkyl, cycloalkyl, cycloalkylalkyl aryl, arylalkyl, heterocyclyl, heterocyclylalkyl, heteroaryl or heteroarylalkyl;

$R^5$ is selected from hydrogen, halogen, haloalkyl, cyano or $C_{1-6}$alkyl;

$R^6$ is selected from hydrogen, alkyl, haloalkyl, —$(CR^aR^b)_nOR^6$, —$(CR^aR^b)_nCOOR^6$, —$(CR^aR^b)_nC(O)R^6$ or aminocarbonyl;

$R^7$ and $R^8$ are independently selected from the group consisting of hydrogen, alkyl, haloalkyl, —$(CR^aR^b)_nOR^6$, —$(CR^aR^b)_nC(O)R^6$, aryl, heteroaryl, cycloalkyl and heterocyclyl;

$R^a$ and $R^b$ are independently selected from the group consisting of hydrogen, —$OR^6$, halogen, haloalkyl, perhaloalkyl and alkyl; or $R^a$ and $R^b$ taken together form a monocyclic or a bicyclic ring system which is saturated or partially unsaturated;

m is independently selected from 0, 1, 2, 3 or 4;

n is an integer and selected from 0, 1, 2, 3 or 4; and p is an integer selected from 0, 1 or 2.

According to an embodiment, the present disclosure relates to an intermediate of formula (II)

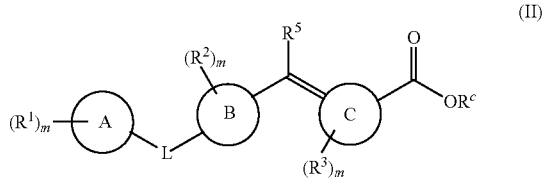

(II)

wherein;
ring A is selected from;

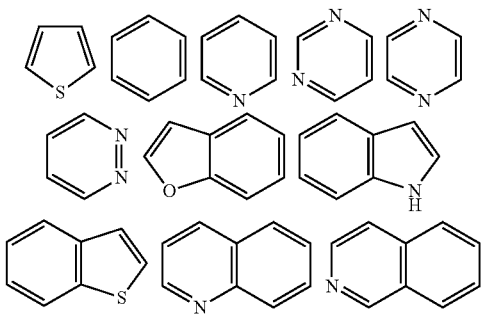

ring B is selected from;

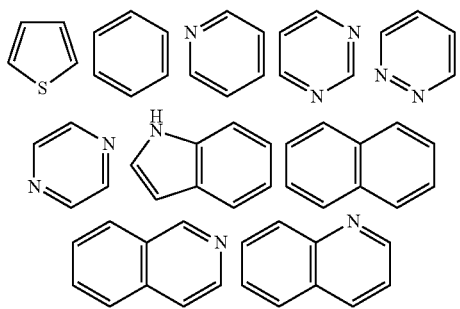

ring C is selected from;

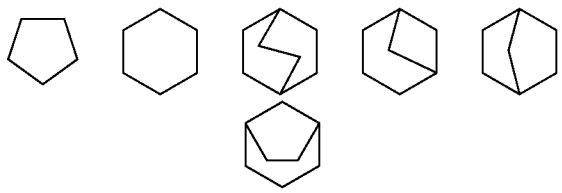

L is $C_{1-4}$alkylene wherein one or more methylene groups is optionally replaced by hetero atoms or groups such as —O—, —N(R)—, —C(O)— or —(CR$^a$R$^b$)—;

R is selected from hydrogen, cyano, alkyl or haloalkyl;

R$^1$, R$^2$ and R$^3$ are independently selected from hydrogen, halo, cyano, nitro, —(CR$^a$R$^b$)$_n$OR$^6$, —(CR$^a$R$^b$)$_n$C(O)R$^6$, —(CR$^a$R$^b$)$_n$SR$^6$, —(CR$^a$R$^b$)$_n$COOR$^6$, —(CR$^a$R$^b$)$_n$NR$^7$R$^8$, —(CR$^a$R$^b$)$_n$C(O)NR$^7$R$^8$, —(CR$^a$R$^b$)$_n$NR$^7$C(O)OR$^6$, —(CR$^a$R$^b$)$_n$NR$^7$C(O)NR$^7$R$^8$, —NR$^7$S(O)$_2$R$^6$, —S(O)$_p$R$^6$, —SO$_3$H, —S(O)$_2$NR$^7$R$^8$, azido, oxo, thiocarbonyl, $C_{1-6}$alkyl, cyanoalkyl, cyanoalkylcarbonyl, haloalkyl, perhaloalkyl, haloalkoxy, perhaloalkoxy, alkoxyalkoxy, alkoxyalkoxyalkyl, cycloalkyl, cycloalkylalkyl aryl, arylalkyl, heterocyclyl, heterocyclylalkyl, heteroaryl or heteroarylalkyl;

R$^5$ is selected from hydrogen, halogen, haloalkyl, cyano or $C_{1-6}$alkyl;

R$^6$ is selected from hydrogen, alkyl, haloalkyl, —(CR$^a$R$^b$)$_n$OR$^6$, —(CR$^a$R$^b$)$_n$COOR$^6$, —(CR$^a$R$^b$)$_n$C(O)R$^6$ or aminocarbonyl;

R$^7$ and R$^8$ are independently selected from the group consisting of hydrogen, alkyl, haloalkyl, —(CR$^a$R$^b$)$_n$OR$^6$, —(CR$^a$R$^b$)$_n$C(O)R$^6$, aryl, heteroaryl, cycloalkyl and heterocyclyl;

R$^a$ and R$^b$ are independently selected from the group consisting of hydrogen, —OR$^6$, halogen, haloalkyl, perhaloalkyl and alkyl; or R$^a$ and R$^b$ taken together form a monocyclic or a bicyclic ring system which is saturated or partially unsaturated;

R$^c$ is selected from hydrogen, alkyl, arylalkyl;

m is independently selected from 0, 1, 2, 3 or 4;

n is an integer and selected from 0, 1, 2, 3 or 4; and p is an integer selected from 0, 1 or 2.

In another aspect, pharmaceutical compositions are provided comprising a compound of the invention, and a pharmaceutical carrier, excipient or diluent. The pharmaceutical composition can comprise one or more of the compounds described herein. In a further embodiment, the pharmaceutical compositions of the invention can comprise a compound in combination with one or more other compounds and/or compositions having a like therapeutic effect.

In another aspect, methods are provided for treatment, prevention, prophylaxis, management, or adjunct treatment in a mammal, of all medical conditions related to modulation of Fatty Acid Amide Hydrolase (FAAH), such as pain including acute such as post operative pain, chronic pain, cancer pain, cancer chemotherapy induced pain, neuropathic pain, nociceptive pain, inflammatory pain, back pain, pain due to disease of various origin such as: diabetic neuropathy, neurotropic viral disease including human immunodeficient virus (HIV), herpes zoster such as post herpetic neuralgia; polyneuropathy, neurotoxicity, mechanical nerve injury, carpal tunnel syndrome, immunologic mechanisms like multiple sclerosis.

In yet another aspect, methods are provided for treatment, prevention, prophylaxis, management, or adjunct treatment of sleep disorders, anxiety and depression disorders, inflammatory disorders, weight and eating disorders, Parkinson's disease, Alzheimer's disease, asthma, myocardial infarction, inflammatory bowel disease, addiction, spasticity, hypertension or other disorders. The disclosure also relates to the process of preparation of the amide compounds.

In another aspect, the compounds of formula I described herein and their pharmaceutically acceptable compositions either alone or in combination with other therapeutic agents are useful in methods for treating or lessening the severity of pain syndromes or indications, including but not limited to acute such as post operative pain, as well as chronic pain, cancer pain, cancer chemotherapy induced pain, neuropathic pain, nociceptive pain, inflammatory pain, back pain including lumbosacral radiculopathy, pain due to disease of various origin such as: diabetic neuropathy, neurotropic viral disease including human immunodeficient virus (HIV), herpes zoster such as post herpetic neuralgia; polyneuropathy, neurotoxicity, mechanical nerve injury, carpal tunnel syndrome, immunologic mechanisms like multiple sclerosis.

In another aspect, the compounds of formula I described herein and their pharmaceutical compositions can be used in combination with other FAAH inhibitors, including reversible and irreversible inhibitors of FAAH known in the literature e.g. OL-135, PF-3845, PF-04457845, PF-750, JNJ-116101, URB-597, URB-524, URB-937, V-158866, IW-6118, SAR-411298 and IPI-940.

Compounds of general formula I may be administered in combination with other classes of pharmaceutically active drugs for the treatment of one or more related disorders to above mentioned syndromes or indications. The pharmacologically active compounds can be selected from opioid analgesic, nonsteroidal antiinflammatory drug (NSAID), barbiturate, benzodiazepine, $H_1$ antagonist, Tramadol, cannabinoid receptor agonist or antagonist, TRPV1 agonist or antagonist, 5-HT receptor agonist or antagonist, mGluR1 antagonist, leukotriene B4 antagonist, NMDA receptor antagonist, 5-HT3 antagonist, prostaglandin $E_2$ subtype 4 antagonist, tachykinin (NK) antagonist, inducible nitric oxide synthase (iNOS) inhibitor, serotonin reuptake inhibitor, noradrenaline reuptake inhibitor, dual serotonin-noradrenaline reuptake inhibitor, PDE inhibitor, COX-2 inhibitor, 5-lipoxygenase inhibitor, acetylcholinesterase inhibitor, tricyclic antidepressant, anticonvulsant, alpha-adrenergic, coal-tar analgesic, neuroleptic, cholinergic analgesic, alph-2-delta ligand, sodium channel blocker calcium channel inhibitor N-type, p38 MAP kinase inhibitor, nicoticic acid receptor agonist, angiotensin II AT-2 receptor antagonist, Beta-2 adrenoceptor agonist, $GABA_A$ receptor modulators, anti-nerve growth factor antibodies.

Compounds of general formula I may be useful to lower dose of classical opioid therapy as well as opioid resistance/tolerance/non-responsiveness.

In addition to the methods of treatment set forth above, the present invention extends to the use of any of the compounds of the invention for the preparation of medicaments that may be administered for such treatments, as well as to such compounds for the treatments disclosed and specified.

Accordingly, it is a principal object of the invention to provide a novel series of compounds, which can modify any aberrant activity of FAAH and thus may have the ability to treat certain of the conditions in which FAAH is believed to play a role.

A still further object of the invention is to provide a method for the treatment of the disease states recited above, by the administration of a therapeutically effective amount of the compounds of the invention, and/or the pharmaceutical compositions of the invention.

A yet further object of the invention is to provide formulations for the treatment of the diseases as aforesaid, by the combination of at least one of the compounds of the invention, a pharmaceutical composition of the invention, combinations thereof with other compounds and compositions having a like therapeutic effect.

According to an embodiment, the present disclosure relates to a process for the preparation of a compound of formula (I), their stereoisomers, tautomers, prodrugs, pharmaceutically acceptable salts, polymorphs and solvates.

According to an embodiment, the present disclosure also relates to a process for the preparation of a compound of formula (I), their key intermediates (II) and (IV) including their stereoisomers and tautomers.

General Schemes

Compounds of formula (I) may be prepared following below mentioned general synthetic routes as outlined in schemes 1-6.

Scheme-1: Compounds of formula (II) wherein $R^c$ is selected from hydrogen, alkyl, arylalkyl and all other symbols are defined herein above may be reacted with compounds of formula (III) under amide coupling reaction conditions to obtain compounds of formula (I) wherein Z is —C(O)NR—$(CR^aR^b)_q$— and all other symbols are defined herein above.

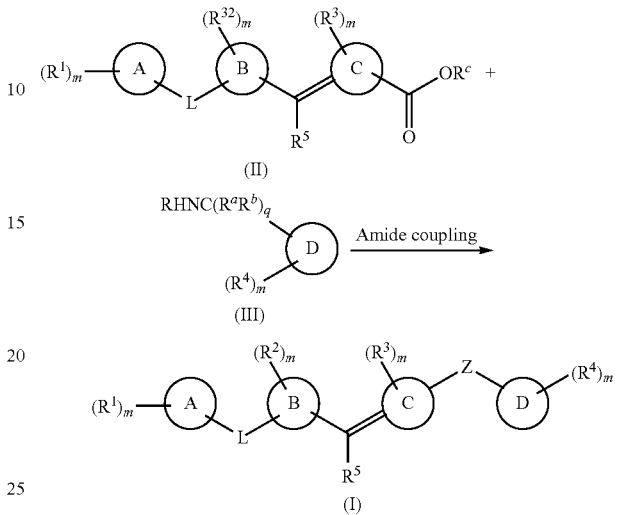

Scheme-2: Compounds of formula (IV) may be reacted with compounds of formula (V) wherein R" is selected from hydrogen, alkyl, arylalkyl under amide coupling reaction conditions to furnish compounds of formula (I) wherein Z is —NRC(O)—$(CR^aR^b)_q$— and all other symbols are defined herein above.

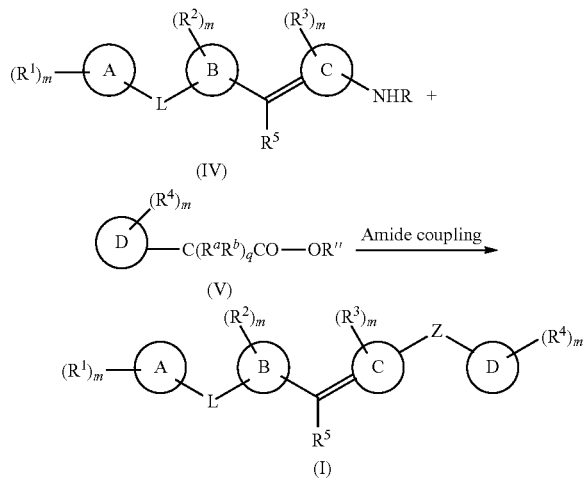

Scheme 3A: Compounds of formula (IA) wherein LG is leaving group such as Cl, Br, I, F, OTf, OTs, OMs and all other symbols are defined herein above may be subjected to nucleophilic substitution reaction with compounds of formula (VI-A) wherein $R^4$ is selected from O, S, $NR^d$ ($R^d$ is selected from hydrogen, alkyl, arylalkyl, heteroarylalkyl) aryl, alkyl, cycloalkyl, heteroaryl, heteroarylalkyl, arylalkyl, heterocycloalkyl to furnish compounds of formula (I) wherein $R^4$ is selected from —$(CR^aR^b)_n OR^6$, —$(CR^aR^b)_n NR^7R^8$, —$S(O)_p R^6$ and all other symbols are defined herein above.

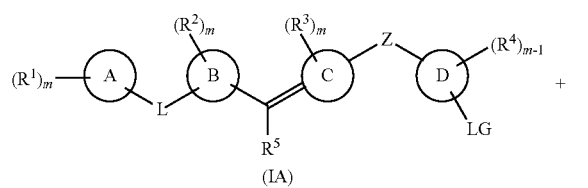

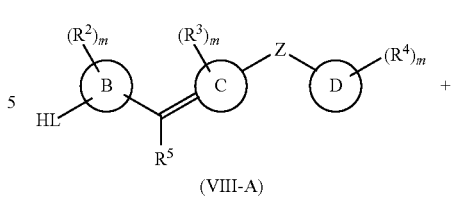

Scheme 3B: Compounds of formula (IB) wherein G is either Cl, Br, I, OTf, may be subjected to palladium catalyzed coupling with compounds of formula (VII-A) wherein $R^f$ may be hydrogen, alkyl or two $R^f$ groups combined together as cyclic boronate esters and $R^g$ is one of the $R^4$ groups such as aryl, heteroaryl, alkyl, cycloalkyl, cycloalkylalkyl, arylalkyl, heteroarylalkyl, heterocycloalkyl to furnish compounds of formula (I) wherein all symbols are defined herein above.

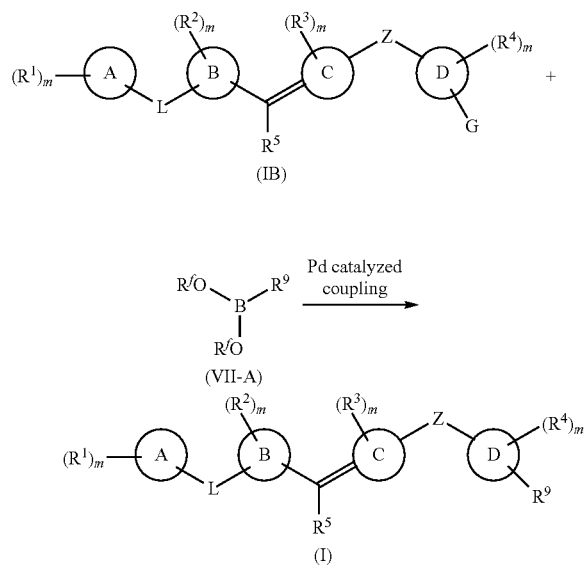

Scheme 4A: Compounds of formula (VIII-A) wherein L is selected from O, NR or S may be reacted with the compounds of formula (IX-A) wherein LG is leaving group such as Cl, Br, F, I, OTf, OTs, OMs, OH under nucleophilic substitution reaction conditions or Buchwald-Hartwig coupling reaction or Ullman coupling reaction conditions to give compounds of formula (I) wherein all other symbols are defined herein above.

Scheme 4B: Compounds of formula (VIII-A) wherein L may preferentially be O, S or NR may be reacted with the compounds of formula (IX-B) wherein $R^f$ is selected from hydrogen, alkyl or two $R^f$ groups combined together as cyclic boronate ester under metal catalyzed reaction conditions like Chan-Lam coupling reaction to furnish compounds of formula (I) wherein all symbols are defined herein above.

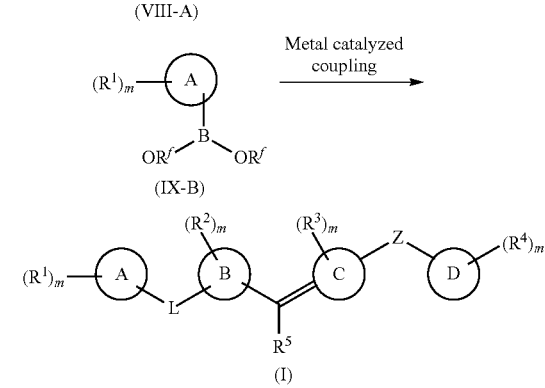

Scheme 4C: Compounds of formula (VIII-B) wherein LG is leaving group such as Cl, Br, F, I, OTf, OTs, OMs may be reacted with the compounds of formula (IX-C) wherein L is selected from O, NR or S under nucleophilic substitution reaction conditions to give compounds of formula (I) wherein all other symbols are defined herein above.

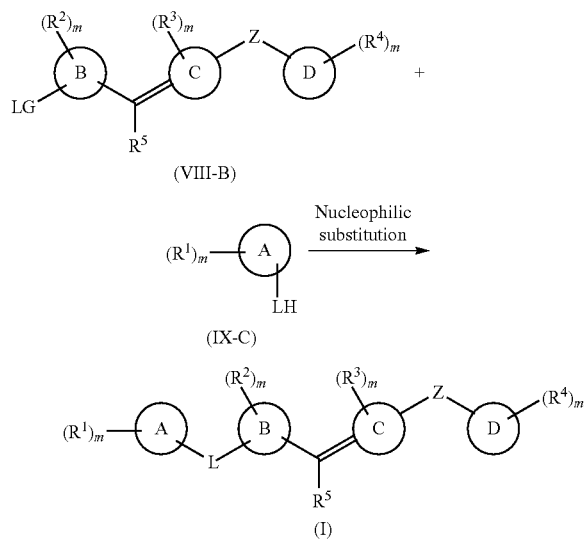

Scheme-5: Alternatively, compounds of formula (IC) (X=Br, Cl, I) may be reacted with compounds of formula (VII-B) wherein $R^f$ is selected from hydrogen, alkyl or two $R^f$ groups combined together as cyclic boronate ester under palladium catalyzed reaction conditions to furnish compounds of formula (I) wherein $R^5$ is selected from alkyl, cycloalkyl, cycloalkylalkyl, aryl, arylalkyl, heterocycloalkyl, heteroaryl, heteroarylalkyl and other symbols are defined herein above.

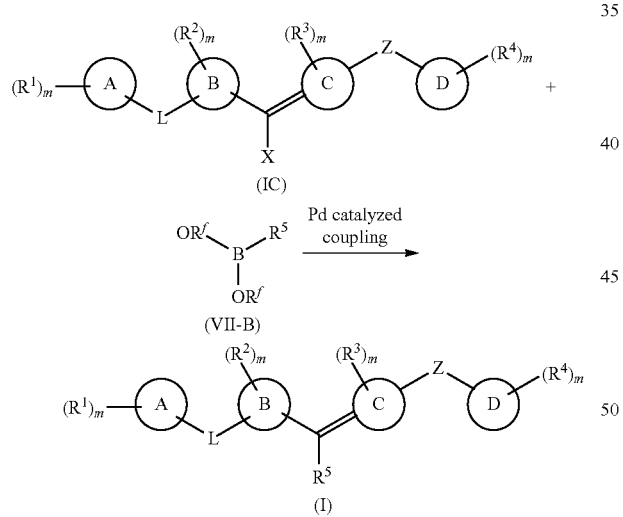

Scheme 6A: Compounds of formula (ID) wherein LG is leaving group such as Cl, Br, F, I, OTf, OTs, OMs may be reacted with compounds of formula (VI-C) wherein $L^1$ is selected from O, S, NR and $R^h$ may preferentially be hydrogen, alkyl, cycloalkyl, cycloalkylalkyl, aryl, heteroaryl, arylalkyl, heteroarylalkyl, heterocycloalkyl, heterocycloalkylalkyl under nucleophilic substitution reaction conditions to furnish compounds of formula (I) wherein collectively $L^1$-$R^h$ is one of the $R^1$ groups such as —$(CR^aR^b)_nOR^6$, —$(CR^aR^b)_nNR^7R^8$—, —$S(O)_pR^6$ and all symbols are defined herein above.

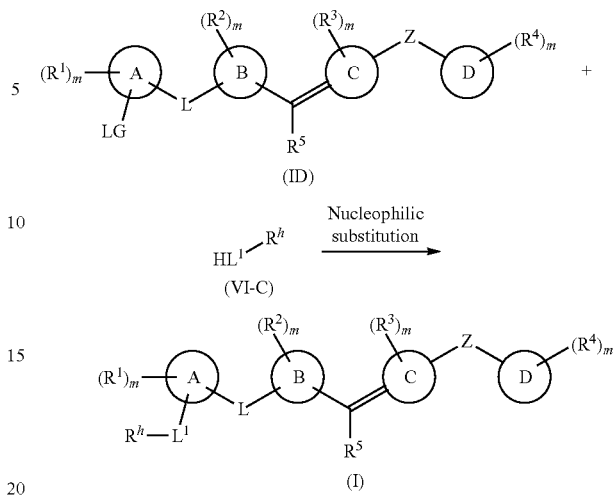

Scheme 6B: Compounds of formula (ID) wherein LG is leaving group such as Cl, Br, I, OTf, OTs may be reacted with compounds of formula (VII-C) wherein $R^f$ is selected from hydrogen, alkyl or two $R^f$ groups combined together as cyclic boronate ester and $R^i$ is one of the $R^1$ groups such as aryl, heteroaryl, alkyl, cycloalkyl, arylalkyl, heteroarylalkyl, heterocycloalkyl under palladium catalyzed reaction conditions to furnish compounds of formula (I) wherein all symbols are defined herein above.

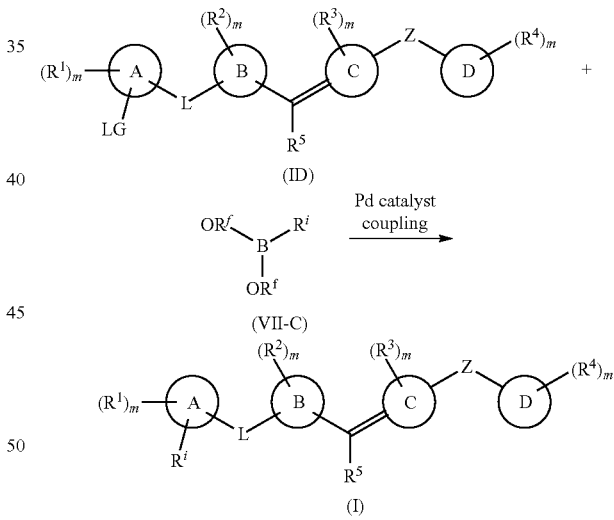

Intermediates described above for synthesis of compounds of formula (I) can be synthesized by following general synthetic routes.

Scheme 7: Compounds of formula (X) wherein Alk is alkyl and other symbols are defined herein above may be treated with compounds of formula (XI) wherein $R^c$ can be selected from alkyl, arylalkyl under Wittig-Horner reaction conditions to give compounds of formula (IIA). Compounds of formula (IIA) wherein $R^c$ is alkyl, arylalkyl may be optionally hydrolyzed to compounds of formula (II) wherein $R^c$ is hydrogen and all other symbols are defined herein above.

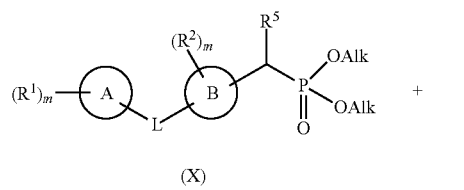

(X)

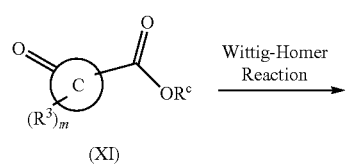

(XI)

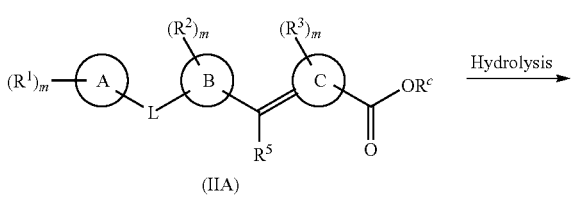

(IIA)

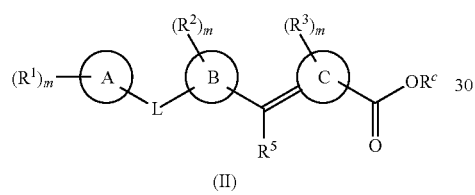

(II)

Scheme 8: Compounds of formula (X) wherein Alk is alkyl and other symbols are defined herein above may be reacted with compounds of formula (XII) wherein all the symbols are defined herein above under Wittig-Horner reaction conditions to furnish compounds of formula (XIII) wherein all symbols are defined herein above. Compounds of formula (XIII) may be deprotected to furnish compounds of formula (XIV) which upon subsequent reductive amination may furnish compounds of formula (IV) wherein R may preferentially be from hydrogen, alkyl, cycloalkyl, aryl, arylalkyl, heteroaryl, heterocycloalkyl, heteroarylalkyl and other symbols are defined herein above.

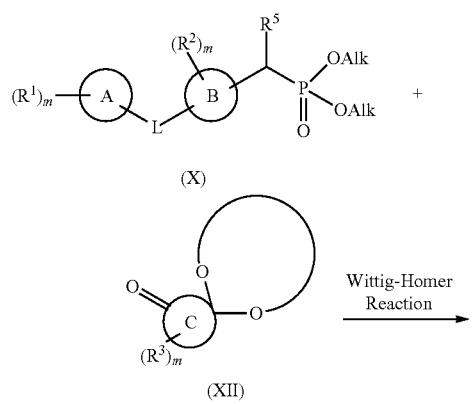

-continued

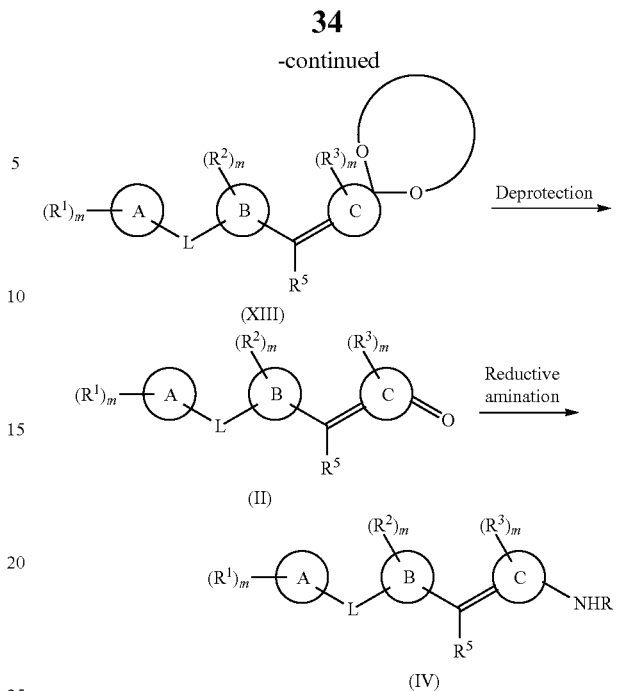

Scheme 9: Alternatively, compounds of formula (X) wherein Alk is alkyl and other symbols are defined herein above may be reacted with compounds of formula (XV) under Wittig-Horner reaction conditions to give compounds of formula (XVI) wherein all symbols are defined herein above. Compounds of formula (XVI) may be deprotected to furnish compounds of formula (IV) wherein R may preferentially be hydrogen, alkyl, cycloalkyl, aryl, arylalkyl, heteroaryl, heterocycloalkyl, heteroarylalkyl and other symbols are defined herein above.

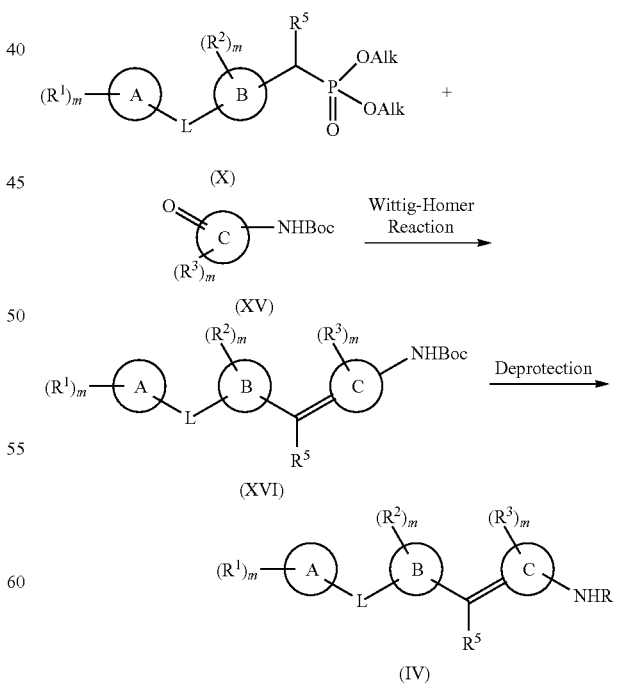

Scheme 10: Compounds of formula (XVII-A) may be converted to compounds of formula (XVIII-A) under Apple reaction conditions which upon treatment with zinc may give compounds of formula (XIX-A) wherein all symbols are defined herein above. Compounds of formula (XIX-A) may be reacted with boronic acids of formula (XX) under Suzuli coupling reaction conditions to furnish compounds of formula (XIII) wherein all symbols are defined herein above.

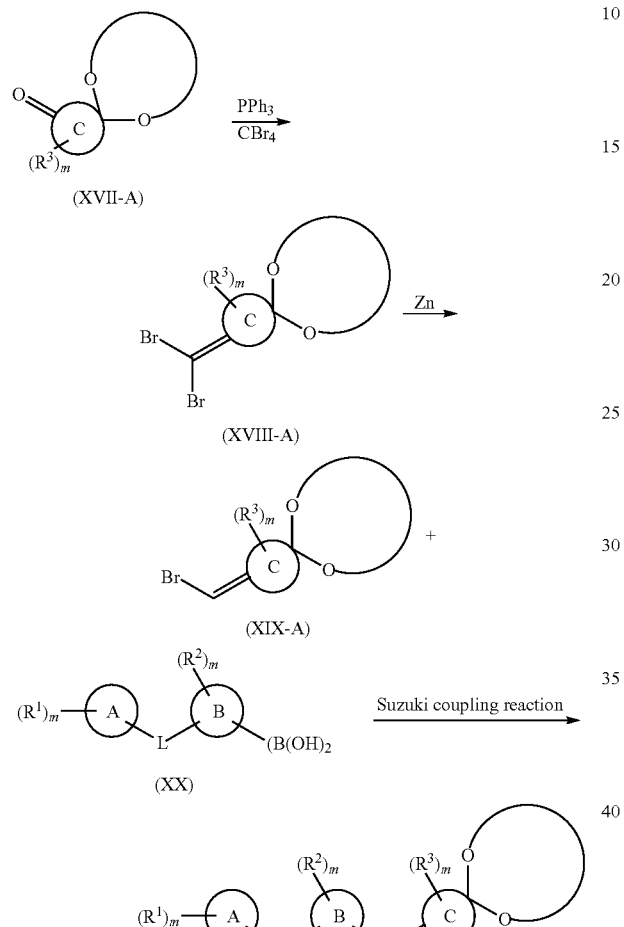

Scheme 11: Compounds of formula (XVII-B) may be converted to compounds of formula (XVIII-B) under Apple reaction conditions which upon treatment with zinc may give compounds of formula (XIX-B) wherein all symbols are defined herein above. Compounds of formula (XIX-B) may be reacted with boronic acids of formula (XX) under Suzuki coupling reaction conditions to furnish compounds of formula (XVI) wherein all symbols are defined herein above.

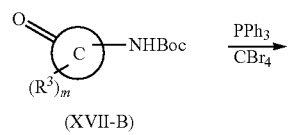

Scheme 12: Compounds of formula (XIX-A) may be reacted with compounds of formula (XXI) under Suzuki coupling reaction conditions to furnish compounds of formula (XXII) wherein all the symbols are defined herein above. Compounds of formula (XXII) may be reacted with compounds of formula (VII-C) wherein LG is leaving group such as Br, I, Cl, F, OTs, OTf under nucleophilic substitution reaction conditions to furnish compounds of formula (XIII) wherein all the symbols are defined herein above.

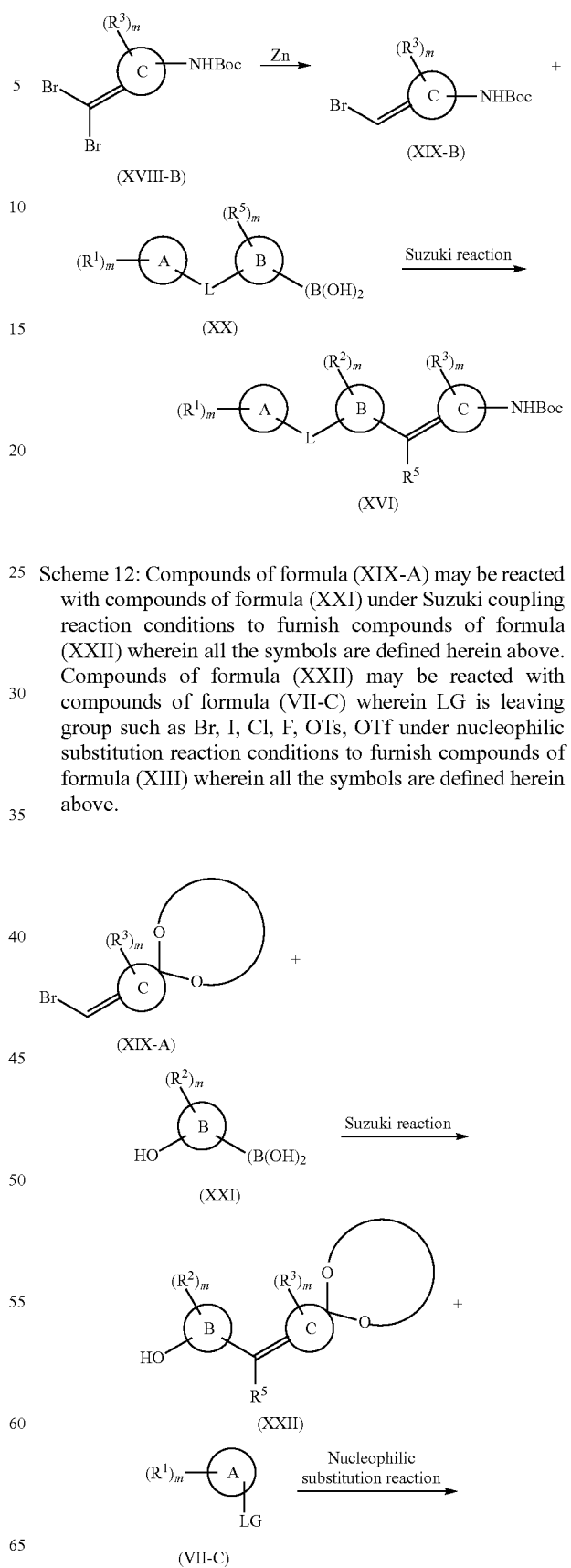

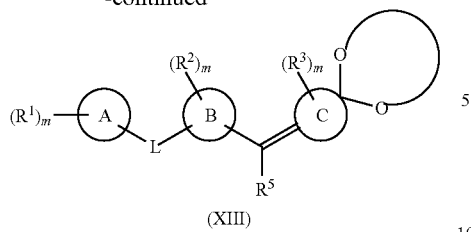

(XIII)

Scheme 13: Compounds of formula (XXIV) wherein X is selected from Br, Cl, I and PG is suitable protecting group while all other symbols are defined herein above can be reacted with trialkylphosphite to give Wittig salts of formula (XXV). The compounds of formula (XVII-A) may be reacted with the salts of formula (XXV) under Wittig-Horner reaction conditions to furnish compounds of formula (XXVI) wherein all the symbols are defined herein above. Compounds of formula (XXVI) may be deprotected to keto compounds of formula (XXVII) which upon subsequent reductive amination may furnish compounds of formula (XXVIII) wherein all symbols are defined herein above. Compounds of formula (XXVIII) may be reacted with compounds of formula (V) wherein R' may preferentially be hydrogen, alkyl, arylalkyl to furnish compounds of formula (XXIX) wherein Z is —NRC(O)—(CR$^a$R$^b$)$_q$— and all other symbols are defined herein above. Compounds of formula (XXIX) may be deprotected to compounds of formula (VIII) wherein L is O, NR, S wherein R may preferentially be hydrogen, alkyl, cycloalkyl, aryl, arylalkyl, heteroaryl, heterocycloalkyl, heteroarylalkyl and other symbols are defined herein above.

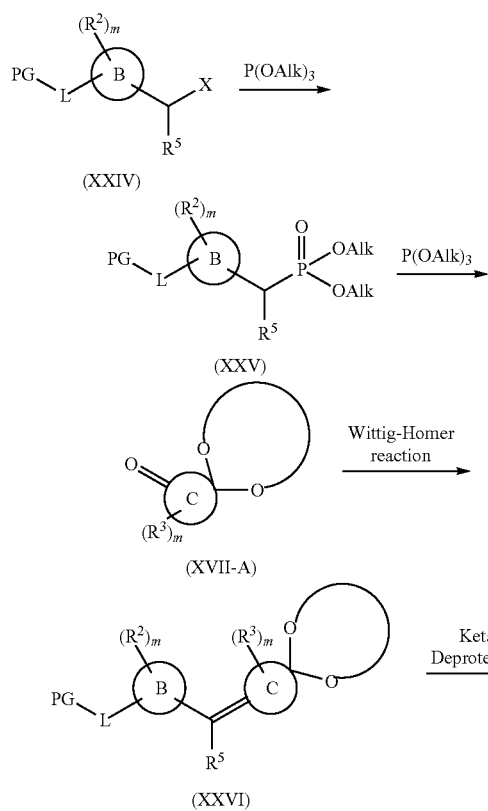

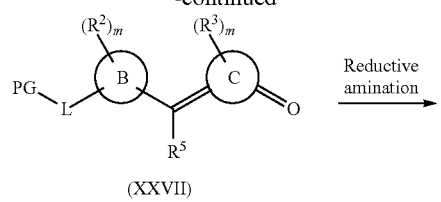

(XXVII)

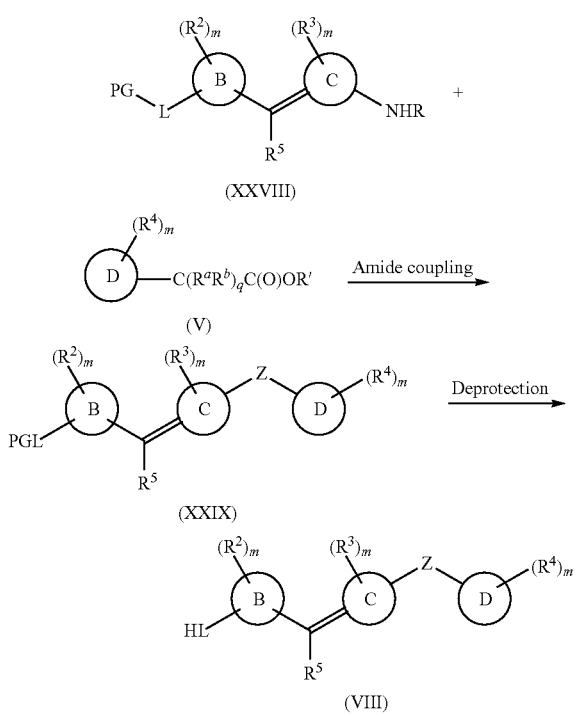

Scheme 14: Compounds of formula (ID) wherein R is hydrogen and other symbols are defined herein above may be subjected to addition reaction to furnish compounds of formula (IE) wherein X is selected from Br, Cl, I and all other symbols are defined herein above. Compounds of formula (IE) may be subjected to elimination reaction under basic conditions preferably using sodium hydroxide, potassium hydroxide, lithium hydroxide, calcium hydroxide to give compounds (IB) wherein X is selected from Br, Cl, I and all other symbols are defined herein above.

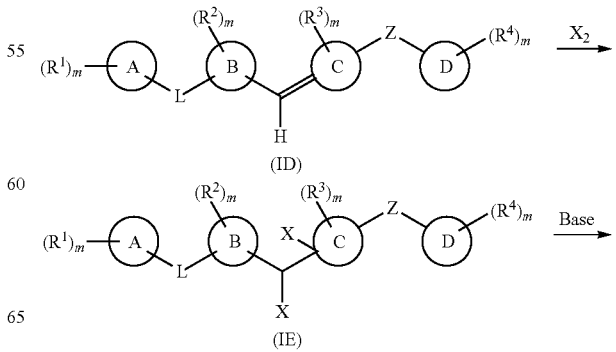

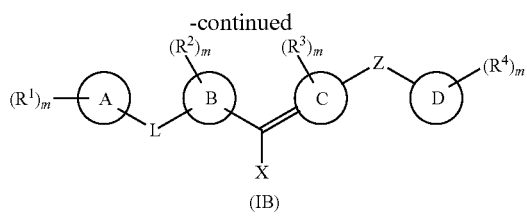

(IB)

Scheme 15: The compounds of formula (XXX) wherein all symbols are defined herein above can be halogenated to furnish compounds (XXXI) wherein X is Cl, Br, I. Compounds of formula (XXXI) which may be treated with PO(Alk)₃ wherein Alk is alkyl to furnish Wittig salts (X) wherein all symbols are defined herein above.

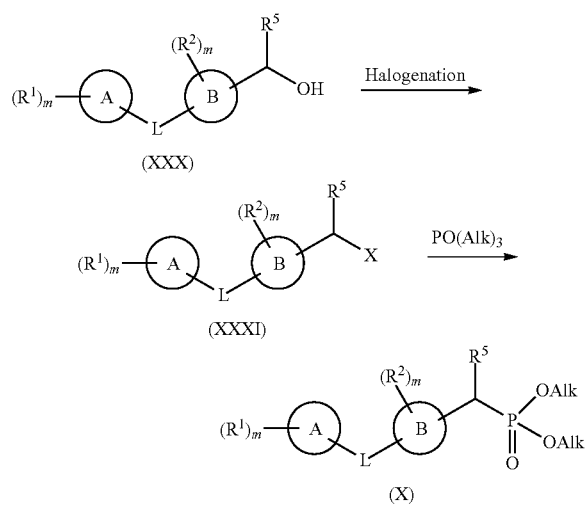

Scheme 16: Compounds of formula (XXXII) wherein L is selected from O, NR or S may be treated with compounds of formula (VII-C) wherein LG is leaving group such as Cl, Br, F, I, OTf, OTs, OMs under nucleophilic substitution reaction conditions to furnish compounds of formula (XXX) wherein all symbols are defined herein above.

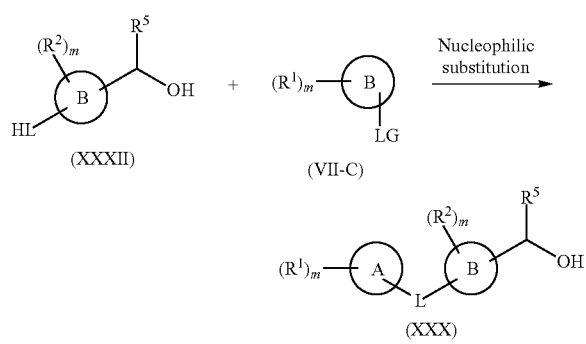

Scheme 17: Compounds of formula (VII-C) wherein LG is leaving group such as Cl, F, Br, OTf, OTs, OMs and all other symbols are defined herein above may be subjected to nucleophilic substitution reaction with the compounds of formula (XXXIII) wherein all symbols are defined herein above to furnish carbonyl compounds of formula (XXXIV). The compounds (XXXIV) may be reduced to yield hydroxy compounds of formula (XXX) wherein all symbols are defined herein above.

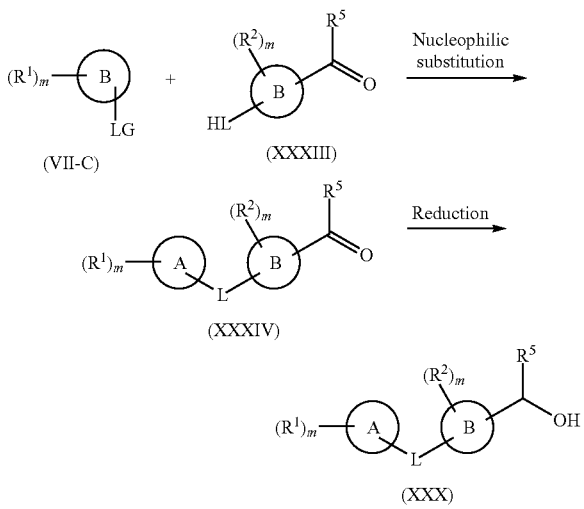

Amide Coupling Conditions: Condition-I: When $R^c$=H, the amide coupling may be carried out using any suitable activating agent or amide coupling regents such as oxalyl chloride, thionyl chloride, BOP-Cl, DCC, HOBt, HOAt, HATU, EDCI, alkylchloroformate and the like in the presence of organic non-nucleophilic bases such as triethyl amine, di-isopropylethyl amine, pyridine, N-methylpyrrolidine, N,N-dimethylaminopyridine, DBU, DABCO, other hindered amines and pyridines. The amide coupling reaction may be carried out in the presence of solvents such as dichloromethane, dichloroethane, DMF, dimethylacetamide, THF, acetonitrile or mixture of them may be used at a temperature ranging from −5 to 150° C. The reaction may be carried out optionally in presence of catalytic amount of DMF. Condition-II: When $R^c$ is lower alkyl, the amide coupling may be carried out by heating the ester and amine either in the absence of solvent or in presence of high boiling solvent like toluene, xylene, DMSO. Such reaction may be carried out in presence of trialkyl aluminium (*Chem. Commun.,* 2008, 1100-1102).

Conditions for Nucleophilic Substitution: Condition-1: For heteroatom based nucleophile: Nucleophilic substitution reaction may be carried out using any suitable organic or inorganic bases. Organic bases may be selected from a group consisting of mono, di or trialkyl amines particularly methylamine, ethylamine, dimethylamine, diethylamine and triethylamine. Inorganic bases may be selected from a group consisting of alkali and alkaline earth metal hydrides, hyroxides, carbonates and bicarbonates or mixtures thereof. Solvents used for this reaction may be selected from a group consisting of lower alcohols, acetone, acetonitrile, DMSO, DMF, dimethylacetamide, THF and toluene, or mixtures thereof. The reaction may be carried out at a temperature in the range of 0 to 150° C. Condition 2: For Carbon centered nucleophile. The reactions can be carried out using strong non nucleophilic bases like, n-BuLi, LDA, LiHMDS, KO'Bu, NaHMDS to generate carbon centered nucleophile. Reactions can be done in anhydrous condition and using aprotic solvents like THF, diethylether, dioxane, benzene etc.

Conditions for Hydrolysis: Ester hydrolysis of carboxylic acids may be carried out using general saponification conditions employing inorganic bases such as alkali and alkaline earth metal hyroxides, carbonates and bicarbonates, for example lithium hydroxide, sodium hydride, sodium carbonate, potassium carbonate, cesium carbonate and the like; in the presence of solvents such as water, methanol, ethanol, THF and diethyl ether or mixtures thereof. These reactions may be done at 0° C. to refluxing temperature.

Reductive Amination Condition: Reductive amination is a form of reaction that involves the conversion of a carbonyl group to an amine via an intermediate imine. The carbonyl group is most commonly a ketone or an aldehyde. The reaction is carried out with reducing agents that are more reactive toward protonated imines than ketones, and that are stable under moderately acidic conditions. The imine formation may be carried out in presence of lewis acid such as titanium (IV) tetrachloride, titanium (IV) isoproposxide, Indium chloride. The reducing agents preferentially include sodium borohydride ($NaBH_4$) sodium cyanoborohydride ($NaBH_3CN$) and sodium triacetoxyborohydride ($NaBH(OCOCH_3)_3$), triethylsilane. [*Organic Reactions*, 1, 59, 2002]

Palladium Catalyzed Reaction: Condition I: Suzuki coupling reaction: Suzuki coupling reaction is the organic reaction of an aryl- or vinyl-boronic acid with an aryl- or vinyl-halide catalyzed by a palladium complex such as tetrakis(triphenylphosphine)palladium, Tris(dibenzylideneacetone)dipalladium(0), palladium (II) acetate, [1,1'-Bis(diphenylphosphino)ferrocene]dichloropalladium(II), complex with dichloromethane, palladium (II) chloride, Bis(tricyclohexylphosphine)palladium(0), Bis(triphenylphosphine)palladium(II) acetate and or in presence of ligands such as 1,1'-Bis-(diphenylphosphino) ferrocene, 1,1'-Bis(diphenylphosphino)ferrocene, 2,2'-Bis(di-p-tolylphosphino)-1,1'-binaphthyl, [*Chemical Reviews* 95 (7): 2457-2483]. Condition II: Buchwald-Hartwig cross coupling: Buchwald-Hartwig coupling is the organic reaction which allows C—N bond formation via palladium catalyzed cross coupling of amine with aryl halide or aryl triflate in presence of ligands such as xantphos, 2,2-bis(diphenylphosphino)-1,1'-binaphinyl. [*Topics in Curr. Chem.* 219, 131-209]. Condition III: Ullman coupling reaction: Ullman coupling reaction allows C—O bond formation via copper catalyzed (catalyst such as copper (I) iodide, copper (II) oxide) coupling of aryl halide and phenol in presence of ligands. [*Org. Lett.*, 2003, 5, 3799-3802, *Org. Lett.* 2004, 6, 913-916].

Metal Ctalyzed Reaction: Condition I: Chan Lam Coupling: Chan Lam coupling is the organic reaction which allows aryl carbon-heteroatom bond formation via an oxidative coupling of an aryl boronic acid with N—H or O—H containing compounds catalyzed by copper catalyst such as copper (II) acetate, copper(II) triflate. [Tet. Lett., 1998, 39, 2933-2936].

Wittig-Horner Reaction condition: The reaction of aldehydes or ketones with stabilized phosphorus ylides (phosphonate carbanions) leads to olefins with excellent E-selectivity. The reaction is carried out in presence of bases such as sodium hydride, potassium tert. butoxide, n-butyl lithium and the like; in the presence of solvents such as THF and diethyl ether or mixtures thereof. These reactions may be done at 0° C. to refluxing temperature.

Conditions for Reduction: Reduction may be carried out using appropriate reduction conditions for transforming carbonyls to sec-alcohols employing reducing agents like hydrogenation in presence of catalysts such as Pd/C, Pt/C, $PtO_2$ and the like. Such reduction by hydrogenation can also be done using organo-metallic complexes as catalyst from metals like Iron, Rhodium, Ruthenium, and phosphorus-based organic ligands like triphenylphosphine, bidentate phosphine ligands such as bis(diphenylphosphino)ethane. Such hydrogenation based reductions can also be done under asymmetric reduction conditions to yield chiral products (in individual enantiomers and in enantiomerically enriched form) if employed appropriate chiral phosphine ligands such as chiral 2,2'-bis(diphenylphosphino)-1,1'-binaphthyl (BINAP) to form the organo-metallic complex. Such reductions can also be done using metal hydrides such as sodium borohydride, lithium aluminiumhydride, borane reagents and like. Such metal hydride or borane reagent based reductions can also be done in asymmetric way to yield chiral products (in individual enantiomers and in enantiomerically enriched form) by using appropriate chiral ligands like tartarate (EP 0320096), chiral 1,1'-bi-2-napthol (BINOL), oxazaborolidines.

Halogenation Conditions: Halogenation reaction may be carried out using reagents such as N-halosuccinimide, dihalogens and the like, in presence of radical generating reagents like peroxides such as benzoylperoxide. Solvents used for this reaction include, but are not limited to, carbontetrachloride and ethers or mixtures thereof. The reaction may be carried out at a temperature ranging from −5 to 80° C.

Conditions for Deprotection: Type-I: Ketal deprotection: Usually, O,O'-ketal deprotection is done by aqueous acid hydrolysis, to furnish carbonyl compounds such as ketone or aldehyde. Also, this deprotection can be done in presence of CeCl3.7H2O, $FeCl_3$, $TMSN(SO_2F)_2$, Magtrieve, Cerric ammonium nitrate, $Bi(NO_3)_3.5H_2O$, Ce—$(OTf)_3$, $Bi(OTf)_3$, hydrothermal conditions, $I_2$/Acetone and IBX, [*J. Org. Chem.*, 2004, 69, 8932-8934]

Type-II: N-Boc deprotection: N-Boc can be deprotected using mild acidic conditions such as trifluoroacetic acid in dichloromethane, hydrochloric acid in ethyl acetate, H2SO4 in t-BuOAc, TsOH and MsOH in t-BuOAc—$CH_2Cl_2$, aqueous phosphoric acid in THF, or with Lewis acids such as $BF_3.OEt_2$, TMSI, TMSOTf, $TiCl_4$, $SnCl_4$, $AlCl_3$, $Sn(OTf)_2$ and $ZnBr_2$ Montmorillonite K10 clay catalyst (Shaikh et al., 2000) and silica gel or thermolytic conditions at high temperature (150° C.). [*Inter. Journal of Chem.*; 2012, 4, 73-79]

Above mentioned conditions, for the respective functional group transformations are only to illustrate the type of synthesis. More specific conditions for above transformations are well documented and referred in the literature (R. C. Larock in Comprehensive Organic Transformations, Wiley-VCH Publication; B. M. Trost and I. Fleming Ed. Comprehensive Organic Synthesis, Elsevier Publication; Greene, T. W. and Wuts, P.G.M., Protecting Groups in Organic Synthesis, 3$^{rd}$ Edition, 1999 [Wiley]).

Wherever desired or necessary, in any of the above mentioned processes, functional groups is transformed to different functional groups such as an ester function being converted to an acid, amide, hydroxymethyl, keto, aldehyde as well as an ester. The said conversions are carried out using reagents and conditions well documented in the literature.

Wherever desired or necessary, in any of the above mentioned processes, any of the compounds of formula (I) is converted into a pharmaceutically acceptable salt or vice versa or converting one salt form into another pharmaceutically acceptable salt form.

When employed as pharmaceuticals, the compounds of this invention are typically administered in the form of a pharmaceutical composition. Such compositions can be prepared in a manner well known in the pharmaceutical art and comprise at least one active compound. In certain embodiments, the pharmaceutical composition may comprise a compound of the invention in combination with one or more compounds or compositions of like therapeutic utility and effect.

Generally, the compounds of this invention are administered in a pharmaceutically effective amount. The amount of the compound actually administered will typically be determined by a physician, in the light of the relevant circumstances, including the condition to be treated, the chosen route of administration, the actual compound -administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Abbreviations

The following abbreviations are employed in the examples and elsewhere herein:
DMF: N,N-dimethylformamide,
THF: Tetrahydrofuran,
HCl: Hydrochloric acid,
DMA: Dimethylacetamide
DMSO: Dimethyl sulfoxide,
DMAP: 4-Dimethylaminopyridine,
POCl$_3$: Phosphoryl chloride,
HOBt: 1-Hydroxybenzotriazole,
DIPEA: N,N-Diisopropylethylamine,
MeOH: Methanol

EXAMPLES

The invention is further illustrated by the following examples which in no way should be construed as being further limiting. One skilled in the art will readily appreciate that the specific methods and results described are merely illustrative. Structures of the intermediates as well as the final compounds were confirmed by nuclear magnetic resonance spectra for proton ($^1$H NMR) and LCMS.

The compounds of the present disclosure are prepared using the reactions and techniques described below, together with conventional techniques known to those skilled in the art of organic synthesis, or variations thereon as appreciated by those skilled in the art.

The reactions are performed in solvents appropriate to the reagents and materials employed and are suitable for the transformations being affected. Preferred methods include, but not limited to those described below, where all symbols are as defined earlier and otherwise defined below.

Intermediate 1A

4-[[3-[[5-(Trifluoromethyl)-2-pyridyl]oxy]phenyl]methylene]-cyclohexane carboxylic acid

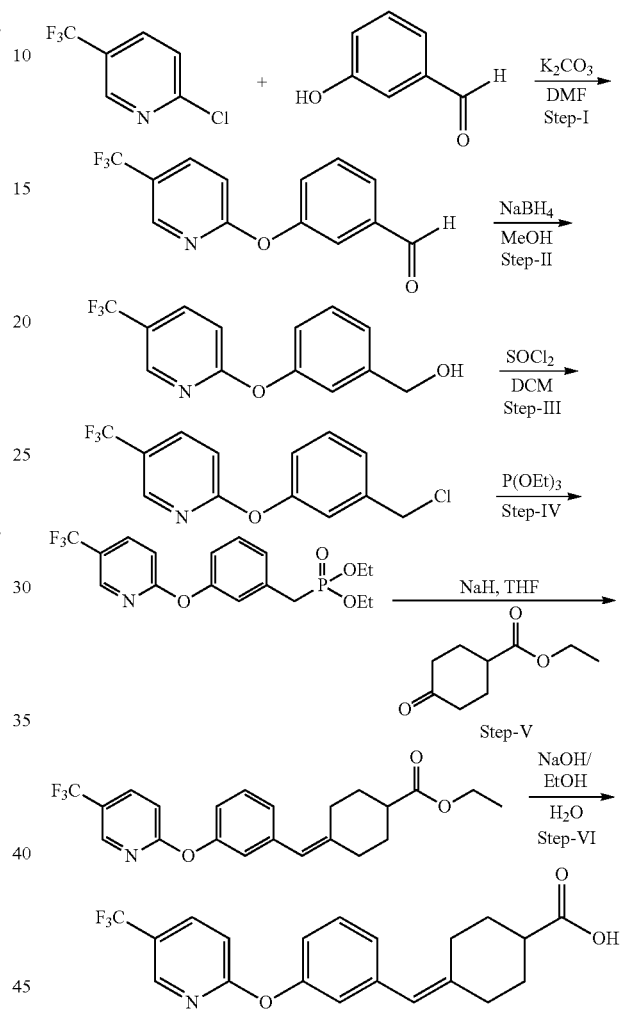

Step-I:
3-[[5-(Trifluoromethyl)-2-pyridyl]oxy]benzaldehyde

To a mixture of 3-hydroxybenzaldehyde (67.3 g, 550.8 mmol), 2-chloro-5-trifluoromethylpyridine (100.0 g. 550.8 mmol) in DMF (1000 mL) was added potassium carbonate (152.2 g, 1101.7 mmol) and heated at 100° C. for 18 h. After cooling to room temperature, water (3000 mL) was added and extracted with ethyl acetate (2×2000 mL). Combined organic layer was washed with water (3000 mL), brine (3000 mL), dried over anhydrous sodium sulfate, filtered, concentrated and dried under vacuum to give 140.0 g (95%) of 3-[[5-(trifluoromethyl)-2-pyridyl]oxy]benzaldehyde.

$^1$H NMR (400 MHz, CDCl$_3$): δ 7.10 (d, J=8.5 Hz, 1H), 7.43-7.44 (m, 1H), 7.62 (t, J=7.8 Hz, 1H), 7.69 (s, 1H), 7.78 (d, J=7.6 Hz, 1H), 7.95 (dd, J=8.8, 2.4 Hz, 1H), 8.43 (s, 1H), 10.03 (s, 1H). MS (ES) m/z 267.9 (M+1).

Step-II: [3-[[5-(Trifluoromethyl)-2-pyridyl]oxy]phenyl]methanol

To a stirred solution of 3-[[5-(trifluoromethyl)-2-pyridyl]oxy]benzaldehyde (140.0 g, 523.9 mmol) in methanol (1200 mL) was added sodium borohydride (39.7 g, 1047.9 mmol) in portions at 0° C. After stirring for 1 h, methanol was evaporated under reduced pressure. To the resulting residue, water was added and extracted with ethyl acetate (3×1000 mL). Combined organic layer was washed with brine (3000 mL), dried over anhydrous sodium sulfate, filtered and concentrated to give 140.0 g (99%) of [3-[[5-(trifluoromethyl)-2-pyridyl]oxy]phenyl]methanol.

$^1$H NMR (400 MHz, CDCl$_3$): δ 1.91 (brs, 1H), 4.73 (s, 2H), 7.02 (d, J=8.2 Hz, 1H), 7.07 (d, J=7.9 Hz, 1H), 7.18 (s, 1H), 7.25 (d, J=7.6 Hz, 1H), 7.43 (t, J=7.8 Hz, 1H), 7.90 (dd, J=8.5, 2.2 Hz, 1H), 8.43 (s, 1H). MS (ES) m/z 269.8 (M+1).

Step-III: 2-[3-(Chloromethyl)phenoxy]-5-(trifluoromethyl)pyridine

To a cooled solution of [3-[[5-(trifluoromethyl)-2-pyridyl]oxy]phenyl]methanol (140.0 g, 523.9 mmol) in DCM (1000 mL) was added thionyl chloride (76.0 mL, 1047.8 mmol) at 0° C. After stirring for 1 h at room temperature, volatiles were evaporated under reduced pressure. The resulting residue was taken in DCM (2000 mL), washed with aqueous saturated sodium bicarbonate solution (2000 mL), water (2000 mL), brine (2000 mL), dried over anhydrous sodium sulfate, filtered and concentrated to give 149.0 g (99%) of 2-[3-(chloromethyl)phenoxy]-5-(trifluoromethyl)pyridine.

$^1$H NMR (400 MHz, CDCl$_3$): δ 4.60 (s, 2H), 7.03 (d, J=8.5 Hz, 1H), 7.11 (dd, J=8.0, 1.9 Hz, 1H), 7.21 (s, 1H), 7.28 (d, J=7.6 Hz, 1H), 7.43 (t, J=7.9 Hz, 1H), 7.91 (dd, J=8.8, 2.4 Hz, 1H), 8.44 (s, 1H). MS (ES) m/z 288.0 (M+1).

Step-IV: 2-[3-(Diethoxyphosphorylmethyl)phenoxy]-5-(trifluoromethyl)pyridine Mixture of 2-[3-(chloromethyl)phenoxy]-5-(trifluoromethyl)pyridine (149.0 g, 517.9 mmol) and triethyl phosphite (172.1 mL, 1035.9 mmol) was heated at 150° C. After 18 h, reaction mixture was cooled to 0° C.; n-pentane (1500 mL) was added, stirred for 2 h. The solid precipitated was filtered through Buchner funnel, dried under vacuum to give 195.0 g (97%) of 2-[3-(diethoxyphosphorylmethyl)phenoxy]-5-(trifluoromethyl)pyridine as a solid.

$^1$H NMR (400 MHz, CDCl$_3$): δ 1.25 (t, J=7.2 Hz, 6H), 3.14 (s, 1H), 3.20 (s, 1H), 4.00-4.07 (q, J=7.2 Hz, 4H), 7.00 (d, J=8.8 Hz, 1H), 7.04 (d, J=8.2 Hz, 1H), 7.10 (d, J=1.8 Hz, 1H), 7.20 (d, J=7.5 Hz, 1H), 7.37 (t, J=7.8 Hz, 1H), 7.89 (dd, J=8.8, 2.5 Hz, 1H), 8.42 (s, 1H). MS (ES) m/z 390.1 (M+1).

Step-V: Ethyl 4-[[3-[[5-(trifluoromethyl)-2-pyridyl]oxy]phenyl]methylene]-cyclohexane carboxylate To a suspension of sodium hydride (60% in mineral oil; 1.8 g, 44.9 mmol) in THF (30 mL) was added a solution of 2-[3-(diethoxyphosphorylmethyl)phenoxy]-5-(trifluoromethyl)pyridine (9.0 g, 23.1 mmol) in THF (40 mL) at 0° C. After stirring for 2 h at room temperature, reaction mixture was cooled to 0° C., added a solution of ethyl 4-oxocyclohexanecarboxylate (3.6 g, 20.2 mmol) in THF (10 mL) and stirring continued for 18 h at room temperature. Reaction mixture was poured onto ice-cold water; this was extracted with ethyl acetate (2×50 mL). Combined organic layer was washed with brine (100 mL), dried over anhydrous sodium sulfate, filtered, concentrated and purified by column chromatography to give 5.4 g (63%) of ethyl 4-[[3-[[5-(trifluoromethyl)-2-pyridyl]oxy]phenyl]methylene]-cyclohexanecarboxylate.

$^1$H NMR (400 MHz, CDCl$_3$): δ 1.25 (t, J=7.1 Hz, 3H), 1.55-1.62 (m, 1H), 1.67 (qd, J=12.2, 4.1 Hz, 1H), 1.96-2.08 (m, 3H), 2.23 (td, J=12.3, 3.5 Hz, 1H), 2.41 (dt, J=15.4, 3.9 Hz, 1H), 2.51 (tt, J=11.0, 3.9 Hz, 1H), 2.86 (dt, J=15.2, 4.4 Hz, 1H), 4.13 (q, J=7.1 Hz, 2H), 6.27 (s, 1H), 6.96-7.01 (m, 3H), 7.07 (d, J=7.5 Hz, 1H), 7.36 (t, J=7.8 Hz, 1H), 7.89 (dd, J=8.6, 2.5 Hz, 1H), 8.45 (s, 1H). MS (ES) m/z 406.2 (M+1).

Step-VI: 4-[[3-[[5-(Trifluoromethyl)-2-pyridyl]oxy]phenyl]methylene]cyclohexane carboxylic acid To a solution of ethyl 4-[[3-[[5-(trifluoromethyl)-2-pyridyl]oxy]phenyl]methylene]-cyclohexanecarboxylate (2.9 g, 7.2 mmol) in ethanol (20 mL) was added a solution of sodium hydroxide (430 mg, 10.7 mmol) in water (10 mL) at room temperature. After stirring for 20 h, volatiles were evaporated under reduced pressure. Resulting residue was taken in water (30 mL), acidified by 5% aqueous citric acid, extracted with ethyl acetate (3×30 mL). Combined organic layer was washed with brine (50 mL), dried over anhydrous sodium sulfate, filtered and concentrated to give 2.5 g (93%) of 4-[[3-[[5-(trifluoromethyl)-2-pyridyl]oxy]phenyl]methylene]cyclohexanecarboxylic acid.

$^1$H NMR (400 MHz, CD$_3$OD): δ 1.51 (qd, J=12.2, 3.6 Hz, 1H), 1.63 (qd, J=12.0, 4.1 Hz, 1H), 1.95-2.12 (m, 3H), 2.27 (td, J=12.2, 4.1 Hz, 1H), 2.43 (dt, J=13.7, 4.1 Hz, 1H), 2.54 (tt, J=10.8, 3.7 Hz, 1H), 2.85 (dt, J=13.7, 3.9 Hz, 1H), 6.30 (s, 1H), 6.97-7.00 (m, 2H), 7.09-7.12 (m, 2H), 7.38 (t, J=7.6 Hz, 1H), 8.08 (dd, J=8.6, 2.5 Hz, 1H), 8.43 (s, 1H). MS (ES) m/z 378.1 (M+1).

Intermediates 2A-2F were obtained from commercial source

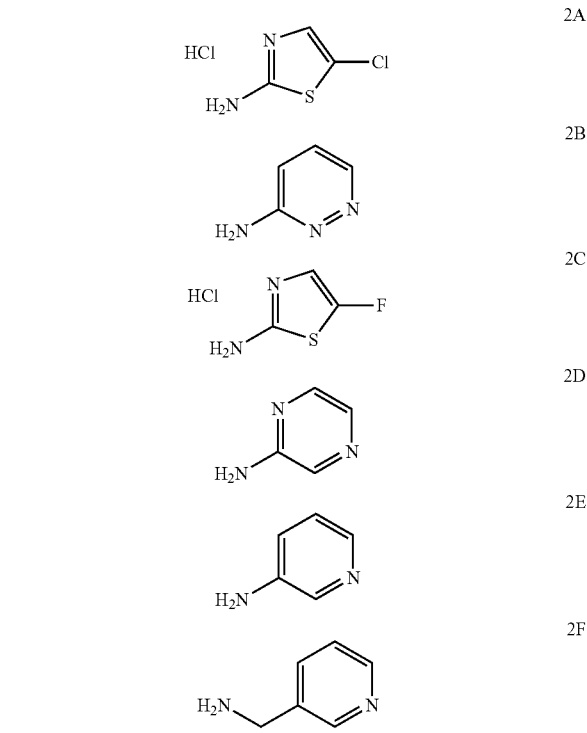

Intermediate 3A

4-[[3-[[5-(Trifluoromethyl)-2-pyridyl]oxy]phenyl] methylene]-cyclohexanamine

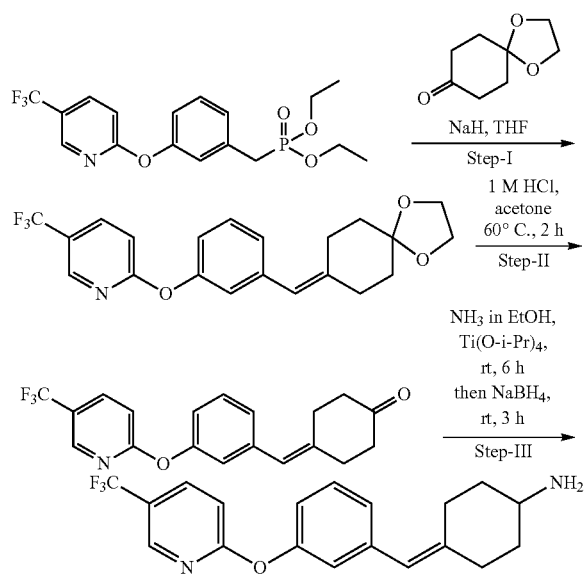

Step-I: 2-[3-(1,4-Dioxaspiro[4.5]decan-8-ylidenemethyl)phenoxy]-5-(trifluoromethyl)pyridine To a suspension of sodium hydride (60% in mineral oil; 9.5 g, 211.3 mmol) in THF (100 mL) was added a solution of 2-[3-(diethoxyphosphorylmethyl)phenoxy]-5-(trifluoromethyl)pyridine (49.3 g, 126.8 mmol) (Intermediate 1A, Step-IV) in THF (300 mL) at 0° C. After stirring for 4 h at room temperature, reaction mixture was cooled to 0° C., added a solution of 1,4-dioxaspiro[4.5]decan-8-one (16.5 g, 105.6 mmol) in THF (250 mL) and stirring continued for 18 h at room temperature. Reaction mixture was poured onto ice-cold water; this was extracted with ethyl acetate (2×900 mL), combined organic layer was washed with brine (1500 mL), dried over anhydrous sodium sulfate, filtered, concentrated and purified by column chromatography to give 40.0 g (97%) of 2-[3-(1,4-dioxaspiro[4.5]decan-8-ylidenemethyl)phenoxy]-5-(trifluoromethyl)pyridine.

$^1$H NMR (400 MHz, CDCl$_3$): δ 1.68 (t, J=6.6 Hz, 2H), 1.79 (t, J=6.4 Hz, 2H), 2.42 (t, J=6.4 Hz, 2H), 2.53 (t, J=6.4 Hz, 2H), 3.98 (s, 4H), 6.30 (s, 1H), 6.98-7.01 (m, 3H), 7.09 (d, J=7.5 Hz, 1H), 7.37 (t, J=8.6 Hz, 1H), 7.89 (dd, J=8.6, 2.4 Hz, 1H), 8.45 (s, 1H). MS (ES) m/z 392.0 (M+1).

Step-II: 4-[[3-[[5-(Trifluoromethyl)-2 pyridyl]oxy]phenyl]methylene]cyclohexanone To a stirred solution of 2-[3-(1,4-dioxaspiro[4.5]decan-8-ylidenemethyl)phenoxy]-5-(trifluoromethyl)pyridine (40.0 g, 102.2 mmol) in acetone (1000 mL) was added 1 N HCl (400 mL). After stirring for 4 h at 60° C., volatiles were evaporated under reduced pressure. The resulting residue was taken in ethyl acetate (1000 mL) and washed with aqueous saturated sodium bicarbonate solution (1000 mL), water (1000 mL), brine (1000 mL), dried over anhydrous sodium sulfate, filtered and concentrated to give 35.0 g (99%) of 4-[[3-[[5-(trifluoromethyl)-2 pyridyl]oxy]phenyl] methylene]cyclohexanone.

$^1$H NMR (400 MHz, CDCl$_3$): δ 2.44 (t, J=7.1 Hz, 2H), 2.52 (t, J=7.3 Hz, 2H), 2.68 (t, J=7.0 Hz, 2H), 2.78 (t, J=6.8 Hz, 2H), 6.48 (s, 1H), 7.01-7.04 (m, 3H), 7.13 (d, J=7.7 Hz, 1H), 7.41 (t, J=8.6 Hz, 1H), 7.91 (dd, J=8.6, 2.4 Hz, 1H), 8.44 (s, 1H). MS (ES) m/z 348.0 (M+1).

Step-III: 4-[[3-[[5-(Trifluoromethyl)-2-pyridyl]oxy] phenyl]methylene]-cyclohexanamine A mixture of 4-[[3-[[5-(trifluoromethyl)-2-pyridyl] oxy]phenyl]methylene]cyclohexanone (20.0 g, 57.6 mmol), ammonia in ethyl alcohol (2 M solution; 150.0 mL, 287.9 mmol) and titanium (IV) isopropoxide (34.0 mL, 115.2 mmol) was stirred under argon atmosphere at ambient temperature for 6 h. Sodium borohydride (3.3 g, 86.4 mmol) was added and the resulting mixture stirred at room temperature for 18 h. Reaction was quenched by the addition of ammonium hydroxide (~30% in water, 500 mL), stirred for 1 h. Resulting precipitate was filtered through celite bed and washed with methanol (2×200 mL). The organic layer was evaporated under reduced pressure and aqueous layer extracted with ethyl acetate (2×500 mL). Combined organic layer was washed with brine (1000 mL), dried over anhydrous sodium sulfate, filtered, concentrated and purified by column chromatography to give 11.5 g (57%) of 4-[[3-[[5-(trifluoromethyl)-2-pyridyl]-oxy]phenyl]methylene]cyclohexanamine.

$^1$H NMR (400 MHz, CDCl$_3$): δ 1.13-1.23 (m, 1H), 1.25-1.34 (m, 1H), 1.87-1.94 (m, 1H), 1.95-2.04 (m, 2H), 2.25 (td, J=12.9, 3.4 Hz, 1H), 2.38 (d, J=13.7 Hz, 1H), 2.84-2.95 (m, 2H), 3.48 (s, 2H), 6.26 (s, 1H), 6.97-7.01 (m, 3H), 7.08 (d, J=7.6 Hz, 1H), 7.37 (t, J=8.8 Hz, 1H), 7.89 (dd, J=8.5, 2.2 Hz, 1H), 8.45 (s, 1H). MS (ES) m/z 349.2 (M+1).

Intermediate 3B

4-[[3-[(5-Bromo-2-pyridyl)oxy]phenyl]methylene]-cyclohexanamine

The titled intermediate was prepared from 5-bromo-2-chloropyridine using the procedure for Intermediate 3A.

$^1$H NMR (400 MHz, CDCl$_3$): δ 1.15 (qd, J=12.4, 4.1 Hz, 1H), 1.27 (qd, J=12.5, 4.4 Hz, 1H), 1.86-2.02 (m, 3H), 2.25 (td, J=12.5, 3.2 Hz, 1H), 2.36 (d, J=13.5 Hz, 1H), 2.83-2.93 (m, 2H), 6.24 (s, 1H), 6.82 (d, J=8.6 Hz, 1H), 6.93-6.95 (m, 2H), 7.04 (d, J=7.9 Hz, 1H), 7.33 (t, J=8.6 Hz, 1H), 7.75 (dd, J=8.8, 2.7 Hz, 1H), 8.21 (d, J=2.2 Hz, 1H). MS (ES) m/z 359.0 (M+1)

Intermediate 3C

4-[[3-[5-(Trifluoromethyl)pyrazin-2-yl]oxyphenyl] methylene]-cyclohexanamine The titled intermediate was prepared from 2-chloro-5-trifluoromethylpyrazine using the procedure for Intermediate 3A.

MS (ES) m/z 350.2 (M+1).

Intermediate 3D

4-[[3-[(5-chloro-6-methyl-2-pyridyl)oxy]phenyl] methylene]-cyclohexanamine

The titled intermediate was prepared from 2-bromo-5-chloro-6-methylpyridine using the procedure for Intermediate 3A.

MS (ES) m/z 329.2 (M+1).

Intermediate 3E

(2E)-2-[[3-[[5-(Trifluoromethyl)-2-pyridyl]oxy]phenyl]methylene]-bicyclo[2.2.2]octan-5-amine The titled intermediate was prepared from spiro[1,3-dioxolane-2,2'-bicyclo[2.2.2]octane]-5'-one using the procedure for Intermediate 3A.

$^1$H NMR (400 MHz, CDCl$_3$): δ 1.14-1.30 (m, 1H), 1.34-1.44 (m, 1H), 1.50-1.70 (m, 4H), 1.71-1.85 (m, 2H), 1.88-2.13 (m, 2H), 2.15-2.36 (m, 1H), 3.10-3.20 (m, 2H), 6.23 (d, J=10.1 Hz, 1H), 7.01-7.07 (m, 1H), 7.16 (d, J=9.0 Hz, 1H), 7.22-7.27 (m, 2H), 7.37-7.43 (m, 1H), 8.24 (d, J=8.6 Hz, 1H), 8.57 (s, 1H). MS (ES) m/z 375.1 (M+1).

Intermediate 3F

4-[[2-Fluoro-5-[[5-(trifluoromethyl)-2-pyridyl]oxy]phenyl]-methylene]cyclohexanamine The titled intermediate was prepared from 2-fluoro-5-hydroxy-benzaldehyde using the procedure for Intermediate 3A.

MS (ES) m/z 367.2 (M+1).

Intermediate 3G

4-[[3-[[3-Chloro-5-(trifluoromethyl)-2-pyridyl]oxy]phenyl]-methylene]cyclohexanamine

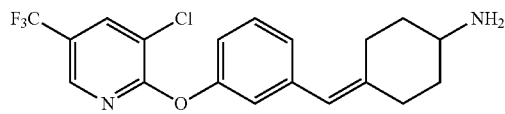 [SMILES: NC1CCC(=Cc2cccc(Oc3ncc(C(F)(F)F)cc3Cl)c2)CC1]

The titled intermediate was prepared from 2,3-dichloro-(5-trifluoromethyl)pyridine using the procedure for Intermediate 3A.

$^1$H NMR (400 MHz, CDCl$_3$): δ 1.02-1.21 (m, 2H), 1.56-1.65 (m, 2H), 1.73-1.85 (m, 2H), 1.91-2.00 (m, 1H), 2.12-2.17 (m, 1H), 2.29-2.34 (m, 1H), 2.68-2.78 (m, 2H), 6.22 (s, 1H), 7.00 (s, 1H), 7.05 (d, J=7.8 Hz, 1H), 7.09 (d, J=7.6 Hz, 1H), 7.38 (t, J=8.1 Hz, 1H), 8.49 (s, 1H), 8.55 (s, 1H). MS (ES) m/z 383.1 (M+1).

Intermediate 3H

4-[[3-[[6-Methyl-5-(trifluoromethyl)-2-pyridyl]oxy]phenyl]-methylene]cyclohexanamine

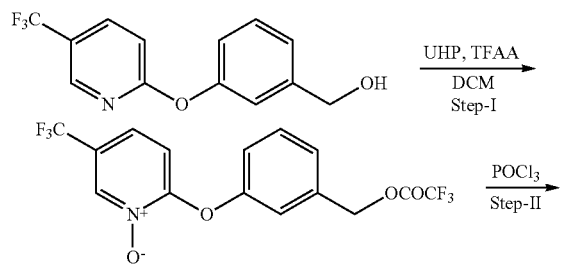

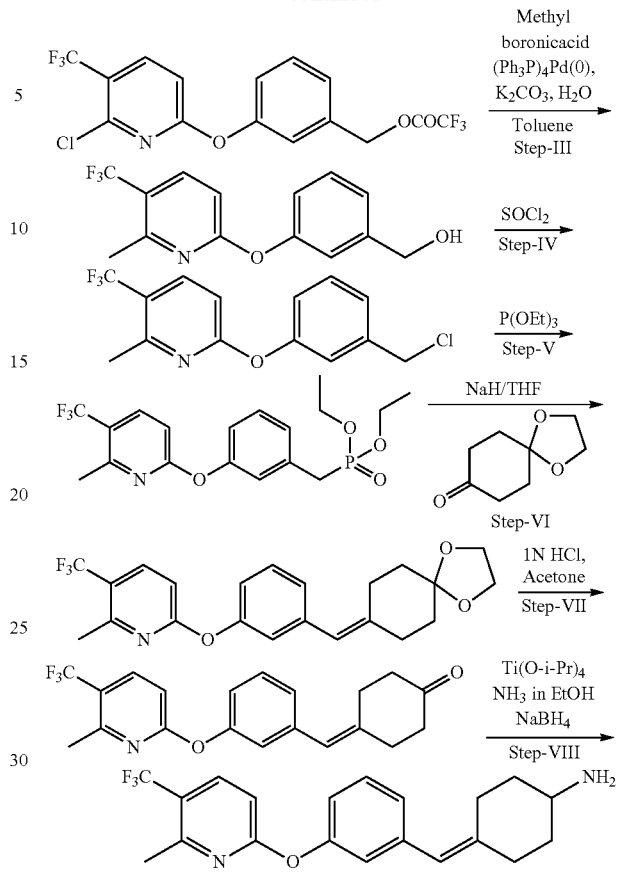

Step-I: [3-[[1-Oxo-5-(trifluoromethyl)-2-pyridyl]oxy]phenyl]methyl 2,2,2-trifluoroacetate To a stirred solution of [3-[[5-(trifluoromethyl)-2-pyridyl]oxy]phenyl]methanol (7.50 g, 27.9 mmol) (Intermediate 1A, step-II) in DCM (100 mL) was added trifluoroacetic anhydride (7.7 mL, 55.8 mmol) at 0° C. followed by urea hydrogen peroxide (5.5 g, 58.5 mmol). After stirring for 2 h at room temperature, reaction mixture was diluted with DCM (100 mL), washed with aqueous saturated sodium bicarbonate solution (100 mL), water (100 mL), brine (100 mL), dried over anhydrous sodium sulfate, filtered and concentrated under reduced pressure and purified by column chromatography to afford 5.0 g (63%) of [3-[[1-oxo-5-(trifluoromethyl)-2-pyridyl]oxy]phenyl]methyl 2,2,2-trifluoroacetate.

Step-II: [3-[[6-Chloro-5-(trifluoromethyl)-2-pyridyl]oxy]phenyl]methyl 2,2,2-trifluoroacetate A mixture of [3-[[1-oxo-5-(trifluoromethyl)-2-pyridyl]oxy]phenyl]methyl 2,2,2-trifluoroacetate (5.0 g, 17.5 mmol) and POCl$_3$ (8.2 mL) was heated at 130° C. for 2 h. Excess of POCl$_3$ was removed under reduced pressure. Reaction mixture was diluted with ethyl acetate (100 mL), neutralized with aqueous saturated sodium bicarbonate solution (100 mL). Organic layer was separated, washed with water (100 mL), brine (100 mL), dried over anhydrous sodium sulfate, filtered, concentrated and purified by column chromatography to afford 3.0 g (56%) of [3-[[6-chloro-5-(trifluoromethyl)-2-pyridyl]-oxy]phenyl]methyl 2,2,2-trifluoroacetate.

¹H NMR (400 MHz, CDCl₃): δ 5.38 (s, 2H), 6.91 (d, J=8.3 Hz, 1H), 7.10-7.25 (m, 2H), 7.30 (d, J=7.6 Hz, 1H), 7.48 (t, J=7.5 Hz, 1H), 7.99 (d, J=8.6 Hz, 1H).

Step-III: [3-[[6-Methyl-5-(trifluoromethyl)-2-pyridyl]oxy]phenyl]methanol

To a stirred solution of [3-[[6-chloro-5-(trifluoromethyl)-2-pyridyl]oxy]phenyl]methyl 2,2,2-trifluoroacetate (2.4 g, 6.0 mmol) in 1,4-dioxane (30 mL) was added methyl boronic acid (0.53 g, 7.2 mmol) followed by potassium carbonate (2.5 g, 18.0 mmol) and degassed with argon for 30 min. To this was added tetrakis-(triphenylphosphine) palladium(0) (347 mg, 0.3 mmol) and stirred at 80° C. for 18 h. Reaction mixture was cooled to room temperature, diluted with ethyl acetate (50 mL), washed with aqueous saturated sodium bicarbonate solution (50 mL), water (50 mL), brine (50 mL), dried over anhydrous sodium sulfate, filtered, concentrated and purified by silica gel column chromatography to furnish 1.25 g (70%) of [3-[[6-methyl-5-(trifluoromethyl)-2-pyridyl]-oxy]phenyl]methanol.

¹H NMR (400 MHz, CDCl₃): δ 1.81 (brs, 1H), 2.57 (s, 3H), 4.73 (s, 2H), 6.68 (d, J=8.6 Hz, 1H), 7.06-7.08 (m, 1H), 7.17-7.18 (m, 1H), 7.22-7.25 (m, 1H), 7.40 (t, J=7.8 Hz, 1H), 7.84 (d, J=8.5 Hz, 1H). MS (ES) m/z 283.9 (M+1).

Step-IV: 6-[3-(Chloromethyl)phenoxy]-2-methyl-3-(trifluoromethyl)pyridine

To a stirred solution [3-[[6-methyl-5-(trifluoromethyl)-2-pyridyl]oxy]phenyl]methanol (1.2 g, 4.2 mmol) in DCM (10 mL) was added thionyl chloride (0.4 mL, 5.0 mmol) at 0° C. After stirring for 1 h at room temperature, volatiles were evaporated under reduced pressure. The resulting residue was taken in DCM (50 mL), washed with aqueous saturated sodium bicarbonate solution (20 mL), water (20 mL), brine (20 mL), dried over anhydrous sodium sulfate, filtered and concentrated to give 1.20 g (93%) of 6-[3-(chloromethyl)phenoxy]-2-methyl-3-(trifluoromethyl)pyridine.

¹H NMR (400 MHz, CDCl₃): δ 2.73 (s, 3H), 4.59 (s, 2H), 6.74 (d, J=8.3 Hz, 1H), 7.13-7.18 (m, 1H), 7.20-7.23 (m, 1H), 7.27-7.31 (m, 1H), 7.40-7.45 (m, 1H), 7.97 (d, J=8.3 Hz, 1H). MS (ES) m/z 301.9 (M+1).

Step-V: 6-[3-(Diethoxyphosphorylmethyl)phenoxy]-2-methyl-3-(trifluoromethyl)pyridine A mixture of 6-[3-(chloromethyl)phenoxy]-2-methyl-3-(trifluoromethyl)pyridine (1.2 g, 4.0 mmol) and triethyl phosphite (1.5 mL, 8.7 mmol) was heated at 140° C. After 18 h, reaction mixture was cooled to 0° C. The reaction mixture was diluted with ethyl acetate (50 mL), washed with aqueous saturated sodium bicarbonate solution (50 mL), water (50 mL), brine (50 mL), dried over anhydrous sodium sulfate, filtered and concentrated under reduced pressure to give crude compound 1.55 g (97%).

MS (ES) m/z 403.9 (M+1).

Step-VI: 6-[3-(1,4-Dioxaspiro[4.5]decan-8-ylidenemethyl)phenoxy]-2-methyl-3-(trifluoromethyl)pyridine To a cooled suspension of sodium hydride (60% in mineral oil; 280 mg, 7.04 mmol) in THF (20 mL) was added a solution of 6-[3-(diethoxyphosphorylmethyl)phenoxy]-2-methyl-3-(trifluoromethyl)pyridine (1.55 g, 3.87 mmol) in THF (10 mL) at 0° C. After stirring for 4 h at room temperature, reaction mixture was cooled to 0° C., added a solution of cyclohexane-1,4-dione-mono ethylene ketal (550 mg, 105.6 mmol) in THF (5 mL) and stirring continued for 18 h at room temperature. Reaction mixture was poured onto ice-cold water; this was extracted with ethyl acetate (3×50 mL), combined organic layer washed with brine (100 mL), dried over anhydrous sodium sulfate, filtered and concentrated under reduced pressure to give crude compound which was purified by column chromatography to afford 1.02 g (65%) of 6-[3-(1,4-dioxaspiro[4.5]decan-8-ylidenemethyl)phenoxy]-2-methyl-3-(trifluoromethyl)pyridine.

¹H NMR (400 MHz, CDCl₃): δ 1.68 (t, J=6.6 Hz, 2H), 1.79 (t, J=6.6 Hz, 2H), 2.42 (t, J=6.6 Hz, 2H), 2.54 (t, J=6.6 Hz, 2H), 2.57 (s, 3H), 3.98 (s, 4H), 6.30 (s, 1H), 6.67 (d, J=8.5 Hz, 1H), 6.97-7.01 (m, 2H), 7.06 (d, J=7.6 Hz, 1H), 7.35 (t, J=8.3 Hz, 1H), 7.83 (d, J=8.5 Hz, 1H). MS (ES) m/z 406.0 (M+1).

Step-VII: 4-[[3-[[6-Methyl-5-(trifluoromethyl)-2-pyridyl]oxy]phenyl]methylene]cyclohexanone To a stirred solution of 6-[3-(1,4-dioxaspiro[4.5]decan-8-ylidenemethyl)phenoxy]-2-methyl-3-(trifluoromethyl)pyridine (1.0 g, 2.5 mmol) in acetone (25 mL) was added 1 N HCl (6 mL). After stirring for 2 h at 60° C., volatiles were evaporated under reduced pressure. The resulting residue was diluted with ethyl acetate (50 mL) and washed with aqueous saturated sodium bicarbonate solution (20 mL), water (20 mL), brine (20 mL), dried over anhydrous sodium sulfate, filtered, concentrated and purified by silica gel column chromatography to afford 600 mg (67%) of 4-[[3-[[6-methyl-5-(trifluoromethyl)-2-pyridyl]oxy]phenyl]methylene]cyclohexanone.

¹H NMR (400 MHz, CDCl₃): δ 2.44 (t, J=6.8 Hz, 2H), 2.53 (t, J=6.6 Hz, 2H), 2.57 (s, 3H), 2.69 (t, J=7.1 Hz, 2H), 2.79 (t, J=7.1 Hz, 2H), 6.48 (s, 1H), 6.70 (d, J=8.8 Hz, 1H), 7.00-7.04 (m, 2H), 7.10 (d, J=7.9 Hz, 1H), 7.39 (t, J=8.6 Hz, 1H), 7.85 (d, J=8.5 Hz, 1H). MS (ES) m/z 362.0 (M+1).

Step-VIII: 4-[[3-[[6-Methyl-5-(trifluoromethyl)-2-pyridyl]oxy]phenyl]methylene]cyclohexanamine A mixture of 4-[[3-[[6-methyl-5-(trifluoromethyl)-2-pyridyl]oxy]phenyl]methylene]cyclohexanone (600 mg, 1.7 mmol), ammonia in ethanol (2 M solution, 4.15 mL, 8.3 mmol) and titanium (IV) isopropoxide (0.98 mL, 3.3 mmol) was stirred under argon at ambient temperature for 6 h. Sodium borohydride (95 mg, 2.5 mmol) was added and the resulting mixture was stirred at room temperature for 18 h. Reaction was quenched by addition of ammonium hydroxide solution (~30% in water, 10 mL). The resulting inorganic precipitate was filtered off, washed with ethyl acetate (2×50 mL). Aqueous layer was separated, extracted with ethyl acetate (2×50 mL). Combined organic layer was washed with brine (100 mL), dried over anhydrous sodium sulfate, filtered, concentrated and purified column chromatography afford 280 mg (47%) of 4-[[3-[[6-methyl-5-(trifluoromethyl)-2-pyridyl]oxy]phenyl]methylene]cyclohexanamine.

¹H NMR (400 MHz, CDCl₃): δ 1.12-1.23 (m, 1H), 1.25-1.34 (m, 1H), 1.48 (brs, 2H), 1.87-1.94 (m, 1H), 1.95-2.04 (m, 2H), 2.25 (td, J=12.9, 3.4 Hz, 1H), 2.36-2.40 (m, 1H), 2.58 (s, 3H), 2.84-2.95 (m, 2H), 6.26 (s, 1H), 6.67 (d, J=8.6 Hz, 1H), 6.96-7.01 (m, 2H), 7.06 (d, J=7.6 Hz, 1H), 7.32-7.36 (m, 1H), 7.83 (d, J=8.6 Hz, 1H). MS (ES) m/z 363.0 (M+1).

Intermediate 3I

4-[[3-[[6-Cyclopropyl-5-(trifluoromethyl)-2-pyridyl]oxy]phenyl]-methylene]cyclohexanamine

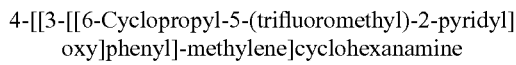

The titled intermediate was prepared from cyclopropyl boronic acid by using the procedure for Intermediate 3H.
MS (ES) m/z 389.0 (M+1).

Intermediate 3J

4-[[3-[[6-Ethyl-5-(trifluoromethyl)-2-pyridyl]oxy]phenyl]-methylene]cyclohexanamine

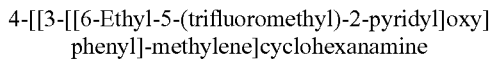

The titled intermediate was prepared from ethyl boronic acid by using the procedure for Intermediate 3H.
MS (ES) m/z 377.1 (M+1).

Intermediate 3K

(3E)-3-[[3-[[5-(Trifluoromethyl)-2-pyridyl]oxy]phenyl]methylene]-cyclohexanamine

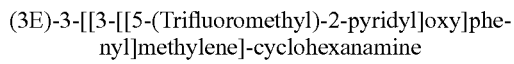

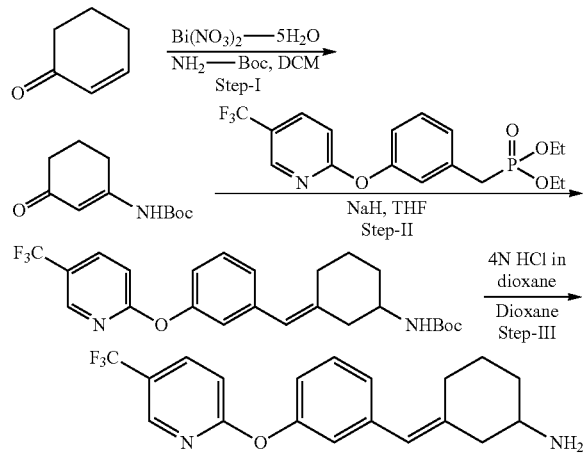

Step-I: tert-Butyl 2-(3-oxocyclohexyl)acetate

Prepared according to the procedure disclosed in the literature (WO2006/114260)

Step-II: tert-Butyl N-[(3E)-3-[[3-[[5-(trifluoromethyl)-2-pyridyl]oxy]phenyl]-methylene]cyclohexyl]carbamate To a stirred suspension of sodium hydride (60% in mineral oil; 169 mg, 3.5 mmol) in THF (5 mL) was added a solution of 2-[3-(diethoxyphosphorylmethyl)phenoxy]-5-(trifluoromethyl)pyridine (1.1 g, 2.8 mmol) (Intermediate 1A step-IV) in THF (15 mL) at 0° C. After stirring for 3.5 h at room temperature, reaction mixture was cooled to 0° C., added a solution of tert-butyl 2-(3-oxocyclohexyl)acetate (500 mg, 2.3 mmol) in THF (10 mL) and stirring continued for 19 h at ambient temperature. Reaction was quenched by the addition of saturated ammonium chloride solution. This was extracted with ethyl acetate (3×30 mL), combined organic layer was washed with brine (50 mL), dried over anhydrous sodium sulfate, filtered, concentrated and purified by column chromatography to give 700 mg (66%) of tert-butyl N-[(3E)-3-[[3-[[5-(trifluoromethyl)-2-pyridyl]oxy]phenyl]methylene]cyclohexyl]carbamate.
MS (ES) m/z 449.2 (M+1).

Step-III: (3E)-3-[[3-[[5-(Trifluoromethyl)-2-pyridyl]oxy]phenyl]methylene]-cyclohexanamine To a stirred solution of tert-butyl N-[(3E)-3-[[3-[[5-(trifluoromethyl)-2-pyridyl]oxy]phenyl]methylene]cyclohexyl]carbamate (700 mg, 1.56 mmol) in dioxane (1 mL) was added 4 N HCl in dioxane (5 mL) at ambient temperature and stirred for 8 h. Volatiles were evaporated under reduced pressure, resulting residue was taken in ethyl acetate (15 mL), washed with aqueous saturated sodium bicarbonate solution (15 mL), dried over anhydrous sodium sulfate, filtered, concentrated to give 501 mg (92%) of (3E)-3-[[3-[[5-(trifluoromethyl)-2-pyridyl]oxy]phenyl]methylene]-cyclohexanamine.
MS (ES) m/z 349.3 (M+1).

Intermediate 3L

(3E)-3-[[3-[[5-(Trifluoromethyl)-2-pyridyl]oxy]phenyl]methylene]-cyclopentanamine

The titled intermediate was prepared from cyclopent-2-en-1-one using the procedure for Intermediate 3K.
MS (ES) m/z 335.3 (M+1).

Intermediate 3M

4-[[3-Methyl-5-[[5-(trifluoromethyl)-2-pyridyl]oxy]phenyl]-methylene]cyclohexanamine

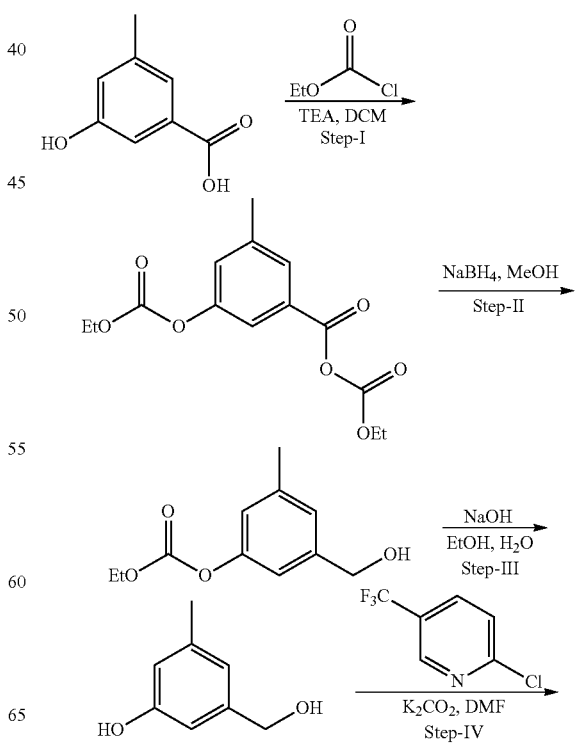

55

-continued

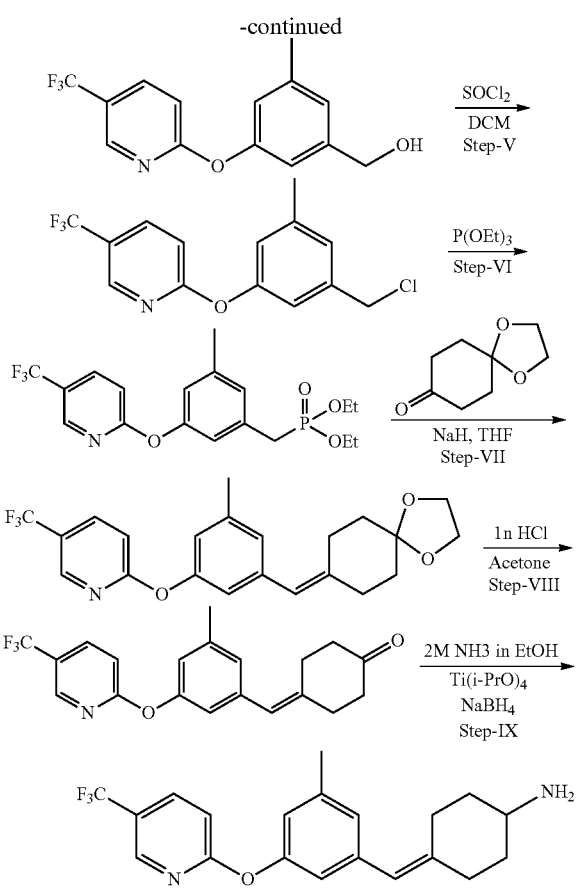

Step-I: Ethoxycarbonyl 3-ethoxycarbonyloxy-5-methyl-benzoate

To a stirred solution of 3-hydroxy-5-methyl benzoic acid (1.5 g, 9.8 mmol) in DCM (20 mL) was added triethylamine (4.2 mL, 29.5 mmol) and ethyl chloroformate (1.6 g, 14.8 mmol) at 0° C. After stirring for 30 min at room temperature, reaction mixture was diluted with DCM (50 mL), washed with water (50 mL), brine (50 mL), dried over anhydrous sodium sulfate, filtered and concentrated to give 2.2 g (75%) of ethoxycarbonyl 3-ethoxycarbonyloxy-5-methyl-benzoate.
$^1$H NMR (400 MHz, CDCl$_3$): δ 1.35-142 (m, 6H), 2.43 (s, 3H), 4.30-4.43 (m, 4H), 7.28 (s, 1H), 7.69 (s, 1H), 7.79 (s, 1H).

Step-II: Ethyl [3-(hydroxymethyl)-5-methyl-phenyl]carbonate

To a solution of ethoxycarbonyl 3-ethoxycarbonyloxy-5-methyl-benzoate (2.0 g, 6.7 mmol) in MeOH (20 mL) was added sodium borohydride (510 mg, 13.5 mmol) at room temperature.
After stirring for 30 min, methanol was evaporated under reduced pressure. The resulting residue was taken in ethyl acetate (40 mL), washed with water (40 mL), brine (40 mL), dried over anhydrous sodium sulfate, filtered and concentrated to give 1.4 g (99%) of ethyl [3-(hydroxymethyl)-5-methyl-phenyl]carbonate.
$^1$H NMR (400 MHz, CDCl$_3$): δ 1.39 (t, J=7.4 Hz, 3H), 1.73 (brs, 1H), 2.36 (s, 3H), 4.32 (q, J=7.1 Hz, 2H), 4.67 (s, 2H), 6.91 (s, 1H), 7.00 (s, 1H), 7.07 (s, 1H).

Step-III: 3-(Hydroxymethyl)-5-methyl-phenol

A mixture of ethyl [3-(hydroxymethyl)-5-methyl-phenyl] carbonate (1.4 g, 6.7 mmol), ethanol (15 mL) and water (15 mL) was refluxed for 1 h. Ethanol was evaporated under reduced pressure. The resulting aqueous layer was acidified with 1N HCl. This was extracted with ethyl acetate (3×15 mL), combined organic layer washed with brine (40 mL), dried over anhydrous sodium sulfate, filtered and concentrated to give 850 mg (92%) of 3-(hydroxymethyl)-5-methyl-phenol.
$^1$H NMR (400 MHz, CDCl$_3$): δ 2.29 (s, 3H), 4.64 (s, 2H), 6.59 (s, 1H), 6.66 (s, 1H), 6.72 (s, 1H).

Step-IV: [3-Methyl-5-[[5-(trifluoromethyl)-2-pyridyl]oxy]phenyl]methanol

To a mixture of 3-(hydroxymethyl)-5-methyl-phenol (850 mg, 6.1 mmol), 2-chloro-5-trifluoromethylpyridine (1.67 g. 9.2 mmol) in DMF (10 mL) was added potassium carbonate (1.7 g, 12.3 mmol) and heated at 100° C. for 2 h. After cooling to room temperature, water (60 mL) was added and extracted with ethyl acetate (2×40 mL). Combined organic layer was washed with water (30 mL), brine (50 mL), dried over anhydrous sodium sulfate, concentrated and purified by column chromatography to give 1.4 g (80%) of [3-methyl-5-[[5-(trifluoromethyl)-2-pyridyl]oxy]phenyl]methanol.
MS (ES) m/z 283.9 (M+1).

Step-V: 2-[3-(Chloromethyl)-5-methyl-phenoxy]-5-(trifluoromethyl)pyridine

To a stirred solution of [3-methyl-5-[[5-(trifluoromethyl)-2-pyridyl]oxy]phenyl]methanol (1.4 g, 4.9 mmol) in DCM (20 mL) was added thionyl chloride (0.7 mL, 9.9 mmol) at 0° C. After stirring for 1 h at room temperature, volatiles were evaporated under reduced pressure. The resulting residue was taken in DCM (30 mL), washed with aqueous saturated sodium bicarbonate solution (30 mL), water (30 mL), brine (30 mL), dried over anhydrous sodium sulfate and concentrated to afford 1.3 g (87%) of 2-[3-(chloromethyl)-5-methyl-phenoxy]-5-(trifluoromethyl)pyridine.
MS (ES) m/z 301.9 (M+1).

Step-VI: 2-[3-(Diethoxyphosphorylmethyl)-5-methyl-phenoxy]-5-(trifluoromethyl)-pyridine A mixture of 2-[3-(chloromethyl)-5-methyl-phenoxy]-5-(trifluoromethyl)pyridine (1.3 g, 7.8 mmol) and triethyl phosphite (2.65 mL, 15.6 mmol) was heated at 130° C. After 18 h, reaction mixture was cooled to room temperature; excess triethyl phosphite was evaporated under reduced pressure to furnish 2.0 g of 2-[3-(diethoxyphosphorylmethyl)-5-methyl-phenoxy]-5-(trifluoromethyl)pyridine. Crude product was taken up for further conversion.
MS (ES) m/z 404.0 (M+1).

Step-VII: 2-[3-(1,4-Dioxaspiro[4.5]decan-8-ylidenemethyl)-5-methyl-phenoxy]-5-(trifluoromethyl) pyridine To a suspension of sodium hydride (60% in mineral oil; 310 mg, 7.6 mmol) in THF (5 mL) was added a solution of 2-[3-(diethoxyphosphorylmethyl)-5-methyl-phenoxy]-5-(trifluoromethyl)pyridine (1.7 g, 4.2 mmol) in THF (10 mL) at 0° C. After stirring for 4 h at room temperature, reaction mixture was cooled to 0° C. and added a solution of 1,4-dioxaspiro[4.5]decan-8-one (600 mg, 3.8 mmol) in THF (5 mL). After stirring for 18 h at room temperature, reaction mixture was poured onto ice-cold water; this was extracted with ethyl acetate (2×20 mL), combined organic layer was washed with brine (40 mL), dried over anhydrous sodium sulfate, filtered, concentrated and purified by column chromatography to give 1.2 g (77%) of 2-[3-(1,4-dioxaspiro[4.5]decan-8-ylidenemethyl)-5-methyl-phenoxy]-5-(trifluoromethyl)pyridine.

$^1$H NMR (400 MHz, CDCl$_3$): δ 1.67 (t, J=6.5 Hz, 2H), 1.78 (t, J=6.4 Hz, 2H), 2.36 (s, 3H), 2.41 (t, J=6.4 Hz, 2H), 2.53 (t, J=6.5 Hz, 2H), 3.98 (s, 4H), 6.26 (s, 1H), 6.79 (d, J=9.0 Hz, 2H), 6.90 (s, 1H), 6.99 (d, J=8.7 Hz, 1H), 7.88 (d, J=8.7 Hz, 1H), 8.45 (s, 1H).

Step-VIII: 4-[[3-Methyl-5-[[5-(trifluoromethyl)-2-pyridyl]oxy]phenyl]methylene]-cyclohexanone To a stirred solution of 2-[3-(1,4-dioxaspiro[4.5]decan-8-ylidenemethyl)-5-methyl-phenoxy]-5-(trifluoromethyl)pyridine (1.2 g, 2.9 mmol) in acetone (20 mL) was added 1 N HCl (12 mL). After refluxing for 1 h, volatiles were evaporated under reduced pressure. The resulting residue was taken in ethyl acetate (40 mL) and washed with aqueous saturated sodium bicarbonate solution (30 mL), water (30 mL), brine (30 mL), dried over anhydrous sodium sulfate and concentrated to afford 1.0 g (93%) of 4-[[3-methyl-5-[[5-(trifluoromethyl)-2-pyridyl]oxy]phenyl]methylene]cyclohexanone.

$^1$H NMR (400 MHz, CDCl$_3$): δ 2.38 (s, 3H), 2.43 (t, J=6.9 Hz, 2H), 2.51 (t, J=7.1 Hz, 2H), 2.67 (t, J=6.8 Hz, 2H), 2.78 (t, J=7.7 Hz, 2H), 6.45 (s, 1H), 6.84 (d, J=7.9 Hz, 2H), 6.94 (s, 1H), 7.01 (d, J=8.7 Hz, 1H), 7.90 (dd, J=8.6, 2.5 Hz, 1H), 8.45 (s, 1H). MS (ES) m/z 362.0 (M+1).

Step-IX: 4-[[3-Methyl-5-[[5-(trifluoromethyl)-2-pyridyl]oxy]phenyl]methylene]-cyclohexanamine A mixture of 4-[[3-methyl-5-[[5-(trifluoromethyl)-2-pyridyl]oxy]phenyl]methylene]-cyclohexanone (1.0 g, 2.8 mmol), ammonia in ethyl alcohol (2 M solution, 7.0 mL, 13.8 mmol) and titanium (IV) isopropoxide (1.2 mL, 4.1 mmol) was stirred under argon atmosphere at ambient temperature for 6 h. Sodium borohydride (210 mg, 5.5 mmol) was added and stirred for 18 h. Reaction was quenched by addition of ammonium hydroxide (~30% in water, 15 mL); the resulting inorganic precipitate was filtered off through celite bed and washed with methanol (2×20 mL). The organic layer was evaporated under reduced pressure. Aqueous layer was extracted with ethyl acetate (2×20 mL), washed with brine (20 mL), dried over anhydrous sodium sulfate, concentrated and purified by column chromatography to give 400 mg (40%) of 4-[[3-Methyl-5-[[5-(trifluoromethyl)-2-pyridyl]oxy]phenyl]methylene]cyclohexanamine.

$^1$H NMR (400 MHz, CDCl$_3$): δ 1.29-1.36 (m, 1H), 1.37-1.47 (m, 1H), 1.96-2.10 (m, 3H), 2.20-2.28 (m, 1H), 2.36 (s, 3H), 2.35-2.42 (m, 1H), 2.86-2.91 (m, 1H), 3.02-3.09 (m, 1H), 3.49 (s, 2H), 6.23 (s, 1H), 6.76 (s, 1H), 6.80 (s, 1H), 6.88 (s, 1H), 6.98 (d, J=8.8 Hz, 1H), 7.88 (dd, J=8.6, 2.3 Hz, 1H), 8.45 (s, 1H). MS (ES) m/z 363.0 (M+1).

Intermediate 3N

4-[[2-Methyl-5-[[5-(trifluoromethyl)-2-pyridyl]oxy]phenyl]-methylene]cyclohexanamine The titled intermediate was prepared from 2-methyl-5-hydroxybenzaldehyde and 2-chloro-5-trifluoromethylpyridine using the procedure for Intermediate 3M.
MS (ES) m/z 363.1 (M+1).

Intermediate 3O

4-[[3-[(5-Cyclopropyl-2-pyridyl)oxy]phenyl]methylene]cyclohexanamine

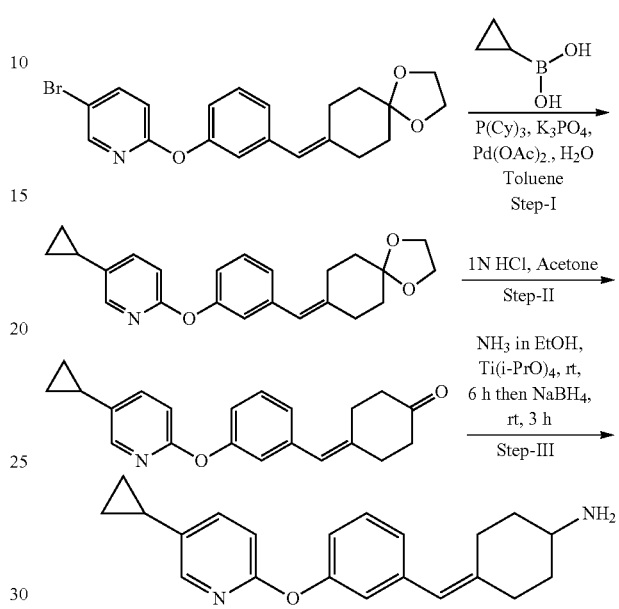

Step-I: 5-Cyclopropyl-2-[3-(1,4-dioxaspiro[4.5]decan-8-ylidenemethyl)phenoxy]-pyridine To a stirred solution of 5-bromo-2-[3-(1,4-dioxaspiro[4.5]decan-8-ylidenemethyl)phenoxy]pyridine (prepared from 5-bromo-2-chloropyridine using the procedure for Intermediate 3A) (200 mg, 0.5 mmol) in toluene (5 mL) was added tricyclohexylphosphine (14 mg, 0.05 mmol) followed by a solution of potassium phosphate tribasic (370 mg, 1.7 mmol) in water (0.5 mL), cyclopropyl boronic acid (56 mg, 0.7 mmol) and degassed with argon for 20 min. To this was added palladium acetate (6 mg, 0.03 mmol) and heated to 100° C. for 18 h. Reaction mixture was cooled to room temperature, filtered through celite bed, washed with ethyl acetate. Filtrate was washed with water (20 mL), brine (20 mL), dried over anhydrous sodium sulfate, filtered, concentrated and purified by column chromatography to furnish 60 mg (33%) of 5-cyclopropyl-2-[3-(1,4-dioxaspiro[4.5]decan-8-ylidenemethyl)phenoxy]-pyridine.
MS (ES) m/z 364.2 (M+1).

Step-II: 4-[[3-[(5-Cyclopropyl-2-pyridyl)oxy]phenyl]methylene]cyclohexanone

To a solution of 5-cyclopropyl-2-[3-(1,4-dioxaspiro[4.5]decan-8-ylidenemethyl)phenoxy]pyridine (1.7 g, 4.7 mmol) in acetone (50 mL) was added 1 N HCl (20 mL). After stirring for 1 h at 60° C., volatiles were evaporated under reduced pressure. The resulting residue was taken in ethyl acetate (30 mL) and washed with aqueous saturated sodium bicarbonate solution (30 mL), water (30 mL), brine (30 mL), dried over anhydrous sodium sulfate, filtered and concentrated to afford 1.45 g (97%) of 4-[[3-[(5-cyclopropyl-2-pyridyl)oxy]phenyl]methylene]cyclohexanone.

$^1$H NMR (400 MHz, CDCl$_3$): δ 0.63-0.67 (m, 2H), 0.95-1.00 (m, 2H), 1.83-1.90 (m, 1H), 2.42 (t, J=7.1 Hz, 2H), 2.51 (t, J=7.1 Hz, 2H), 2.67 (t, J=7.1 Hz, 2H), 2.77 (t, J=7.1 Hz, 2H), 6.46 (s, 1H), 6.82 (d, J=8.6 Hz, 1H), 6.97-6.98 (m, 2H), 7.03 (d, J=7.6 Hz, 1H), 7.32-7.36 (m, 2H), 8.01 (d, J=2.2 Hz, 1H). MS (ES) m/z 320.2 (M+1).

Step-III: 4-[[3-[(5-Cyclopropyl-2-pyridyl)oxy]phenyl]methylene]cyclohexanamine

A mixture of 4-[[3-[(5-cyclopropyl-2-pyridyl)oxy]phenyl]methylene]cyclohexanone (1.4 g, 4.3 mmol), ammonia in ethanol (2 M solution, 15.0 mL, 21.9 mmol) and titanium (IV) isopropoxide (2.6 mL, 8.8 mmol) was stirred under argon at ambient temperature for 6 h. Sodium borohydride (250 mg, 6.5 mmol) was added and the resulting mixture was stirred at room temperature for 18 h. Reaction was quenched by addition of ammonium hydroxide (~30% in water, 50 mL), the resulting inorganic precipitate was filtered off and washed with methanol (20 mL×2). The organic layer was evaporated under reduced pressure. The resulting residue was extracted with ethyl acetate (2×20 mL), combined organic layer washed with brine (1000 mL), dried over anhydrous sodium sulfate, filtered, concentrated and purified by column chromatography to give 11.5 g (57%) of 4-[[3-[(5-cyclopropyl-2-pyridyl)oxy]phenyl]methylene]cyclohexanamine.

MS (ES) m/z 321.3 (M+1).

Intermediate 3P

4-[[3-[[6-chloro-5-(trifluoromethyl)-2-pyridyl]oxy]phenyl]-methylene]cyclohexanamine

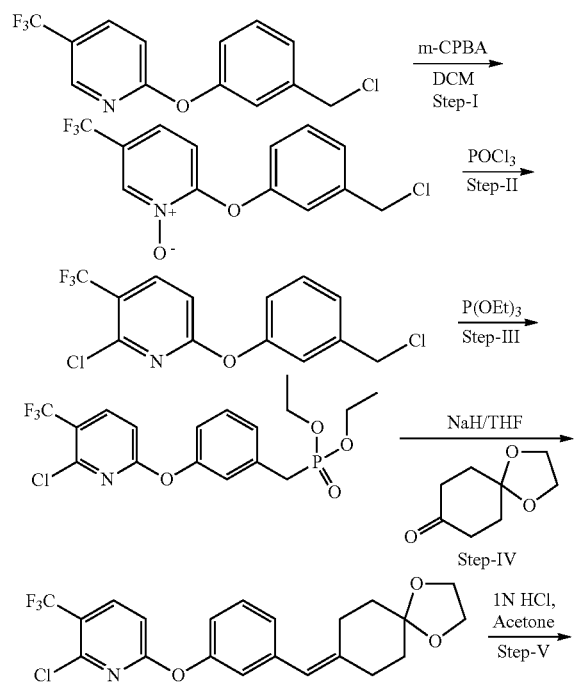

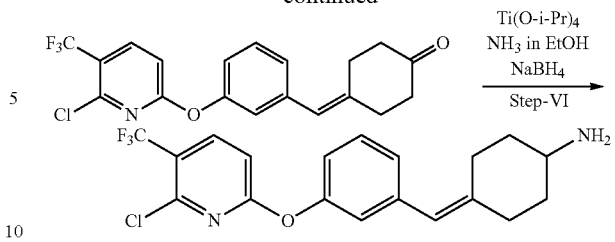

Step-I: 2-[3-(Chloromethyl)phenoxy]-1-oxido-5-(trifluoromethyl)pyridin-1-ium

To a stirred solution of 2-[3-(chloromethyl)phenoxy]-5-(trifluoromethyl)pyridine (1.0 g, 3.5 mmol) (Intermediate 1A, step-III) in DCM (10 mL) was added m-chloroperbenzoic acid (~70% in water; 2.0 g, 8.1 mmol) at room temperature. After stirring for 3 days, reaction mixture was filtered through celite bed. Celite bed was washed with DCM, Filtrate was washed with aqueous saturated sodium bicarbonate solution (50 mL), water (50 mL), brine (50 mL), dried over anhydrous sodium sulfate, filtered, concentrated and purified by column chromatography to afford 440 mg (42%) of titled compound.

MS (ES) m/z 303.9 (M+1).

Step-II: 2-Chloro-6-[3-(chloromethyl)phenoxy]-3-(trifluoromethyl)pyridine

A mixture of 2-[3-(Chloromethyl)phenoxy]-1-oxido-5-(trifluoromethyl)pyridin-1-ium (440 mg, 1.4 mmol) and POCl$_3$ (4.0 mL), was heated at 130° C. for 2 h. Excess of POCl$_3$ was removed under reduced pressure. Reaction mixture was diluted with ethyl acetate (10 mL), neutralized with aqueous saturated sodium bicarbonate solution (10 mL). Organic layer was separated, washed with water (10 mL), brine (10 mL), dried over anhydrous sodium sulfate, filtered, concentrated and purified by column chromatography to afford 448 mg (96%) of 2-chloro-6-[3-(chloromethyl)phenoxy]-3-(trifluoromethyl)pyridine.

MS (ES) m/z 321.8 (M+1).

Step-III: 2-Chloro-6-[3-(diethoxyphosphorylmethyl)phenoxy]-3-(trifluoromethyl)pyridine A mixture of 2-chloro-6-[3-(chloromethyl)phenoxy]-3-(trifluoromethyl)pyridine (400 mg, 1.2 mmol) and triethyl phosphite (3.0 mL, 17.5 mmol) was heated at 140° C. After 18 h, reaction mixture was cooled to 0° C. The reaction mixture was diluted with ethyl acetate (10 mL), washed with aqueous saturated sodium bicarbonate solution (10 mL), water (10 mL), brine (10 mL), dried over anhydrous sodium sulfate, filtered and concentrated under reduced pressure to give 354 mg (67%) of titled compound.

MS (ES) m/z 423.9 (M+1).

Step-IV: 2-Chloro-6-[3-(1,4-dioxaspiro[4.5]decan-8-ylidenemethyl)phenoxy]-3-(trifluoromethyl)pyridine To a cooled suspension of sodium hydride (60% in mineral oil; 80 mg, 2.0 mmol) in THF (3 mL) was added a solution of 2-chloro-6-[3-(diethoxyphosphorylmethyl)phenoxy]-3-(trifluoromethyl)pyridine (354 mg, 0.8 mmol) in THF (4 mL) at 0° C. After stirring for 4 h at room temperature, reaction mixture was cooled to 0° C. and added a solution of cyclohexane-1,4-dione-mono ethylene ketal (156 mg, 1.0 mmol) in THF (3 mL). After stirring for 18 h at room temperature, reaction was poured onto ice-cold water; this was extracted with ethyl acetate (3×10 mL), combined organic layer washed with brine (15 mL), dried over anhydrous sodium sulfate, filtered and concentrated under reduced pressure to give crude compound which was purified by column chromatography to afford 350 mg (98%) of 2-chloro-6-[3-(1,4-dioxaspiro[4.5]decan-8-ylidenemethyl)phenoxy]-3-(trifluoromethyl)pyridine.

MS (ES) m/z 425.9 (M+1).

Step-V: 4-[[3-[[6-Chloro-5-(trifluoromethyl)-2-pyridyl]oxy]phenyl]methylene]cyclohexanone To a stirred solution of 2-chloro-6-[3-(1,4-dioxaspiro[4.5]decan-8-ylidenemethyl)phenoxy]-3-(trifluoromethyl)pyridine (330 mg, 0.8 mmol) in acetone (5 mL) was added 1 N HCl (5 mL). After stirring for 2 h at 60° C., volatiles were evaporated under reduced pressure. The resulting residue was diluted with ethyl acetate (15 mL) and washed with aqueous saturated sodium bicarbonate solution (10 mL), water (10 mL), brine (10 mL), dried over anhydrous sodium sulfate, filtered, concentrated and purified by silica gel column chromatography to afford 210 mg (71%) of 4-[[3-[[6-chloro-5-(trifluoromethyl)-2-pyridyl]oxy]phenyl]methylene]cyclohexanone.

MS (ES) m/z 382.0 (M+1).

Step-VI: 4-[[3-[[6-chloro-5-(trifluoromethyl)-2-pyridyl]oxy]phenyl]-methylene]cyclohexanamine A mixture of 4-[[3-[[6-chloro-5-(trifluoromethyl)-2-pyridyl]oxy]phenyl]methylene]cyclohexanone (200 mg, 0.5 mmol), ammonia in ethanol (2 M solution, 1.3 mL, 2.6 mmol) and titanium (IV) isopropoxide (0.3 mL, 1.0 mmol) was stirred under argon at ambient temperature for 6 h. Sodium borohydride (30 mg, 0.8 mmol) was added and the resulting mixture was stirred at room temperature for 18 h. Reaction was quenched by addition of ammonium hydroxide solution (~30% in water, 5 mL). The resulting inorganic precipitate was filtered off, washed with ethyl acetate (2×25 mL). Aqueous layer was separated, extracted with ethyl acetate (2×10 mL). Combined organic layer was washed with brine (10 mL), dried over anhydrous sodium sulfate, filtered, concentrated and purified column chromatography afford 110 mg (55%) of titled intermediate.

$^1$H NMR (400 MHz, CDCl$_3$): δ 1.25 (qd, J=10.9, 4.2 Hz, 1H), 1.36 (qd, J=10.6, 3.5 Hz, 1H), 1.94-2.07 (m, 3H), 2.21-2.30 (m, 1H), 2.37-2.43 (m, 1H), 2.86-2.93 (m, 1H), 2.95-3.02 (m, 1H), 3.49 (s, 2H), 6.27 (s, 1H), 6.84 (d, J=8.5 Hz, 1H), 6.97-7.00 (m, 2H), 7.08 (d, J=7.7 Hz, 1H), 7.34 (t, J=8.1 Hz, 1H), 7.95 (d, J=8.6 Hz, 1H). MS (ES) m/z 383.0 (M+1).

Intermediate 3Q

6-[3-[(4-Aminocyclohexylidene)methyl]phenoxy]-3-(trifluoromethyl)pyridine-2-carbonitrile

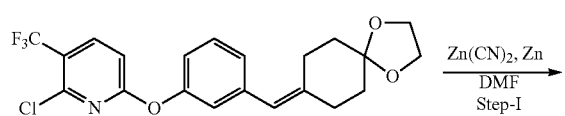

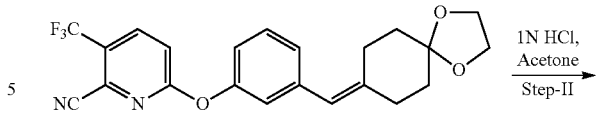

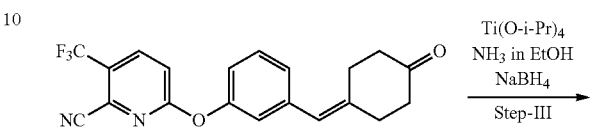

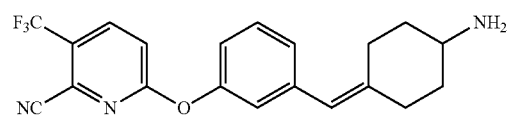

Step-I: 6-[3-(1,4-Dioxaspiro[4.5]decan-8-ylidenemethyl)phenoxy]-3-(trifluoromethyl)pyridine-2-carbonitrile A solution of 2-chloro-6-[3-(1,4-dioxaspiro[4.5]decan-8-ylidenemethyl)phenoxy]-3-(trifluoromethyl)pyridine (Intermediate 3P, Step-IV) (120 mg, 0.2 mmol) zinc cyanide (17 mg, 0.1 mmol) zinc dust (6 mg, 0.09 mmol) in DMF (5 mL) was degassed for 5 min. To this was added 1,1'-bis(diphenylphosphino)ferrocene dipalladium (II) dichloromethane complex (10 mg, 0.01 mmol) and heated at 120° C. for 2 h. Reaction mixture was cooled to room temperature, quenched with the addition of water (15 mL). This was extracted with ethyl acetate (2×10 mL), combined organic layer was washed with brine (20 mL), dried over anhydrous sodium sulfate, concentrated and purified by column chromatography to give 230 mg (98%) of 6-[3-(1,4-dioxaspiro[4.5]decan-8-ylidenemethyl)phenoxy]-3-(trifluoromethyl)pyridine-2-carbonitrile.

MS (ES) m/z 417.2 (M+1).

Step-II: 6-[3-[(4-Oxocyclohexylidene)methyl]phenoxy]-3-(trifluoromethyl)pyridine-2-carbonitrile The titled compound was prepared from 6-[3-(1,4-dioxaspiro[4.5]decan-8-ylidenemethyl)phenoxy]-3-(trifluoromethyl)pyridine-2-carbonitrile in analogous manner of Intermediate 3P step-V.

MS (ES) m/z 373.2 (M+1).

Step-III: 6-[3-[(4-Aminocyclohexylidene)methyl]phenoxy]-3-(trifluoromethyl)-pyridine-2-carbonitrile The titled compound was prepared from 6-[3-[(4-oxocyclohexylidene)methyl]phenoxy]-3-(trifluoromethyl)pyridine-2-carbonitrile in analogous manner of Intermediate 3P step-VI.

MS (ES) m/z 374.3 (M+1).

Chemical Resolution of Racemic Intermediate 3A Through Diastereomeric Salt Formation with (+)-O,O'-Di-p-toluoyl-D-tartaric acid Intermediate 3R (−)-4-[[3-[[5-(trifluoromethyl)-2-pyridyl]oxy]phenyl]methylene]-cyclohexanamine

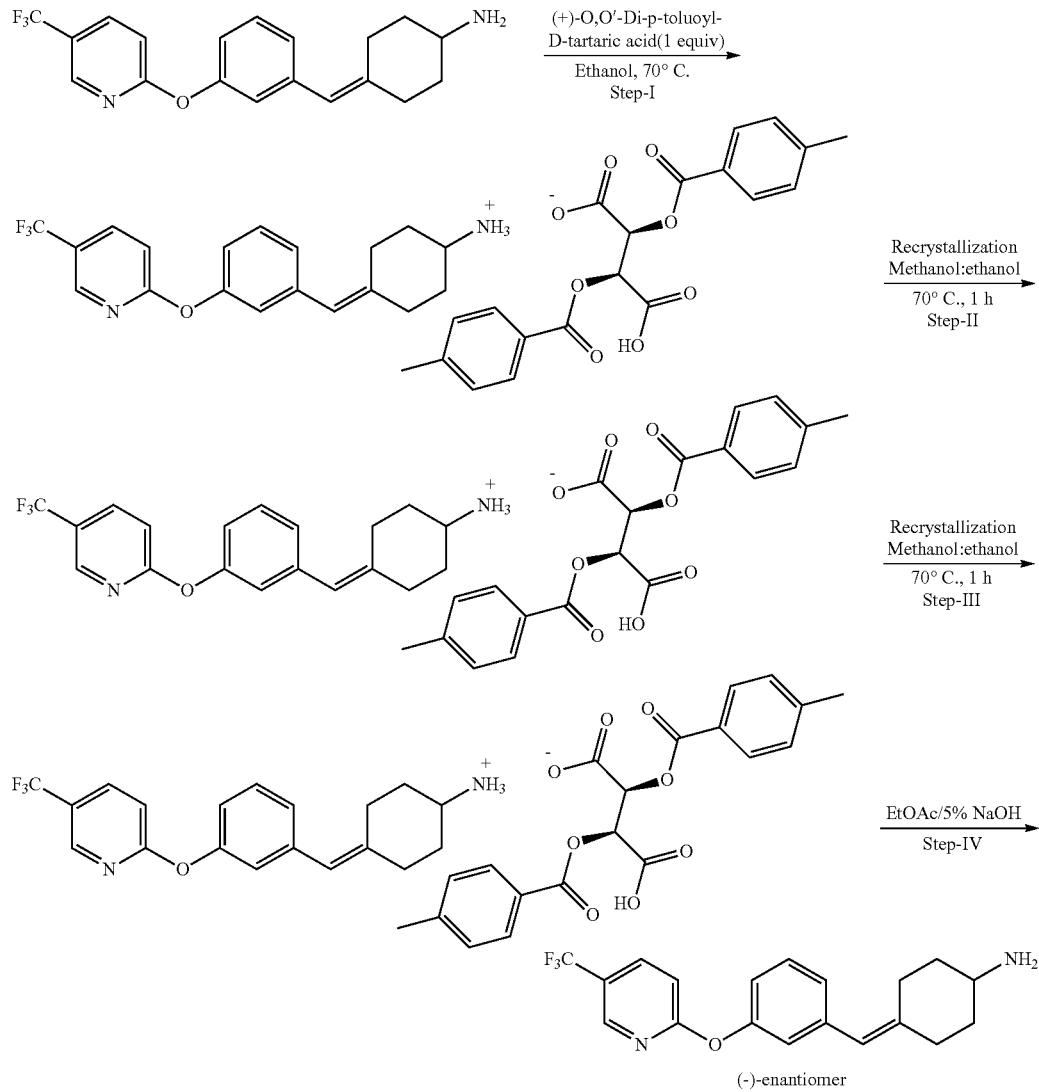

Step-I: 4-[[3-[[5-(trifluoromethyl)-2-pyridyl]oxy]phenyl]methylene]-cyclohexanamine (+)-O,O'-Di-p-toluoyl-D-tartarate salt To a stirred solution of 4-[[3-[[5-(trifluoromethyl)-2-pyridyl]oxy]phenyl]methylene]cyclohexanamine (5.0 g, 14.4 mmol) in ethanol (100 mL, 20 vol/wt) was added (+)-O,O'-Di-p-toluoyl-D-tartaric acid (5.5 g, 14.4 mmol) at 70° C. to give clear solution. Within 2 min reaction mixture turned turbid and started precipitation. Reaction mixture became thick suspension, which was heated for 2 h. Reaction mixture was allowed to cool to 25° C. gradually (~2 h). This thick suspension was filtered through Buchner funnel, washed with ethanol (20 mL) and dried under vacuum to give 5.5 g (52%) of tartarate salt.

Chiral HPLC purity of solid tartarate salt: 62%

Step-II: Crystallization

Tartarate salt (Step-I) (5.24 g) was suspended in methanol:ethanol (3:1, 105 mL, 20 vol/wt). This suspension was stirred at 70° C. for 1 h. During this period, suspension became turbid (not completely soluble). After stirring for 1 h, reaction mixture was allowed to cool to 25° C. gradually (~2 h). Thick suspension was filtered through Buchner funnel, washed with ethanol (10 mL) and dried under vacuum to give solid tartarate salt (3.12 g). Chiral HPLC purity of solid tartarate salt: 90%

Step-III: Re-crystallization

Tartarate salt (step-II) (3.12 g) was suspended in methanol:ethanol (1:1, 62 mL, 20 vol/wt). This suspension was stirred at 70° C. for 1 h. Reaction mixture was allowed to cool to 25° C. gradually (~2 h). During cooling thick suspension was obtained, which filtered through Buchner funnel, washed with ethanol (10 mL) and dried under vacuum to furnish (2.43 g) of solid tartarate salt.

Chiral HPLC purity of solid tartarate salt: 97

Step-IV: (−)-4-[[3-[[5-(trifluoromethyl)-2-pyridyl] oxy]phenyl]methylene]-cyclohexanamine To a suspension of tartarate salt (4.15 g) (Step-III) in ethyl acetate (200 mL) was added 5% aqueous sodium hydroxide solution till the solution reached pH 10 at 10° C. After stirring for 30 min at 10° C., aqueous layer was separated, extracted with ethyl acetate (2×100 mL). Combined organic layer was washed with brine (100 mL), dried over anhydrous sodium sulfate, filtered and concentrated under reduced pressure to give 1.90 g of (−)-4-[[3-[[5-(trifluoromethyl)-2-pyridyl]oxy]phenyl]methylene]-cyclohexanamine as viscous oil.

Chiral HPLC purity: 97%. $[\alpha]^{20}_D$-28.8 (c 0.5, MeOH).

Following carboxylic acid and carboxylic acid chloride Intermediates 4A-4AZ were obtained from commercial source.

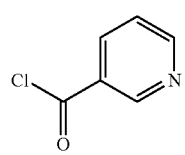
4A

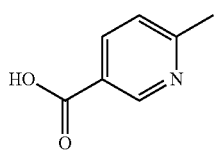
4B

4C

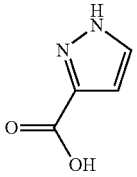
4D

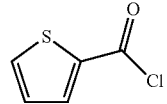
4E

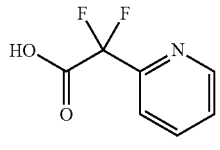
4F

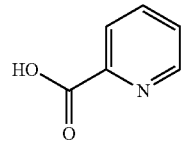
4G

-continued

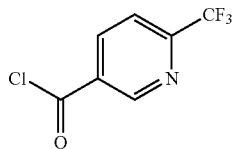
4H

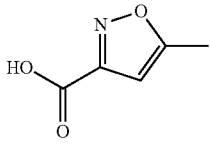
4I

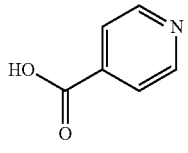
4J

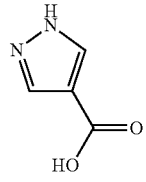
4K

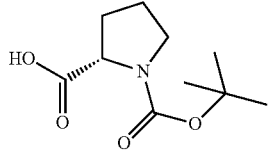
4L

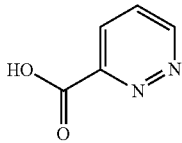
4M

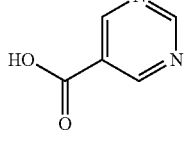
4N

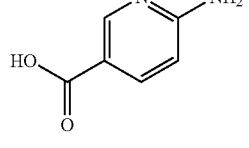
4O

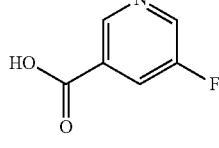
4P

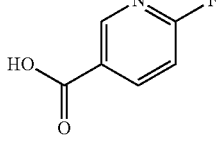
4Q

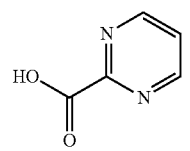    4R
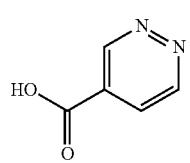    4S
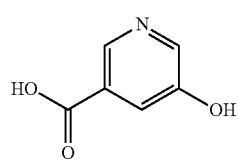    4T
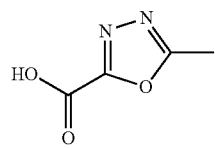    4U
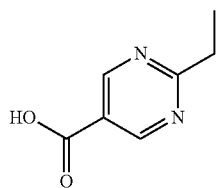    4V
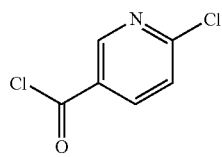    4W
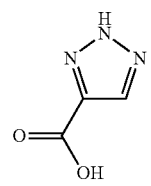    4X
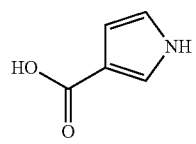    4Y
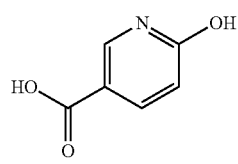    4Z
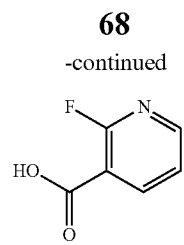    4AA
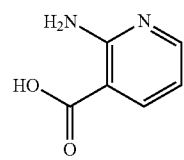    4AB
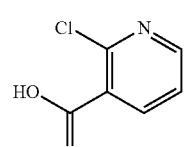    4AC
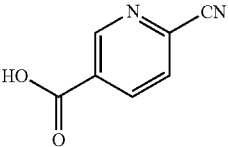    4AD
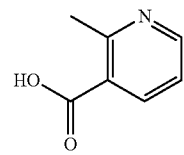    4AE
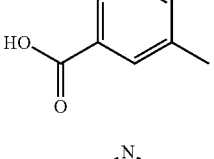    4AF
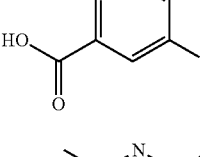    4AG
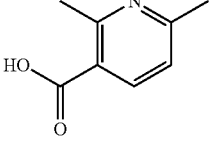    4AH
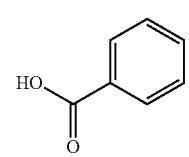    4AI
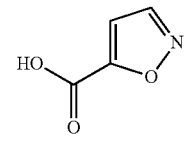    4AJ -continued
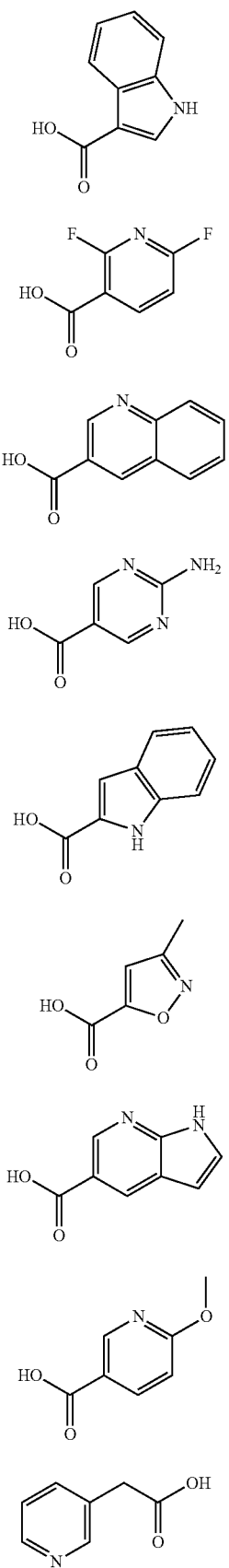
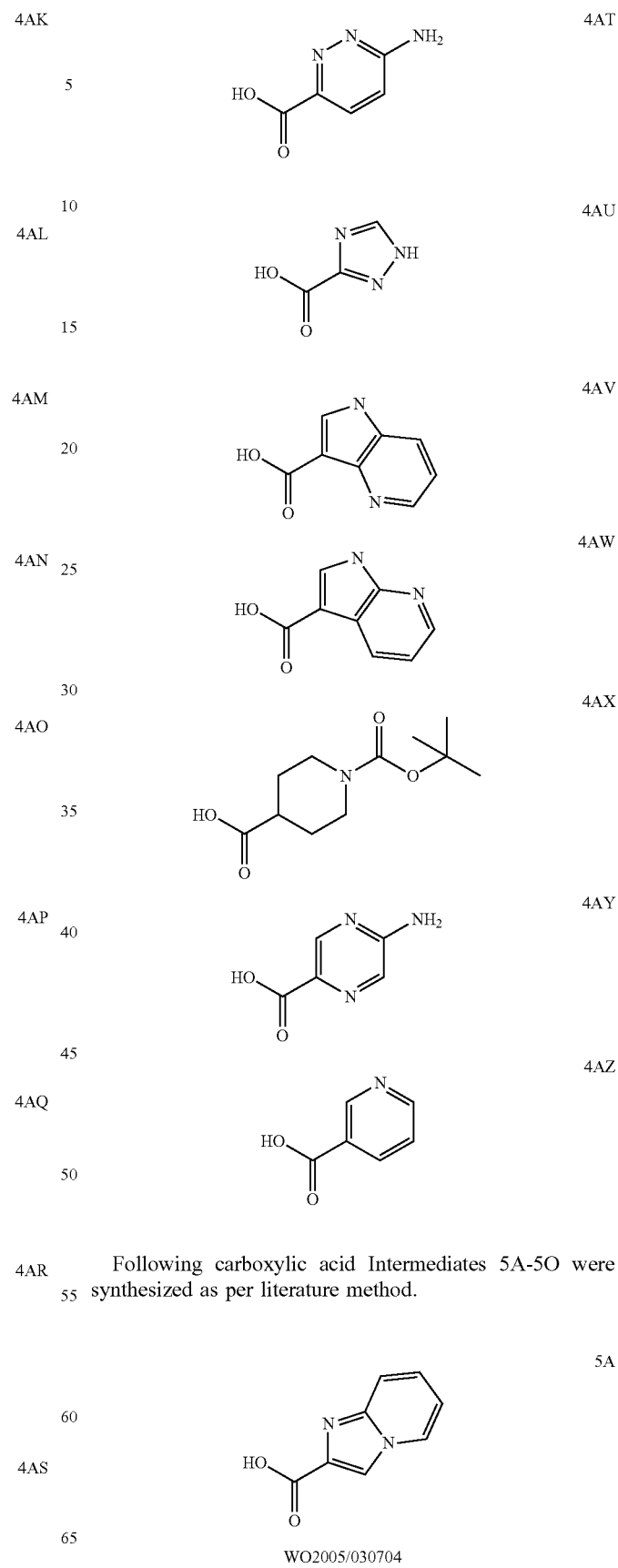
Following carboxylic acid Intermediates 5A-5O were synthesized as per literature method.
WO2005/030704

-continued
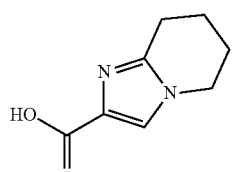
WO2007/108750
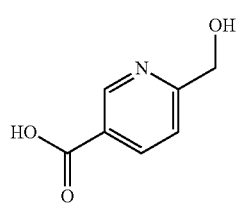
WO2009/027283
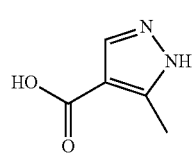
WO2009/137338
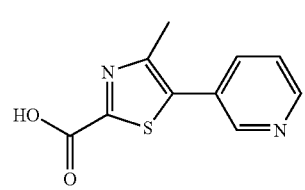
WO2010/129497
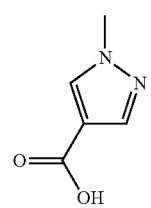
WO2003/06459
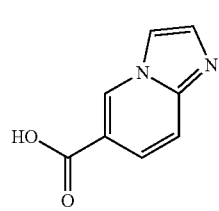
WO2005/030704
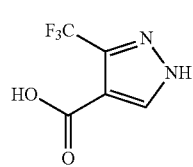 [SMILES: O=C(O)c1c[nH]nc1C(F)(F)F]
*J. Org. Chem.*, 2012, 77, 1, 45-56
-continued
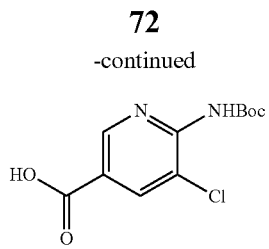 5I
*Bio. Med. Chem.*, 2004, 12, 5, 1151-1175
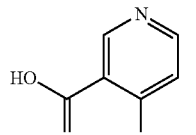 5J
*Bio. Med. Chem.*, 2004, 12, 5, 1151-1175
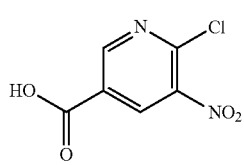 5K
WO/2005/021544
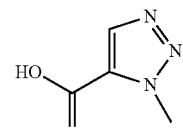 5L
WO2008/035826
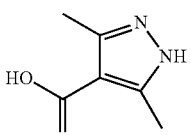 5M
*J. Am. Chem. Soc.*, 2011, 133, 31, 11888-11891
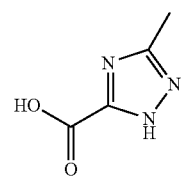 5N
*Chem Pharma Bull.*, 1966, 14, 5, 523-528
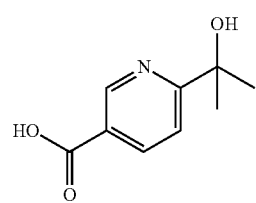 5O
WO2010/086406

Intermediate 6A

5-Isopropyl-3-methyl-1H-pyrazole-4-carboxylic acid

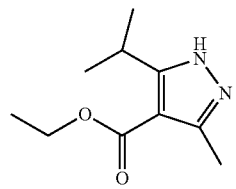 NaOH, EtOH, H₂O → 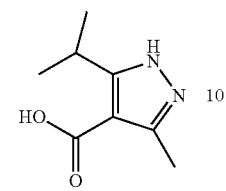

Ethyl 5-isopropyl-3-methyl-1H-pyrazole-4-carboxylate (WO2009/013211) (2.1 g, 10.7 mmol) was dissolved in ethanol:water (2:1, 10 mL), to it was added sodium hydroxide (857 mg, 21.4 mmol) and refluxed for 20 h. Volatiles were evaporated under reduced pressure. Aqueous layer was diluted with water (20 mL) and extracted with ethyl acetate (2×20 mL). Combined organic layer was washed with brine (25 mL), dried over anhydrous sodium sulfate, filtered and concentrated to give 750 mg (73%) of 5-isopropyl-3-methyl-1H-pyrazole-4-carboxylic acid.

$^1$H NMR (400 MHz, CDCl$_3$): δ 1.17 (d, J=6.9 Hz, 6H), 2.32 (s, 3H), 3.45-3.54 (m, 1H), 12.23 (brs, 2H). MS (ES) m/z 169.1 (M+1).

Following intermediates were synthesized from appropriate starting materials using the procedure for Intermediate 6A.

6B
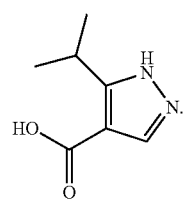
MS (ES) m/z 155.1 (M + 1)

6C
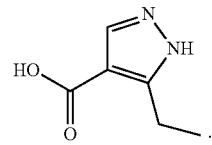
MS (ES) m/z 141.1 (M + 1)

6D
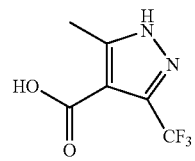
MS (ES) m/z 195.1 (M + 1)

6E
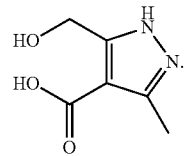
MS (ES) m/z 156.2 (M + 1)

6F
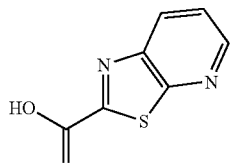
MS (ES) m/z 181.1 (M + 1)

Intermediate 6G

Imidazo[1,2-b]pyridazine-3-carboxylic acid

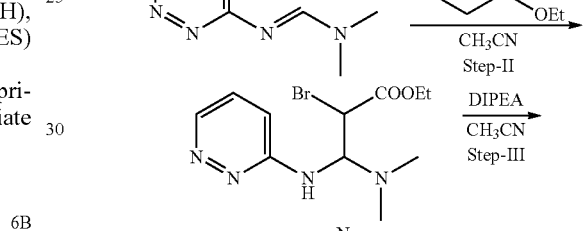

Step-I: N,N-Dimethyl-N'-pyridazin-3-yl-formamidine

A mixture of pyridazin-3-amine (2.0 g, 21.0 mmol) and DMF.DMA (2.86 mL, 21.5 mmol) was refluxed for 2 h. After cooling to room temperature, reaction mixture was concentrated under reduced pressure. To the resulting residue was added ethyl acetate (20 mL). Solid precipitated was filtered through Buckner funnel and dried under vacuum to furnish 3 g (95%) of the titled compound as a solid.

Step-II: Ethyl 2-bromo-3-(dimethylamino)-3-(pyridazin-3-ylamino)propanoate

To a stirred solution of N,N-dimethyl-N'-pyridazin-3-yl-formamidine (3.0 g, 20.0 mmol) in acetonitrile (50 mL) was added ethyl-2-bromoacetate (6.64 mL, 59.9 mmol) and refluxed for 16 h. Solvent was partially evaporated, to the residue diethyl ether was added. Precipitated solid was filtered through Buckner funnel, dried under vacuum to afford 5.0 g (78%) of the titled compound as a solid.

Step-III: Ethyl imidazo[1,2-b]pyridazine-3-carboxylate

To a stirred solution of ethyl 2-bromo-3-(dimethylamino)-3-(pyridazin-3-ylamino)propanoate (4.0 g, 12.6 mmol) in acetonitrile (100 mL) was added N,N di-isopropyl ethylamine (4.4 mL, 25.1 mmol). After stirring for 4 h, solvent was evaporated and residue was triturated with water. Solid precipitated was filtered through Buckner funnel and dried under vacuum to give 2.0 g (83%) of the titled compound as a solid.

Step-IV: Imidazo[1,2-b]pyridazine-3-carboxylic acid

Ethyl imidazo[1,2-b]pyridazine-3-carboxylate was hydrolyzed according to the procedure for Intermediate 6A. MS (ES) m/z 164.2 (M+1).

Intermediate 6 H

6-Pyrazol-1-ylpyridine-3-carboxylic acid

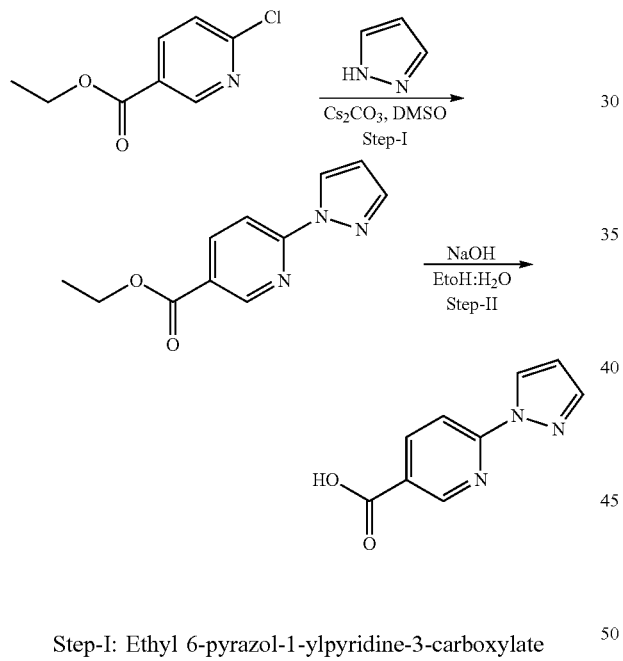

Step-I: Ethyl 6-pyrazol-1-ylpyridine-3-carboxylate

A stirred suspension of ethyl 6-chloropyridine-3-carboxylate (500 mg, 2.7 mmol), 1H-pyrazole (270 mg, 4.0 mmol) and cesium carbonate (1.32 g, 4.0 mmol) in DMSO (5 mL) was heated at 100° C. for 16 h. Reaction mixture was cooled to room temperature and quenched with water (20 mL). This was extracted with ethyl acetate (2×25 mL), combined organic layer washed with water (20 mL), brine (20 mL), dried over anhydrous sodium sulfate, filtered, concentrated and purified by column chromatography to give 500 mg (85%) of ethyl 6-pyrazol-1-ylpyridine-3-carboxylate.

$^1$H NMR (400 MHz, CDCl$_3$): δ 1.42 (t, J=7.1 Hz, 3H), 4.42 (q, J=7.1 Hz, 2H), 6.50 (t, J=1.8 Hz, 1H), 7.78 (s, 1H), 8.04 (d, J=8.6 Hz, 1H), 8.40 (dd, J=8.5, 2.1 Hz, 1H), 8.62 (d, J=2.5 Hz, 1H), 9.03 (d, J=2.0 Hz, 1H). MS (ES) m/z 218.0 (M+1).

Step-II: 6-Pyrazol-1-ylpyridine-3-carboxylic acid

The titled intermediate was prepared from ethyl 6-pyrazol-1-ylpyridine-3-carboxylate using the procedure for Intermediate 6A.

$^1$H NMR (400 MHz, CDCl$_3$): δ 6.64 (t, J=2.1 Hz, 1H), 7.91 (s, 1H), 8.03 (d, J=8.4 Hz, 1H), 8.44 (dd, J=8.6, 2.1 Hz, 1H), 8.70 (d, J=2.5 Hz, 1H), 8.95 (d, J=1.7 Hz, 1H), 13.42 (brs, 1H). MS (ES) m/z 190.0 (M+1).

Following intermediates were prepared from appropriate starting materials using the procedure for Intermediate 6H.

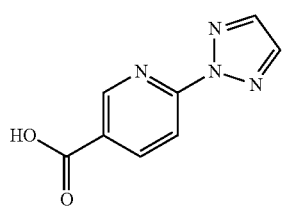

6I

MS (ES) m/z 191.0 (M+1).

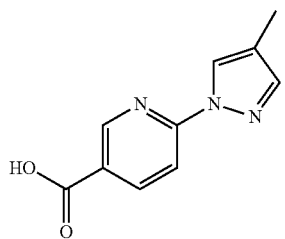

6J

MS (ES) m/z 204.1 (M+1).

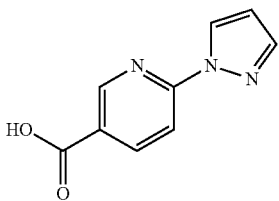

6K

MS (ES) m/z 190.1 (M+1).

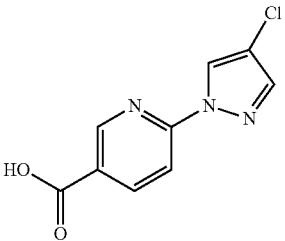

6L

MS (ES) m/z 224.2 (M+1).

77
-continued

6M

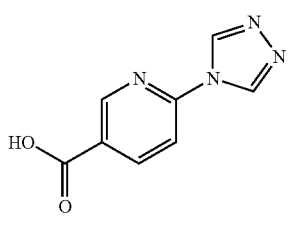

MS (ES) m/z 191.0 (M+1).

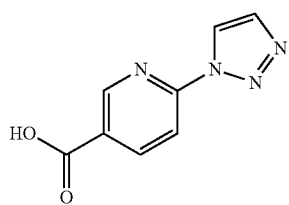

MS (ES) m/z 191.2 (M+1).

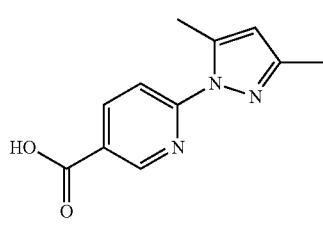

MS (ES) m/z 218.1 (M+1).

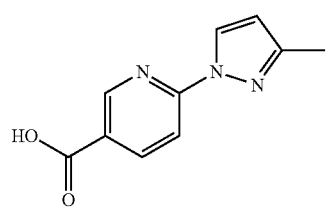

MS (ES) m/z 204.2 (M+1).

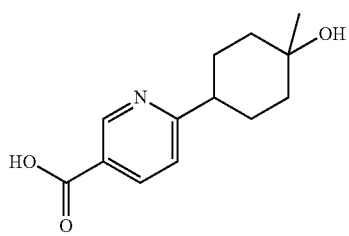

MS (ES) m/z 237.1 (M+1).

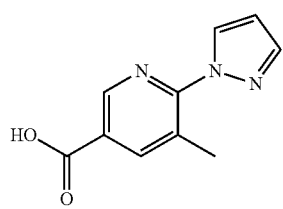

MS (ES) m/z 204.1 (M+1).

MS (ES) m/z 204.1 (M+1).

78

Intermediate 6S

5-Pyrazol-1-ylpyridine-3-carboxylic acid

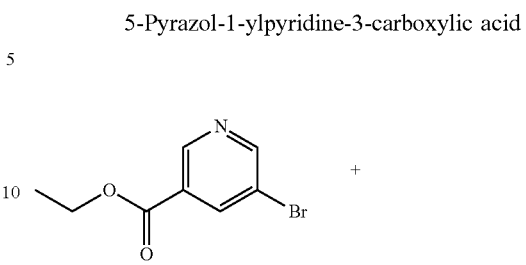

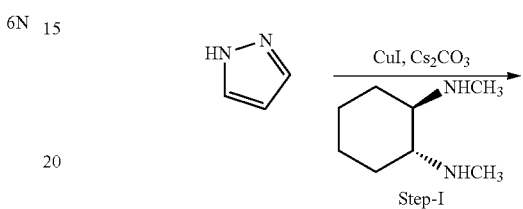

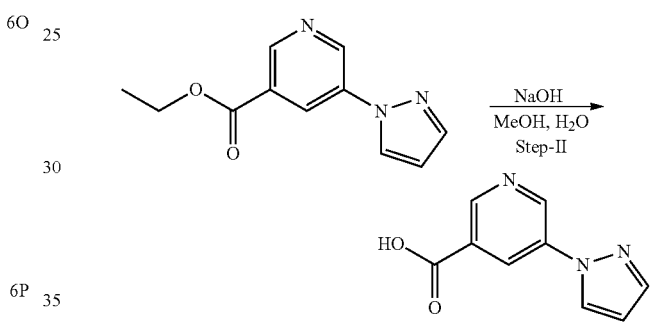

Step-I: Ethyl 5-pyrazol-1-ylpyridine-3-carboxylate

To a solution of ethyl 5-bromopyridine-3-carboxylate (1.0 g, 6.4 mmol), pyrazole (1.32 g, 19.3 mmol) in DMSO (50 mL) under nitrogen atmosphere was added cesium carbonate (4.02 g, 12.9 mmol) followed by trans-N,N'-dimethylcyclohexane-1,2-diamine (918 mg, 6.4 mmol) and copper (I) iodide (980 mg, 5.1 mmol). After heating at 120° C. for 5 h, reaction mixture was cooled to room temperature, added diethyl ether (25 mL), washed with water (10 mL), brine (10 mL), dried over anhydrous sodium sulfate, concentrated and purified by column chromatography to give 580 mg of ethyl 5-pyrazol-1-ylpyridine-3-carboxylate.

$^1$H NMR (400 MHz, CDCl$_3$): δ 1.44 (t, J=7.1 Hz, 3H), 4.46 (q, J=7.3 Hz, 2H), 6.57 (s, 1H), 7.81 (s, 1H), 8.03 (d, J=2.5 Hz, 1H), 8.59 (t, J=1.7 Hz, 1H), 9.14 (s, 1H), 9.20 (d, J=2.5 Hz, 1H). MS (ES) m/z 218.1 (M+1).

Step-II: 5-Pyrazol-1-ylpyridine-3-carboxylic acid

Ethyl 5-pyrazol-1-ylpyridine-3-carboxylate was hydrolyzed using the procedure for Intermediate 6A to give titled intermediate.

$^1$H NMR (400 MHz, DMSO-d$_6$): δ 6.64 (s, 1H), 7.87 (s, 1H), 8.64 (s, 1H), 8.76 (d, J=2.4 Hz, 1H), 8.98 (d, J=1.9 Hz, 1H), 9.33 (d, J=2.4 Hz, 1H). MS (ES) m/z 190.0 (M+1).

Intermediate 6T

6-(1H-Pyrazol-4-yl)pyridine-3-carboxylic acid

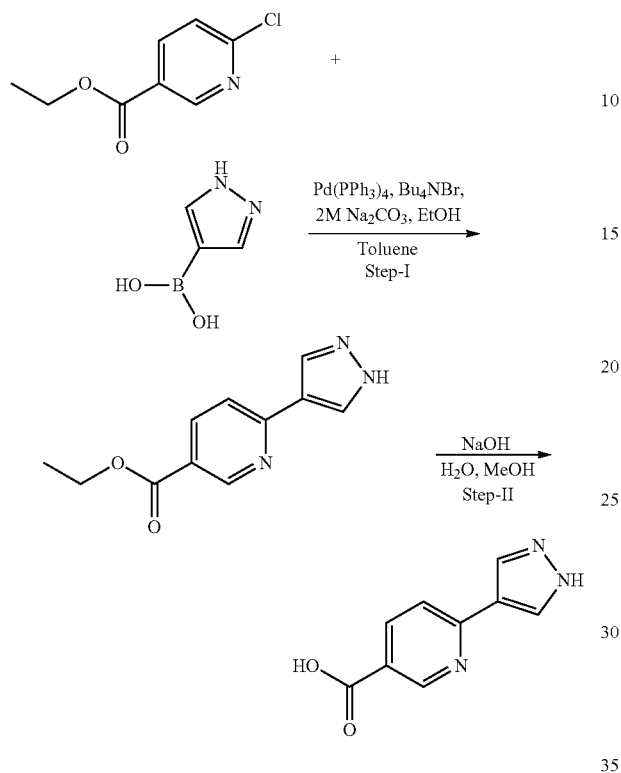

Step-I: Ethyl 6-(1H-pyrazol-4-yl)pyridine-3-carboxylate

A mixture of ethyl 6-chloropyridine-3-carboxylate (450 mg, 2.4 mmol), 1H-pyrazole-4-ylboronic acid (540 mg, 4.8 mmol), tetra-n-butyl ammonium bromide (30 mg), 2M sodium carbonate solution in water (1.5 mL), toluene (18 mL) and ethanol (18 mL) was degassed for 30 min using argon. To this was added tertakis-(triphenylphosphine) palladium (0) (70 mg) and refluxed for 19 h. Reaction mixture was cooled to room temperature, diluted with ethyl acetate (30 mL), filtered through celite bed. Fitrate was washed with water (2×20 mL), brine (20 mL), dried over anhydrous sodium sulfate, filtered, concentrated and purified by column chromatography to furnish 270 mg (51%) of ethyl 6-(1H-pyrazol-4-yl)pyridine-3-carboxylate.

$^1$H NMR (400 MHz, CDCl$_3$): δ 1.41 (t, J=7.0 Hz, 3H), 4.41 (q, J=7.1 Hz, 2H), 6.36 (s, 1H), 7.56 (d, J=8.3 Hz, 1H), 7.63 (d, J=1.8 Hz, 1H), 8.19 (s, 1H), 8.27 (dd, J=8.3, 2.2 Hz, 1H), 9.17 (d, J=1.9 Hz, 1H). MS (ES) m/z 218.1 (M+1).

Step-II: 6-(1H-Pyrazol-4-yl)pyridine-3-carboxylic acid

Ethyl 6-(1H-pyrazol-4-yl)pyridine-3-carboxylate was converted to the titled intermediate using procedure for Intermediate 6A.

MS (ES) m/z 190.1 (M+1).

Following carboxylic acid Intermediates 6U-6Y were prepared from appropriate starting material using procedure for Intermediate 6T.

6U

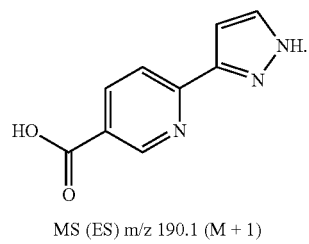

MS (ES) m/z 190.1 (M+1)

6V

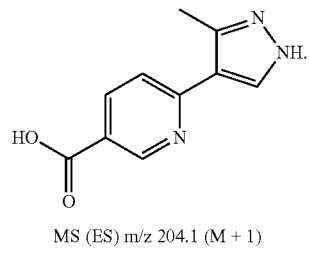

MS (ES) m/z 204.1 (M+1)

6W

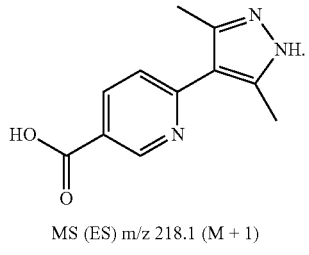

MS (ES) m/z 218.1 (M+1)

6X

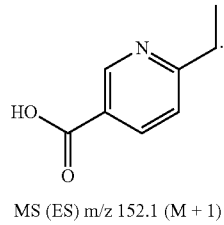

MS (ES) m/z 152.1 (M+1)

6Y

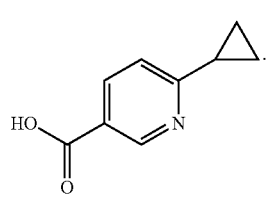

MS (ES) m/z 164.1 (M+1)

Intermediate 6Z

1-Methylpyrrolo[2,3-b]pyridine-5-carboxylic acid

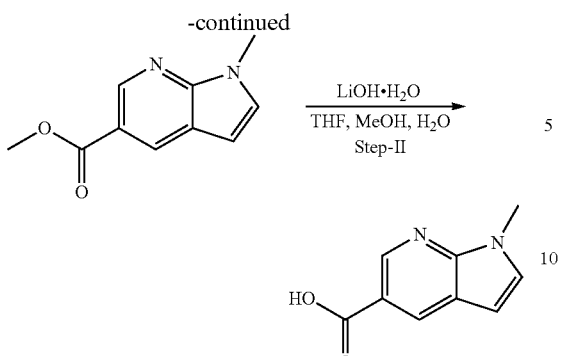

Step-I: Methyl 1-methylpyrrolo[2,3-b]pyridine-5-carboxylate

To a suspension of sodium hydride (60% in mineral oil; 62 mg, 1.5 mmol) in DMF (2 mL) was added a solution of 7-azaindole 5-carboxylic acid (100 mg, 0.6 mmol) in DMF (2 mL) at 0° C. After 10 min, to it was added methyl iodide (0.1 mL, 1.9 mmol) and stirred at room temperature for 30 min. Reaction was quenched by the addition of water (10 mL), extracted with ethyl acetate (2×10 mL). Combined organic layer was washed with brine (20 mL), dried over anhydrous sodium sulfate, concentrated to give quantitative methyl 1-methylpyrrolo[2,3-b]pyridine-5-carboxylate as a brown solid. The crude as such was taken up for further conversion.

MS (ES) m/z 191.1 (M+1).

Step-II: 1-Methylpyrrolo[2,3-b]pyridine-5-carboxylic acid

Methyl 1-methylpyrrolo[2,3-b]pyridine-5-carboxylate (137 mg, 0.7 mmol) was dissolved in THF:methanol:water (3:2:1, 6 mL), to it was added lithium hydroxide monohydrate (91 mg, 2.2 mmol) and stirred for 20 h. Volatiles were evaporated under reduced pressure. Aqueous layer was diluted with water (5 mL) and extracted with ethyl acetate (2×10 mL). Combined organic layer was washed with brine (20 mL), dried over anhydrous sodium sulfate, filtered and concentrated to give 130 mg of methylpyrrolo[2,3-b]pyridine-5-carboxylic acid.

$^1$H NMR (400 MHz, DMSO-$d_6$): δ 3.82 (s, 3H), 6.47 (d, J=3.5 Hz, 1H), 7.47 (d, J=3.1 Hz, 1H), 8.39 (d, J=1.5 Hz, 1H), 8.81 (s, J=1.5 Hz, 1H). MS (ES) m/z 177.1 (M+1).

Following Intermediates 6AA-6AB were synthesized in analogous manner of Intermediate 6Z.

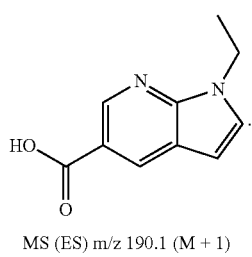

6AA

MS (ES) m/z 190.1 (M + 1)

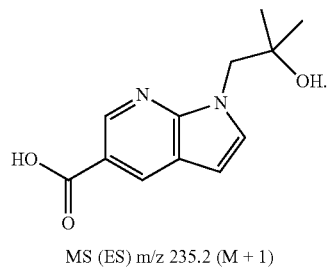

6AB

MS (ES) m/z 235.2 (M + 1)

Intermediate 6AC

2-Methyl-1H-pyrrolo[2,3-b]pyridine-5-carboxylic acid

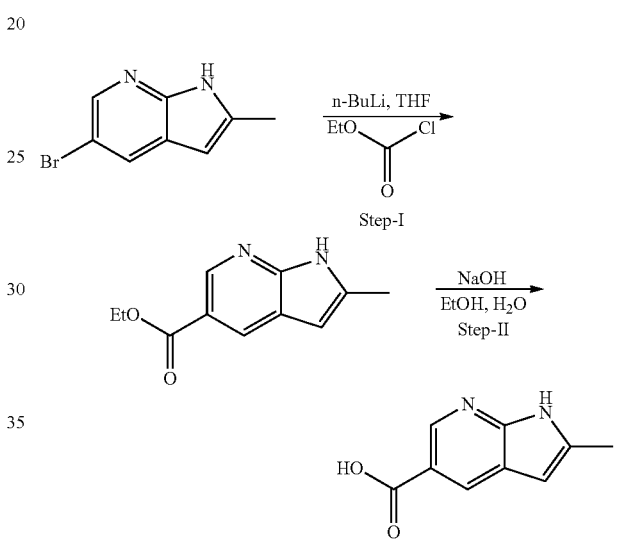

Step-I: Ethyl 2-methyl-1H-pyrrolo[2,3-b]pyridine-5-carboxylate

To a cooled solution of 5-bromo-2-methyl-1H-pyrrolo[2,3-b]pyridine (WO2011/149950) (150 mg, 0.7 mmol) in THF (2 mL) was added n-butyl lithium (1.6M in hexane, 0.9 mL, 1.4 mmol) at −78° C. and stirred for 1 h. To it was added ethyl chloroformate (70 μL, 0.84 mmol) and allowed to attain room temperature. After stirring for 20 h, reaction was quenched by the addition of water (5 mL). This was extracted with ethyl acetate (2×5 mL), combined organic layer was washed with brine (10 mL), dried over anhydrous sodium sulfate, filtered and concentrated to afford crude 150 mg of ethyl 2-methyl-1H-pyrrolo[2,3-b]pyridine-5-carboxylate. The crude material was taken up as such for further conversion.

MS (ES) m/z 205.1 (M+1).

Step-II: 2-Methyl-1H-pyrrolo[2,3-b]pyridine-5-carboxylic acid

Following the analogous procedure for Intermediate 6A, titled compound was prepared from ethyl 2-methyl-1H-pyrrolo[2,3-b]pyridine-5-carboxylate.

MS (ES) m/z 177.1 (M+1).

Intermediate 6AD

6-(3-Cyclopropyl-1H-pyrazol-4-yl)pyridine-3-carboxylic acid

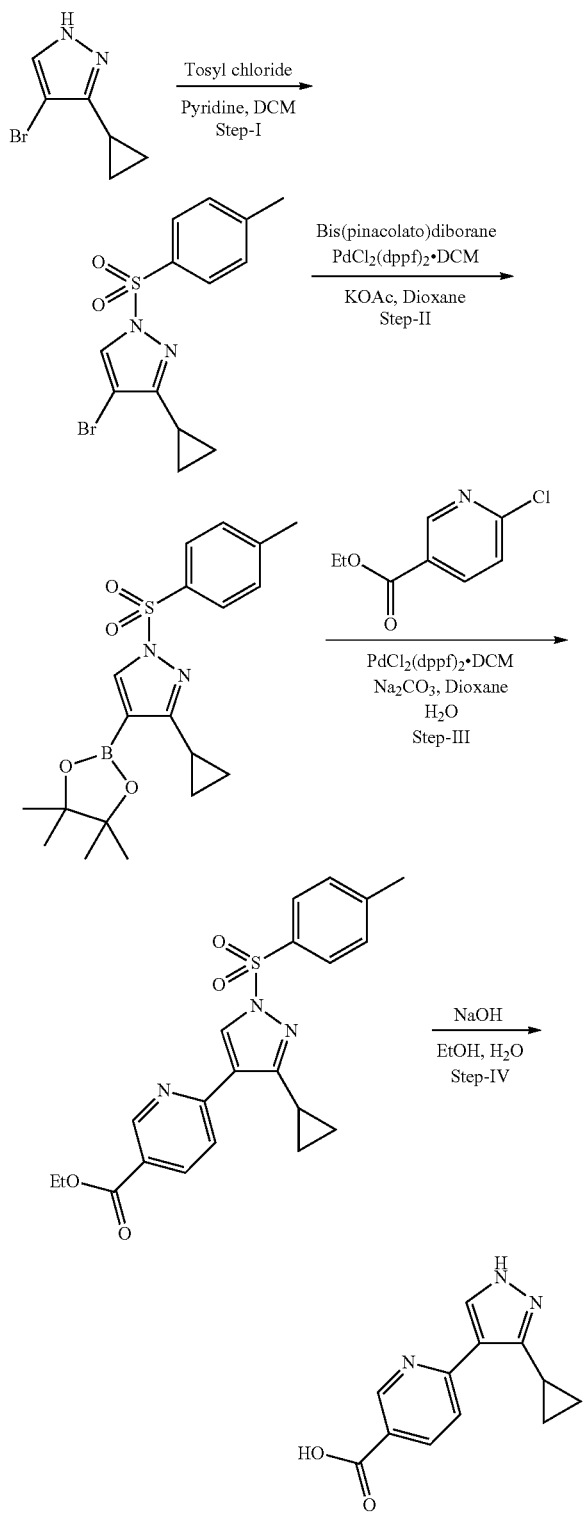

Step-I: 4-Bromo-3-cyclopropyl-1-(p-tolylsulfonyl)pyrazole

4-Bromo-3-cyclopropyl-1H-pyrazole (500 mg, 2.7 mmol) was dissolved in DCM (15 mL), to it added pyridine (316 mg, 4.0 mmol) and tosyl chloride (662 mg, 3.5 mmol) at ambient temperature. After stirring for 20 h, reaction mixture was diluted with DCM (10 mL), washed with water (20 mL), brine (20 mL), dried over anhydrous sodium sulfate, filtered, concentrated and purified by column chromatography to give 800 mg (88%) of titled compound.
MS (ES) m/z 343.0 (M+2).

Step-II: 3-Cyclopropyl-1-(p-tolylsulfonyl)-4-(4,4,5,5-tetramethyl-1,3,2-dioxaborolan-2-yl)pyrazole A mixture of 4-bromo-3-cyclopropyl-1-(p-tolylsulfonyl)pyrazole (1.0 g, 2.9 mmol), bis(pinacolato)diborane (894 mg, 3.5 mmol), potassium acetate (577 mg, 5.9 mmol) in dioxane (20 mL) was degassed by argon for 20 min. To this was added 1,1'-Bis(diphenylphosphino)ferrocene-palladium(II)dichloride dichloromethane complex (111 mg, 0.1 mmol) and heated at 110° C. for 20 h. Reaction mixture was diluted with ethyl acetate (25 mL), washed with water (20 mL), brine (20 mL), dried over anhydrous sodium sulfate, filtered, concentrated and purified by column chromatography to give 600 mg of titled compound.
MS (ES) m/z 389.2 (M+1).

Step-III: Ethyl 6-[3-cyclopropyl-1-(p-tolylsulfonyl)pyrazol-4-yl]pyridine-3-carboxylate A mixture of 3-cyclopropyl-1-(p-tolylsulfonyl)-4-(4,4,5,5-tetramethyl-1,3,2-dioxaborolan-2-yl)pyrazole (600 mg, 1.5 mmol), ethyl 6-chloronicotinate (285 mg, 1.5 mmol), sodium carbonate (489 mg, 4.6 mmol) in dioxane:water (3:1, 8 mL) was degassed by argon for 20 min. To this was added 1,1'-Bis(diphenylphosphino)ferrocene-palladium(II) dichloride dichloromethane complex (62 mg, 0.08 mmol) and heated at 110° C. for 20 h. Reaction mixture was diluted with ethyl acetate (15 mL), washed with water (15 mL), brine (15 mL), dried over anhydrous sodium sulfate, filtered, concentrated and purified by column chromatography to furnish 96 mg of ethyl 6-[3-cyclopropyl-1-(p-tolylsulfonyl)pyrazol-4-yl]pyridine-3-carboxylate.
$^1$H NMR (400 MHz, CDCl$_3$): δ 0.95-1.05 (m, 4H), 1.41 (t, J=7.1 Hz, 3H), 2.27-2.37 (m, 1H), 2.41 (s, 3H), 4.41 (q, J=7.1 Hz, 2H), 7.32 (d, J=8.1 Hz, 2H), 7.71 (d, J=8.3 Hz, 1H), 7.89 (d, J=8.4 Hz, 2H), 8.30 (dd, J=8.1, 2.0 Hz, 1H), 8.49 (s, 1H), 9.20 (d, J=1.7 Hz, 1H).
MS (ES) m/z 412.2 (M+1).

Step-IV: 6-(3-Cyclopropyl-1H-pyrazol-4-yl)pyridine-3-carboxylic acid

Following the analogous procedure of an Intermediate 6A, titled intermediate was prepared from ethyl 6-[3-cyclopropyl-1-(p-tolylsulfonyl)pyrazol-4-yl]pyridine-3-carboxylate.
MS (ES) m/z 230.1 (M+1).

Intermediate 6AE 6-(3-Isopropyl-1H-pyrazol-4-yl)pyridine-3-carboxylic acid

The titled intermediate was prepared from 4-bromo-3-isopropyl-1H-pyrazole using the procedure for Intermediate 6AD.
MS (ES) m/z 232.1 (M+1).

Intermediate 6AF

6-[1-(2-Hydroxyethyl)pyrazol-4-yl]pyridine-3-carboxylic acid

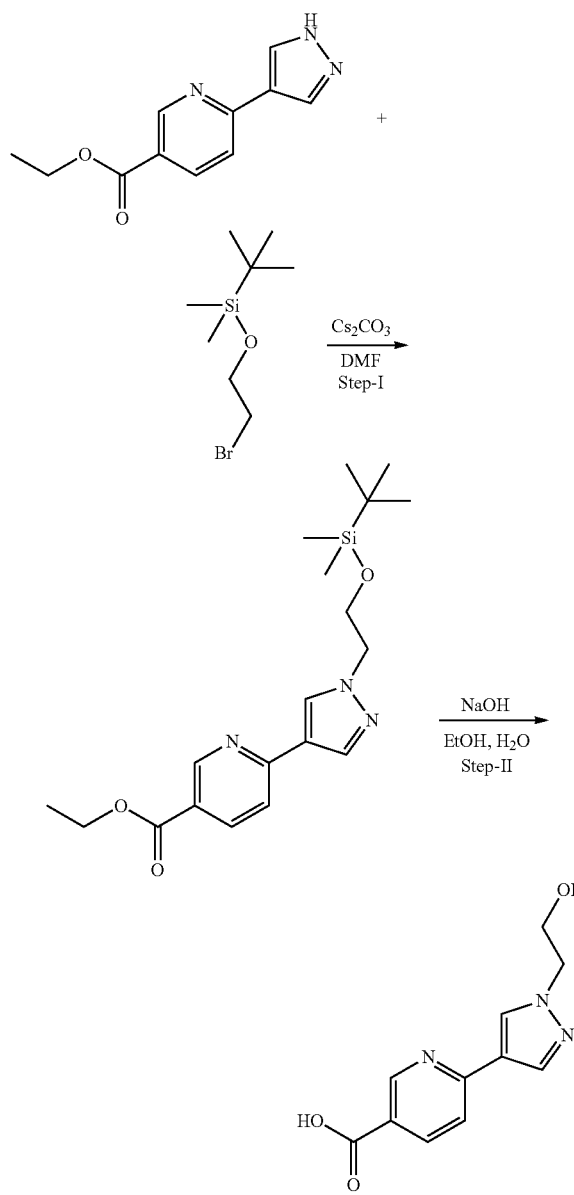

Step-I: Ethyl 6-[1-[2-[tert-butyl(dimethyl)silyl]oxyethyl]pyrazol-4-yl]pyridine-3-carboxylate Ethyl 6-(1H-pyrazol-4-yl)pyridine-3-carboxylate (200 mg, 0.9 mmol) was dissolved in DMF (2 mL), to it added cesium carbonate (387 mg, 1.2 mmol) followed by 2-bromoethoxy-tert-butyl-dimethyl-silane (284 mg, 1.2 mmol). After stirring for 16 h at 60° C., reaction was quenched by the addition of water (15 mL). Solid precipitated was filtered and purified by column chromatography to give 200 mg of ethyl 6-[1-[2-[tert-butyl(dimethyl)silyl]oxyethyl]pyrazol-4-yl]pyridine-3-carboxylate.

$^1$H NMR (400 MHz, CDCl$_3$): δ −0.06 (s, 6H), 0.83 (s, 9H), 1.41 (t, J=7.4 Hz, 3H), 3.97 (t, J=5.1 Hz, 2H), 4.27 (t, J=5.2 Hz, 2H), 4.40 (q, J=7.1 Hz, 2H), 7.48 (d, J=8.1 Hz, 1H), 8.05 (s, 1H), 8.08 (s, 1H), 8.23 (dd, J=8.1, 2.0 Hz, 1H), 9.14 (d, J=1.7 Hz, 1H). MS (ES) m/z 376.3 (M+1).

Step-II: 6-[1-(2-Hydroxyethyl)pyrazol-4-yl]pyridine-3-carboxylic acid

The titled intermediate was prepared from ethyl 6-[1-[2-[tert-butyl(dimethyl)silyl]oxyethyl]pyrazol-4-yl]pyridine-3-carboxylate using the procedure for Intermediate 6A.

$^1$H NMR (400 MHz, DMSO-d$_6$): δ 3.77 (t, J=5.3 Hz, 2H), 4.22 (t, J=5.3 Hz, 2H), 5.32 (brs, 1H), 7.92 (d, J=8.3 Hz, 1H), 8.24 (s, 1H), 8.32 (dd, J=8.3, 1.7 Hz, 1H), 8.56 (s, 1H), 8.95 (d, J=1.5 Hz, 1H). MS (ES) m/z 234.1 (M+1).

Intermediate 6AG 5-(2-Pyridyl)-1,3,4-oxadiazole-2-carboxylic acid

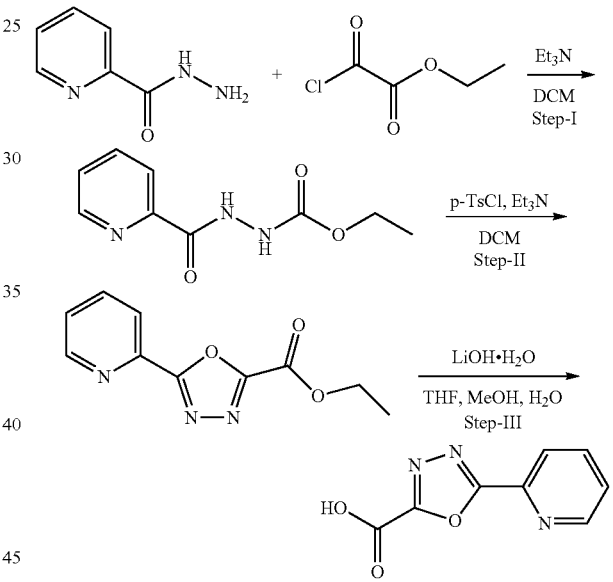

Step-I: Ethyl N-(pyridine-2-carbonylamino)carbamate

To a stirred solution of pyridine-2-carbohydrazide (2.2 g, 16.0 mmol) in DCM (30 mL) was added ethyl chlorooxalate (2.6 g, 19.3 mmol) at 0° C. followed by triethylamine (6.7 mL, 48.2 mmol). After stirring for overnight, reaction mixture was diluted with DCM (30 mL). DCM layer was washed with water (50 mL), brine (50 mL), dried over anhydrous sodium sulfate, filtered, concentrated and purified by column chromatography to give 3.0 g of ethyl N-(pyridine-2-carbonylamino)carbamate.
MS (ES) m/z 238.2 (M+1).

Step-II: Ethyl 5-(2-pyridyl)-1,3,4-oxadiazole-2-carboxylate

To a mixture of ethyl N-(pyridine-2-carbonylamino)carbamate (600 mg, 2.5 mmol) in DCM (10 mL) was added triethylamine (0.5 mL, 3.3 mmol) followed by p-tosylchloride (580 mg, 3.0 mmol) over the period of 10 min. and stirred for overnight at ambient temperature. Reaction mixture was diluted with DCM (20 mL), washed with water (20 mL), brine (20 mL), dried over anhydrous sodium sulfate, filtered, concentrated and purified by column chromatography to give 380 mg of Ethyl 5-(2-pyridyl)-1,3,4-oxadiazole-2-carboxylate.

MS (ES) m/z 220.2 (M+1).

Step-III:
5-(2-Pyridyl)-1,3,4-oxadiazole-2-carboxylic acid

The titled intermediate was prepared from ethyl 5-(2-pyridyl)-1,3,4-oxadiazole-2-carboxylate using the procedure for Intermediate 6A.

$^1$H NMR (400 MHz, DMSO-d$_6$): δ 7.62 (dd, J=6.3, 4.8 Hz, 1H), 8.04 (td, J=7.8, 1.2 Hz, 1H), 8.15 (dd, J=7.8, 0.8 Hz, 1H), 8.77 (d, J=4.7 Hz, 1H). MS (ES) m/z 192.1 (M+1).

Intermediate 6AH 4-(tert-Butoxycarbonylamino)pyridine-3-carboxylic acid

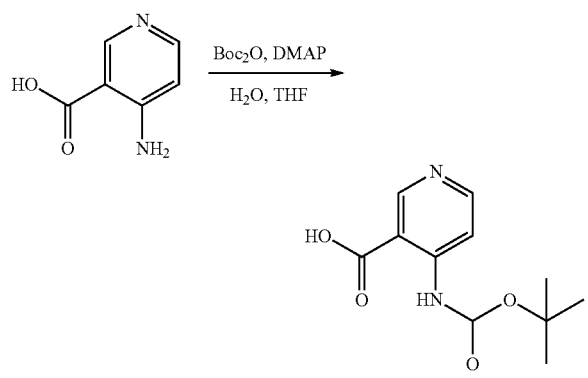

To a stirred solution of 4-aminopyridine-3-carboxylic acid (1.0 g, 7.2 mmol), Boc anhydride in THF:water (1:1, 20 mL) was added DMAP and stirred for 3 h at room temperature. To this was added ethyl acetate (25 mL) and water (25 mL). Aqueous layer was separated, extracted with ethyl acetate (25 mL). Combined organic layer was washed with brine (25 mL), dried over anhydrous sodium sulfate and concentrated under reduced pressure to furnish 1.2 g (69%) of 4-(tert-butoxycarbonylamino)pyridine-3-carboxylic acid.

MS (ES) m/z 239.1 (M+1).

Intermediate 6AI

2-Pyrazol-1-ylpyrimidine-5-carboxylic acid

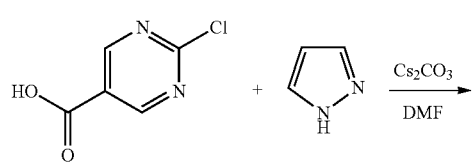

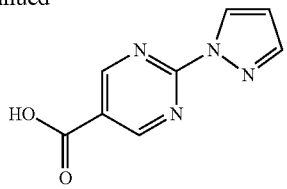

To a solution of 2-chloro-5-pyrimidine carboxylic acid (100 mg, 0.6 mmol) in DMF (3.2 mL) was added pyrazole (47 mg, 0.7 mmol) and cesium carbonate (432 mg, 1.3 mmol). After heating at 100° C. for 19 h, reaction was quenched by the addition of water (10 mL). This was extracted with ethyl acetate (3×10 mL), combined organic layer was washed with brine (10 mL), dried over anhydrous sodium sulfate, filtered and concentrated to give 96 mg (80%) of 2-pyrazol-1-ylpyrimidine-5-carboxylic acid.

$^1$H NMR (400 MHz, CDCl$_3$): δ 6.67-6.68 (m, 1H), 7.91 (s, 1H), 8.87 (d, J=2.7 Hz, 1H), 9.25 (s, 2H), 13.8 (brs, 1H). MS (ES) m/z 191.1 (M+1).

Intermediate 6AJ 6-(4-Ethoxycarbonylpyrazol-1-yl)pyridine-3-carboxylic acid

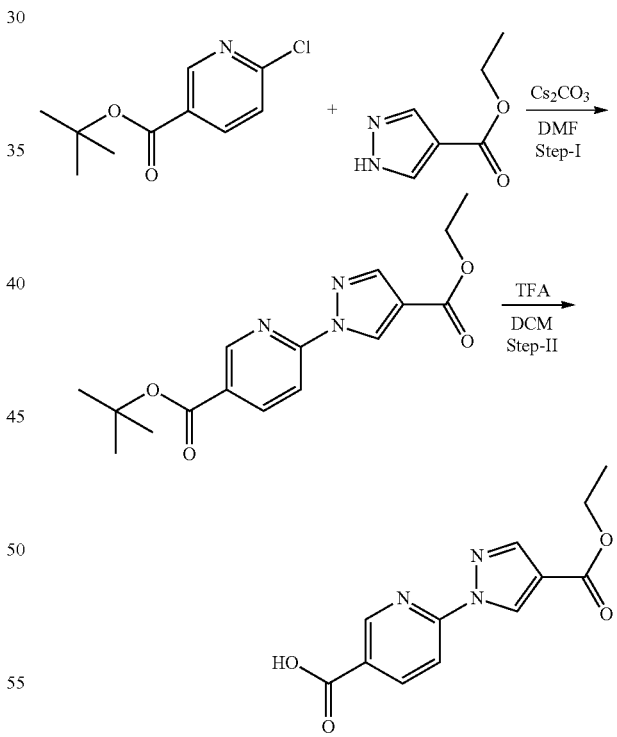

Step I: tert-Butyl 6-(4-ethoxycarbonylpyrazol-1-yl)pyridine-3-carboxylate

A suspension of tert-butyl 6-chloropyridine-3-carboxylate (2.3 g, 10.7 mmol), ethyl 1H-pyrazole-4-carboxylate (1.81 g, 12.8 mmol) and cesium carbonate (8.6 g, 26.7 mmol) in DMF (20 mL) was heated at 80° C. for 16 h. Reaction mixture was cooled to room temperature and added water (60 mL). Precipitated solid was filtered through Buckner funnel, dried under vacuum to give 2.6 g (76%) of tert-butyl 6-(4-ethoxycarbonylpyrazol-1-yl)pyridine-3-carboxylate as a solid.

$^{1}$H NMR (400 MHz, CDCl$_3$): δ 1.38 (t, J=7.1 Hz, 3H), 1.62 (s, 9H), 4.35 (q, J=7.1 Hz, 2H), 8.04 (d, J=8.5 Hz, 1H), 8.14 (s, 1H), 8.38 (dd, J=8.4, 2.0 Hz, 1H), 9.00 (d, J=2.2 Hz, 1H), 9.08 (s, 1H). MS (ES) m/z 318.2 (M+1).

Step I: 6-(4-Ethoxycarbonylpyrazol-1-yl)pyridine-3-carboxylic acid

To a stirred solution of tert-butyl 6-(4-ethoxycarbonylpyrazol-1-yl)pyridine-3-carboxylate (2.5 g, 7.8 mmol) in DCM (20 mL) was added trifluoroacetic acid (11 mL, 78.8 mmol) at room temperature and stirred for 16 h. Solvent was evaporated under reduced pressure, resulting residue was washed with diethyl ether (2×20 mL), dried under vacuum to give 1.8 g (87%) of 6-(4-ethoxycarbonylpyrazol-1-yl)pyridine-3-carboxylic acid as a solid.

$^{1}$H NMR (400 MHz, DMSO-d$_6$): δ 1.31 (t, J=7.1 Hz, 3H), 4.29 (q, J=7.1 Hz, 2H), 8.09 (d, J=8.5 Hz, 1H), 8.30 (s, 1H), 8.50 (dd, J=8.5, 1.9 Hz, 1H), 9.00 (d, J=2.2 Hz, 1H), 9.06 (s, 1H), 13.60 (brs, 1H). MS (ES) m/z 262.1 (M+1).

Intermediate 6AK 6-(3-Ethoxycarbonylpyrazol-1-yl)pyridine-3-carboxylic acid

The titled intermediate was prepared from ethyl 1H-pyrazole-3-carboxylate using the procedure for Intermediate 6AJ.

MS (ES) m/z 262.1 (M+1).

Intermediate 6AL 6-(4-Isopropyl-1H-pyrazol-3-yl)pyridine-3-carboxylic acid

Step-I: 6-(4-Methyl-3-oxo-pentanoyl)pyridine-3-carboxylic acid

To a solution of 6-Ethoxycarbonylpyridine-3-carboxylic acid (WO2008/011131) (500 mg, 2.6 mmol) in DMF (4 mL) was added 3-methyl 2-butanone (0.41 mL, 3.8 mmol). Reaction mixture was cooled to 0° C., sodium hydride (60% in mineral oil, 150 mg, 3.8 mmol) added and stirred under nitrogen atmosphere for 19 h. Reaction mixture was cooled to 0° C., quenched by the addition of brine (5 mL), acidified up to pH 2. This was extracted with ethyl acetate (2×10 mL), combined organic layer was washed with brine (10 mL), dried over anhydrous sodium sulfate, filtered and concentrated to give 330 mg of 6-(4-methyl-3-oxo-pentanoyl)pyridine-3-carboxylic acid as a yellow solid.

MS (ES) m/z 236.1 (M+1).

Step-II: 6-(4-Isopropyl-1H-pyrazol-3-yl)pyridine-3-carboxylic acid

A mixture of 6-(4-Methyl-3-oxo-pentanoyl)pyridine-3-carboxylic acid (320 mg, 1.4 mmol), hydrazine hydrate (73 μL, 1.5 mmol) in ethanol (5 mL) was stirred at room temperature for overnight. Volatiles were evaporated under reduced pressure. Residue obtained was taken in water (10 mL), acidified up to pH 2 with 2N HCl. Solid obtained was filtered and dried under vacuum to furnish 210 mg (67%) of titled compound.

$^{1}$H NMR (400 MHz, DMSO-d$_6$): δ 1.26 (d, J=6.8 Hz, 6H), 2.95-3.02 (m, 1H), 6.70 (s, 1H), 8.01 (d, J=8.3 Hz, 1H), 8.26 (dd, J=8.4, 2.2 Hz, 1H), 9.03 (d, J=1.5 Hz, 1H), 12.99 (brs, 1H), 13.28 (brs, 1H). MS (ES) m/z 232.1 (M+1).

Intermediate 6AM 6-(4-Ethyl-1H-pyrazol-3-yl)pyridine-3-carboxylic acid

The titled intermediate was prepared from ethyl methyl ketone in analogous manner of an Intermediate 6AL.

MS (ES) m/z 218.1 (M+1).

Intermediate 6AN

6-Amino-5-methyl-pyridine-3-carboxylic acid

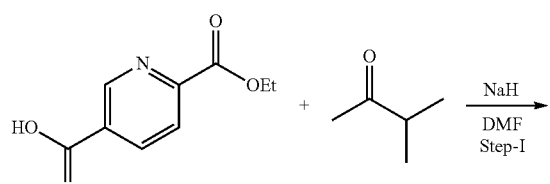

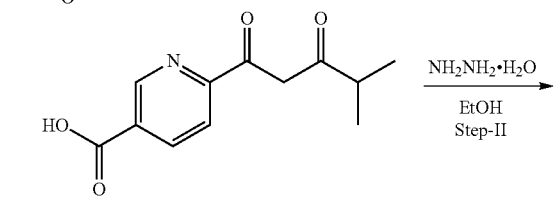

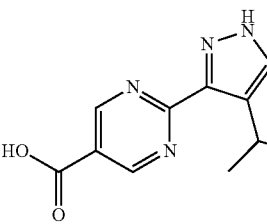

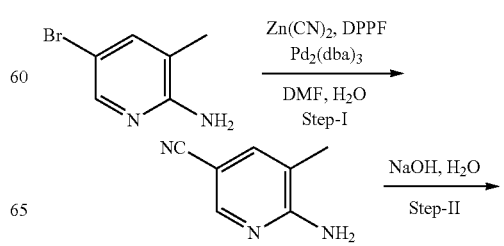

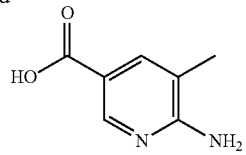

Step-I: 6-Amino-5-methyl-pyridine-3-carbonitrile

To a mixture of DMF:water (100:2, 102 mL) was added 5-bromo-3-methyl-pyridin-2-amine (10 g, 53.47 mmol), zinc cyanide (3.77 g, 32.1 mmol) and 1,1'-Bis(diphenylphosphino)ferrocene (3.56 g, 6.4 mmol) and degassed for 20 mins. To this was added tris(dibenzylideneacetone)dipalladium (0) (2.45 g, 2.67 mmol) and heated at 120° C. After stirring for 16 h, reaction mixture was cooled to room temperature. To it was added mixture of saturated solution of ammonium chloride: ammonium hydroxide:water (4:1:4, 100 mL). Slurry formed was cooled to 0° C. and again mixture of saturated solution of ammonium chloride: ammonium hydroxide:water (4:1:4, 100 mL) added and stirred for 1 h. Solid formed was filtered through Buchner funnel and dried under high vacuum to get 6.0 g (81%) of titled compound as a tan solid.

MS (ES) m/z 134.1 (M+1).

Step II: 6-Amino-5-methyl-pyridine-3-carboxylic acid

To a stirred suspension of 6-amino-5-methyl-pyridine-3-carbonitrile (6.0 g, 45.0 mmol) in water (40 mL) was added sodium hydroxide (5.4 g, 135.2 mmol) and refluxed for 4 h. Reaction mixture was cooled to room temperature and filtered through Buchner funnel. Filtrate was neutralized with 4N HCl. Solid formed was filtered through Buchner funnel and dried under high vacuum to furnish 6.0 g (88%) of titled intermediate as a white solid.

$^1$H NMR (400 MHz, CDCl$_3$): δ 2.05 (s, 3H), 6.53 (s, 2H), 7.66 (s, 1H), 8.37 (d, J=2.0 Hz, 1H), 12.29 (brs, 1H). MS (ES) m/z 153.0 (M+1).

Example 1.1

N-(5-Chlorothiazol-2-yl)-4-[[3-[[5-(trifluoromethyl)-2-pyridyl]oxy]phenyl]methylene]cyclohexanecarboxamide

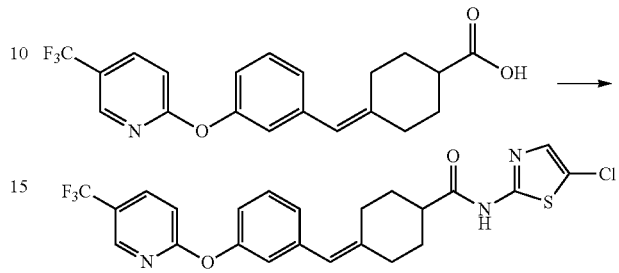

To a cooled solution of 4-[[3-[[5-(Trifluoromethyl)-2-pyridyl]oxy]phenyl]-methylene]cyclohexane carboxylic acid (Intermediate 1A) (1.0 g, 2.7 mmol) in DCM (20 mL) was added DMF (0.01 mL) followed by oxalyl chloride (0.5 mL, 5.3 mmol) at 0° C. After stirring for 2 h at room temperature, volatiles were evaporated. The resulting residue was dissolved in DCM (5 mL) and added to a solution of 2-amino-5-chlorothiazole hydrochloride (Intermediate 2A) (680 mg, 4.0 mmol) in DCM (15 mL) at 0° C. To this was added triethylamine (1.1 mL, 8.0 mmol) and stirred for 2 h. Reaction was quenched by the addition of water (30 mL). Organic layer was diluted with DCM (50 mL), separated, washed with brine (30 mL), dried over anhydrous sodium sulfate, filtered, concentrated and purified by column chromatography to give 400 mg (34%) of the title compound as a solid.

$^1$H NMR (400 MHz, CDCl$_3$): δ 1.50-1.76 (m, 1H), 1.82 (qd, J=12.4, 3.6 Hz, 1H), 2.01-2.13 (m, 3H), 2.29 (t, J=12.4 Hz, 1H), 2.51 (d, J=12.7 Hz, 1H), 2.62 (t, J=11.5 Hz, 1H), 3.00 (d, J=15.1 Hz, 1H), 6.33 (s, 1H), 6.95-7.02 (m, 3H), 7.08 (d, J=7.8 Hz, 1H), 7.23 (s, 1H), 7.38 (t, J=7.8 Hz, 1H), 7.90 (dd, J=8.6, 1.7 Hz, 1H), 8.45 (s, 1H), 10.65 (brs, 1H). MS (ES) m/z 494.1 (M+1). MP=149-152° C.

Following examples were prepared from Intermediate 1A and appropriate amine selected from Intermediates 2B-2F using the procedure described for Example 1.1.

| Example 1.A-1 | N-Pyridazin-3-yl-4-[[3-[[5-(trifluoromethyl)-2-pyridyl]oxy]phenyl]methylene]cyclohexanecarboxamide<br>$^1$H NMR (400 MHz, CDCl$_3$): δ 1.67 (qd, J = 11.7, 3.7 Hz, 1H), 1.78 (qd, J = 13.0, 4.1 Hz, 1H), 2.02-2.12 (m, 2H), 2.14-2.20 (m, 1H), 2.29-2.37 (m, 1H), 2.51 (d, J = 14.5 Hz, 1H), 2.68 (t, J = 11.2 Hz, 1H), 2.99-3.03 (m, 1H), 6.33 (s, 1H), 6.99-7.03 (m, 3H), 7.10 (d, J = 7.6 Hz, 1H), 7.39 (t, J = 7.8 Hz, 1H), 7.48 (dd, J = 9.0, 4.6 Hz, 1H), 7.90 (dd, J = 8.8, 2.4 Hz, 1H), 8.45 (s, 1H), 8.50 (d, J = 9.0 Hz, 1H), 8.76 (brs, 1H), 8.93 (dd, J = 4.6, 1.2 Hz, 1H). MS (ES) m/z 455.2 (M + 1). MP = 72-73° C. |
|---|---|
| Example 1.A-2 | N-(5-Fluorothiazol-2-yl)-4-[[3-[[5-(trifluoromethyl)-2-pyridyl]oxy]phenyl]methylene]cyclohexanecarboxamide<br>$^1$H NMR (400 MHz, CDCl$_3$): δ 1.57-1.81 (m, 2H), 2.01-2.16 (m, 3H), 2.26-2.33 (m, 1H), 2.48-2.61 (m, 2H), 2.99 (d, J = 14.0 Hz, 1H), 6.33 (s, 1H), 6.97-7.03 (m, 4H), 7.08 (d, J = 7.4 Hz, 1H), 7.38 (t, J = 7.8 Hz, 1H), 7.90 (dd, J = 8.6, 2.2 Hz, 1H), 8.45 (s, 1H), 9.42 (brs, 1H). MS (ES) m/z 478.1 (M + 1). MP = 58-60° C. |
| Example 1.A-3 | N-Pyrazin-2-yl-4-[[3-[[5-(trifluoromethyl)-2-pyridyl]oxy]phenyl]methylene]cyclohexanecarboxamide<br>$^1$H NMR (400 MHz, CD$_3$OD): δ 1.59 (qd, J = 11.7, 3.4 Hz, 1H), 1.70 (qd, J = 12.8, 4.2 Hz, 1H), 1.98-2.11 (m, 3H), 2.35 (td, J = 13.0, 3.7 Hz, 1H), 2.50 (d, J = 13.7 Hz, 1H), 2.74 (tt, J = 11.7, 3.4 Hz, 1H), 3.00 (d, J = 14.2 Hz, 1H), 6.34 (s, 1H), 6.98-7.00 (m, 2H), 7.12 (d, J = 8.3 Hz, 2H), 7.39 (t, J = 8.6 Hz, 1H), 8.08 (dd, J = 8.8, 2.4 Hz, 1H), 8.27 (d, J = 2.4 Hz, 1H), 8.35 (s, 1H), 8.43 (s, 1H), 9.36 (s, 1H). MS (ES) m/z 455.2 (M + 1). Sticky solid. |

| Example 1.A-4 | N-(3-Pyridylmethyl)-4-[[3-[[5-(trifluoromethyl)-2-pyridyl]oxy]phenyl]methylene]cyclohexanecarboxamide |
|---|---|
| | ¹H NMR (400 MHz, CDCl₃): δ 1.58 (qd, J = 12.3, 4.2 Hz, 1H), 1.69 (qd, J = 12.2, 3.9 Hz, 1H), 1.92-2.10 (m, 3H), 2.24 (td, J = 12.7, 3.6 Hz, 1H), 2.37 (tt, J = 11.5, 3.2 Hz, 1H), 2.45 (d, J = 13.4 Hz, 1H), 2.94- 2.98 (m, 1H), 4.47 (d, J = 6.0 Hz, 2H), 5.85 (brs, 1H), 6.29 (s, 1H), 6.96-7.01 (m, 3H), 7.07 (d, J = 7.6 Hz, 1H), 7.26-7.28 (m, 1H), 7.37 (t, J = 7.9 Hz, 1H), 7.62 (d, J = 7.8 Hz, 1H), 7.89 (dd, J = 8.8, 2.5 Hz, 1H), 8.45 (s, 1H), 8.52 (s, 2H). MS (ES) m/z 468.3 (M + 1). Sticky solid. |

Example 1.2

N-(3-Pyridyl)-4-[[3-[[5-(trifluoromethyl)-2-pyridyl]oxy]phenyl]-methylene]cyclohexanecarboxamide hydrochloride

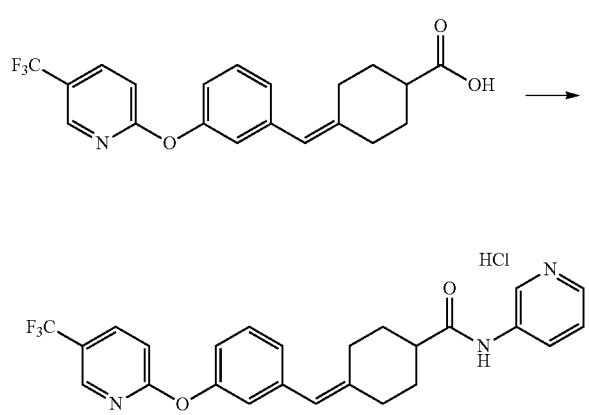

To a stirred solution of 4-[[3-[[5-(Trifluoromethyl)-2-pyridyl]oxy]phenyl]-methylene]cyclohexanecarboxylic acid (300 mg, 0.8 mmol) in DCM (50 mL) was added DMF (0.01 mL) followed by oxalyl chloride (0.2 mL, 1.6 mmol) at 0° C. After stirring for 2 h at room temperature, volatiles were evaporated. The resulting residue was dissolved in DCM (2 mL) and added to a stirred solution of 3-aminopyridine (Intermediate 2F) (75 mg, 0.8 mmol) in DCM (3 mL) at 0° C. To this was added triethylamine (0.1 mL, 0.9 mmol) and stirred for 2 h. Reaction was quenched by the addition of water (10 mL). Organic layer was diluted with DCM (10 mL), separated, washed with brine (30 mL), dried over anhydrous sodium sulfate, filtered, concentrated and purified by column chromatography. The resulting product was stirred with 4 N HCl in dioxane (5 ml) for 1 h. Excess solvent was evaporated under reduced pressure to give 150 mg (38%) of the titled compound.

¹H NMR (400 MHz, DMSO-d₆): δ 1.46-1.65 (m, 2H), 1.94-2.12 (m, 3H), 2.24-2.35 (m, 1H), 2.42-2.50 (m, 1H), 2.57-2.68 (m, 1H), 2.89 (d, J=12.0 Hz, 1H), 6.33 (s, 1H), 7.03-7.07 (m, 2H), 7.13 (d, J=6.4 Hz, 1H), 7.25 (d, J=8.3 Hz, 1H), 7.42 (brs, 1H), 7.91 (brs, 1H), 8.23 (d, J=8.8 Hz, 1H), 8.45-8.58 (m, 3H), 9.21 (s, 1H), 11.08 (brs, 1H). MS (ES) m/z 454.2 (M+1).

Example 2.1

N-[4-[[3-[[5-(Trifluoromethyl)-2-pyridyl]oxy]phenyl]methylene]cyclohexyl]pyridine-3-carboxamide

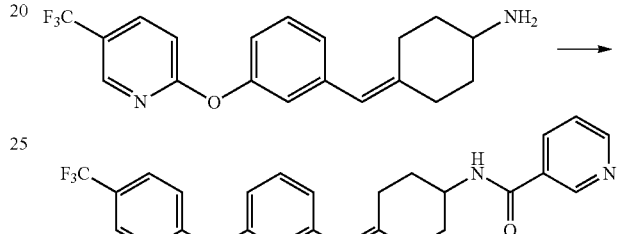

To a mixture of 4-[[3-[[5-(Trifluoromethyl)-2-pyridyl]oxy]phenyl]methylene]cyclohexanamine (Intermediate 3A) (200 mg, 0.57 mmol) and nicotinoyl chloride (Intermediate 4A) (150 mg, 0.86 mmol) in DCM (10 mL) was added triethylamine (0.5 mL, 3.5 mmol) slowly at 0° C. After stirring for 2 h at room temperature, volatiles were evaporated under reduced pressure. The resulting residue was taken in ethyl acetate (25 mL) and washed with aqueous saturated sodium bicarbonate solution (20 mL), water (20 mL), brine (20 mL), dried over anhydrous sodium sulfate, filtered, concentrated and purified by preparative HPLC to give 75 mg (30%) of N-[4-[[3-[[5-(trifluoromethyl)-2-pyridyl]oxy]phenyl]methylene]cyclohexyl]-pyridine-3-carboxamide.

¹H NMR (400 MHz, CDCl₃): δ 1.37 (qd, J=11.0, 5.6 Hz, 1H), 1.48 (qd, J=11.3, 5.1 Hz, 1H), 2.15-2.59 (m, 3H), 2.37-2.49 (m, 2H), 2.88-2.94 (m, 1H), 4.18-4.28 (m, 1H), 6.00 (d, J=7.4 Hz, 1H), 6.32 (s, 1H), 6.99-7.03 (m, 3H), 7.00 (d, J=7.9 Hz, 1H), 7.37-7.41 (m, 2H), 7.90 (dd, J=8.8, 2.4 Hz, 1H), 8.10 (dt, J=7.8, 1.7 Hz, 1H), 8.45 (s, 1H), 8.72 (dd, J=4.9, 1.7 Hz, 1H), 8.94 (d, J=1.7 Hz 1H). MS (ES) m/z 454.3 (M+1). MP=60-62° C.

Example 2.2

6-Methyl-N-[4-[[3-[[5-(trifluoromethyl)-2-pyridyl]oxy]phenyl]-methylene]cyclohexyl]pyridine-3-carboxamide

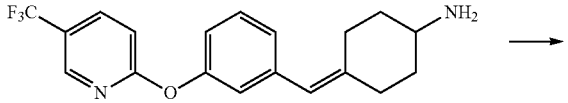

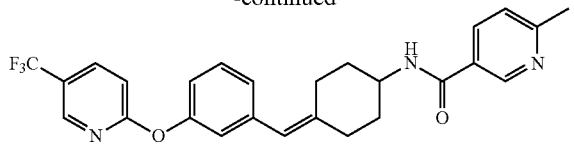

To a stirred solution 6-Methylnicotinic acid (Intermediate 4B) (95 mg, 0.7 mmol) in DMF (3 mL) was added EDCI·HCl (220 mg, 1.1 mmol), HOBt (175 mg, 1.1 mmol) stirred for 10 min at room temperature. To this was added 4-[[3-[[5-(trifluoromethyl)-2-pyridyl]oxy]phenyl]methylene]cyclohexanamine (Intermediate 3A) (200 mg, 0.6 mmol) and N-methylmorpholine (0.25 mL, 1.7 mmol). After stirring for 18 h, reaction was quenched by the addition of water (10 mL). This was extracted with ethyl acetate (2×10 mL), combined organic layer was washed with brine (20 mL), dried over anhydrous sodium sulfate, filtered, concentrated and purified by column chromatography to give 220 mg (81%) of titled compound.

$^1$H NMR (400 MHz, CDCl$_3$): δ 1.35 (qd, J=13.4, 3.6 Hz, 1H), 1.46 (qd, J=11.5, 5.2 Hz, 1H), 2.13-2.22 (m, 3H), 2.37-2.43 (m, 2H), 2.60 (s, 3H), 2.92 (d, J=14.4 Hz, 1H), 4.18-4.25 (m, 1H), 6.03 (d, J=8.3 Hz, 1H), 6.31 (s, 1H), 6.99-7.03 (m, 3H), 7.10 (d, J=7.5 Hz, 1H), 7.23 (d, J=8.0 Hz, 1H), 7.39 (t, J=7.9 Hz, 1H), 7.90 (dd, J=8.8, 2.2 Hz, 1H), 7.99 (dd, J=8.1, 1.7 Hz, 1H), 8.45 (s, 1H), 8.82 (d, J=2.0 Hz, 1H). MS (ES) m/z 468.2 (M+1). MP=152-153° C.

Example 2.3

N-[(3E)-3-[[3-[[5-(Trifluoromethyl)-2-pyridyl]oxy]phenyl]methylene]-cyclohexyl]pyrazine-2-carboxamide

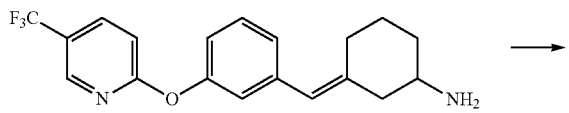

To a mixture of (3E)-3-[[3-[[5-(trifluoromethyl)-2-pyridyl]oxy]phenyl]methylene]cyclohexanamine (Intermediate 3K) (125 mg, 0.4 mmol) and 2-pyrazine carboxylic acid (Intermediate 4C) (44 mg, 0.4 mmol) in DMF (1.5 mL) was added HATU (205 mg, 0.5 mmol), DIPEA (0.11 mg, 0.9 mmol) and stirred for 19 h at room temperature. DMF was evaporated under reduced pressure. To the resulting residue was added ice water (10 mL). This was extracted with ethyl acetate (2×10 mL), combined organic layer was washed with brine (20 mL), dried over anhydrous sodium sulfate, filtered, concentrated and purified by column chromatography to furnish 101 mg (62%) of titled compound.

$^1$H NMR (400 MHz, CDCl$_3$) mixture of stereoisomers: δ 1.50-1.71 (m, 2H), 1.73-1.82 (m, 0.5H), 1.83-1.92 (m, 0.5H), 2.01-2.09 (m, 1H), 2.23-2.31 (m, 2H), 2.33-2.38 (m, 0.5H), 2.56-2.62 (m, 0.5H), 2.72 (dd, J=13.0, 3.9 Hz, 0.5H), 2.94 (dd, J=13.2, 3.9, 0.5H), 4.13-4.22 (m, 0.5H), 4.23-4.31 (m, 0.5H), 6.38 (s, 0.5H), 6.46 (s, 0.5H), 6.94-6.98 (m, 1H), 7.01-7.04 (m, 2H), 7.12 (d, J=7.6 Hz, 1H), 7.33-7.42 (m, 1H), 7.80-7.92 (m, 2H), 8.39 (s, 0.5H), 8.64 (d, J=1.5 Hz, 1H), 8.51 (s, 0.5H), 8.71 (d, J=2.2 Hz, 0.5H), 8.75 (d, J=2.2 Hz, 0.5H), 9.34 (s, 0.5H), 9.42 (s, 0.5H). MS (ES) m/z 455.3 (M+1). Sticky solid.

Following examples were prepared from Intermediate 3A and appropriate carboxylic acid or carboxylic acid chloride selected from Intermediates 4-6 using either of the procedure described for Example 2.1, Example 2.2, Example 2.3.

| Example | |
|---|---|
| 2.A-1 | N-[4-[[3-[[5-(Trifluoromethyl)-2-pyridyl]oxy]phenyl] methylene]cyclohexyl]-1H-pyrazole-3-carboxamide<br>$^1$H NMR (400 MHz, CDCl$_3$): δ 1.37 (qd, J = 11.8, 3.7 Hz, 1H), 1.49 (qd, J = 11.2, 4.9 Hz, 1H), 1.67 (brs, 1H), 2.07-2.19 (m, 3H), 2.33-2.45 (m, 2H), 2.87 (dt, J = 14.2, 3.7 Hz, 1H), 4.16-4.26 (m, 1H), 6.29 (s, 1H), 6.80 (d, J = 8.0 Hz, 1H), 6.86 (d, J = 2.4 Hz, 1H), 6.98-7.02 (m, 3H), 7.09 (d, J = 7.6 Hz, 1H), 7.38 (t, J = 8.1 Hz, 1H), 7.58 (d, J = 2.4 Hz, 1H), 7.90 (dd, J = 8.8, 2.4 Hz, 1H), 8.45 (s, 1H). MS (ES) m/z 443.3 (M + 1). MP = 56-57° C. |
| 2.A-2 | N-[4-[[3-[[5-(Trifluoromethyl)-2-pyridyl]oxy]phenyl] methylene]cyclohexyl]thiophene-2-carboxamide<br>$^1$H NMR (400 MHz, CDCl$_3$): δ 1.31-1.62 (m, 2H), 2.11-2.24 (m, 3H), 2.40-2.47 (m, 2H), 2.89-2.94 (m, 1H), 4.16-4.25 (m, 1H), 5.83 (d, J = 8.0 Hz, 1H), 6.33 (s, 1H), 7.01-7.05 (m, 3H), 7.09 (d, J = 4.8 Hz, 1H), 7.12 (d, J = 9.6 Hz, 1H), 7.41 (t, J = 8.0 Hz, 1H), 7.48 (td, J = 4.0, 2.8 Hz, 2H), 7.92 (dd, J = 8.8, 2.4 Hz, 1H), 8.47 (s, 1H). MS (ES) m/z 459.3 (M + 1). MP = 52-53° C. |
| 2.A-3 | 2,2-Difluoro-2-(2-pyridyl)-N-[4-[[3-[[5-(trifluoromethyl)-2-pyridyl]oxy]phenyl]methylene]cyclohexyl]acetamide<br>$^1$H NMR (400 MHz, CDCl$_3$): δ 1.35 (qd, J = 11.6, 4.0 Hz, 1H), 1.50 (qd, J = 12.0, 4.8 Hz, 1H), 2.02-2.14 (m, 3H), 2.29-2.43 (m, 2H), 2.83-2.87 (m, 1H), 4.04-4.06 (m, 1H), 6.30 (s, 1H), 6.78 (d, J = 7.2 Hz, 1H), 6.96-7.02 (m, 3H), 7.08 (d, J = 7.6 Hz, 1H), 7.36 (t, J = 7.8 Hz, 1H), 7.42 (dd, J = 7.2, 2.0 Hz, 1H), 7.77 (d, J = 7.8 Hz, 1H), 7.85 (td, J = 8.1, 1.5 Hz, 1H), 7.90 (dd, J = 8.8, 2.4 Hz, 1H), 8.45 (bs, 1H), 8.64 (d, J = 4.8 Hz, 1H). MS (ES) m/z 504.3 (M + 1). Sticky solid |
| 2.A-4 | N-[4-[[3-[[5-(Trifluoromethyl)-2-pyridyl]oxy]phenyl] methylene]cyclohexyl]pyridine-2-carboxamide<br>$^1$H NMR (400 MHz, CDCl$_3$): δ 1.44 (qd, J = 12.0, 4.1 Hz, 1H), 1.51-1.61 (m, 1H), 2.07-2.23 (m, 3H), 2.36-2.47 (m, 2H), 2.87 (dt, J = 10.0, 3.6 Hz, 1H), 4.17-4.26 (m, 1H), 6.31 (s, 1H), 6.99-7.02 (m, 3H), 7.10 (d, J = 7.6 Hz, 1H), |

| | |
|---|---|
| | 7.34-7.43 (m, 2H), 7.85 (td, J = 7.6, 1.5 Hz, 1H), 7.89 (dd, J = 8.8, 2.4 Hz, 1H), 8.00 (d, J = 8.0 Hz, 1H), 8.20 (d, J = 7.9 Hz, 1H), 8.45 (s, 1H), 8.52 (d, J = 4.7 Hz, 1H). MS (ES) m/z 454.2 (M + 1). Sticky solid. |
| Example 2.A-5 | N-[4-[[3-[[5-(Trifluoromethyl)-2-pyridyl]oxy]phenyl] methylene]cyclohexyl]pyrazine-2-carboxamide<br>¹H NMR (400 MHz, CDCl₃): δ 1.43 (qd, J = 12.0, 3.7 Hz, 1H), 1.51-1.61 (m, 1H), 2.07-2.24 (m, 3H), 2.35-2.49 (m, 2H), 2.87-2.92 (m, 1H), 4.18-4.28 (m, 1H), 6.32 (s, 1H), 6.99-7.02 (m, 3H), 7.10 (d, J = 7.6 Hz, 1H), 7.38 (t, J = 7.6 Hz, 1H), 7.73 (d, J = 12.1 Hz, 1H), 7.90 (dd, J = 8.6, 2.2 Hz, 1H), 8.45 (s, 1H), 8.51 (s, 1H), 8.74 (d, J = 2.2 Hz, 1H), 9.41 (s, 1H). MS (ES) m/z 455.3 (M + 1). MP = 114-115° C. |
| Example 2.A-6 | 6-(Trifluoromethyl)-N-[4-[[3-[[5-(trifluoromethyl)-2-pyridyl]oxy]phenyl]methylene]cyclohexyl]pyridine-3-carboxamide<br>¹H NMR (400 MHz, CDCl₃): δ 1.38 (qd, J = 13.2, 5.6 Hz, 1H), 1.50 (qd, J = 10.8, 5.2 Hz, 1H), 2.13-2.25 (m, 3H), 2.38-2.48 (m, 2H), 2.90-2.95 (m, 1H), 4.20-4.28 (m, 1H), 6.06 (d, J = 7.6 Hz, 1H), 6.33 (s, 1H), 6.99-7.03 (m, 3H), 7.10 (d, J = 7.5 Hz, 1H), 7.39 (t, J = 7.8 Hz, 1H), 7.78 (d, J = 8.0 Hz, 1H), 7.90 (dd, J = 8.6, 2.5 Hz, 1H), 8.28 (dd, J = 8.1, 1.7 Hz, 1H), 8.45 (s, 1H), 9.02 (d, J = 1.5 Hz, 1H). MS (ES) m/z 522.2 (M + 1). MP = 160-161° C. |
| Example 2.A-7 | 5-Methyl-N-[4-[[3-[[5-(trifluoromethyl)-2-pyridyl]oxy]phenyl]methylene]cyclohexyl]isoxazole-3-carboxamide<br>¹H NMR (400 MHz, CDCl₃): δ 1.33-1.41 (m, 1H), 1.46-1.54 (m, 1H), 2.06-2.18 (m, 3H), 2.33-2.42 (m, 2H), 2.48 (s, 3H), 2.88 (d, J = 13.7 Hz, 1H), 4.13-4.18 (m, 1H), 6.30 (s, 1H), 6.44 (s, 1H), 6.69 (d, J = 7.9 Hz, 1H), 6.98-7.02 (m, 3H), 7.09 (d, J = 7.6 Hz, 1H), 7.38 (t, J = 7.6 Hz, 1H), 7.90 (dd, J = 8.5 Hz, 1H), 8.45 (s, 1H). MS (ES) m/z 458.3 (M + 1). MP = 124-125° C. |
| Example 2.A-8 | N-[4-[[3-[[5-(Trifluoromethyl)-2-pyridyl]oxy]phenyl] methylene]cyclohexyl]pyridine-4-carboxamide<br>¹H NMR (400 MHz, CDCl₃): δ 1.30-1.40 (m, 1H), 1.47 (qd, J = 11.5, 5.4 Hz, 1H), 2.11-2.23 (m, 3H), 2.36-2.47 (m, 2H), 2.92 (dt, J = 16.9, 6.6 Hz, 1H), 4.17-4.27 (m, 1H), 6.03 (d, J = 7.6 Hz, 1H), 6.32 (s, 1H), 6.98-7.03 (m, 3H), 7.09 (d, J = 7.6 Hz, 1H), 7.39 (t, J = 7.9 Hz, 1H), 7.59 (d, J = 5.9 Hz, 2H), 7.90 (dd, J = 8.6, 2.5 Hz, 1H), 8.45 (s, 1H), 8.74 (d, J = 5.8 Hz, 2H). MS (ES) m/z 454.3 (M + 1). MP = 121-124° C. |
| Example 2.A-9 | N-[4-[[3-[[5-(Trifluoromethyl)-2-pyridyl]oxy]phenyl] methylene]cyclohexyl]-1H-pyrazole-4-carboxamide<br>¹H NMR (400 MHz, CDCl₃): δ 1.26-1.36 (m, 1H), 1.43 (qd, J = 11.7, 5.1 Hz, 1H), 2.08-2.17 (m, 3H), 2.32-2.42 (m, 2H), 2.85-2.89 (m, 1H), 4.16-4.21 (m, 1H), 5.85 (d, J = 8.4 Hz, 1H), 6.28 (s, 1H), 6.98-7.03 (m, 3H), 7.08 (d, J = 7.6 Hz, 1H), 7.37 (t, J = 8.4 Hz, 1H), 7.89-7.92 (m, 3H), 8.45 (s, 1H). MS (ES) m/z 443.3 (M + 1). MP = 172-174° C. |
| Example 2.A-10 | tert-Butyl-(2S)-2-[[4-[[3-[[5-(trifluoromethyl)-2-pyridyl]oxy]phenyl] methylene]cyclohexyl]carbamoyl]pyrrolidine-1-carboxylate<br>¹H NMR (400 MHz, CD₃OD): δ 1.21-1.45 (m, 2H), 1.41 (s, 9H), 1.81-1.96 (m, 3H), 2.01-2.13 (m, 2H), 2.17-2.24 (m, 1H), 2.33-2.44 (m, 2H), 2.86-2.90 (m, 1H), 3.37-3.43 (m, 1H), 3.48-3.53 (m, 1H), 3.85-3.93 (m, 1H), 4.08-4.12 (m, 1H), 6.86-3.93 (m, 1H), 4.10 (dd, J = 8.0, 3.6 Hz, 1H), 6.32 (s, 1H), 6.97-7.01 (m, 2H), 7.11 (t, J = 8.3 Hz, 2H), 7.38 (t, J = 7.9 Hz, 1H), 8.09 (dd, J = 8.6, 2.5 Hz, 1H), 8.42 (s, 1H). MS (ES) m/z 546.4 (M + 1). MP = 55-56° C. |
| Example 2.A-11 | N-[4-[[3-[[5-(Trifluoromethyl)-2-pyridyl]oxy]phenyl] methylene]cyclohexyl]pyridazine-3-carboxamide<br>¹H NMR (400 MHz, CDCl₃): δ 1.46 (qd, J = 11.7, 3.2 Hz, 1H), 1.55-1.63 (m, 1H), 2.09-2.23 (m, 3H), 2.36-2.45 (m, 2H), 2.91 (dt, J = 14.2, 3.9 Hz, 1H), 4.21-4.29 (m, 1H), 6.32 (s, 1H), 6.97-7.02 (m, 3H), 7.10 (d, J = 7.6 Hz, 1H), 7.39 (t, J = 8.6 Hz, 1H), 7.66 (dd, J = 8.3, 4.9 Hz, 1H), 7.89 (dd, J = 8.6, 2.4 Hz, 1H), 8.15 (d, J = 8.4 Hz, 1H), 8.33 (dd, J = 8.6, 1.6 Hz, 1H), 8.44 (s, 1H), 9.27 (dd, J = 4.8, 1.6 Hz, 1H). MS (ES) m/z 455.3 (M + 1). MP = 136-137° C. |
| Example 2.A-12 | N-[4-[[3-[[5-(Trifluoromethyl)-2-pyridyl]oxy]phenyl] methylene]cyclohexyl] pyrimidine-5-carboxamide<br>¹H NMR (400 MHz, CDCl₃): δ 1.32-1.42 (m, 1H), 1.45-1.54 (m, 1H), 2.12-2.22 (m, 3H), 2.36-2.43 (m, 2H), 2.93 (d, J = 14.2 Hz, 1H), 4.22-4.24 (m, 1H), 6.28 (brs, 1H), 6.32 (s, 1H), 6.98-7.03 (m, 3H), 7.09 (d, J = 7.8 Hz, 1H), 7.38 (t, J = 7.6 Hz, 1H), 7.90 (d, J = 7.6 Hz, 1H), 8.44 (s, 1H), 9.09 (s, 2H), 9.30 (s, 1H). MS (ES) m/z 455.3 (M + 1). MP = 54-55° C. |
| Example 2.A-13 | 2-(3-Pyridyl)-N-[4-[[3-[[5-(trifluoromethyl)-2-pyridyl]oxy]phenyl] methylene]cyclohexyl]acetamide<br>¹H NMR (400 MHz, CDCl₃): δ 1.13-1.22 (m, 1H), 1.25-1.34 (m, 1H), 1.95-2.09 (m, 3H), 2.27-2.32 (m, 2H), 2.80 (d, J = 14.1 Hz, 1H), 3.52 (s, 2H), 3.95-4.12 (m, 1H), 5.52 (d, J = 7.5 Hz, 1H), 6.26 (s, 1H), 6.94 (s, 1H), 6.99 (t, J = 8.5 Hz, 2H), 7.05 (d, J = 7.6 Hz, 1H), 7.29 (d, J = 7.1 Hz, 1H), 7.36 (t, J = 7.9 Hz, 1H), 7.66 (d, J = 7.8 Hz, 1H), 7.89 (d, J = 8.6 Hz, 1H), 8.43 (s, 1H), 8.49 (s, 1H), 8.52 (d, J = 4.4 Hz, 1H). MS (ES) m/z 468.2 (M + 1). MP = 105-106° C. |

| | |
|---|---|
| Example 2.A-14 | 6-Fluoro-N-[4-[[3-[[5-(trifluoromethyl)-2-pyridyl]oxy]phenyl]methylene] cyclohexyl]pyridine-3-carboxamide<br>$^1$H NMR (400 MHz, CDCl$_3$): δ 1.31-1.41 (m, 1H), 1.43-1.53 (m, 1H), 2.14-2.23 (m, 3H), 2.39-2.47 (m, 2H), 2.90-2.94 (m, 1H), 4.19-4.28 (m, 1H), 5.94 (d, J = 7.8 Hz, 1H), 6.32 (s, 1H), 7.00-7.03 (m, 4H), 7.09 (d, J = 7.5 Hz, 1H), 7.39 (t, J = 7.8 Hz, 1H), 7.90 (dd, J = 8.6, 2.2 Hz, 1H), 8.23 (td, J = 8.6, 2.5 Hz, 1H), 8.45 (s, 1H), 8.57 (s, 1H). MS (ES) m/z 472.3 (M + 1). MP = 110-111° C. |
| Example 2.A-15 | 5-Fluoro-N-[4-[[3-[[5-(trifluoromethyl)-2-pyridyl]oxy]phenyl]methylene] cyclohexyl]pyridine-3-carboxamide<br>$^1$H NMR (400 MHz, CDCl$_3$): δ 1.31-1.41 (m, 1H), 1.46-1.54 (m, 1H), 2.13-2.23 (m, 3H), 2.39-2.47 (m, 2H), 2.92 (d, J = 14.2 Hz, 1H), 4.19-4.29 (m, 1H), 6.00 (d, J = 8.1 Hz, 1H), 6.33 (s, 1H), 7.00-7.03 (m, 3H), 7.09 (d, J = 7.6 Hz, 1H), 7.39 (t, J = 7.8 Hz, 1H), 7.85 (dd, J = 8.5, 1.7 Hz, 1H), 7.90 (dd, J = 8.8, 2.0 Hz, 1H), 8.45 (s, 1H), 8.59 (d, J = 2.7 Hz, 1H), 8.73 (s, 1H). MS (ES) m/z 472.3 (M + 1). MP = 154-155° C. |
| Example 2.A-16 | N-[4-[[3-[[5-(Trifluoromethyl)-2-pyridyl]oxy]phenyl] methylene]cyclohexyl] pyrimidine-2-carboxamide<br>$^1$H NMR (400 MHz, CDCl$_3$): δ 1.39-1.49 (m, 1H), 1.51-1.61 (m, 1H), 2.11-2.24 (m, 3H), 2.40-2.44 (m, 2H), 2.87-2.91 (m, 1H), 4.28-4.32 (m, 1H), 6.32 (s, 1H), 6.99-7.03 (m, 3H), 7.10 (d, J = 7.8 Hz, 1H), 7.39 (t, J = 7.6 Hz, 1H), 7.44 (t, J = 4.8 Hz, 1H), 7.90 (dd, J = 8.8, 2.2 Hz, 1H), 7.98 (d, J = 8.1 Hz, 1H), 8.46 (s, 1H), 8.88 (d, J = 4.9 Hz, 2H). MS (ES) m/z 455.2 (M + 1). Sticky solid. |
| Example 2.A-17 | N-[4-[[3-[[5-(Trifluoromethyl)-2-pyridyl]oxy]phenyl] methylene]cyclohexyl] pyridazine-4-carboxamide<br>$^1$H NMR (400 MHz, CDCl$_3$): δ 1.40 (qd, J = 11.3, 3.7 Hz, 1H), 1.52 (qd, J = 11.7, 4.6 Hz, 1H), 2.11-2.22 (m, 3H), 2.35-2.47 (m, 2H), 2.90-2.96 (m, 1H), 4.17-4.26 (m, 1H), 6.31 (s, 1H), 6.64 (d, J = 7.2 Hz, 1H), 6.97-7.03 (m, 3H), 7.08 (d, J = 7.5 Hz, 1H), 7.38 (t, J = 7.9 Hz, 1H), 7.85 (d, J = 3.1 Hz, 1H), 7.90 (dd, J = 8.4, 2.0 Hz, 1H), 8.44 (s, 1H), 9.34 (s, 1H), 9.51 (s, 1H). MS (ES) m/z 466.1 (M + 1), 468.3 (M + 3). MP = 55-56° C. |
| Example 2.A-18 | 1-Methyl-N-[4-[[3-[[5-(trifluoromethyl)-2-pyridyl]oxy]phenyl]methylene] cyclohexyl]pyrazole-4-carboxamide<br>$^1$H NMR (400 MHz, CDCl$_3$): δ 1.25-1.45 (m, 2H), 2.06-2.19 (m, 3H), 2.34-2.44 (m, 2H), 2.88 (d, J = 13.9 Hz, 1H), 3.92 (s, 3H), 4.12-4.21 (m, 1H), 5.57 (d, J = 8.1 Hz, 1H), 6.30 (s, 1H), 6.98-7.03 (m, 3H), 7.09 (d, J = 7.9 Hz, 1H), 7.38 (t, J = 8.1 Hz, 1H), 7.68 (s, 1H), 7.82 (s, 1H), 7.90 (d, J = 8.5 Hz, 1H), 8.45 (s, 1H). MS (ES) m/z 457.2 (M + 1). MP = 72-74° C.. |
| Example 2.A-19 | N-[4-[[3-[[5-(Trifluoromethyl)-2-pyridyl]oxy]phenyl] methylene]cyclohexyl]-2H-triazole-4-carboxamide<br>$^1$H NMR (400 MHz, CDCl$_3$): δ 1.34-1.58 (m, 2H), 2.07-2.19 (m, 3H), 2.36-2.44 (m, 2H), 2.88 (d, J = 13.9 Hz, 1H), 4.18-4.28 (m, 1H), 6.31 (s, 1H), 6.90 (brs, 1H), 6.99-7.03 (m, 3H), 7.10 (d, J = 7.5 Hz, 1H), 7.39 (t, J = 7.8 Hz, 1H), 7.90 (d, J = 8.6 Hz, 1H), 8.20 (s, 1H), 8.45 (s, 1H). MS (ES) m/z 444.2 (M + 1). MP = 75-77° C. |
| Example 2.A-20 | 5-Methyl-N-[4-[[3-[[5-(trifluoromethyl)-2-pyridyl]oxy]phenyl]methylene] cyclohexyl]-1,3,4-oxadiazole-2-carboxamide<br>$^1$H NMR (400 MHz, CDCl$_3$): δ 1.34-1.60 (m, 2H), 2.07-2.19 (m, 3H), 2.33-2.47 (m, 2H), 2.62 (s, 3H), 2.89 (d, J = 14.2 Hz, 1H), 4.14-4.22 (m, 1H), 6.32 (s, 1H), 6.97-7.02 (m, 4H), 7.08 (d, J = 7.6 Hz, 1H), 7.38 (t, J = 7.6 Hz, 1H), 7.89 (dd, J = 8.5, 2.2 Hz, 1H), 8.45 (s, 1H). MS (ES) m/z 459.3 (M + 1). MP = 131-133° C. |
| Example 2.A-21 | 2-Ethyl-N-[4-[[3-[[5-(trifluoromethyl)-2-pyridyl]oxy]phenyl]methylene] cyclohexyl]pyrimidine-5-carboxamide<br>$^1$H NMR (400 MHz, CDCl$_3$): δ 1.32-1.1.41 (m, 1H), 1.37 (t, J = 7.5 Hz, 3H), 1.50 (qd, J = 11.4, 5.1 Hz, 1H), 2.11-2.23 (m, 3H), 2.37-2.47 (m, 2H), 2.89-2.94 (m, 1H), 3.04 (q, J = 7.3 Hz, 2H), 4.18-4.28 (m, 1H), 5.92 (d, J = 7.6 Hz, 1H), 6.32 (s, 1H), 6.98-7.02 (m, 3H), 7.09 (d, J = 7.6 Hz, 1H), 7.38 (t, J = 7.5 Hz, 1H), 7.89 (d, J = 8.5 Hz, 1H), 8.45 (s, 1H), 8.99 (s, 2H). MS (ES) m/z 483.3 (M + 1). MP = 180-182° C. |
| Example 2.A-22 | 6-Chloro-N-[4-[[3-[[5-(trifluoromethyl)-2-pyridyl]oxy]phenyl]methylene] cyclohexyl]pyridine-3-carboxamide<br>$^1$H NMR (400 MHz, CDCl$_3$): δ 1.35 (qd, J = 13.5, 5.4 Hz, 1H), 1.47 (qd, J = 11.5, 5.1 Hz, 1H), 2.08-2.22 (m, 3H), 2.35-2.46 (m, 2H), 2.88-2.94 (m, 1H), 4.16-4.25 (m, 1H), 6.02 (d, J = 7.6 Hz, 1H), 6.31 (s, 1H), 6.98-7.02 (m , 3H), 7.08 (d, J = 7.6 Hz, 1H), 7.36-7.41 (m, 2H), 7.89 (dd, J = 8.5, 2.2 Hz, 1H), 8.05 (dd, J = 8.3, 2.4 Hz, 1H), 8.44 (s, 1H), 8.70 (d, J = 2.2 Hz, 1H). MS (ES) m/z 488.2 (M + 1), 489.4 (M + 2). MP = 122-123° C. |
| Example 2.A-23 | 5-Methyl-N-[4-[[3-[[5-(trifluoromethyl)-2-pyridyl]oxy]phenyl]methylene] cyclohexyl]-1H-pyrazole-4-carboxamide<br>$^1$H NMR (400 MHz, CDCl$_3$): δ 1.32 (qd, J = 13.6, 5.6 Hz, 1H), 1.44 (qd, J = 11.7, 5.1 Hz, 1H), 2.07-2.27 (m, 3H), 2.33-2.41 (m, 2H), 2.55 (s, 3H), 2.85-2.90 (m, 1H), 4.12-4.20 (m, 1H), 5.58 (d, J = 7.6 Hz, 1H), 6.29 (s, 1H), 6.97-7.01 (m, 3H), 7.08 (d, J = 7.3 Hz, 1H), 7.37 (t, J = 7.8 Hz, 1H), 7.71 (s, 1H), 7.88 (d, J = 8.8 Hz, 1H), 8.44 (s, 1H). MS (ES) m/z 457.2 (M + 1). MP = 140-141° C. |

| | |
|---|---|
| Example 2.A-24 | 6-(Dimethylamino)-N-[4-[[3-[[5-(trifluoromethyl)-2-pyridyl]oxy]phenyl]methylene]cyclohexyl]pyridine-3-carboxamide<br>¹H NMR (400 MHz, CDCl₃): δ 1.31 (qd, J = 10.8, 4.4 Hz, 1H), 1.44 (qd, J = 11.0, 5.7 Hz, 1H), 2.07-2.19 (m, 3H), 2.33-2.42 (m, 2H), 2.86 (dt, J = 14.4, 3.6 Hz, 1H), 4.13-4.23 (m, 1H), 5.69 (d, J = 8.1 Hz, 1H), 6.28 (s, 1H), 6.39 (d, J = 1.5 Hz, 1H), 6.74-6.75 (m, 1H), 6.98-7.02 (m, 3H), 7.09 (d, J = 7.6 Hz, 1H), 7.33 (d, J = 1.5 Hz, 1H), 7.37 (t, J = 7.6 Hz, 1H), 7.89 (dd, J = 8.5, 2.2 Hz, 1H), 8.44 (s, 1H), 8.89 (brs, 1H). MS (ES) m/z 442.3 (M + 1). MP = 149-151° C. |
| Example 2.A-25 | 2-Chloro-N-[4-[[3-[[5-(trifluoromethyl)-2-pyridyl]oxy]phenyl]methylene]cyclohexyl]pyridine-3-carboxamide<br>¹H NMR (400 MHz, CDCl₃): δ 1.42 (qd, J = 10.7, 2.7 Hz, 1H), 1.54 (qd, J = 11.0, 4.9 Hz, 1H), 2.12-2.23 (m, 3H), 2.38-2.47 (m, 2H), 2.87 (d, J = 14.4 Hz, 1H), 4.22-4.28 (m, 1H), 6.32 (s, 1H), 6.39 (d, J = 7.3 Hz, 1H), 6.99-7.03 (m, 3H), 7.09 (d, J = 7.6 Hz, 1H), 7.34-7.41 (m, 2H), 7.90 (d, J = 8.8 Hz, 1H), 8.10 (dd, J = 7.8, 1.9 Hz, 1H), 8.45-8.47 (m, 2H). MS (ES) m/z 488.0 (M + 1), 489.1 (M + 2). MP = 113-114° C. |
| Example 2.A-26 | 2-Fluoro-N-[4-[[3-[[5-(trifluoromethyl)-2-pyridyl]oxy]phenyl]methylene]cyclohexyl]pyridine-3-carboxamide<br>¹H NMR (400 MHz, CDCl₃): δ 1.41 (qd, J = 11.3, 3.4 Hz, 1H), 1.54 (qd, J = 11.2, 4.9 Hz, 1H), 2.10-2.22 (m, 3H), 2.36-2.47 (m, 2H), 2.86-2.91 (m, 1H), 4.21-4.28 (m, 1H), 6.32 (s, 1H), 6.75 (dd, J = 12.9, 8.3 Hz, 1H), 6.99-7.03 (m, 3H), 7.10 (d, J = 7.8 Hz, 1H), 7.36-7.41 (m, 2H), 7.90 (dd, J = 9.5, 1.9 Hz, 1H), 8.32-8.33 (m, 1H), 8.45 (s, 1H), 8.59 (dt, J = 9.5, 1.7 Hz, 1H). MS (ES) m/z 472.1 (M + 1). MP = 69-70° C. |
| Example 2.A-27 | 6-Cyano-N-[4-[[3-[[5-(trifluoromethyl)-2-pyridyl]oxy]phenyl]methylene]cyclohexyl]pyridine-3-carboxamide<br>¹H NMR (400 MHz, CDCl₃): δ 1.32-1.42 (m, 1H), 1.44-1.54 (m, 1H), 2.13-2.22 (m, 3H), 2.39-2.44 (m, 2H), 2.93 (d, J = 13.5 Hz, 1H), 4.19-4.28 (m, 1H), 6.12 (d, J = 7.4 Hz, 1H), 6.33 (s, 1H), 6.98-7.03 (m, 3H), 7.09 (d, J = 6.9 Hz, 1H), 7.39 (t, J = 7.6 Hz, 1H), 7.79 (d, J = 7.8 Hz, 1H), 7.90 (d, J = 8.3 Hz, 1H), 8.24 (d, J = 5.7 Hz, 1H), 8.44 (s, 1H), 9.02 (s, 1H). MS (ES) m/z 479.2 (M + 1). MP = 81-82° C. |
| Example 2.A-28 | 2-Methyl-N-[4-[[3-[[5-(trifluoromethyl)-2-pyridyl]oxy]phenyl]methylene]cyclohexyl]pyridine-3-carboxamide<br>¹H NMR (400 MHz, CDCl₃): δ 1.34 (qd, J = 11.6, 3.2 Hz, 1H), 1.47 (qd, J = 10.8, 5.2 Hz, 1H), 2.12-2.23 (m, 3H), 2.34-2.46 (m, 2H), 2.66 (s, 3H), 2.87-2.92 (m, 1H), 4.17-4.26 (m, 1H), 5.69 (s, 1H), 6.31 (s, 1H), 6.98-7.03 (m, 3H), 7.09 (d, J = 7.9 Hz, 1H), 7.15 (dd, J = 7.1, 5.1 Hz, 1H), 7.38 (t, J = 7.8 Hz, 1H), 7.63 (d, J = 7.5 Hz, 1H), 7.90 (dd, J = 8.8, 2.4 Hz, 1H), 8.45 (s, 1H), 8.54 (d, J = 4.9 Hz, 1H). MS (ES) m/z 468.2 (M + 1). MP = 134-135° C. |
| Example 2.A-29 | 3-(Trifluoromethyl)-N-[4-[[3-[[5-(trifluoromethyl)-2-pyridyl]oxy]phenyl]methylene]cyclohexyl]-1H-pyrazole-4-carboxamide<br>¹H NMR (400 MHz, CDCl₃): δ 1.32-1.42 (m, 1H), 1.44-1.54 (m, 1H), 2.05-2.22 (m, 3H), 2.32-2.47 (m, 2H), 2.79-2.85 (m, 1H), 4.15-4.25 (m, 1H), 5.99 (d, J = 5.6 Hz, 1H), 6.31 (s, 1H), 6.98-7.03 (m, 3H), 7.09 (d, J = 7.8 Hz, 1H), 7.38 (t, J = 8.1 Hz, 1H), 7.90 (dd, J = 8.6, 1.8 Hz, 1H), 8.13 (s, 1H), 8.45 (s, 1H), 10.92 (brs, 1H). MS (ES) m/z 511.2 (M + 1). MP = 87-89° C. |
| Example 2.A-30 | 5-Methyl-N-[4-[[3-[[5-(trifluoromethyl)-2-pyridyl]oxy]phenyl]methylene]cyclohexyl]pyridine-3-carboxamide<br>¹H NMR (400 MHz, CDCl₃): δ 1.35 (qd, J = 13.5, 5.4 Hz, 1H), 1.48 (qd, J = 11.2, 5.1 Hz, 1H), 2.13-2.24 (m, 3H), 2.37-2.47 (m, 2H), 2.40 (s, 3H), 2.89-2.94 (m, 1H), 4.17-4.27 (m, 1H), 6.03 (d, J = 7.3 Hz, 1H), 6.32 (s, 1H), 6.99-7.03 (m, 3H), 7.10 (d, J = 7.6 Hz, 1H), 7.39 (t, J = 7.6 Hz, 1H), 7.88-7.92 (m, 2H), 8.45 (s, 1H), 8.55 (s, 1H), 8.72 (s, 1H). MS (ES) m/z 468.2 (M + 1). MP = 144-145° C. |
| Example 2.A-31 | tert-Butyl N-[3-[4-[[3-[[5-(trifluoromethyl)-2-pyridyl]oxy]phenyl]methylene]cyclohexyl]carbamoyl]-4-pyridyl]carbamate<br>MS (ES) m/z 569.3 (M + 1). |
| Example 2.A-32 | 5-Chloro-N-[4-[[3-[[5-(trifluoromethyl)-2-pyridyl]oxy]phenyl]methylene]cyclohexyl]pyridine-3-carboxamide<br>¹H NMR (400 MHz, CDCl₃): δ 1.36 (qd, J = 11.2, 3.6 Hz, 1H), 1.48 (qd, J = 11.2, 4.8 Hz, 1H), 2.12-2.23 (m, 3H), 2.36-2.47 (m, 2H), 2.88-2.95 (m, 1H), 4.17-4.26 (m, 1H), 6.04 (d, J = 7.5 Hz, 1H), 6.32 (s, 1H), 6.98-7.03 (m, 3H), 7.10 (d, J = 4.5 Hz, 1H), 7.39 (t, J = 7.8 Hz, 1H), 7.90 (dd, J = 8.6, 2.2 Hz, 1H), 8.09 (t, J = 2.0 Hz, 1H), 8.45 (s, 1H), 8.68 (d, J = 2.4 Hz, 1H), 8.79 (d, J = 1.7 Hz, 1H). MS (ES) m/z 488.2 (M + 1), 489.2 (M + 2). MP = 165-166° C. |
| Example 2.A-33 | 3-Methyl-N-[4-[[3-[[5-(trifluoromethyl)-2-pyridyl]oxy]phenyl]methylene]cyclohexyl]triazole-4-carboxamide<br>¹H NMR (400 MHz, CDCl₃): δ 1.26-1.36 (m, 1H), 1.41-1.52 (m, 1H), 2.07-2.22 (m, 3H), 2.34-2.47 (m, 2H), 2.93 (d, J = 13.2 Hz, 1H), 4.14-4.42 (m, 1H), 4.33 (s, 3H), 5.90 (d, J = 7.2 Hz, 1H), 6.32 (s, 1H), 6.98-7.03 (m, 3H), 7.09 (d, J = 7.5 Hz, 1H), 7.39 (t, J = 7.9 Hz, 1H), 7.87 (s, 1H), 7.90 (d, J = 8.9 Hz, 1H), 8.44 (s, 1H). MS (ES) m/z 458.2 (M + 1). MP = 62-65° C. |
| Example 2.A-34 | N-[4-[[3-[[5-(Trifluoromethyl)-2-pyridyl]oxy]phenyl]methylene]cyclohexyl]benzamide<br>¹H NMR (400 MHz, CDCl₃): δ 1.35 (qd, J = 12.3, 4.2 Hz, 1H), 1.47 (qd, J = 11.0, 5.6 Hz, 1H), 2.11-2.21 (m, 3H), 2.37-2.46 (m, 2H), 2.87-2.93 (m, 1H), 4.18-4.27 (m, 1H), 5.97 (d, J = 7.5 Hz, 1H), 6.31 (s, 1H), 6.99-7.03 (m, 3H), |

| | |
|---|---|
| | 7.10 (d, J = 7.5 Hz, 1H), 7.36-7.52 (m, 4H), 7.75 (d, J = 7.6 Hz, 2H), 7.90 (dd, J = 8.6, 2.2 Hz, 1H), 8.45 (s, 1H). MS (ES) m/z 453.2 (M + 1). MP = 130-133° C. |
| Example 2.A-35 | 3,5-Dimethyl-N-[4-[[3-[[5-(trifluoromethyl)-2-pyridyl]oxy]phenyl] methylene]cyclohexyl]-1H-pyrazole-4-carboxamide<br>$^1$H NMR (400 MHz, CDCl$_3$): δ 1.34 (qd, J = 11.5, 3.6 Hz, 1H), 1.46 (qd, J = 10.7, 5.6 Hz, 1H), 2.07-2.21 (m, 3H), 2.33-2.41 (m, 2H), 2.45 (s, 6H), 2.82-2.87 (m, 1H), 4.15-4.25 (m, 1H), 5.48 (d, J = 7.6 Hz, 1H), 6.30 (s, 1H), 6.99-7.02 (m, 3H), 7.09 (d, J = 7.6 Hz, 1H), 7.38 (t, J = 7.5 Hz, 1H), 7.89 (dd, J = 8.8, 2.0 Hz, 1H), 8.44 (s, 1H), 9.75 (brs, 1H). MS (ES) m/z 471.2 (M + 1). MP = 211-212° C. |
| Example 2.A-36 | 5-Methyl-3-(trifluoromethyl)-N-[4-[[3-[[5-(trifluoromethyl)-2-pyridyl] oxy]phenyl]methylene]cyclohexyl]-1H-pyrazole-4-carboxamide<br>$^1$H NMR (400 MHz, CDCl$_3$): δ 1.35 (qd, J = 11.9, 3.9 Hz, 1H), 1.48 (qd, J = 11.1, 5.0 Hz, 1H), 2.05-2.21 (m, 3H), 2.32-2.44 (m, 2H), 2.53 (s, 3H), 2.83 (dt, J = 13.7, 3.9 Hz, 1H), 4.13-4.22 (m, 1H), 5.91 (d, J = 7.7 Hz, 1H), 6.30 (s, 1H), 6.98-7.02 (m, 3H), 7.09 (d, J = 7.7 Hz, 1H), 7.38 (t, J = 7.7 Hz, 1H), 7.90 (dd, J = 8.5, 2.5 Hz, 1H), 8.45 (s, 1H), 10.65 (brs, 1H). MS (ES) m/z 525.2 (M + 1). MP = 99-102° C. |
| Example 2.A-37 | 2,6-Dimethyl-N-[4-[[3-[[5-(trifluoromethyl)-2-pyridyl]oxy] phenyl]methylene]cyclohexyl]pyridine-3-carboxamide<br>$^1$H NMR (400 MHz, CDCl$_3$): δ 1.33 (qd, J = 11.0, 4.0 Hz, 1H), 1.46 (qd, J = 10.8, 5.6 Hz, 1H), 2.10-2.23 (m, 3H), 2.35-2.42 (m, 2H), 2.46 (s, 3H), 2.64 (s, 3H), 2.86-2.92 (m, 1H), 4.16-4.25 (m, 1H), 5.62 (d, J = 7.9 Hz, 1H), 6.31 (s, 1H), 6.98-7.01 (m, 4H), 7.09 (d, J = 7.7 Hz, 1H), 7.38 (t, J = 7.7 Hz, 1H), 7.56 (d, J = 7.7 Hz, 1H), 7.90 (dd, J = 8.7, 2.3 Hz, 1H), 8.85 (s, 1H). MS (ES) m/z 482.2 (M + 1). MP = 102-103° C. |
| Example 2.A-38 | 5-Isopropyl-3-methyl-N-[4-[[3-[[5-(trifluoromethyl)-2-pyridyl]oxy]phenyl] methylene]cyclohexyl]-1H-pyrazole-4-carboxamide<br>$^1$H NMR (400 MHz, CDCl$_3$): δ 1.30-1.38 (m, 1H), 1.31 (d, J = 6.8 Hz, 6H), 1.46 (qd, J = 10.8, 5.9 Hz, 1H), 2.08-2.20 (m, 3H), 2.34-2.44 (m, 2H), 2.42 (s, 3H), 2.86 (dt, J = 14.2, 4.2 Hz, 1H), 3.41-3.51 (m, 1H), 4.16-4.25 (m, 1H), 5.50 (d, J = 7.8 Hz, 1H), 6.31 (s, 1H), 6.98-7.02 (m, 3H), 7.09 (d, J = 7.6 Hz, 1H), 7.38 (t, J = 7.9 Hz, 1H), 7.90 (dd, J = 8.5, 2.4 Hz, 1H), 8.45 (s, 1H). MS (ES) m/z 499.3 (M + 1). MP = 119-121° C. |
| Example 2.A-39 | 5-Isopropyl-N-[4-[[3-[[5-(trifluoromethyl)-2-pyridyl]oxy]phenyl] methylene]cyclohexyl]-1H-pyrazole-4-carboxamide<br>$^1$H NMR (400 MHz, CDCl$_3$): δ 1.29-1.48 (m, 2H), 1.33 (d, J = 6.9 Hz, 6H), 2.07-2.20 (m, 3H), 2.33-2.44 (m, 2H), 2.87-2.92 (m, 1H), 3.66-3.76 (m, 1H), 4.12-4.21 (m, 1H), 5.60 (d, J = 7.6 Hz, 1H), 6.30 (s, 1H), 6.98-7.03 (m, 3H), 7.09 (d, J = 7.4 Hz, 1H), 7.38 (t, J = 7.6 Hz, 1H), 7.68 (s, 1H), 7.90 (dd, J = 8.5, 2.2 Hz, 1H), 8.45 (s, 1H). MS (ES) m/z 485.2 (M + 1). MP = 94-96° C. |
| Example 2.A-40 | 3-(Hydroxymethyl)-5-methyl-N-[4-[[3-[[5-(trifluoromethyl)-2-pyridyl]oxy] phenyl]methylene]cyclohexyl]-1H-pyrazole-4-carboxamide<br>$^1$H NMR (400 MHz, DMSO-d$_6$): δ 1.32-1.42 (m, 1H), 1.48-1.52 (m, 1H), 1.88-1.94 (m, 3H), 2.19-2.31 (m, 2H), 2.38 (s, 3H), 2.63-2.68 (m, 1H), 3.94-4.04 (m, 1H), 4.49 (d, = 4.9 Hz, 2H), 6.03 (t, J = 4.9 Hz, 1H), 6.31 (s, 1H), 7.01 (s, 1H), 7.05 (d, J = 8.1 Hz, 1H), 7.12 (d, J = 7.6 Hz, 1H), 7.24 (d, J = 8.5 Hz, 1H), 7.41 (t, J = 7.8 Hz, 1H), 8.23 (dd, J = 8.6, 2.2 Hz, 1H), 8.39 (d, J = 7.3 Hz, 1H), 8.58 (s, 1H), 12.67 (brs, 1H). MS (ES) m/z 487.2 (M + 1). MP = 96-98° C. |
| Example 2.A-41 | N-[4-[[3-[[5-(Trifluoromethyl)-2-pyridyl]oxy]phenyl] methylene]cyclohexyl] isoxazole-5-carboxamide<br>$^1$H NMR (400 MHz, CDCl$_3$): δ 1.34-1.44 (m, 1H), 1.47-1.57 (m, 1H), 2.08-2.20 (m, 3H), 2.35-2.48 (m, 2H), 2.90 (d, J = 13.6 Hz, 1H), 4.14-4.23 (m, 1H), 6.32 (s, 1H), 6.46 (d, J = 7.8 Hz, 1H), 6.92 (d, J = 1.7 Hz, 1H), 6.98-7.03 (m, 3H), 7.10 (d, J = 7.6 Hz, 1H), 7.39 (t, J = 7.8 Hz, 1H), 7.90 (dd, J = 8.8, 2.4 Hz, 1H), 8.33 (d, J = 1.7 Hz, 1H), 8.45 (s, 1H). MS (ES) m/z 444.2 (M + 1). MP = 135-137° C. |
| Example 2.A-42 | 6-Cyclopropyl-N-[4-[[3-[[5-(trifluoromethyl)-2-pyridyl]oxy]phenyl] methylene]cyclohexyl]pyridine-3-carboxamide<br>$^1$H NMR (400 MHz, DMSO-d$_6$): δ 0.93-1.02 (m, 4H), 1.31-1.40 (m, 1H), 1.43-1.52 (m, 1H), 1.89-1.97 (m, 2H), 2.04-2.15 (m, 2H), 2.29 (t, J = 12.0 Hz, 1H), 2.38 (d, J = 13.2 Hz, 1H), 2.81 (d, J = 13.4 Hz, 1H), 3.92-4.28 (m, 1H), 6.30 (s, 1H), 6.99 (s, 1H), 7.04 (d, J = 8.0 Hz, 1H), 7.10 (d, J = 7.5 Hz, 1H), 7.23 (d, J = 8.6 Hz, 1H), 7.35 (d, J = 8.1 Hz, 1H), 7.40 (t, J = 7.6 Hz, 1H), 8.00 (d, J = 7.3 Hz, 1H), 8.22 (d, J = 8.6 Hz, 1H), 8.28 (d, J = 7.3 Hz, 1H), 8.56 (s, 1H), 8.78 (s, 1H). MS (ES) m/z 494.2 (M + 1). MP = 140143° C. |
| Example 2.A-43 | 6-Ethyl-N-[4-[[3-[[5-(trifluoromethyl)-2-pyridyl]oxy]phenyl]methylene] cyclohexyl]pyridine-3-carboxamide<br>$^1$H NMR (400 MHz, DMSO-d$_6$): δ 1.23 (t, J = 7.3 Hz, 3H), 1.33-1.42 (m, 1H), 1.45-1.55 (m, 1H), 1.92-2.00 (m, 2H), 2.10 (t, J = 11.8 Hz, 1H), 2.31 (t, J = 11.7 Hz, 1H), 2.40 (d, J = 12.9 Hz, 1H), 2.76-2.85 (m, 3H), 4.00-4.09 (m, 1H), 6.32 (s, 1H), 7.02 (s, 1H), 7.06 (d, J = 7.8 Hz, 1H), 7.13 (d, J = 7.3 Hz, 1H), 7.25 (d, J = 8.6 Hz, 1H), 7.35 (d, J = 8.1 Hz, 1H), 7.43 (t, J = 7.8 Hz, 1H), 8.08 (d, J = 8.1 Hz, 1H), 8.24 (d, J = 7.6 Hz, 1H), 8.36 (d, J = 7.6 Hz, 1H), 8.59 (s, 1H), 8.88 (s, 1H). MS (ES) m/z 482.2 (M + 1). MP = 140-143° C. |

| | -continued |
|---|---|
| Example 2.A-44 | 5-Ethyl-N-[4-[[3-[[5-(trifluoromethyl)-2-pyridyl]oxy]phenyl]methylene]cyclohexyl]-1H-pyrazole-4-carboxamide<br>$^1$H NMR (400 MHz, CDCl$_3$): δ 1.25-1.36 (m, 1H), 1.31 (t, J = 7.6 Hz, 3H), 1.39-1.49 (m, 1H), 2.04-2.20 (m, 3H), 2.33-2.44 (m, 2H), 2.85-2.91 (m, 1H), 3.01 (q, J = 7.6 Hz, 2H), 4.13-4.20 (m, 1H), 5.58 (d, J = 7.8 Hz, 1H), 6.30 (s, 1H), 7.00-7.02 (m, 3H), 7.09 (d, J = 7.8 Hz, 1H), 7.38 (t, J = 7.9 Hz, 1H), 7.69 (s, 1H), 7.89 (dd, J = 8.6, 2.5 Hz, 1H), 8.44 (d, J = 0.9 Hz, 1H). MS (ES) m/z 471.3 (M + 1). MP = 112-114° C. |
| Example 2.A-45 | 3-Methyl-N-[4-[[3-[[5-(trifluoromethyl)-2-pyridyl]oxy]phenyl]methylene]cyclohexyl]-1H-1,2,4-triazole-5-carboxamide<br>$^1$H NMR (400 MHz, DMSO-d$_6$): δ 1.39-1.48 (m, 1H), 1.52-1.61 (m, 1H), 1.82-1.91 (m, 2H), 2.07 (t, J = 13.2 Hz, 1H), 2.28-2.36 (m, 2H), 2.37 (s, 3H), 2.82 (d, J = 14.0 Hz, 1H), 3.95-4.03 (m, 1H), 6.30 (s, 1H), 7.01 (s, 1H), 7.05 (d, J = 8.0 Hz, 1H), 7.12 (d, J = 7.8 Hz, 1H), 7.25 (d, J = 8.5 Hz, 1H), 7.42 (t, J = 7.8 Hz, 1H), 8.17 (d, J = 6.4 Hz, 1H), 8.23 (dd, J = 8.8, 2.4 Hz, 1H), 8.58 (s, 1H), 14.0 (brs, 1H). MS (ES) m/z 458.2 (M + 1). (M + 1). MP = 205-207° C. |
| Example 2.A-46 | N-[4-[[3-[[5-(Trifluoromethyl)-2-pyridyl]oxy]phenyl] methylene]cyclohexyl]-1H-1,2,4-triazole-3-carboxamide<br>$^1$H NMR (400 MHz, DMSO-d$_6$): δ 1.40-1.49 (m, 1H), 1.51-1.62 (m, 1H), 1.84-1.93 (m, 2H), 2.08 (t, J = 13.2 Hz, 1H), 2.27-2.40 (m, 2H), 2.84 (d, J = 13.4 Hz, 1H), 3.97-4.07 (m, 1H), 6.31 (s, 1H), 7.01 (s, 1H), 7.06 (d, J = 8.1 Hz, 1H), 7.12 (d, J = 7.8 Hz, 1H), 7.25 (d, J = 8.6 Hz, 1H), 7.42 (t, J = 7.8, 1H), 8.09 (brs, 0.5H), 8.25 (dd, J = 8.8, 2.4 Hz, 1H), 8.26 (brs, 0.5H), 8.58 (s, 1H), 8.68 (brs, 0.5H), 8.73 (brs, 0.5H), 14.37 (brs, 0.5H), 14.70 (brs, 0.5H). MS (ES) m/z 444.2 (M + 1). MP = 179-181° C. |
| Example 2.A-47 | 3-Methyl-N-[4-[[3-[[5-(trifluoromethyl)-2-pyridyl]oxy]phenyl]methylene]cyclohexyl]isoxazole-5-carboxamide<br>$^1$H NMR (400 MHz, CDCl$_3$): δ 1.34-1.44 (m, 1H), 1.45-1.56 (m, 1H), 2.07-2.19 (m, 3H), 2.40 (s, 3H), 2.40-2.51 (m, 2H), 2.88 (d, J = 14.0 Hz, 1H), 4.12-4.22 (m, 1H), 6.32 (s, 1H), 6.40 (d, J = 7.8 Hz, 1H), 6.74 (s, 1H), 7.00-7.23 (m, 3H), 7.09 (d, J = 7.5 Hz, 1H), 7.38 (t, J = 7.8 Hz, 1H), 7.90 (dd, J = 8.8, 2.2 Hz, 1H), 8.45 (s, 1H). MS (ES) m/z 458.2 (M + 1). MP = 147-149° C. |
| Example 2.A-48 | 6-Chloro-5-nitro-N-[4-[[3-[[5-(trifluoromethyl)-2-pyridyl]oxy]phenyl]methylene]cyclohexyl]pyridine-3-carboxamide<br>MS (ES) m/z 533.1 (M + 1). |
| Example 2.A-49 | 2,6-Difluoro-N-[4-[[3-[[5-(trifluoromethyl)-2-pyridyl]oxy]phenyl]methylene]cyclohexyl]pyridine-3-carboxamide<br>MS (ES) m/z 490.0 (M + 1). |
| Example 2.A-50 | tert-Butyl-4-[[4-[[3-[[5-(trifluoromethyl)-2-pyridyl]oxy]phenyl]methylene]cyclohexyl]carbamoyl]piperidine-1-carboxylate<br>MS (ES) m/z 560.1 (M + 1). |

Following examples were prepared from Intermediate 3A and appropriate carboxylic acid or carboxylic acid chloride selected from Intermediates 4-6 using either of the procedure described for Example 2.1, Example 2.2, Example 2.3.

| | |
|---|---|
| Example 2.B-1 | 4-Methyl-5-(3-pyridyl)-N-[4-[[3-[4-(trifluoromethyl)phenoxy]phenyl]methylene]cyclohexyl]thiazole-2-carboxamide<br>$^1$H NMR (400 MHz, CDCl$_3$): δ 1.31-1.45 (m, 1H), 1.47-1.56 (m, 1H), 2.14-2.24 (m, 3H), 2.38-2.50 (m, 2H), 2.77 (s, 3H), 2.89-2.95 (m, 1H), 4.17-4.27 (m, 1H), 5.70 (d, J = 7.8 Hz, 1H), 6.35 (s, 1H), 7.01-7.05 (m, 3H), 7.12 (d, J = 7.3 Hz, 1H), 7.39-7.44 (m, 2H), 7.93 (dd, J = 8.5, 1.9 Hz, 1H), 8.25 (d, J = 8.3 Hz, 1H), 8.47 (s, 1H), 8.70 (d, J = 3.9 Hz, 1H), 9.16 (s, 1H). MS (ES) m/z 551.3 (M + 1). MP = 136-137° C. |
| Example 2.B-2 | 5-(2-Pyridyl)-N-[4-[[3-[[5-trifluoromethyl)-2-ridyl]oxy]phenyl]methylene]cyclohexyl]-1,3,4-oxadiazole-2-carboxamide<br>$^1$H NMR (400 MHz, CDCl$_3$): δ 1.36-1.57 (m, 2H), 2.11-2.24 (m, 3H), 2.35-2.49 (m, 2H), 2.89-2.95 (m, 1H), 4.20-4.29 (m, 1H), 6.33 (s, 1H), 6.98-7.11 (m, 5H), 7.39 (t, J = 7.6 Hz, 1H), 7.52 (dd, J = 6.8, 4.6 Hz, 1H), 7.88-7.94 (m, 2H), 8.25 (d, J = 7.8 Hz, 1H), 8.45 (s, 1H), 8.84 (d, J = 4.9 Hz, 1H). MS (ES) m/z 522.3 (M + 1). MP = 228-230° C. |
| Example 2.B-3 | 6-(3,5-Dimethylpyrazol-1-yl)-N-[4-[[3-[[5-(trifluoromethyl)-2-pyridyl]oxy]phenyl]methylene]cyclohexyl]pyridine-3-carboxamide<br>$^1$H NMR (400 MHz, DMSO-d$_6$): δ 1.34-1.44 (m, 1H), 1.47-1.56 (m, 1H), 1.93-2.20 (m, 2H), 2.11 (t, J = 12.5 Hz, 1H), 2.21 (s, 3H), 2.32 (t, J = 12.2 Hz, 1H), 2.43 (d, J = 13.3 Hz, 1H), 2.62 (s, 3H), 2.85 (d, J = 13.9 Hz, 1H), 4.02-4.11 (m, 1H), 6.17 (s, 1H), 6.33 (s, 1H), 7.02 (s, 1H), 7.06 (d, J = 8.0 Hz, 1H), 7.13 (d, J = 7.5 Hz, 1H), 7.25 (d, J = 8.6 Hz, 1H), 7.43 (t, J = 7.9 Hz, 1H), 7.90 (d, J = 8.7 Hz, 1H), 8.24 (d, J = 8.5 Hz, 1H), 8.31 (d, J = 8.5 Hz, 1H), 8.46 (d, J = 7.7 Hz, 1H), 8.59 (s, 1H), 8.86 (s, 1H). MS (ES) m/z 548.3 (M + 1). M. P = 103-105° C. |
| Example 2.B-4 | 6-(1H-Pyrazol-3-yl)-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.36-1.46 (m, 1H), 1.47-1.55 (m, 1H), 2.14-2.26 (m, 3H), 2.37-2.48 (m, 2H), 2.90-2.95 (m, 1H), 4.21-4.29 (m, 1H), 6.05 (d, J = 7.8 Hz, 1H), 6.33 (s, 1H), 6.88 (s, 1H), 6.99-7.03 (m, 3H), 7.10 (d, J = 7.6 Hz, 1H), 7.39 (t, J = 7.9 Hz, 1H), 7.67 (d, J = 1.9 Hz, 1H), 7.82 (d, J = 8.1 Hz, 1H), |

| | |
|---|---|
| | 7.90 (dd, J = 8.6, 2.2 Hz, 1H), 8.14 (dd, J = 8.3, 1.9 Hz, 1H), 8.45 (s, 1H), 8.96 (d, J = 2.0 Hz, 1H), 10.95 (brs, 1H). MS (ES) m/z 520.2 (M + 1). MP = 165-166° C. |
| Example 2.B-5 | 6-(1H-Pyrazol-4-yl)-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.31-1.53 (m, 2H), 2.01-2.23 (m, 3H), 2.36-2.44 (m, 2H), 2.87-2.93 (m, 1H), 4.19-4.26 (m, 1H), 5.95 (d, J = 7.6 Hz, 1H), 6.31 (s, 1H), 6.98-7.01 (m, 3H), 7.08 (d, J = 7.4 Hz, 1H), 7.37 (t, J = 7.6 Hz, 1H), 7.54 (d, J = 8.3 Hz, 1H), 7.88 (dd, J = 8.6, 2.0 Hz, 1H), 8.06 (dd, J = 8.1, 2.0 Hz, 1H), 8.14 (s, 2H), 8.44 (s, 1H), 8.87 (d, J = 1.4 Hz, 1H). MS (ES) m/z 520.2 (M + 1). MP = 230-231° C. |
| Example 2.B-6 | 6-(4-Methylpyrazol-1-yl)-N-[4-[[3-[[5-(trifluoromethyl)-2-pyridyl]oxy]phenyl]methylene]cyclohexyl]pyridine-3-carboxamide<br>$^1$H NMR (400 MHz, DMSO-d$_6$): δ 1.39 (qd, J = 12.6, 4.1 HZ, 1H), 1.52 (qd, J = 12.2, 4.1 Hz, 1H), 1.94-2.02 (m, 2H), 2.04-2.15 (m, 3H), 2.11 (s, 3H), 2.32 (t, J = 12.0 Hz, 1H), 2.42 (d, J = 13.6 Hz, 1H), 2.86 (d, J = 14.0 Hz, 1H), 4.03-4.12 (m, 1H), 6.34 (s, 1H), 7.03 (s, 1H), 7.07 (d, J = 8.1 Hz, 1H), 7.14 (d, J = 7.7 Hz, 1H), 7.27 (d, J = 7.7 Hz, 1H), 7.44 (t, J = 8.0 Hz, 1H), 7.72 (s, 1H), 7.94 (d, J = 8.7 Hz, 1H), 8.25 (dd, J = 8.7, 2.2 Hz, 1H), 8.36 (dd, J = 8.5, 2.0 Hz, 1H), 8.45-8.47 (m, 2H), 8.60 (s, 1H), 8.86 (d, J = 1.8 Hz, 1H). MS (ES) m/z 534.2 (M + 1). MP = 204-206° C. |
| Example 2.B-7 | 5-Pyrazol-1-yl-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.38 (qd, J = 11.0, 4.0 Hz, 1H), 1.51 (qd, J = 11.6, 4.9 Hz, 1H), 2.14-2.50 (m, 3H), 2.37-2.46 (m, 2H), 2.90-2.96 (m, 1H), 4.21-4.29 (m, 1H), 6.09 (d, J = 7.7 Hz, 1H), 6.33 (s, 1H), 6.56 (s, 1H), 6.99-7.03 (m, 3H), 7.10 (d, J = 8.5 Hz, 1H), 7.39 (t, J = 7.7 Hz, 1H), 7.79 (s, 1H), 7.90 (dd, J = 8.7, 2.2 Hz, 1H), 8.03 (d, J = 2.4 Hz, 1H), 8.39 (s, 1H), 8.45 (s, 1H), 8.87 (d, J = 1.4 Hz, 1H), 9.12 (d, J = 2.5 Hz, 1H). MS (ES) m/z 520.2 (M + 1). MP = 139-140° C. |
| Example 2.B-8 | 6-(4-Chloropyrazol-1-yl)-N-[4-[[3-[[5-(trifluoromethyl)-2-pyridyl]oxy]phenyl]methylene]cyclohexyl]pyridine-3-carboxamide<br>$^1$H NMR (400 MHz, DMSO-d$_6$): δ 1.38 (qd, J = 11.8, 3.2 Hz, 1H), 1.52 (qd, J = 11.5, 3.7 Hz, 1H), 1.93-2.11 (m, 2H), 2.10 (t, J = 12.9 Hz, 1H), 2.31 (t, J = 10.6 Hz, 1H), 2.41 (d, J = 14.2 Hz, 1H), 2.83 (d, J = 13.7 Hz, 1H), 4.00-4.09 (m, 1H), 6.31 (s, 1H), 7.00 (s, 1H), 7.04 (d, J = 7.8 Hz, 1H), 7.11 (d, J = 7.8 Hz, 1H), 7.23 (d, J = 8.6 Hz, 1H), 7.40 (t, J = 7.8 Hz, 1H), 7.96 (d, J = 8.6 Hz, 1H), 8.00 (s, 1H), 8.21 (dd, J = 8.8, 2.4 Hz, 1H), 8.38 (dd, J = 8.6, 2.0 Hz, 1H), 8.46 (d, J = 7.6 Hz, 1H), 8.56 (s, 1H), 8.85 (s, 1H), 8.87 (d, J = 2.0 Hz, 1H). MS (ES) m/z 554.2 (M + 1), 555.2 (M + 2). MP = 220-222° C. |
| Example 2.B-9 | 6-(3-Methylpyrazol-1-yl)-N-[4-[[3-[[5-(trifluoromethyl)-2-pyridyl]oxy]phenyl]methylene]cyclohexyl]pyridine-3-carboxamide<br>$^1$H NMR (400 MHz, DMSO-d$_6$): δ 1.39 (qd, J = 13.3, 5.6 Hz, 1H), 1.51 (qd, J = 10.2, 4.8 Hz, 1H), 2.13-2.25 (m, 3H), 2.39 (s, 3H), 2.39-2.46 (m, 2H), 2.89-2.95 (m, 1H), 4.19-4.28 (m, 1H), 5.94 (d, J = 1.1 Hz, 1H), 6.29 (d, J = 2.5 Hz, 1H), 6.33 (s, 1H), 6.99-7.03 (m, 3H), 7.10 (d, J = 7.5 Hz, 1H), 7.39 (t, J = 7.7 Hz, 1H), 7.90 (dd, J = 8.8, 2.3 Hz, 1H), 7.96 (d, J = 8.6 Hz, 1H), 8.14 (dd, J = 8.7, 2.3 Hz, 1H), 8.45 (s, 1H), 8.47 (d, J = 2.5 Hz, 1H), 8.75 (d, J = 2.1 Hz, 1H). MS (ES) m/z 534.2 (M + 1). MP = 171-172° C. |
| Example 2.B-10 | 5-Methyl-6-pyrazol-1-yl-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.32-1.43 (m, 1H), 1.45-1.55 (m, 1H), 2.12-2.26 (m, 3H), 2.37-2.48 (m, 2H), 2.67 (s, 3H), 2.89-2.95 (m, 1H), 4.20-4.28 (m, 1H), 5.95 (d, J = 7.8 Hz, 1H), 6.32 (s, 1H), 6.47 (t, J = 1.7 Hz, 1H), 6.99-7.03 (m, 3H), 7.10 (d, J = 7.5 Hz, 1H), 7.39 (t, J = 7.8 Hz, 1H), 7.77 (s, 1H), 7.90 (dd, J = 8.5, 2.4 Hz, 1H), 8.04 (d, J = 1.9 Hz, 1H), 8.35 (d, J = 2.7 Hz, 1H), 8.45 (s, 1H), 8.62 (d, J = 1.9 Hz, 1H). MS (ES) m/z 534.3 (M + 1). MP = 73-75° C. |
| Example 2.B-11 | 6-(3,5-Dimethyl-1H-pyrazol-4-yl)-N-[4-[[3-[[5-(trifluoromethyl)-2-pyridyl]oxy]phenyl]methylene]cyclohexyl]pyridine-3-carboxamide<br>$^1$H NMR (400 MHz, DMSO-d$_6$): δ 1.39 (qd, J = 11.5, 3.9 Hz, 1H), 1.51 (qd, J = 12.2, 3.9 Hz, 1H), 1.93-2.01 (m, 2H), 2.11 (t, J = 13.2 Hz, 1H), 2.30 (s, 3H), 2.40 (s, 3H), 2.29-2.4 (m, 2H), 2.85 (d, J = 13.7 Hz, 1H), 4.02-4.11 (m, 1H), 6.33 (s, 1H), 7.02 (s, 1H), 7.06 (d, J = 8.4 Hz, 1H), 7.13 (d, J = 7.6 Hz, 1H), 7.26 (d, J = 8.8 Hz, 1H), 7.43 (t, J = 7.8 Hz, 1H), 7.48 (d, J = 8.6 Hz, 1H), 8.15 (dd, J = 8.3, 1.9 Hz, 1H), 8.24 (dd, J = 8.6, 2.0 Hz, 1H), 8.38 (d, J = 7.9 Hz, 1H), 8.59 (s, 1H), 9.00 (d, J = 2.2 Hz, 1H), 12.51 (brs, 1H). MS (ES) m/z 548.3 (M + 1). MP = 208-210° C. |
| Example 2.B-12 | Ethyl1-[5-[[4-[[3-[[5-(trifluoromethyl)-2-pyridyl]oxy]phenyl]methylene]cyclohexyl]carbamoyl]-2-pyridyl]pyrazole-4-carboxylate<br>$^1$H NMR (400 MHz, DMSO-d$_6$): δ 1.31 (t, J = 7.3 Hz, 3H), 1.40 (qd, J = 12.0, 4.0 Hz, 1H), 1.53 (qd, J = 12.0, 4.4 Hz, 1H), 1.95-2.04 (m, 2H), 2.08-2.15 (m, 1H), 2.29-2.45 (m, 2H), 2.85 (d, J = 13.9 Hz, 1H), 4.03-4.12 (m, 1H), 4.28 (q, J = 7.1 Hz, 2H), 6.33 (s, 1H), 7.02 (s, 1H), 7.06 (d, J = 8.1 Hz, 1H), 7.13 (d, J = 7.6 Hz, 1H), 7.25 (d, J = 8.8 Hz, 1H), 7.42 (t, J = 8.0 Hz, 1H), 8.05 (d, J = 8.5 Hz, 1H), 8.24 (dd, J = 8.5, 2.4 Hz, 1H), 8.27 (s, 1H), 8.44 (dd, J = 8.6, 2.2 Hz, 1H), 8.55 (d, J = 7.5 Hz, 1H), 8.58 (s, 1H), 8.93 (d, J = 2.0 Hz, 1H), 9.03 (s, 1H). MS (ES) m/z 592.3 (M + 1). |

-continued

| | |
|---|---|
| Example 2.B-13 | 6-(1,2,4-Triazol-4-yl)-N-[4-[[3-[[5-(trifluoromethyl)-2-pyridyl]oxy]phenyl]methylene]cyclohexyl]pyridine-3-carboxamide<br>$^1$H NMR (400 MHz, DMSO-d$_6$): δ 1.36-1.46 (m, 1H), 1.48-1.58 (m, 1H), 1.95-2.04 (m, 2H), 2.12 (t, J = 12.0 Hz, 1H), 2.33 (t, J = 11.9 Hz, 1H), 2.43 (d, J = 14.2 Hz, 1H), 2.85 (d, J = 13.7 Hz, 1H), 4.03-4.12 (m, 1H), 6.33 (s, 1H), 7.02 (s, 1H), 7.06 (d, J = 8.1 Hz, 1H), 7.13 (d, J = 7.4 Hz, 1H), 7.25 (d, J = 8.8 Hz, 1H), 7.43 (t, J = 7.9 Hz, 1H), 7.96 (d, J = 8.5 Hz, 1H), 8.24 (d, J = 8.1 Hz, 1H), 8.37 (s, 1H), 8.46 (d, J = 6.8 Hz, 1H), 8.55-8.59 (m, 2H), 8.94 (s, 1H), 9.46 (s, 1H). MS (ES) m/z 521.2 (M + 1). MP = 243-244° C |
| Example 2.B-14 | 6-(Triazol-1-yl)-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.38 (qd, J = 11.0, 7.3 Hz, 1H), 1.51 (qd, J = 11.5, 5.2 Hz, 1H), 2.14-2.28 (m, 3H), 2.38-2.50 (m, 2H), 2.91-2.96 (m, 1H), 4.21-4.30 (m, 1H), 6.00 (d, J = 7.6 Hz, 1H), 6.34 (s, 1H), 7.00-7.04 (m, 3H), 7.10 (d, J = 7.6 Hz, 1H), 7.39 (t, J = 7.6 Hz, 1H), 7.86 (s, 1H), 7.91 (dd, J = 8.6, 2.2 Hz, 1H), 8.29 (s, 2H), 8.45 (s, 1H), 8.63 (s, 1H), 8.88 (s, 1H). MS (ES) m/z 521.2 (M + 1). MP = 147-149° C. |
| Example 2.B-15 | 6-(Triazol-2-yl)-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.36-1.45 (m, 1H), 1.46-1.56 (m, 1H), 2.14-2.26 (m, 3H), 2.38-2.50 (m, 2H), 2.94 (d, J = 13.9 Hz, 1H), 4.21-4.30 (m, 1H), 5.98 (d, J = 7.6 Hz, 1H), 6.33 (s, 1H), 6.99-7.03 (m, 3H), 7.10 (d, J = 8.0 Hz, 1H), 7.39 (t, J = 7.6 Hz, 1H), 7.90 (dd, J = 8.8, 2.2 Hz, 1H), 7.95 (s, 2H), 8.16 (d, J = 8.3 Hz, 1H), 8.31 (dd, J = 8.8, 2.0 Hz, 1H), 8.45 (s, 1H), 8.89 (s, 1H). MS (ES) m/z 521.2 (M + 1). MP = 176-178° C. |
| Example 2.B-16 | Ethyl-1-[5-[[4-[[3-[[5-(trifluoromethyl)-2-pyridyl]oxy]phenyl]methylene]cyclohexyl]carbamoyl]-2-pyridyl]pyrazole-3-carboxylate<br>MS (ES) m/z 592.2 (M + 1). |
| Example 2.B-17 | 2-Pyrazol-1-yl-N-[4-[[3-[[5-(trifluoromethyl)-2-pyridyl]oxy]phenyl]methylene]cyclohexyl]pyrimidine-5-carboxamide<br>$^1$H NMR (400 MHz, DMSO-d$_6$): δ 1.41 (qd, J = 12.5, 4.0 Hz, 1H), 1.53 (qd, J = 12.2, 3.9 Hz, 1H), 1.96-2.06 (m, 2H), 2.10-2.17 (m, 1H), 2.31-2.46 (m, 2H), 2.85 (d, J = 13.6 Hz, 1H), 4.03-4.12 (m, 1H), 6.34 (s, 1H), 6.65 (t, J = 2.2 Hz, 1H), 7.02 (s, 1H), 7.07 (dd, J = 8.1, 2.0 Hz, 1H), 7.13 (d, J = 7.8 Hz, 1H), 7.25 (d, J = 8.6 Hz, 1H), 7.43 (t, J = 7.8 Hz, 1H), 7.92 (s, 1H), 8.24 (dd, J = 8.8, 2.7 Hz, 1H), 8.58 (s, 1H), 8.62 (d, J = 7.8 Hz, 1H), 8.72 (d, J = 2.7 Hz, 1H), 9.20 (s, 2H). MS (ES) m/z 521.2 (M + 1). MP = 202-204° C. |
| Example 2.B-18 | 6-(3-Methyl-1H-pyrazol-4-yl)-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.32-1.42 (m, 1H), 1.45-1.55 (m, 1H), 2.02-2.25 (m, 3H), 2.37-2.49 (m, 2H), 2.65 (s, 3H), 2.92 (d, J = 14.1 Hz, 1H), 4.21-4.30 (m, 1H), 5.99 (d, J = 7.6 Hz, 1H), 6.33 (s, 1H), 7.00-7.04 (m, 3H), 7.11 (d, J = 7.7, 1H), 7.39 (t, J = 7.6 Hz, 1H), 7.53 (d, J = 8.2 Hz, 1H), 7.60 (s, 1H), 7.90 (d, J = 8.2 Hz, 1H), 8.01 (s, 1H), 8.09 (d, J = 7.8 Hz, 1H), 8.46 (s, 1H), 8.93 (s, 1H). MS (ES) m/z 534.3 (M + 1). (M + 1). MP = 184-186° C. |
| Example 2.B-19 | 6-(5-Isopropyl-1H-pyrazol-3-yl)-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.34 (d, J = 6.9 Hz, 6H), 1.33-1.43 (m, 1H), 1.45-1.55 (m, 1H), 2.12-2.26 (m, 3H), 2.37-2.48 (m, 2H), 2.89-2.95 (m, 1H), 3.01-3.11 (m, 1H), 4.20-4.29 (m, 1H), 6.00 (d, J = 7.8 Hz, 1H), 6.32 (s, 1H), 6.69-7.03 (m, 4H), 7.10 (d, J = 7.6 Hz, 1H), 7.38 (t, J = 7.8 Hz, 1H), 7.82 (d, J = 8.1 Hz, 1H), 7.90 (dd, J = 8.8, 2.4 Hz, 1H), 8.11 (dd, J = 8.3, 2.2 Hz, 1H), 8.45 (s, 1H), 8.92 (d, J = 1.7 Hz, 1H). MS(ES) m/z 562.1 (M + 1). MP = 131-133° C. |
| Example 2.B-20 | 6-(5-Ethyl-1H-pyrazol-3-yl)-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.45-1.55 (m, 1H), 1.33-1.42 (m, 1H), 1.33 (t, J = 7.6 Hz, 3H), 2.11-2.25 (m, 3H), 2.38-2.48 (m, 2H), 2.75 (q, J = 7.6 Hz, 2H), 2.89-2.95 (m, 1H), 4.19-4.30 (m, 1H), 6.01 (d, J = 7.8 Hz, 1H), 6.32 (s, 1H), 6.68 (s, 1H), 6.99-7.03 (m, 3H), 7.10 (d, J = 7.6 Hz, 1H), 7.39 (t, J = 7.6 Hz, 1H), 7.81 (d, J = 8.3 Hz, 1H), 7.90 (dd, J = 8.5, 2.2 Hz, 1H), 8.11 (dd, J = 8.4, 2.0 Hz, 1H), 8.45 (s, 1H), 8.92 (d, J = 1.4 Hz, 1H). MS(ES) m/z 548.3 (M + 1). MP = 182-184° C. |
| Example 2.B-21 | 6-(3-Cyclopropyl-1H-pyrazol-4-yl)-N-[4-[[3-[[5-(trifluoromethyl)-2-pyridyl]oxy]phenyl]methylene]cyclohexyl]pyridine-3-carboxamide<br>$^1$H NMR (400 MHz, DMSO-d$_6$): δ 0.82-0.87 (m, 2H), 0.97 (brs, 2H), 1.40 (qd, J = 11.0, 3.2 Hz, 1H), 1.52 (qd, J = 11.7, 3.7 Hz, 1H), 1.92-2.03 (m, 2H), 2.11 (t, J = 12.7 Hz, 1H), 2.33 (t, J = 13.0 Hz, 1H), 2.43 (d, J = 13.7 Hz, 1H), 2.64-2.71 (m, 1H), 2.84 (d, J = 13.9 Hz, 1H), 4.02-4.10 (m, 1H), 6.32 (s, 1H), 7.02 (s, 1H), 7.06 (d, J = 8.0 Hz, 1H), 7.13 (d, J = 7.5 Hz, 1H), 7.25 (d, J = 8.6 Hz, 1H), 7.43 (t, J = 7.9 Hz, 1H), 7.78 (d, J = 8.6 Hz, 1H), 8.03 (brs, 1H), 8.14 (dd, J = 8.3, 2.2 Hz, 1H), 8.25 (dd, J = 8.8, 2.4 Hz, 1H), 8.35 (d, J = 7.9 Hz, 1H), 8.58 (s, 1H), 8.95 (d, J = 2.0 Hz, 1H), 12.65 (brs, 1H). MS (ES) m/z 560.3 (M + 1). MP = 108-110° C. |
| Example 2.B-22 | 6-(3-Isopropyl-1H-pyrazol-4-yl)-N-[4-[[3-[[5-(trifluoromethyl)-2-pyridyl]oxy]phenyl]methylene]cyclohexyl]pyridine-3-carboxamide<br>$^1$H NMR (400 MHz, DMSO-d$_6$): δ 1.26 (d, J = 6.9 Hz, 6H), 1.39 (qd, J = 11.3, 4.9 Hz, 1H), 1.52 (qd, J = 11.2, 3.7 Hz, 1H), 1.92-2.02 (m, 2H), 2.11 (t, J = 12.5 Hz, 1H), 2.33 (t, J = 13.2 Hz, 1H), 2.43 (d, J = 13.7 Hz, 1H), 2.85 (d, J = 13.9 Hz, 1H), 4.02-4.08 (m, 1H), 4.09-4.14 (m, 1H), 6.32 (s, 1H), 7.02 (s, 1H), 7.05 |

-continued

| | |
|---|---|
| | (d, J = 8.0 Hz, 1H), 7.13 (d, J = 7.9 Hz, 1H), 7.25 (d, J = 8.8 Hz, 1H), 7.42 (t, J = 7.8 Hz, 1H), 7.69 (d, J = 8.3 Hz, 1H), 8.03 (brs, 1H), 8.11 (dd, J = 8.6, 2.2 Hz, 1H), 8.24 (dd, J = 8.6, 2.2 Hz, 1H), 8.34 (d, J = 8.8 Hz, 1H), 8.58 (s, 1H), 8.96 (d, J = 2.0 Hz, 1H), 12.87 (brs, 1H). MS (ES) m/z 562.1 (M + 1). MP = 97-99° C. |
| Example 2.B-23 | 6-(4-Hydroxy-4-methyl-1-piperidyl)-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.25-1.36 (m, 1H), 1.30 (s, 3H), 1.45 (qd, J = 11.0, 6.9 Hz, 1H), 1.64-1.67(m, 4H), 2.07-2.22 (m, 3H), 2.35-2.45 (m, 2H), 2.88 (d, J = 14.0 Hz, 1H), 3.42-3.49 (m, 2H), 4.02 (dt, J = 13.2, 4.1 Hz, 2H), 4.15-4.24 (m, 1H), 5.76 (d, J = 7.9 Hz, 1H), 6.30 (s, 1H), 6.64 (d, J = 9.0 Hz, 1H), 6.98-7.02 (m, 3H), 7.09 (d, J = 7.8 Hz, 1H), 7.38 (t, J = 7.8 Hz, 1H), 7.86 (dd, J = 9.1, 2.5 Hz, 1H), 7.90 (dd, J = 8.8, 2.2 Hz, 1H), 8.45 (s, 1H), 8.51 (d, J = 2.2 Hz, 1H). MS(ES) m/z 567.1 (M + 1). MP = 86-87° C. |
| Example 2.B-24 | 6-[1-(2-Hydroxyethyl)pyrazol-4-yl]-N-[4-[[3-[[5-(trifluoromethyl)-2-pyridyl]oxy]phenyl]methylene]cyclohexyl]pyridine-3-carboxamide<br>$^1$H NMR (400 MHz, DMSO-d$_6$): δ 1.35-1.45 (m, 1H), 1.47-1.57 (m, 1H), 1.92-2.01 (m, 2H), 2.07-2.14 (m, 1H), 2.28-2.45 (m, 2H), 2.84 (d, J = 13.7 Hz, 1H), 3.77 (q, J = 5.4 Hz, 2H), 4.01-4.11 (m, 1H), 4.19 (t, J = 5.4 Hz, 2H), 4.96 (t, J = 5.1 Hz, 1H), 6.33 (s, 1H), 7.02 (s, 1H), 7.06 (d, J = 8.1 Hz, 1H), 7.13 (d, J = 7.6 Hz, 1H), 7.25 (d, J = 8.6 Hz, 1H), 7.43 (t, J = 8.1 Hz, 1H), 7.74 (d, J = 8.3 Hz, 1H), 8.08 (s, 1H), 8.15 (d, J = 8.3 Hz, 1H), 8.25 (d, J = 8.6 Hz, 1H), 8.35-8.37 (m, 2H), 8.59 (s, 1H), 8.92 (s, 1H). MS (ES) m/z 564.1 (M + 1). MP = 138-141° C. |

Following examples were prepared from Intermediate 3A and appropriate carboxylic acid or carboxylic acid chloride selected from Intermediates 4-6 using either of the procedure described for Example 2.1, Example 2.2, Example 2.3.

| | |
|---|---|
| Example 2.C-1 | 6-Amino-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.28-1.39 (m, 1H), 1.41-1.50 (m, 1H), 2.09-2.20 (m, 3H), 2.35-2.45 (m, 2H), 2.90 (d, J = 14.2 Hz, 1H), 4.15-4.23 (m, 1H), 4.79 (brs, 2H), 5.80 (d, J = 7.6 Hz, 1H), 6.31 (s, 1H), 6.49 (d, J = 8.5 Hz, 1H), 6.99-7.02 (m, 3H), 7.10 (d, J = 7.6 Hz, 1H), 7.38 (t, J = 7.8 Hz, 1H), 7.85-7.91 (m, 2H), 8.44 (brs, 2H). MS (ES) m/z 469.3 (M + 1). MP = 156-157° C. |
| Example 2.C-2 | 6-Methoxy-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.30-1.51 (m, 2H), 2.11-2.22 (m, 3H), 2.35-2.44 (m, 2H), 2.90 (d, J = 14.0 Hz, 1H), 3.97 (s, 3H), 4.14-4.24 (m, 1H), 5.89 (d, J = 7.6 Hz, 1H), 6.31 (s, 1H), 6.77 (d, J = 8.8 HZ, 1H), 6.99-7.03 (m, 3H), 7.10 (d, J = 7.9 Hz, 1H), 7.38 (t, J = 7.8 Hz, 1H), 7.90 (d, J = 8.6 Hz, 1H), 7.97 (dd, J = 8.6, 2.2 Hz, 1H), 8.45 (s, 1H), 8.55 (s, 1H). MS (ES) m/z 484.2 (M + 1). MP = 43-44° C. |
| Example 2.C-3 | 6-Hydroxy-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.32 (qd, J = 12.0, 4.4 Hz, 1H), 11.44 (qd, d, J = 11.7, 4.6 Hz, 1H), 2.05-2.17 (m, 3H), 2.33-2.44 (m, 2H), 2.9 (d, J = 13.7 Hz, 1H), 4.10-4.29 (m, 1H), 6.09 (t, J = 7.6 Hz, 1H), 6.30 (s, 1H), 6.54 (d, J = 9.6 Hz, 1H), 6.98-7.02 (m, 3H), 7.08 (d, J = 7.6 Hz, 1H), 7.38 (t, J = 7.6 Hz, 1H), 7.78 (dd, J = 9.6, 2.2 Hz, 1H), 7.90 (dd, J = 8.6, 2.0 Hz, 1H), 8.03 (d, J = 1.7 Hz, 1H), 8.44 (s, 1H), 12.76 (brs, 1H). MS (ES) m/z 470.2 (M + 1). MP = 165-166° C. |
| Example 2.C-4 | 5-Hydroxy-N-[4-[[3-[[5-(trifluoromethyl)-2-pyridyl]oxy]phenyl]methylene]cyclohexyl]pyridine-3-carboxamide<br>$^1$H NMR (400 MHz, DMSO-d$_6$): δ 1.32-1.42 (m, 1H), 1.45-1.55 (m, 1H), 1.91-1.99 (m, 2H), 2.09 (t, J = 10.8 Hz, 1H), 2.28-2.50 (m, 2H), 2.84 (d, J = 13.5 Hz, 1H), 3.98-4.18 (m, 1H), 6.31 (s, 1H), 7.01 (s, 1H), 7.06 (d, J = 8.1 Hz, 1H), 7.12 (d, J = 7.6 Hz, 1H), 7.25 (d, J = 8.5 Hz, 1H), 7.42 (t, J = 7.8 Hz, 1H), 7.50 (brs, 1H), 8.21-8.25 (m, 2H), 8.37 (d, J = 7.5 Hz, 1H), 8.43 (s, 1H), 8.58 (s, 1H), 10.34 (brs, 1H). MS (ES) m/z 470.1 (M + 1). MP = 210-211° C. |
| Example 2.C-5 | 2-Amino-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.28-1.50 (m, 2H), 2.08-2.19 (m, 3H), 2.35-2.44 (m, 2H), 2.88-2.92 (m, 1H), 4.12-4.21 (m, 1H), 5.88 (d, J = 7.0 Hz, 1H), 6.31 (s, 1H), 6.34 (brs, 2H), 6.59 (dd, J = 7.6, 4.9 Hz, 1H), 6.98-7.03 (m, 3H), 7.09 (d, J = 7.3 Hz, 1H), 7.38 (t, J = 7.8 Hz, 1H), 7.56 (dd, J = 7.4, 1.0 Hz, 1H), 7.90 (dd, J = 7.8, 2.4 Hz, 1H), 8.15 (d, J = 3.4 Hz, 1H), 8.45 (s, 1H). MS (ES) m/z 469.2 (M + 1). MP = 59-61° C. |
| Example 2.C-6 | 2-Amino-N-[4-[[3-[[5-(trifluoromethyl)-2-pyridyl]oxy]phenyl]methylene]cyclohexyl]pyrimidine-5-carboxamide<br>$^1$H NMR (400 MHz, DMSO-d$_6$): δ 1.27-1.37 (m, 1H), 1.40-1.49 (m, 1H), 1.80-1.96 (m, 2H), 2.06 (t, J = 12.8 Hz, 1H), 2.27 (t, J = 13.2 Hz, 1H), 2.38 (d, J = 13.6 Hz, 1H), 2.80 (d, J = 13.6 Hz, 1H), 3.93-4.02 (m, 1H), 6.29 (s, 1H), 6.99 (s, 1H), 7.03 (d, J = 8.1 Hz, 1H), 7.10 (d, J = 7.8 Hz, 1H), 7.17 (s, 2H), 7.22 (d, J = 8.6 Hz, 1H), 7.40 (t, J = 7.8 Hz, 1H), 8.02 (d, J = 7.9 Hz, 1H), 8.22 (dd, J = 8.6, 2.0 Hz, 1H), 8.56 (s, 1H), 8.63 (s, 2H). MS (ES) m/z 470.2 (M + 1). MP = 187-190° C. |

| | |
|---|---|
| Example 2.C-7 | 6-Amino-5-methyl-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.25-1.38 (m, 1H), 1.41-1.51 (m, 1H), 2.10-2.21 (m, 6H), 2.35-2.45 (m, 2H), 2.87-2.92 (m, 1H), 4.15-4.25 (m, 1H), 4.74 (brs, 2H), 5.79 (d, J = 7.3 Hz, 1H), 6.31 (s, 1H), 6.99-7.02 (m, 3H), 7.10 (d, J = 7.5 Hz, 1H), 7.38 (t, J = 7.6 Hz, 1H), 7.72 (s, 1H), 7.88-7.91 (m, 1H), 8.30 (s, 1H), 8.45 (s, 1H). MS (ES) m/z 483.1 (M + 1). MP = 165-168° C. |
| Example 2.C-8 | 6-(1-Hydroxy-1-methyl-ethyl)-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.31-1.42 (m, 1H), 1.48 (qd, J = 11.6, 5.2 Hz, 1H), 1.55 (s, 6H), 2.10-2.25 (m, 3H), 2.36-2.48 (m, 2H), 2.89-2.95 (m, 1H), 4.19-4.29 (m, 1H), 4.72 (s, 1H), 6.00 (d, J = 7.7 Hz, 1H), 6.32 (s, 1H), 6.98-7.03 (m, 3H), 7.09 (d, J = 7.5 Hz, 1H), 7.39 (t, J = 7.7 Hz, 1H), 7.46 (d, J = 8.3 Hz, 1H), 7.90 (dd, J = 8.5, 2.5 Hz, 1H), 8.11 (dd, J = 8.3, 2.3 Hz, 1H), 8.44 (s, 1H), 8.84 (d, J = 2.1 Hz, 1H). MS (ES) m/z 512.0 (M + 1). MP = 62-63° C. |
| Example 2.C-9 | 6-(Hydroxymethyl)-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.36 (qd, J = 12.1, 5.4 Hz, 1H), 1.49 (qd, J = 11.5, 5.3 Hz, 1H), 2.10-2.26 (m, 3H), 2.36-2.48 (m, 2H), 2.89-2.95 (m, 1H), 3.61 (brs, 1H), 4.18-4.28 (m, 1H), 4.81 (s, 2H), 6.02 (d, J = 7.9 Hz, 1H), 6.32 (s, 1H), 6.99-7.03 (m, 3H), 7.10 (d, J = 7.7 Hz, 1H), 7.34 (d, J = 8.4 Hz, 1H), 7.38 (t, J = 7.9 Hz, 1H), 7.90 (dd, J = 8.8, 2.3 Hz, 1H), 8.08 (dd, J = 8.2, 2.1 Hz, 1H), 8.45 (s, 1H), 8.89 (d, J = 1.2 Hz, 1H). MS (ES) m/z 484.0 (M + 1). MP = 117-118° C. |
| Example 2.C-10 | 5-Amino-N-[4-[[3-[[5-(trifluoromethyl)-2-pyridyl]oxy]phenyl]methylene]cyclohexyl]pyrazine-2-carboxamide<br>$^1$H NMR (400 MHz, DMSO-d$_6$): δ 1.47 (qd, J = 12.0, 4.0 Hz, 1H), 1.57 (qd, J = 12.0, 4.4 Hz, 1H), 1.85-1.93 (m, 2H), 2.06-2.14 (m, 1H), 2.29-2.41 (m, 3H), 2.83 (d, J = 14.4 Hz, 1H), 3.98-4.06 (m, 1H), 6.31 (s, 1H), 7.03 (s, 1H), 7.05-7.08 (m, 2H), 7.14 (d, J = 7.8 Hz, 1H), 7.26 (d, J = 8.8 Hz, 1H), 7.43 (t, J = 7.9 Hz, 1H), 7.83 (s, 1H), 8.08 (d, J = 8.6 Hz, 1H), 8.25 (dd, J = 8.8, 2.6 Hz, 1H), 8.48 (s, 1H), 8.59 (s, 1H). MS (ES) m/z 470.1 (M + 1). MP = 105-106° C. |
| Example 2.C-11 | 6-Amino-N-[4-[[3-[[5-(trifluoromethyl)-2-pyridyl]oxy]phenyl]methylene]cyclohexyl]pyridazine-3-carboxamide<br>$^1$H NMR (400 MHz, DMSO-d$_6$): δ 1.49 (qd, J = 12.4, 4.0 Hz, 1H), 1.60 (qd, J = 12.3, 4.4 Hz, 1H), 1.85-1.94 (m, 2H), 2.06-2.14 (m, 1H), 2.28-2.42 (m, 2H), 2.81-2.85 (m, 1H), 3.98-4.09 (m, 1H), 6.30 (s, 1H), 6.83 (d, J = 9.2 Hz, 1H), 6.93 (s, 2H), 7.01 (s, 1H), 7.05 (d, J = 8.1 Hz, 1H), 7.13 (d, J = 7.7 Hz, 1H), 7.25 (d, J = 8.8 Hz, 1H), 7.41 (t, J = 8.0 Hz, 1H), 7.75 (d, J = 9.2 Hz, 1H), 8.23 (dd, J = 8.6, 2.5 Hz, 1H), 8.50 (d, J = 8.6 Hz, 1H), 8.58 (s, 1H). MS (ES) m/z 470.2 (M + 1). MP = 110-112° C. |

Following examples were prepared from Intermediate 3A and appropriate carboxylic acid or carboxylic acid chloride selected from Intermediates 4-6 using the procedure described for Example 2.1, Example 2.2, Example 2.3.

| | |
|---|---|
| Example 2.D-1 | N-[4-[[3-[[5-(Trifluoromethyl)-2-pyridyl]oxy]phenyl]methylene]cyclohexyl]imidazo[1,2-a]pyridine-2-carboxamide<br>$^1$H NMR (400 MHz, CDCl$_3$): δ 1.45 (qd, J = 10.8, 2.8 Hz, 1H), 1.5 (qd, J = 10.8, 2.8 Hz, 1H), 2.10-2.21 (m, 3H), 2.39-47 (, 2H), 2.91 (d, J = 14.0 Hz, 1H), 4.22-4.25 (m, 1H), 6.30 (s, 1H), 6.85 (t, J = 6.8 Hz, 1H), 6.98-7.02 (m, 3H), 7.10 (d, J = 7.6 Hz, 1H), 7.22-7.25 (m, 1H), 7.29 (d, J = 8.8 Hz, 1H), 7.38 (t, J = 8.4 Hz, 1H), 7.56 (d, J = 8.8 Hz, 1H), 7.90 (dd, J = 8.4, 2.0 Hz, 1H), 8.14-8.15 (m, 2H), 8.45 (brs, 1H). MS (ES) m/z 493.3 (M + 1). MP = 68-70° C. |
| Example 2.D-2 | N-[4-[[3-[[5-(Trifluoromethyl)-2-pyridyl]oxy]phenyl]methylene]cyclohexyl]-5,6,7,8-tetrahydroimidazo[1,2-a]pyridine-2-carboxamide<br>$^1$H NMR (400 MHz, CDCl$_3$): δ 1.35 (qd, J = 11.6, 4.0 Hz, 1H), 1.47 (qd, J = 12.0, 4.8 Hz, 1H), 1.93-1.99 (m, 4H), 2.02-2.07 (m, 1H), 2.09-2.14 (m, 2H), 2.35-2.43 (m, 2H), 2.81-2.88 (m, 3H), 3.98 (t, J = 6.0 Hz, 2H), 4.11-4.16 (m, 1H), 6.27 (s, 1H), 6.92 (d, J = 8.4 Hz, 1H), 6.98-6.02 (m, 3H), 7.08 (d, J = 7.6 Hz, 1H), 7.36 (t, J = 7.6 Hz, 1H), 7.40 (s, 1H), 7.89 (dd, J = 8.8, 2.4 Hz, 1H), 8.45 (brs, 1H). MS (ES) m/z 497.3 (M + 1). MP = 64-66° C. |
| Example 2.D-3 | N-[4-[[3-[[5-(Trifluoromethyl)-2-pyridyl]oxy]phenyl]methylene]cyclohexyl]thiazolo[5,4-b]pyridine-2-carboxamide<br>$^1$H NMR (400 MHz, CDCl$_3$): δ 1.45-1.49 (m, 2H), 2.01-2.24 (m, 3H), 2.40-2.46 (m, 2H), 2.91 (d, J = 13.2 Hz, 1H), 4.22-4.25 (m, 1H), 6.33 (s, 1H), 6.99-7.03 (m, 3H), 7.10 (d, J = 7.6 Hz, 1H), 7.32 (d, J = 8.1 Hz, 1H), 7.39 (t, J = 7.9 Hz, 1H), 7.50 (dd, J = 8.4, 4.7 Hz, 1H), 7.90 (dd, J = 8.8, 2.4 Hz, 1H), 8.30 (dd, J = 8.3, 1.2 Hz, 1H), 8.45 (s, 1H), 8.70 (dd, J = 4.7, 1.5 Hz, 1H). MS (ES) m/z 511.3 (M + 1). MP = 141-143° C. |
| Example 2.D-4 | N-[4-[[3-[[5-(Trifluoromethyl)-2-pyridyl]oxy]phenyl]methylene]cyclohexyl]imidazo[1,2-b]pyridazine-3-carboxamide<br>$^1$H NMR (400 MHz, CDCl$_3$): δ 1.43 (qd, J = 12.0, 4.4 Hz, 1H), 1.55 (qd, J = 11.7, 4.8 Hz, 1H), 2.11-2.21 (m, 3H), 2.36-2.48 (m, 2H), 2.91 (d, J = 13.7 Hz, 1H), 4.19-4.29 (m, 1H), 6.31 (s, 1H), 6.86 (t, J = 6.6 Hz, 1H), 6.99-7.03 (m, 3H), 7.11 (d, J = 7.5 Hz, 1H), 7.23-7.31 (m, 1H), 7.39 (t, J = 7.8 Hz, 1H), 7.56 |

-continued

|  |  |
|---|---|
|  | (d, J = 9.3 Hz, 1H), 7.90 (dd, J = 8.5, 2.2 Hz, 1H), 8.15 (t, J = 3.4 Hz, 2H), 8.46 (s, 1H). MS (ES) m/z 493.3 (M + 1). MP = 72-74° C. |
| Example 2.D-5 | N-[4-[[3-[[5-(Trifluoromethyl)-2-pyridyl]oxy]phenyl]methylene] cyclohexyl]-1H-pyrrolo[2,3-b]pyridine-5-carboxamide<br>$^1$H NMR (400 MHz, CDCl$_3$): δ 1.39 (qd, J = 11.2, 2.4 Hz, 1H), 1.51 (qd, J = 11.1, 5.9 Hz, 1H), 2.14-2.26 (m, 3H), 2.38-2.48 (m, 2H), 2.89-2.94 (m, 1H), 4.22-4.31 (m, 1H), 6.01 (d, J = 7.9 Hz, 1H), 6.32 (s, 1H), 6.59-6.60 (m, 1H), 6.99-7.03 (m, 3H), 7.11 (d, J = 7.7 Hz, 1H), 7.37-7.40 (m, 2H), 7.90 (dd, J = 8.7, 2.2 Hz, 1H), 8.36 (d, J = 1.6 Hz, 1H), 8.45 (s, 1H), 8.73 (s, 1H), 9.34 (brs, 1H). MS (ES) m/z 493.3 (M + 1). MP = 217-218° C. |
| Example 2.D-6 | N-[4-[[3-[[5-(Trifluoromethyl)-2-pyridyl]oxy]phenyl]methylene] cyclohexyl]-1H-indole-3-carboxamide<br>$^1$H NMR (400 MHz, CDCl$_3$): δ 1.36-1.46 (m, 1H), 1.48-1.56 (m, 1H), 2.16-2.27 (m, 3H), 2.38-2.45 (m, 2H), 2.87-2.93 (m, 1H), 4.26-4.36 (m, 1H), 5.86 (d, J = 7.8 Hz, 1H), 6.32 (s, 1H), 6.99-7.03 (m, 3H), 7.10 (d, J = 7.8 Hz, 1H), 7.25-7.28 (m, 2H), 7.39 (t, J = 8.0 Hz, 1H), 7.42-7.45 (m, 1H), 7.78 (d, J = 2.7 Hz, 1H), 7.90 (d, J = 8.5 Hz, 2H), 8.45 (s, 1H), 8.52 (brs, 1H). MS (ES) m/z 492.2 (M + 1). MP = 90-93° C. |
| Example 2.D-7 | N-[4-[[3-[[5-(Trifluoromethyl)-2-pyridyl]oxy]phenyl]methylene] cyclohexyl]-1H-indole-2-carboxamide<br>$^1$H NMR (400 MHz, CDCl$_3$): δ 1.38 (qd, J = 11.5, 3.4 Hz, 1H), 1.50 (qd, J = 11.2, 4.9 Hz, 1H), 2.12-2.25 (m, 3H), 2.37-2.48 (m, 2H), 2.90-2.95 (m, 1H), 4.20-4.29 (m, 1H), 6.03 (d, J = 7.1 Hz, 1H), 6.32 (s, 1H), 6.81 (s, 1H), 7.00-7.03 (m, 3H), 7.10 (d, J = 7.6 Hz, 1H), 7.15 (d, J = 7.6 Hz, 1H), 7.29 (t, J = 7.3 Hz, 1H), 7.39 (t, J = 7.8 Hz, 1H), 7.44 (d, J = 8.3 Hz, 1H), 7.64 (d, J = 8.1 Hz, 1H), 7.90 (d, J = 8.6 Hz, 1H), 8.45 (s, 1H), 9.29 (brs, 1H). MS (ES) m/z 492.2 (M + 1). MP = 151-152° C. |
| Example 2.D-8 | N-[4-[[3-[[5-(Trifluoromethyl)-2-pyridyl]oxy]phenyl]methylene] cyclohexyl]quinoline-3-carboxamide<br>$^1$H NMR (400 MHz, CDCl$_3$): δ 1.37-1.48 (m, 1H), 1.50-1.59 (m, 1H), 2.17-2.29 (m, 3H), 2.39-2.50 (m, 2H), 2.92-2.97 (m, 1H), 4.25-4.34 (m, 1H), 6.16 (d, J = 7.8 Hz, 1H), 6.33 (s, 1H), 6.99-7.03 (m, 3H), 7.10 (d, J = 7.3 Hz, 1H), 7.39 (t, J = 7.8 Hz, 1H), 7.63 (t, J = 7.3 Hz, 1H), 7.81 (t, J = 7.1 Hz, 1H), 7.89-7.93 (m, 2H), 8.16 (d, J = 8.3 Hz, 1H), 8.45 (s, 1H), 8.58 (d, J = 2.0 Hz, 1H), 9.24 (d, J = 1.9, 1H). MS (ES) m/z 504.2 (M + 1). MP = 94-96° C. |
| Example 2.D-9 | 1-Methyl-N-[4-[[3-[[5-(trifluoromethyl)-2-pyridyl]oxy]phenyl]methylene] cyclohexyl]pyrrolo[2,3-b]pyridine-5-carboxamide<br>$^1$H NMR (400 MHz, DMSO-d$_6$): δ 1.41 (qd, J = 11.5, 3.0 Hz, 1H), 1.53 (qd, J = 11.5, 4.0 Hz, 1H), 1.95-2.03 (m, 2H), 2.11 (t, J = 12.4 Hz, 1H), 2.33 (t, J = 9.6 Hz, 1H), 2.43 (d, J = 13.2 Hz, 1H), 2.85 (d, J = 13.7 Hz, 1H), 3.85 (s, 3H), 4.01-4.11 (m, 1H), 6.33 (s, 1H), 6.57 (d, J = 3.4 Hz, 1H), 7.03 (s, 1H), 7.06 (d, J = 8.0 Hz, 1H), 7.14 (d, J = 7.6 Hz, 1H), 7.25 (d, J = 8.5 Hz, 1H), 7.43 (t, J = 7.8 Hz, 1H), 7.61 (d, J = 3.4 Hz, 1H), 8.24 (dd, J = 8.8, 2.5 Hz, 1H), 8.30 (d, J = 7.8 Hz, 1H), 8.43 (d, J = 1.7 Hz, 1H), 8.59 (s, 1H), 8.74 (d, J = 1.7 Hz, 1H). MS (ES) m/z 507.3 (M + 1). MP = 108-109° C. |
| Example 2.D-10 | 1-Ethyl-N-[4-[[3-[[5-(trifluoromethyl)-2-pyridyl]oxy]phenyl]methylene] cyclohexyl]pyrrolo[2,3-b]pyridine-5-carboxamide<br>$^1$H NMR (400 MHz, DMSO-d$_6$): δ 1.38 (t, J = 7.1 Hz, 3H), 1.38-1.48 (m, 1H), 1.49-1.57 (m, 1H), 1.98-2.03 (m, 2H), 2.11 (t, J = 13.2 Hz, 1H), 2.33 (t, J = 12.0 Hz, 1H), 2.47 (d, J = 13.6 Hz, 1H), 2.85 (d, J = 13.7 Hz, 1H), 4.13-4.21 (m, 1H), 4.31 (q, J = 7.3 Hz, 2H), 6.33 (s, 1H), 6.57 (d, J = 3.5 Hz, 1H), 7.02 (s, 1H), 7.06 (d, J = 8.3 Hz, 1H), 7.13 (d, J = 7.6 Hz, 1H), 7.25 (d, J = 8.8 Hz, 1H), 7.43 (t, J = 8.1 Hz, 1H), 7.67 (d, J = 3.1 Hz, 1H), 8.24 (d, J = 8.7 Hz, 1H), 8.28 (d, J = 7.8 Hz, 1H), 8.42 (d, J = 1.9 Hz, 1H), 8.59 (s, 1H), 8.72 (d, J = 1.9 Hz, 1H). MS (ES) m/z 521.3 (M + 1). (M + 1). MP = 144-146° C. |
| Example 2.D-11 | 2-Methyl-N-[4-[[3-[[5-(trifluoromethyl)-2-pyridyl]oxy]phenyl]methylene] cyclohexyl]-1H-pyrrolo[2,3-b]pyridine-5-carboxamide<br>$^1$H NMR (400 MHz, CDCl$_3$): δ 1.37 (qd, J = 11.3, 4.1 Hz, 1H), 1.49 (qd, J = 11.7, 5.4 Hz, 1H), 2.11-2.26 (m, 3H), 2.29 (s, 3H), 2.34-2.48 (m, 2H), 2.89-2.95 (m, 1H), 4.20-4.29 (m, 1H), 6.05 (d, J = 7.8 Hz, 1H), 6.33 (s, 1H), 6.99-7.03 (m, 3H), 7.10 (d, J = 7.6 Hz, 1H), 7.32 (d, J = 8.0 Hz, 1H), 7.39 (t, J = 7.5 Hz, 1H), 7.90 (dd, J = 8.5, 2.2 Hz, 1H), 8.22 (dd, J = 8.1, 2.2 Hz, 1H), 8.45 (s, 1H), 8.90 (d, J = 2.2 Hz, 1H). MS (ES) m/z 507.2 (M + 1). MP = 204-205° C. |
| Example 2.D-12 | N-[4-[[3-[[5-(Trifluoromethyl)-2-pyridyl]oxy]phenyl]methylene]cyclohexyl]-1H-pyrrolo[3,2-b]pyridine-3-carboxamide<br>$^1$H NMR (400 MHz, DMSO-d$_6$): δ 1.43-1.56 (m, 2H), 2.00-2.10 (m, 2H), 2.25 (t, J = 10.8 Hz, 1H), 2.33-2.38 (m, 1H), 2.42-2.46 (m, 1H), 2.74 (d, J = 14.5 Hz, 1H), 4.10-4.19 (m, 1H), 6.34 (s, 1H), 7.04 (s, 1H), 7.05 (d, J = 7.6 Hz, 1H), 7.15 (d, J = 7.5 Hz, 1H), 7.22-7.25 (m, 2H), 7.42 (t, J = 7.8 Hz, 1H), 7.91 (d, J = 8.1 Hz, 1H), 8.16 (d, J = 2.4 Hz, 1H), 8.23 (d, J = 8.6 Hz, 1H), 8.45 (d, J = 4.2 Hz, 1H), 8.58 (s, 1H), 8.87 (d, J = 7.6 Hz, 1H), 11.94 (s, 1H). MS(ES) m/z 493.3 (M + 1). MP = 124-126° C. |
| Example 2.D-13 | N-[4-[[3-[[5-(Trifluoromethyl)-2-pyridyl]oxy]phenyl]methylene] cyclohexyl]-1H-pyrrolo[2,3-b]pyridine-3-carboxamide<br>$^1$H NMR (400 MHz, DMSO-d$_6$): δ 1.29-1.41 (m, 1H), 1.49 (qd, J = 12.5, 3.9 Hz, 1H), 1.93-2.04 (m, 2H), 2.10 (t, J = 12.8 Hz, 1H), 2.28-2.36 (m, 1H), 2.42(d, J = 14.0 Hz, 1H), 2.84 (d, J = 13.7 Hz, 1H), 4.02-4.12 (m, 1H), 6.32 (s, 1H), 7.02 (s, 1H), 7.06 (d, J = 8.0 Hz, 1H), 7.12-7.17 (m, 2H), 7.25 (d, J = 8.8 Hz, 1H), 7.43 (t, J = 7.8 Hz, 1H), 7.77 (d, J = 7.8 Hz, 1H), 8.15 (d, J = 3.0 Hz, |

| | -continued |
|---|---|
| | 1H), 8.23 (d, J = 2.2 Hz, 1H), 8.25 (d, J = 3.0 Hz, 1H), 8.43 (d, J = 7.9 Hz, 1H), 8.58 (s, 1H), 12.04 (s, 1H). MS(ES) m/z 493.3 (M + 1). MP = 225-227° C. |
| Example 2.D-14 | 1-(2-Hydroxy-2-methyl-propyl)-N-[4-[[3-[[5-(trifluoromethyl)-2-pyridyl] oxy]phenyl]methylene]cyclohexyl]pyrrolo[2,3-b]pyridine-5-carboxamide<br>¹H NMR (400 MHz, CDCl₃): δ 1.22 (s, 6H), 1.31-1.42 (m, 1H), 1.45-1.55 (m, 1H), 2.09-2.26 (m, 3H), 2.36-2.47 (m, 2H), 2.92 (d, J = 12.5 Hz, 1H), 4.22-4.32 (m, 1H), 4.30 (s, 2H), 5.99 (d, J = 6.6 Hz, 1H), 6.32 (s, 1H), 6.55 (s, 1H), 6.99-7.02 (m, 3H), 7.10 (d, J = 7.1 Hz, 1H), 7.26-7.31 (m, 1H), 7.39 (t, J = 7.6 Hz, 1H), 7.90 (d, J = 7.8 Hz, 1H), 8.36 (s, 1H), 8.45 (s, 1H), 8.66 (s, 1H). MS (ES) m/z 565.1 (M + 1). MP = 157-159° C. |

Following examples were prepared from appropriate amine intermediate selected from Intermediate 3B-3Q and appropriate carboxylic acid or carboxylic acid chloride selected from Intermediates 4-6 using either of the procedure described for Example 2.1, Example 2.2, Example 2.3.

| | |
|---|---|
| Example 2.E-1 | N-[(3E)-3-[[3-[[5-(Trifluoromethyl)-2-pyridyl]oxy]phenyl]methylene] cyclohexyl]pyridine-3-carboxamide<br>¹H NMR (400 MHz, CDCl₃) mixture of stereoisomers: δ 1.58-1.66 (m, 2H), 1.68-1.80 (m, 2H), 1.81-1.90 (m, 0.5H), 2.02-2.10 (m, 1H), 2.25-2.42 (m, 2H), 2.55-2.61 (m, 0.5H), 2.77 (dd, J = 13.0, 3.7 Hz, 0.5H), 2.94 (dd, J = 13.2, 3.7 Hz, 0.5H), 4.20-4.27 (m, 0.5H), 4.29-4.37 (m, 0.5H), 6.08 (d, J = 7.8 Hz, 0.5H), 6.17 (d, J = 8.1 Hz, 0.5H), 6.41 (s, 0.5H), 6.48 (m, 0.5H), 7.01-7.06 (m, 3H), 7.15 (t, J = 8.5 Hz, 1H), 7.34-7.44 (m, 2H), 7.89 (dd, J = 8.6, 2.2 Hz, 0.5H), 7.93 (dd, J = 8.8, 2.4 Hz, 0.5H), 8.03 (d, J = 8.1 Hz, 0.5H), 8.14 (d, J = 7.8 Hz, 0.5H), 8.42 (s, 0.5H), 8.48 (s, 0.5H), 8.72 (d, J = 4.6 Hz, 0.5H), 8.75 (d, J = 4.9 Hz, 0.5H), 8.88 (s, 0.5H), 8.97 (s, 0.5H). MS (ES) m/z 454.3 (M + 1). Sticky solid. |
| Example 2.E-2 | N-[(3E)-3-[[3-[[5-(Trifluoromethyl)-2-pyridyl]oxy]phenyl]methylene] cyclopentyl]pyridine-3-carboxamide<br>¹H NMR (400 MHz, CDCl₃) mixture of stereoisomers: δ 1.71-1.80 (m, 0.5H), 1.83-1.94 (m, 0.5H), 2.17-2.33 (m, 1H), 2.49-2.58 (m, 1H), 2.59-2.79 (m, 2H), 3.02 (dd, J = 16.2, 6.1 Hz, 0.5H), 3.16 (dd, J = 17.6, 7.1 Hz, 0.5H), 4.50-4.58 (m, 0.5H), 4.59-4.66 (m, 0.5H), 6.12 (dd, J = 16.4, 7.4 Hz, 1H), 6.42-6.46 (m, 1H), 6.97-7.02 (m, 2H), 7.07 (brs, 0.5H), 7.11 (brs, 0.5H), 7.17 (d, J = 7.8 Hz, 0.5H), 7.21 (d, J = 7.8 Hz, 0.5H), 7.37-7.41 (m, 2H), 7.90 (dt, J = 8.5, 2.4 Hz, 1H), 8.10 (dt, J = 8.1, 1.9 Hz, 1H), 8.43-8.62 (m, 1H), 8.73 (dd, J = 4.7, 1.3 Hz, 1H), 8.94 (s, 1H). MS (ES) m/z 440.3 (M + 1). Sticky solid. |
| Example 2.E-3 | N-[(3E)-3-[[3-[[5-(Trifluoromethyl)-2-pyridyl]oxy]phenyl]methylene] cyclohexyl]-1H-pyrazole-3-carboxamide<br>¹H NMR (400 MHz, CDCl₃) mixture of stereoisomers: δ 1.49-1.69 (m, 2H), 1.72-1.89 (m, 1H), 1.87-2.08 (m, 1H), 2.16-2.26 (m, 2H), 2.30-2.36 (m, 0.5H), 2.54-2.61 (m, 0.5H), 2.71 (dd, J = 12.5, 3.4 Hz, 0.5H), 2.94 (dd, J = 13.2, 4.1 Hz, 0.5H), 4.09-4.17 (m, 0.5H), 4.18-4.27 (m, 0.5H), 6.36 (s, 0.5H), 6.42 (s, 0.5H), 6.79-7.03 (m, 6H), 7.12 (t, J = 5.9 Hz, 1H), 7.38-7.40 (m, 1H), 7.55 (d, J = 2.2 Hz, 0.5H), 7.58 (d, J = 1.9 Hz, 0.5H), 7.85 (dd, J = 8.5, 2.4 Hz, 0.5H), 7.90 (dd, J = 8.8, 2.4 Hz, 0.5H), 8.42 (s, 0.5H), 8.46 (s, 0.5H). MS (ES) m/z 443.3 (M + 1). Sticky solid. |
| Example 2.E-4 | N-[4-[[3-[(5-Bromo-2-pyridyl)oxy]phenyl]methylene]cyclohexyl]pyridine-3-carboxamide<br>¹H NMR (400 MHz, CDCl₃): δ 1.34 (qd, J = 11.0, 4.1 Hz, 1H), 1.48 (qd, J = 11.3, 5.4 Hz, 1H), 2.12-2.23 (m, 3H), 2.30-2.43 (m, 2H), 2.88-2.93 (m, 1H), 4.19-4.25 (m, 1H), 5.99 (d, J = 7.6 Hz, 1H), 6.31 (s, 1H), 6.85 (d, J = 8.8 Hz, 1H), 6.95-7.04 (m, 2H), 7.05 (d, J = 7.9 Hz, 1H), 7.35 (t, J = 7.9 Hz, 1H), 7.58 (dd, J = 7.8, 4.6 Hz, 1H), 7.77 (dd, J = 8.8, 2.7 Hz, 1H), 8.10 (dt, J = 7.8, 1.7 Hz, 1H), 8.22 (d, J = 2.2 Hz, 1H), 8.72 (dd, J = 4.7, 1.5 Hz, 1H), 8.94 (d, J = 1.5 Hz, 1H). MS (ES) m/z 466.1 (M + 1), 468.3 (M + 3). Sticky solid. |
| Example 2.E-5 | N-[4-[[3-[5-(Trifluoromethyl)pyrazin-2-yl]oxyphenyl]methylene]cyclohexyl]-1H-pyrazole-4-carboxamide<br>¹H NMR (400 MHz, CD₃OD): δ 1.39 (qd, J = 12.3, 3.5 Hz, 1H), 1.52 (qd, J = 12.2, 4.2 Hz, 1H), 2.00-2.15 (m, 3H), 2.35-2.48 (m, 2H), 2.94 (d, J = 13.6 Hz, 1H), 4.03-4.11 (m, 1H), 6.34 (s, 1H), 7.05 (brs, 2H), 7.14 (d, J = 7.6 Hz, 1H), 7.40 (t, J = 7.9 Hz, 1H), 7.97 (brs, 1H), 8.12 (brs, 1H), 8.51 (s, 1H), 8.54 (s, 1H). MS (ES) m/z 444.2 (M + 1). MP = 85-86° C. |
| Example 2.E-6 | N-[4-[[3-[(5-Chloro-2-pyridyl)oxy]phenyl]methylene]cyclohexyl]-1H-pyrazole-4-carboxamide<br>¹H NMR (400 MHz, CDCl₃): δ 1.25-1.48 (m, 2H), 2.04-2.14 (m, 3H), 2.29-2.38 (m, 2H), 2.85 (d, J = 12.5 Hz, 1H), 4.10-4.29 (m, 1H), 6.10 (brs, 1H), 6.24 (s, 1H), 6.87 (d, J = 8.6 Hz, 1H), 6.93-6.95 (m, 3H), 7.02 (d, J = 7.3 Hz, 1H), 7.32 (t, J = 7.5 Hz, 1H), 7.63 (dd, J = 8.8, 2.5 Hz, 1H), 7.86-7.96 (m, 2H), 8.11 (s, 1H). MS (ES) m/z 409.1 (M + 1). MP = 133-134° C. |
| Example 2.E-7 | N-[4-[[3-[(5-Bromo-2-pyridyl)oxy]phenyl]methylene]cyclohexyl]pyridazine-4-carboxamide<br>¹H NMR (400 MHz, CDCl₃): δ 1.32-1.53 (m, 2H), 2.12-2.24 (m, 3H), 2.36-2.48 (m, 2H), 2.90-2.95 (m, 1H), 4.19-4.28 (m, 1H), 6.09 (d, J = 7.1 Hz, 1H), |

| | |
|---|---|
| | 6.32 (s, 1H), 6.85 (d, J = 8.8 Hz, 1H), 6.95-6.99 (m, 2H), 7.05 (d, J = 7.6 Hz, 1H), 7.35 (t, J = 7.8 Hz, 1H), 7.75-7.78 (m, 2H), 8.22 (s, 1H), 9.37 (d, J = 5.1 Hz, 1H), 9.47 (s, 1H). MS (ES) m/z 465.1 (M⁺), 467.1 (M + 2). MP = 75-77° C. |
| Example 2.E-8 | N-[4-[[3-[(5-Bromo-2-pyridyl)oxy]phenyl]methylene]cyclohexyl]-6-fluoro-pyridine-3-carboxamide<br>¹H NMR (400 MHz, CDCl₃): δ 1.25-1.36 (m, 1H), 1.46 (qd, J = 11.5, 6.7 Hz, 1H), 2.11-2.22 (m, 3H), 2.36-2.46 (m, 2H), 2.88-2.93 (m, 1H), 4.17-4.25 (m, 1H), 5.93 (d, J = 7.6 Hz, 1H), 6.30 (s, 1H), 6.84 (d, J = 8.8 Hz, 1H), 6.95-7.02 (m, 3H), 7.04 (d, J = 7.6 Hz, 1H), 7.35 (t, J = 7.8 Hz, 1H), 7.77 (dd, J = 8.8, 2.7 Hz, 1H), 8.20-8.25 (m, 2H), 8.57 (d, J = 2.2 Hz, 1H). MS (ES) m/z 482.1 (M + 1), 484.1 (M + 3). MP = 80-82° C. |
| Example 2.E-9 | 6-Amino-N-[4-[[3-[(5-bromo-2-pyridyl)oxy]phenyl]methylene]cyclohexyl]pyridine-3-carboxamide<br>¹H NMR (400 MHz, CDCl₃): δ 1.28-1.37 (m, 1H), 1.41-1.48 (m, 1H), 1.54 (s, 9H), 2.10-2.22 (m, 3H), 2.38-2.48 (m, 2H), 2.87-2.93 (m, 1H), 4.17-4.24 (m, 1H), 5.85 (d, J = 7.6 Hz, 1H), 6.30 (s, 1H), 6.84 (d, J = 8.5 Hz, 1H), 6.95-6.99 (m, 2H), 7.05 (d, J = 7.9 Hz, 1H), 7.35 (t, J = 7.9 Hz, 1H), 7.47 (s, 1H), 7.77 (dd, J = 8.8, 2.5 Hz, 1H), 7.98-8.03 (m, 2H), 8.22 (d, J = 2.4 Hz, 1H), 8.62 (s, 1H). MS (ES) m/z 579.1 (M + 1), |
| Example 2.E-10 | N-[4-[[3-[(5-Cyclopropyl-2-pyridyl)oxy]phenyl]methylene]cyclohexyl]-1H-pyrazole-4-carboxamide<br>¹H NMR (400 MHz, CDCl₃): δ 0.63-0.67 (m, 2H), 0.95-1.00 (m, 2H), 1.25-1.48 (m, 2H), 1.83-1.89 (m, 1H), 2.06-2.19 (m, 3H), 2.32-2.42 (m, 2H), 2.85-2.89 (m, 1H), 4.12-4.22 (m, 1H), 5.67 (d, J = 7.6 Hz, 1H), 6.27 (s, 1H), 6.82 (d, J = 8.3 Hz, 1H), 6.93 (s, 1H), 6.94 (d, J = 8.1 Hz, 1H), 7.00 (d, J = 7.6 Hz, 1H), 7.30-7.35 (m, 2H), 7.91 (s, 2H), 8.02 (s, 1H), 10.60 (s, 1H). MS (ES) m/z 415.3 (M + 1). MP = 102-104° C. |
| Example 2.E-11 | 6-Chloro-N-[(2E-2-[[3-[[5-(trifluoromethyl)-2-pyridyl]oxy]phenyl]methylene]-5-bicyclo[2.2.2]octanyl]pyridine-3-carboxamide<br>¹H NMR (400 MHz, DMSO-d₆) mixture of isomers: δ 1.39-1.84 (m, 4H), 1.88-2.23 (m, 3H), 2.24-2.62 (m, 2H), 2.55-2.95 (m, 1H), 3.98-4.20 (m, 1H), 6.26 (s, 1H), 6.98-7.09 (m, 2H), 7.18-7.29 (m, 2H), 7.41 (t, J = 7.6 Hz, 1H), 7.60-7.66 (m, 1H), 8.22-8.27 (m, 2H), 8.53-8.57 (m, 2H), 8.83 (d, J = 8.4 Hz, 1H). MS (ES) m/z 514.2 (M + 1), 515.2 (M + 2). Sticky solid. |
| Example 2.E-12 | N-[4-[[2-Fluoro-5-[[5-(trifluoromethyl)-2-pyridyl]oxy]phenyl]methylene]cyclohexyl]-3-(trifluoromethyl)-1H-pyrazole-4-carboxamide<br>¹H NMR (400 MHz, DMSO-d₆): δ 1.41 (qd, J = 11.2, 4.4 Hz, 1H), 1.53 (qd, J = 12.5, 3.9 Hz, 1H), 1.87-2.09 (m, 3H), 2.25-2.58 (m, 3H), 3.89-3.98 (m, 1H), 6.20 (s, 1H), 7.06 (dd, J = 6.1, 2.7 Hz, 1H), 7.12-7.16 (m, 1H), 7.25-7.30 (m, 2H), 7.99 (d, J = 7.8 Hz, 1H), 8.24 (dd, J = 8.8, 2.5 Hz, 1H), 8.36 (s, 1H), 8.58 (s, 1H), 13.74 (brs, 1H). MS (ES) m/z 529.1 (M + 1). MP = 142-144° C. |
| Example 2.E-13 | N-[4-[[2-Fluoro-5-[[5-(trifluoromethyl)-2-pyridyl]oxy]phenyl]methylene]cyclohexyl]-6-pyrazol-1-yl-pyridine-3 -carboxamide<br>¹H NMR (400 MHz, DMSO-d₆): δ 1.36-1.45 (m, 1H), 1.50-1.59 (m, 1H), 1.93-2.12 (m, 4H), 2.33 (t, J = 11.3 Hz, 1H), 2.61 (d, J = 13.9 Hz, 1H), 4.02-4.10 (m, 1H), 6.22 (s, 1H), 6.63 (s, 1H), 7.06-7.08 (m, 1H), 7.13-7.18 (m, 1H), 7.26-7.32 (m, 2H), 7.89 (s, 1H), 7.99 (d, J = 8.5 Hz, 1H), 8.25 (d, J = 8.5 Hz, 1H), 8.39 (d, J = 8.5 Hz, 1H), 8.50 (d, J = 7.9 Hz, 1H), 8.59 (s, 1H), 8.68 (s, 1H), 8.88 (s, 1H). MS (ES) m/z 538.2 (M + 1). MP = 193-196° C. |
| Example 2.E-14 | N-[4-[[3-[[3-Chloro-5-(trifluoromethyl)-2-pyridyl]oxy]phenyl]methylene]cyclohexyl]-6-pyrazol-1-yl-pyridine-3-carboxamide<br>¹H NMR (400 MHz, DMSO-d₆): δ 1.40 (qd, J = 12.2, 3.4 Hz, 1H), 1.52 (qd, J = 11.7, 3.7 Hz, 1H), 1.95-2.04 (m, 2H), 2.12 (t, J = 12.5 Hz, 1H), 2.33 (t, J = 11.3 Hz, 1H), 2.43 (d, J = 13.9 Hz, 1H), 2.85 (d, J = 13.4 Hz, 1H), 4.02-4.11 (m, 1H), 6.33 (s, 1H), 6.62 (t, J = 1.7 Hz, 1H), 7.07 (s, 1H), 7.10 (d, J = 8.1 Hz, 1H), 7.15 (d, J = 7.8 Hz, 1H), 7.45 (t, J = 7.8 Hz, 1H), 7.89 (s, 1H), 7.99 (d, J = 8.6 Hz, 1H), 8.39 (dd, J = 8.6, 2.0 Hz, 1H), 8.49 (d, J = 7.6 Hz, 1H), 8.53 (s, 1H), 8.59 (d, J = 1.9 Hz, 1H), 8.68 (d, J = 2.4 Hz, 1H), 8.88 (d, J = 2.2 Hz, 1H). MS (ES) m/z 554.3 (M + 1). MP = 150-151° C. |
| Example 2.E-15 | N-[4-[[3-[[3-Chloro-5-(trifluoromethyl)-2-pyridyl]oxy]phenyl]methylene]cyclohexyl]-3-(trifluoromethyl)-1H-pyrazole-4-carboxamide<br>¹H NMR (400 MHz, DMSO-d₆): δ 1.23-1.35 (m, 1H), 1.38-1.47 (m, 1H), 1.77-1.99 (m, 2H), 2.09 (t, J = 11.7 Hz, 1H), 2.26-2.42 (m, 2H), 2.81 (d, J = 14.5 Hz, 1H), 3.90-3.99 (m, 1H), 6.31 (s, 1H), 7.05 (s, 1H), 7.09 (d, J = 8.0 Hz, 1H), 7.14 (d, J = 7.6 Hz, 1H), 7.43 (t, J = 7.6 Hz, 1H), 8.00 (d, J = 8.0 Hz, 1H), 8.34 (s, 1H), 8.52 (s, 1H), 8.59 (s, 1H), 13.74 (brs, 1H). MS (ES) m/z 545.2 (M + 1). (M + 1). MP = 99-100° C. |
| Example 2.E-16 | 6-Amino-N-[4-[[3-[(5-chloro-6-methyl-2-pyridyl)oxy]phenyl]methylene]cyclohexyl]pyridine-3-carboxamide<br>¹H NMR (400 MHz, CDCl₃): δ 1.32 (qd, J = 13.0, 5.4 Hz, 1H), 1.46 (qd, J = 10.7, 4.8 Hz, 1H), 2.07-2.20 (m, 3H), 2.34-2.42 (m, 2H), 2.50 (s, 3H), 2.89 (d, J = 14.4 Hz, 1H), 4.16-4.24 (m, 1H), 4.77 (brs, 2H), 5.81 (d, J = 7.3 Hz, 1H), 6.29 (s, 1H), 6.50 (d, J = 8.6 Hz, 1H), 6.61 (d, J = 8.5 Hz, 1H), 6.95-6.96 (m, 2H), 7.02 (d, J = 7.5 Hz, 1H), 7.33 (t, J = 8.6 Hz, 1H), 7.57 (d, J = 8.6 Hz, 1H), 7.87 (d, J = 8.8 Hz, 1H), 8.44 (s, 1H). MS (ES) m/z 450.0 (M + 1). MP = 140-143° C. |
| Example 2.E-17 | 6-Amino-N-[4-[[3-[[6-methyl-5-(trifluoromethyl)-2-pyridyl]oxy]phenyl]methylene]cyclohexyl]pyridine-3-carboxamide<br>¹H NMR (400 MHz, DMSO-d₆): δ 1.35 (qd, J = 12.0, 4.1 Hz, 1H), 1.47 (qd, J = 12.2, 3.9 Hz, 1H), 1.91 (dd, J = 26.5, 9.8 Hz, 2H), 2.06 (td, J = 13.0, 2.9 Hz, |

| | |
|---|---|
| | 1H), 2.25-2.33 (m, 1H), 2.38-2.45 (m, 1H), 2.45 (s, 3H), 2.85 (d, J = 13.7 Hz, 1H), 3.95-4.04 (m, 1H), 6.32 (s, 1H), 6.40 (d, J = 8.6 Hz, 1H), 6.46 (s, 2H), 6.96 (d, J = 8.8 Hz, 1H), 7.00 (s, 1H), 7.04 (dd, J = 7.8, 1.4 Hz, 1H), 7.10 (d, J = 7.9 Hz, 1H), 7.41 (t, J = 8.1 Hz, 1H), 7.79 (dd, J = 8.5, 2.2 Hz, 1H), 7.88 (d, J = 7.9 Hz, 1H), 8.11 (d, J = 8.8 Hz, 1H), 8.42 (d, J = 2.0 Hz, 1H). MS (ES) m/z 483.1 (M⁺). MP = 151-154° C. |
| Example 2.E-18 | N-[4-[[3-[[6-Methyl-5-(trifluoromethyl)-2-pyridyl]oxy]phenyl]methylene]cyclohexyl]-3-(trifluoromethyl)-1H-pyrazole-4-carboxamide<br>¹H NMR (400 MHz, DMSO-d₆): δ 1.29 (qd, J = 11.2, 3.6 Hz, 1H), 1.41 (qd, J = 11.6, 3.6 Hz, 1H), 1.85-1.97 (m, 2H), 2.03-2.12 (m, 1H), 2.22-2.41 (m, 2H), 2.43 (s, 3H), 2.81 (d, J = 13.9 Hz, 1H), 3.88-3.98 (m, 1H), 6.30 (s, 1H), 6.94 (d, J = 8.5 Hz, 1H), 6.98 (s, 1H), 7.03 (dd, J = 8.0, 2.1 Hz, 1H), 7.08 (d, J = 7.7 Hz, 1H), 7.39 (t, J = 7.9 Hz, 1H), 7.96 (d, J = 7.7 Hz, 1H), 8.09 (d, J = 8.7 Hz, 1H), 8.34 (s, 1H), 13.75 (brs, 1H). MS (ES) m/z 525.0 (M + 1). MP = 94-97° C. |
| Example 2.E-19 | 6-Amino-N-[4-[[3-[[6-cyclopropyl-5-(trifluoromethyl)-2-pyridyl]oxy]phenyl]methylene]cyclohexyl]pyridine-3-carboxamide<br>¹H NMR (400 MHz, DMSO-d₆): δ 0.72-0.76 (m, 2H), 0.90-0.94 (m, 2H), 1.33 (qd, J = 11.9, 4.2 Hz, 1H), 1.45 (qd, J = 11.7, 3.8 Hz, 1H), 1.85-1.96 (m, 2H), 2.01-2.16 (m, 2H), 2.21-2.32 (m, 1H), 2.38 (d, J = 13.2 Hz, 1H), 2.78 (d, J = 13.5 Hz, 1H), 3.93-4.02 (m, 1H), 6.29 (s, 1H), 6.38 (d, J = 8.6 Hz, 1H), 6.43 (s, 2H), 6.84 (d, J = 8.7 Hz, 1H), 6.93 (s, 1H), 6.98 (d, J = 8.1 Hz, 1H), 7.08 (d, J = 7.7 Hz, 1H), 7.39 (t, J = 8.0 Hz, 1H), 7.77 (dd, J = 8.5, 2.3 Hz, 1H), 7.86 (d, J = 8.3 Hz, 1H), 8.03 (d, J = 8.7 Hz, 1H), 8.41 (d, J = 2.1 Hz, 1H). MS (ES) m/z 509.0 (M + 1). MP = 182-185° C. |
| Example 2.E-20 | 6-Amino-N-[4-[[3-[[6-chloro-5-(trifluoromethyl)-2-pyridyl] oxy]phenyl]methylene]cyclohexyl]pyridine-3-carboxamide<br>¹H NMR (400 MHz, CDCl₃): δ 1.34 (qd, J = 11.2, 3.5 Hz, 1H), 1.46 (qd, J = 11.2, 5.2 Hz, 1H), 2.09-2.23 (m, 3H), 2.36-2.47 (m, 2H), 2.88-2.94 (m, 1H), 4.16-4.25 (m, 1H), 4.78 (s, 2H), 5.79 (d, J = 7.8 Hz, 1H), 6.31 (s, 1H), 6.50 (d, J = 8.8 Hz, 1H), 6.86 (d, J = 8.8 Hz, 1H), 6.99 (s, 2H), 7.09 (d, J = 7.5 Hz, 1H), 7.38 (t, J = 8.6 Hz, 1H), 7.87 (dd, J = 8.8, 1.6 Hz, 1H), 7.96 (d, J = 8.8 Hz, 1H), 8.44 (m, 1H). MS (ES) m/z 503.0 (M⁺). MP = 119-122° C. |
| Example 2.E-21 | 6-Amino-N-[4-[[3-methyl-5-[[5-(trifluoromethyl)-2-pyridyl]oxy]phenyl]methylene]cyclohexyl]pyridine-3-carboxamide<br>¹H NMR (400 MHz, CDCl₃): δ 1.32 (qd, J = 10.8, 3.7 Hz, 1H), 1.44 (qd, J = 11.7, 5.4 Hz, 1H), 2.09-2.20 (m, 3H), 2.36 (s, 3H), 2.34-2.44 (m, 2H), 2.88 (dt, J = 14.2, 3.8 Hz, 1H), 4.15-4.24 (m, 1H), 4.75 (s, 2H), 5.79 (d, J = 7.8 Hz, 1H), 6.27 (s, 1H), 6.48 (d, J = 8.5 Hz, 1H), 6.78 (s, 1H), 6.81 (s, 1H), 6.91 (s, 1H), 6.99 (d, J = 8.5 Hz, 1H), 7.85-7.90 (m, 2H), 8.43-8.44 (m, 2H). MS (ES) m/z 483.0 (M + 1). MP = 110-112° C. |
| Example 2.E-22 | 2-Amino-N-[4-[[3-[[6-methyl-5-(trifluoromethyl)-2-pyridyl]oxy]phenyl]methylene]cyclohexyl]pyrimidine-5-carboxamide<br>¹H NMR (400 MHz, (CD₃)₂CO): δ 1.43 (qd, J = 11.5, 4.2 Hz, 1H), 1.53 (qd, J = 11.4, 4.4 Hz, 1H), 2.09-2.21 (m, 3H), 2.39 (td, J = 13.0, 3.6 Hz, 1H), 2.43-2.48 (m, 2H), 2.48 (s, 3H), 2.96 (d, J = 13.9 Hz, 1H), 4.10-4.19 (m, 1H), 6.35 (s, 1H), 6.46 (s, 1H), 6.94 (d, J = 8.6 Hz, 1H), 7.04-7.06 (m, 2H), 7.11 (d, J = 7.7 Hz, 1H), 7.35-7.43 (m, 2H), 8.07 (d, J = 8.6 Hz, 1H), 8.69 (s, 2H). MS (ES) m/z 484.1 (M + 1). MP = 168-170° C. |
| Example 2.E-23 | 6-Amino-5-methyl-N-[4-[[3-[[6-methyl-5-(trifluoromethyl)-2-pyridyl]oxy]phenyl]methylene]cyclohexyl]pyridine-3-carboxamide<br>¹H NMR (400 MHz, CD₃OD): δ 1.40 (qd, J = 11.7, 3.9 Hz, 1H), 1.53 (qd, J = 11.7, 3.9 Hz, 1H), 2.00-2.16 (m, 3H), 2.23 (s, 3H), 2.38 (t, J = 12.6 Hz, 1H), 2.45-2.51 (m, 1H), 2.51 (s, 3H), 2.97 (d, J = 13.5 Hz, 1H), 4.04-4.13 (m, 1H), 6.35 (s, 1H), 6.83 (d, J = 8.6 Hz, 1H), 6.97-7.00 (m, 2H), 7.09 (d, J = 7.5 Hz, 1H), 7.38 (t, J = 7.5 Hz, 1H), 7.99-8.01 (m, 2H), 8.26 (s, 1H). MS (ES) m/z 497.1 (M + 1). MP = 97-100° C. |
| Example 2.E-24 | 6-Amino-N-[4-[[3-[[6-ethyl-5-(trifluoromethyl)-2-pyridyl]oxy]phenyl]methylene]cyclohexyl]pyridine-3-carboxamide<br>¹H NMR (400 MHz, DMSO-d₆): δ 1.07 (t, J = 7.3 Hz, 3H), 1.28-1.38 (m, 1H), 1.39-1.50 (m, 1H), 1.83-1.94 (m, 2H), 2.04 (t, J = 12.5 Hz, 1H), 2.27 (t, J = 14.5 Hz, 1H), 2.38 (d, J = 13.9 Hz, 1H), 2.65-2.74 (m, 2H), 2.81 (d, J = 13.5 Hz, 1H), 3.92-4.02 (m, 1H), 6.29 (s, 1H), 6.38 (d, J = 8.8 Hz, 1H), 6.42 (s, 2H), 6.94 (d, J = 8.8 Hz, 1H), 6.98 (s, 1H), 7.04 (d, J = 8.0 Hz, 1H), 7.09 (d, J = 7.5 Hz, 1H), 7.40 (t, J = 7.9 Hz, 1H), 7.77 (d, J = 8.6 Hz, 1H), 7.86 (d, J = 7.5 Hz, 1H), 8.09 (d, J = 8.3 Hz, 1H), 8.40 (s, 1H). MS (ES) m/z 497.1 (M + 1). MP = 128-131° C. |
| Example 2.E-25 | 6-Amino-N-[4-[[3-[(5-chloro-6-methyl-2-pyridyl)oxy]phenyl]methylene]cyclohexyl]-5-methyl-pyridine-3-carboxamide<br>¹H NMR (400 MHz, CDCl₃): δ 1.32 (qd, J = 12.3, 3.5 Hz, 1H), 1.45 (qd, J = 11.7, 5.3 Hz, 1H), 2.08-2.22 (m, 3H), 2.16 (s, 3H), 2.37-2.44 (m, 2H), 2.50 (s, 3H), 2.86-2.92 (m, 1H), 4.15-4.24 (m, 1H), 4.71 (s, 2H), 5.80 (d, J = 7.7 Hz, 1H), 6.29 (s, 1H), 6.62 (d, J = 8.6 Hz, 1H), 6.95-6.96 (m, 2H), 7.02 (d, J = 7.7 Hz, 1H), 7.32 (t, J = 8.2 Hz, 1H), 7.57 (d, J = 8.6 Hz, 1H), 7.72 (s, 1H), 8.31 (d, J = 1.8 Hz, 1H). MS (ES) m/z 463.3 (M + 1). MP = 260-265° C. |
| Example 2.E-26 | 6-Amino-N-[4-[[2-methyl-5-[[5-(trifluoromethyl)-2-pyridyl]oxy]phenyl]methylene]cyclohexyl]pyridine-3-carboxamide<br>¹H NMR (400 MHz, CDCl₃): δ 1.25-1.33 (m, 1H), 1.45 (qd, J = 11.7, 4.5 Hz, 1H), 2.02-2.11 (m, 2H), 2.17-2.23 (m, 1H), 2.26 (s, 3H), 2.34-2.48 (m, 2H), 2.62-2.67 (m, 1H), 4.13-4.23 (m, 1H), 4.74 (s, 2H), 5.78 (d, J = 7.8 Hz, 1H), |

| | -continued |
|---|---|
| | 6.23 (s, 1H), 6.50 (d, J = 8.8 Hz, 1H), 6.88 (d, J = 2.5 Hz, 1H), 6.94 (dd, J = 8.1, 2.4 Hz, 1H), 6.99 (d, J = 8.8 Hz, 1H), 7.23 (d, J = 8.2 Hz, 1H), 7.85-7.89 (m, 2H), 8.43 (s, 2H). MS (ES) m/z 483.1 (M + 1). MP = 167-170° C. |
| Example 2.E-27 | 2-Amino-N-[4-[[3-[(5-chloro-6-methyl-2-pyridyl)oxy]phenyl]methylene]cyclohexyl]pyrimidine-5-carboxamide<br>$^1$H NMR (400 MHz, CDCl$_3$): δ 1.32 (qd, J = 11.0, 3.9 Hz, 1H), 1.45 (qd, J = 11.4, 5.2 Hz, 1H), 2.09-2.22 (m, 3H), 2.36-2.45 (m, 2H), 2.50 (s, 3H), 2.88-2.93 (m, 1H), 4.16-4.25 (m, 1H), 5.44 (s, 2H), 5.75 (d, J = 7.9 Hz, 1H), 6.29 (s, 1H), 6.62 (d, J = 8.7 Hz, 1H), 6.95-6.97 (m, 2H), 7.08 (d, J = 7.7 Hz, 1H), 7.33 (t, J = 7.5 Hz, 1H), 7.57 (d, J = 8.5 Hz, 1H), 8.67 (s, 2H). MS (ES) m/z 450.1 (M + 1). MP = 142-143° C. |
| Example 2.E-28 | 6-Amino-N-[4-[[3-[[6-cyano-5-(trifluoromethyl)-2-pyridyl]oxy]phenyl]methylene]cyclohexyl]pyridine-3-carboxamide<br>$^1$H NMR (400 MHz, CDCl$_3$): δ 1.38 (qd, J = 10.6, 3.5 Hz, 1H), 1.47 (qd, J = 11.7, 5.8 Hz, 1H), 2.11-2.25 (m, 3H), 2.37-2.46 (m, 2H), 2.87-2.93 (m, 1H), 4.17-4.26 (m, 1H), 4.72 (s, 2H), 5.78 (d, J = 7.7 Hz, 1H), 6.31 (s, 1H), 6.50 (d, J = 8.6 Hz, 1H), 6.98-7.00 (m, 2H), 7.12 (d, J = 7.7 Hz, 1H), 7.22-7.26 (m, 1H), 7.38 (t, J = 7.7 Hz, 1H), 7.86 (dd, J = 8.6, 2.2 Hz, 1H), 8.04 (d, J = 8.8 Hz, 1H), 8.45 (d, J = 1.9 Hz, 1H). MS (ES) m/z 494.1 (M + 1). MP = 98-101° C. |
| Example 2.E-29 | N-[(5E)-5-[[3-[[5-(Trifluoromethyl)-2-pyridyl]oxy]phenyl]methylene]norbornan-2-yl]-1H-pyrazole-4-carboxamide<br>MS (ES) m/z 455.2 (M + 1). MP = 101-103° C. |
| Example 2.E-30 | N-[4-[[3-[(5-chloro-6-methyl-2-pyridyl)oxy]phenyl]methylene]cyclohexyl]-3-(trifluoromethyl)-1H-pyrazole-4-carboxamide<br>$^1$H NMR (400 MHz, CDCl$_3$): δ 1.28-1.42 (m, 1H), 1.43-1.54 (m, 1H), 2.05-2.20 (m, 3H), 2.34-2.48 (m, 2H), 2.51 (s, 3H), 2.83 (d, J = 14.0 Hz, 1H), 4.15-4.24 (m, 1H), 5.99 (brs, 1H), 6.29 (s, 1H), 6.62 (d, J = 8.3 Hz, 1H), 6.95-6.97 (m, 2H), 7.02 (d, J = 7.5 Hz, 1H), 7.33 (t, J = 7.7 Hz, 1H), 7.58 (d, J = 8.6 Hz, 1H), 8.14 (s, 1H). MS (ES) m/z 491.2 (M + 1). MP = 97-98° C. |
| Example 2.E-31 | N-[4-[[3-[(5-chloro-6-methyl-2-pyridyl)oxy]phenyl]methylene]cyclohexyl]-6-(3,5-dimethyl-1H-pyrazol-4-yl)pyridine-3-carboxamide<br>$^1$H NMR (400 MHz, CDCl$_3$): δ 1.36 (qd, J = 11.1, 3.8 Hz, 1H), 1.49 (qd, J = 11.4, 5.0 Hz, 1H), 2.10-2.25 (m, 3H), 2.38-2.47 (m, 2H), 2.47 (s, 6H), 2.51 (s, 3H), 2.90-2.95 (m, 1H), 4.21-4.30 (m, 1H), 5.98 (d, J = 8.1 Hz, 1H), 6.31 (s, 1H), 6.62 (d, J = 8.5 Hz, 1H), 6.96-6.98 (m, 2H), 7.02 (d, J = 7.7 Hz, 1H), 7.33 (t, J = 8.0 Hz, 1H), 7.41 (d, J = 8.3 Hz, 1H), 7.57 (d, J = 8.6 Hz, 1H), 8.11 (dd, J = 8.4, 2.3 Hz, 1H), 8.98 (d, J = 1.8 Hz, 1H). MS (ES) m/z 528.1 (M + 1). MP = 194-195° C. |

Example 3.1

N-[4-[[3-[(5-Cyclopropyl-2-pyridyl)oxy]phenyl]methylene]-cyclohexyl]pyridine-3-carboxamide

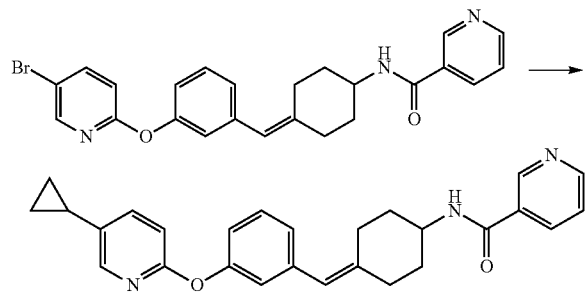

To a stirred solution of N-[4-[[3-[(5-bromo-2-pyridyl)oxy]phenyl]methylene]-cyclohexyl]pyridine-3-carboxamide (Example 2.E-4) (200 mg, 0.4 mmol) in toluene (5 mL) was added tricyclohexylphosphine (11 mg, 0.04 mmol) followed by a solution of potassium phosphate tribasic (297 mg, 1.4 mmol) in water (0.3 mL), cyclopropyl boronic acid (43 mg, 0.5 mmol) and degassed with argon for 45 min. To this was added palladium acetate (5 mg, 0.02 mmol) and reaction mixture heated to 100° C. for 18 h. Reaction mixture was cooled room temperature, filtered through celite bed, washed with ethyl acetate. Organic layer was washed with water (20 mL), brine (20 mL), dried over anhydrous sodium sulfate, filtered, concentrated and purified by column chromatography to give 100 mg (55%) of the title compound.

$^1$H NMR (400 MHz, CDCl$_3$): δ 0.63-0.67 (m, 2H), 0.88-0.96 (m, 2H), 1.30-1.40 (m, 1H), 1.43-1.54 (m, 1H), 1.84-1.89 (m, 1H), 2.11-2.22 (m, 3H), 2.35-2.42 (m, 2H), 2.89-2.94 (m, 1H), 4.19-4.35 (m, 1H), 6.03 (brs, 1H), 6.30 (s, 1H), 6.81 (d, J=8.6 Hz, 1H), 6.94-7.01 (m, 3H), 7.30 (t, J=7.6 Hz, 2H), 7.39 (dd, J=7.6, 4.9 Hz, 1H), 8.02 (s, 1H), 8.10 (d, J=7.8 Hz, 1H), 8.72 (d, J=3.4 Hz, 1H), 8.95 (s, 1H). MS (ES) m/z 426.2 (M+1). MP=50-51° C.

Following examples were prepared from the appropriate starting material selected from Example 2 using the procedure described for Example 3.1.

| Example 3.A-1 | N-[4-[[3-[(5-Cyclopropyl-2-pyridyl)oxy]phenyl]methylene]cyclohexyl]pyridazine-4-carboxamide<br>$^1$H NMR (400 MHz, CDCl$_3$): δ 0.63-0.67 (m, 2H), 0.94-0.99 (m, 2H), 1.29-1.53 (m, 2H), 1.82-1.92 (m, 1H), 2.09-2.22 (m, 3H), 2.35-2.46 (m, 2H), 2.93 (d, J = 14.7 Hz, 1H), 4.20-4.28 (m, 1H), 6.26 (d, J = 7.4 Hz, 1H), 6.30 (s, 1H), 6.81 (d, J = 8.6 Hz, 1H), 6.93-7.00 (m, 3H), 7.30-7.34 (m, 2H), 7.79-7.81 (m, |

| Example 3.A-2 | N-[4-[[3-[(5-Cyclopropyl-2-pyridyl)oxy]phenyl]methylene]cyclohexyl]-6-fluoro-pyridine-3-carboxamide<br>$^1$H NMR (400 MHz, CDCl$_3$): δ 0.63-0.65 (m, 2H), 0.95-0.99 (m, 2H), 1.25-1.36 (m, 1H), 1.41-1.52 (m, 1H), 1.83-1.89 (m, 1H), 2.08-2.21 (m, 3H), 2.35-2.41 (m, 2H), 2.88-2.93 (m, 1H), 4.17-4.24 (m, 1H), 6.00 (d, J = 7.6 Hz, 1H), 6.29 (s, 1H), 6.81 (d, J = 8.6 Hz, 1H), 6.93-7.03 (m, 4H), 7.29-7.34 (m, 2H), 8.01 (s, 1H), 8.22 (t, J = 6.6 Hz, 1H), 8.57 (s, 1H). MS (ES) m/z 444.2 (M + 1). MP = 49-50° C. |
|---|---|
| Example 3.A-3 | N-[4-[[3-[(5-Cyclopropyl-2-pyridyl)oxy]phenyl]methylene]cyclohexyl]pyridazine-3-carboxamide<br>$^1$H NMR (400 MHz, CDCl$_3$): δ 0.63-0.67 (m, 2H), 0.94-0.99 (m, 2H), 1.44 (qd, J = 11.5, 3.4 Hz, 1H), 1.53-1.59 (m, 1H), 1.83-1.90 (m, 1H), 2.08-2.21 (m, 3H), 2.34-2.48 (m, 2H), 2.90 (d, J = 13.9 Hz, 1H), 4.19-4.29 (m, 1H), 6.30 (s, 1H), 6.81 (d, J = 8.6 Hz, 1H), 6.94-6.97 (m, 2H), 7.01 (d, J = 7.8 Hz, 1H), 7.32-7.35 (m, 2H), 7.67 (dd, J = 8.3, 5.1 Hz, 1H), 8.02 (d, J = 2.2 Hz, 1H), 8.15 (d, J = 8.0 Hz, 1H), 8.33 (dd, J = 8.6, 1.7 Hz, 1H), 9.28 (dd, J = 4.9, 1.5 Hz, 1H). MS (ES) m/z 427.3 (M + 1). MP = 135-136° C. |
| Example 3.A-4 | 6-Amino-N-[4-[[3-[(5-cyclopropyl-2-pyridyl)oxy]phenyl]methylene]cyclohexyl]pyridine-3-carboxamide<br>MS (ES) m/z 541.3 (M + 1). |

Example 4.1

(2S)—N-[4-[[3-[[5-(Trifluoromethyl)-2-pyridyl]oxy]phenyl]methylene]-cyclohexyl]pyrrolidine-2-carboxamide

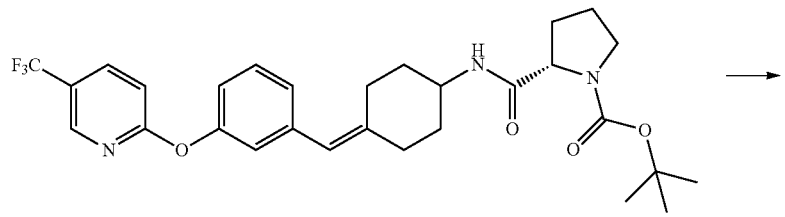

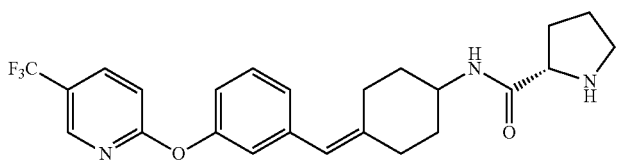

To a cooled solution of tert-butyl (2S)-2-[[4-[[3-[[5-(Trifluoromethyl)-2-pyridyl]oxy]phenyl]methylene]cyclohexyl]carbamoyl]pyrrolidine-1-carboxylate (Example 2.A-10) (200 mg, 0.4 mmol) in DCM (8.5 mL) was added trifluoroacetic acid (2.5 mL) at 0° C. After stirring for 18 h at room temperature, volatiles were evaporated. Resulting residue was dissolved in DCM (15 mL) and washed with aqueous saturated sodium bicarbonate (20 mL), water (20 mL), brine (20 mL), dried over anhydrous sodium sulfate, filtered, concentrated and purified by column chromatography to give 33 mg (20%) of the title compound.

$^1$H NMR (400 MHz, CD$_3$OD): δ 1.27-1.37 (m, 1H), 1.44 (qd, J=12.0, 4.5 Hz, 1H), 1.72-1.80 (m, 3H), 1.89-2.03 (m, 2H), 2.07-2.16 (m, 2H), 2.33 (td, J=12.5, 3.6 Hz, 1H), 2.41 (dt, J=13.6, 4.0 Hz, 1H), 2.83-2.89 (m, 1H), 2.91-2.95 (m, 1H), 2.99-3.06 (m, 1H), 3.62-3.65 (m, 1H), 3.85-3.92 (m, 1H), 6.32 (s, 1H), 6.97-7.00 (m, 2H), 7.11 (t, J=8.3 Hz, 2H), 7.38 (t, J=7.9 Hz, 1H), 8.08 (dd, J=8.9, 2.5 Hz, 1H), 8.42 (s, 1H). MS (ES) m/z 446.3 (M+1). MP=50-51° C.

Following examples were prepared from the appropriate starting examples 2 using the procedure described for Example 4.1.

| Example 4.A-1 | N-[4-[[3-[[5-(Trifluoromethyl)-2-pyridyl]oxy]phenyl]methylene]cyclohexyl]piperidine-4-carboxamide<br>$^1$H NMR (400 MHz, DMSO-d$_6$): δ 1.14-1.24 (m, 1H), 1.32 (qd, J = 12.2, 4.2 Hz, 1H), 1.59-1.87 (m, 7H), 2.02-2.08 (m, 1H), 2.21 (td, J = 12.9, 2.6 Hz, 1H), 2.26-2.36 (m, 2H), 2.68-2.81 (m, 3H), 3.21 (d, J = 12.7 Hz, 1H), 3.71-3.79 (m, 1H), 6.26 (s, 1H), 6.97 (s, 1H), 7.02 (dd, J = 7.8, 1.7 Hz, 1H), 7.08 (d, J = 7.6 Hz, 1H), 7.23 (d, J = 8.6 Hz, 1H), 7.39 (t, J = 7.9 Hz, 1H), 7.79 (d, J = 7.3 Hz, 1H), 7.92 (brs, 1H), 8.22 (dd, J = 8.5, 2.4 Hz, 1H), 8.55 (s, 1H). MS (ES) m/z 460.1 (M + 1). MP = 155-165° C. |
|---|---|
| Example 4.A-2 | 4-Amino-N-[4-[[3-[[5-(trifluoromethyl)-2-pyridyl] oxy]phenyl]methylene]cyclohexyl]pyridine-3-carboxamide<br>$^1$H NMR (400 MHz, CDCl$_3$): δ 1.33 (qd, J = 10.8, 3.2, 1H), 1.44 (qd, J = 11.2, 4.8 Hz, 1H), 2.08-2.20 (m, 3H), 2.36-2.43 (m, 2H), 2.87-2.93 (m, 1H), 4.11-4.21 (m, 1H), 5.88 (d, J = 9.3 Hz, 1H), 6.31 (s, 1H), 6.34 (brs, 1H), 6.60 (dd, J = 7.6, 4.8 Hz, 1H), 6.98-7.03 (m, 3H), 7.09 (d, J = 7.9 Hz, 1H), 7.39 (t, J = 7.5 Hz, 1H), 7.56 (d, J = 7.6 Hz, 1H), 7.90 (dd, J = 8.8, 2.5 Hz, 1H), 8.15 (d, J = 3.7 Hz, 1H), 8.45 (s, 1H). MS (ES) m/z 469.2 (M + 1). M. P = 62-65° C. |
| Example 4.A-3 | 6-Amino-5-chloro-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.33 (qd, J = 11.5, 3.2 Hz, 1H), 1.45 (qd, J = 11.2, 4.8 Hz, 1H), 2.08-2.20 (m, 3H), 2.35-2.42 (m, 2H), 2.87-2.93 (m, 1H), 4.13-4.23 (m, 1H), 5.21 (brs, 2H), 5.81 (d, J = 7.6 Hz, 1H), 6.31 (s, 1H), 6.99-7.03 (m, 3H), 7.09 (d, J = 7.6 Hz, 1H), 7.38 (t, J = 7.6 Hz, 1H), 7.90 (d, J = 8.5 Hz, 1H), 7.95 (s, 1H), 8.34 (s, 1H), 8.45 (s, 1H). MS (ES) m/z 503.2 (M + 1), 504.2 (M + 2). MP = 162-163° C. |
| Example 4.A-4 | 6-Amino-N-[4-[[3-[(5-cyclopropyl-2-pyridyl)oxy]phenyl]methylene]cyclohexyl]pyridine-3-carboxamide<br>$^1$H NMR (400 MHz, CDCl$_3$): δ 0.63-0.68 (m, 2H), 0.94-0.99 (m, 2H), 1.28-1.49 (m, 2H), 1.84-1.89 (m, 1H), 2.07-2.17 (m, 3H), 2.33-2.41 (m, 2H), 2.88 (d, J = 13.9 Hz, 1H), 4.15-4.24 (m, 1H), 4.95 (brs, 2H), 5.82 (d, J = 7.3 Hz, 1H), 6.28 (s, 1H), 6.51 (d, J = 8.6 Hz, 1H), 6.81 (d, J = 8.3 Hz, 1H), 6.93-6.95 (m, 2H), 7.00 (d, J = 7.6 Hz, 1H), 7.32 (t, J = 8.4 Hz, 2H), 7.88 (d, J = 8.6 Hz, 1H), 8.02 (s, 1H), 8.43 (s, 1H). MS (ES) m/z 441.2 (M + 1). MP = 155-157° C. |

Example 5.1

6-(Dimethylamino)-N-[4-[[3-[[5-(trifluoromethyl)-2-pyridyl]oxy]-phenyl]methylene]cyclohexyl]pyridine-3-carboxamide

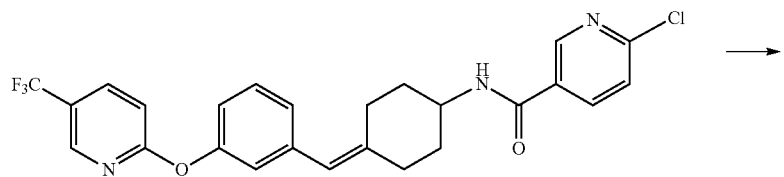

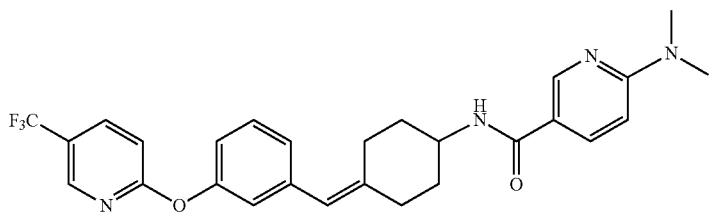

To a stirred solution of 6-chloro-N-[4-[[3-[[5-(trifluoromethyl)-2-pyridyl]oxy]phenyl]-methylene]cyclohexyl]pyridine-3-carboxamide (Example 2.A-22) (200 mg, 0.2 mmol) in DMF (1 mL) was added 2 N dimethylamine in methanol (4 mL) and heated at 50° C. for 19 h in sealed tube. Volatiles were evaporated under reduced pressure. The resulting residue was taken ethyl acetate (15 mL) and washed with water (15 mL), brine (15 mL), dried over anhydrous sodium sulfate, filtered, concentrated and purified by preparative HPLC to give 61 mg (30%) of titled compound.

$^1$H NMR (400 MHz, CDCl$_3$): δ 1.27-1.37 (m, 1H), 1.39-1.49 (m, 1H), 2.07-2.20 (m, 3H), 2.38-2.41 (m, 2H), 2.87 (d, J=13.2 Hz, 1H), 3.13 (s, 6H), 4.15-4.23 (m, 1H), 5.76 (d, J=7.5 Hz, 1H), 6.30 (s, 1H), 6.49 (d, J=8.8 Hz, 1H), 6.98-7.02 (m, 3H), 7.09 (d, J=7.6 Hz, 1H), 7.37 (t, J=7.6 Hz, 1H), 7.84-7.91 (m, 2H), 8.45 (s, 1H), 8.52 (d, J=2.2 Hz, 1H). MS (ES) m/z 497.4 (M+1). MP=153-155° C.

Following examples were prepared from the appropriate starting materials using the procedure described for Example 5.1.

| | |
|---|---|
| Example 5.A-1 | 6-(Methylamino)-N-[4-[[3-[[5-(trifluoromethyl)-2-pyridyl]oxy]phenyl] methylene]cyclohexyl]pyridine-3-carboxamide<br>$^1$H NMR (400 MHz, CDCl$_3$): δ 1.33 (qd, J = 14.9, 4.2 Hz, 1H), 1.45 (qd, J = 10.7, 5.4 Hz, 1H), 2.08-2.22 (m, 3H), 2.38-2.44 (m, 2H), 2.86-2.92 (m, 1H), 2.96 (d, J = 5.1 Hz, 3H), 4.15-4.24 (m, 1H), 4.90 (d, J = 4.1 Hz, 1H), 5.77 (d, J = 7.6 Hz, 1H), 6.30 (s, 1H), 6.39 (d, J = 8.8 Hz, 1H), 6.98-7.02 (m, 3H), 7.10 (d, J = 7.5 Hz, 1H), 7.38 (t, J = 7.6 Hz, 1H), 7.85-7.91 (m, 2H), 8.45 (s, 1H), 8.46 (d, J = 2.0 Hz, 1H). MS (ES) m/z 483.3 (M + 1). MP = 156-157° C. |
| Example 5.A-2 | 6-Pyrrolidin-1-yl-N-[4-[[3-[[5-(trifluoromethyl)-2-pyridyl]oxy]phenyl] methylene]cyclohexyl]pyridine-3-carboxamide<br>$^1$H NMR (400 MHz, CDCl$_3$): δ 1.33 (qd, J = 11.7, 4.4 Hz, 1H), 1.45 (qd, J = 12.0, 5.7 Hz, 1H), 2.01-2.21 (m, 7H), 2.35-2.42 (m, 2H), 2.88 (d, J = 14.0 Hz, 1H), 3.49 (brs, 4H), 4.16-4.24 (m, 1H), 5.75 (d, J = 7.8 Hz, 1H), 6.30 (s, 1H), 6.34 (d, J = 8.9 Hz, 1H), 6.99-7.02 (m, 3H), 7.10 (d, J = 7.5 Hz, 1H), 7.38 (t, J = 7.8 Hz, 1H), 7.85 (dd, J = 8.8, 2.2 Hz, 1H), 7.90 (dd, J = 8.8, 2.4 Hz, 1H), 8.45 (s, 1H), 8.52 (d, J = 2.0 Hz, 1H). MS (ES) m/z 523.1 (M + 1). MP = 153-154° C. |
| Example 5.A-3 | 6-[[(1R)-2-Hydroxy-1-methyl-ethyl]amino]-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.27 (d, J = 6.6 Hz, 3H), 1.27-1.50 (m, 2H), 2.08-2.12 (m, 2H), 2.15-2.20 (m, 2H), 2.36-2.43 (m, 2H), 2.87-2.91 (m, 1H), 3.60 (dd, J = 11.2, 7.2 Hz, 1H), 3.75 (dd, J = 10.8, 2.8 Hz, 1H), 4.05-4.11 (m, 1H), 4.15-4.23 (m, 1H), 4.86 (d, J = 6.1 Hz, 1H), 5.80 (d, J = 7.8 Hz, 1H), 6.30 (s, 1H), 6.43 (d, J = 8.5 Hz, 1H), 6.99-7.03 (m, 3H), 7.10 (d, J = 7.8 Hz, 1H), 7.38 (t, J = 7.8 Hz, 1H), 7.83 (dd, J = 8.8, 2.2 Hz, 1H), 7.90 (dd, J = 8.5, 2.2 Hz, 1H), 8.40 (d, J = 1.8 Hz, 1H), 8.45 (s, 1H). MS (ES) m/z 527.2 (M + 1). MP = 152-154° C. |
| Example 5.A-4 | 6-Morpholino-N-[4-[[3-[[5-(trifluoromethyl)-2-pyridyl]oxy]phenyl] methylene]cyclohexyl]pyridine-3-carboxamide<br>$^1$H NMR (400 MHz, DMSO-d$_6$): δ 1.31-1.41 (m, 1H), 1.43-1.54 (m, 1H), 1.85-2.00 (m, 2H), 2.08 (t, J = 11.2 Hz, 1H), 2.26-2.34 (m, 1H), 2.40 (d, J = 14.2 Hz, 1H), 2.83 (d, J = 14.1 Hz, 1H), 3.51-3.55 (m, 4H), 3.66-3.72 (m, 4H), 3.96-4.06 (m, 1H), 6.31 (s, 1H), 6.85 (d, J = 9.1 Hz, 1H), 7.01 (s, 1H), 7.06 (d, J = 7.6 Hz, 1H), 7.12 (d, J = 7.6 Hz, 1H), 7.25 (d, J = 8.6 Hz, 1H), 7.42 (t, J = 7.8 Hz, 1H), 7.97 (d, J = 9.1 Hz, 1H), 8.02 (d, J = 7.6 Hz, 1H), 8.24 (d, J = 7.5 Hz, 1H), 8.58 (s, 1H), 8.61 (s, 1H). MS (ES) m/z 539.3 (M + 1). M.P. = 87-89° C. |
| Example 5.A-5 | 6-Piperazin-1-yl-N-[4-[[3-[[5-(trifluoromemyl)-2-pyridyl] oxy]phenyl] methylene]cyclohexyl]pyridine-3-carboxamide<br>$^1$H NMR (400 MHz, DMSO-d$_6$): δ 1.31-1.41 (m, 1H), 1.44-1.54 (m, 1H), 1.89-1.98 (m, 2H), 2.08 (t, J = 13.0 Hz, 1H), 2.30 (t, J = 12.0 Hz, 1H), 2.40 (d, J = 13.4 Hz, 1H), 2.83 (d, J = 13.7 Hz, 1H), 2.91 (brs, 4H), 3.62 (brs, 4H), 3.97-4.07 (m, 1H), 6.31 (s, 1H), 6.85 (d, J = 9.1 Hz, 1H), 7.01 (s, 1H), 7.06 (d, J = 8.1 Hz, 1H), 7.12 (d, J = 7.6 Hz, 1H), 7.25 (d, J = 8.8 Hz, 1H), 7.42 (t, J = 7.8 Hz, 1H), 7.97 (d, J = 8.8 Hz, 1H), 8.01 (d, J = 7.6 Hz, 1H), 8.22-8.26 (m, 2H), 8.58 (s, 1H), 8.60 (s, 1H). MS (ES) m/z 538.3 (M + 1). M.P. = 138-140° C. |
| Example 5.A-6 | 6-Pyrazol-1-yl-N-[4-[[3-[[5-(trifluoromemyl)-2-pyridyl]oxy]phenyl] methylene]cyclohexyl]pyridine-3-carboxamide<br>$^1$H NMR (400 MHz, DMSO-d$_6$): δ 1.34-1.46 (m, 1H), 1.47-1.58 (m, 1H), 1.94-2.06 (m, 2H), 2.07-2.16 (m, 1H), 2.28-2.45 (m, 2H), 2.85 (d, J = 12.7 Hz, 1H), 4.01-4.11 (m, 1H), 6.33 (s, 1H), 6.62 (t, J = 2.4 Hz, 1H), 7.02 (s, 1H), 7.06 (d, J = 8.1 Hz, 1H), 7.13 (d, J = 7.6 Hz, 1H), 7.25 (d, J = 8.6 Hz, 1H), 7.43 (t, J = 8.1 Hz, 1H), 7.88 (s, 1H), 7.99 (d, J = 8.5 Hz, 1H), 8.24 (dd, J = 8.8, 2.2 Hz, 1H), 8.39 (dd, J = 8.5, 2.2 Hz, 1H), 8.48 (d, J = 7.8 Hz, 1H), 8.58 (s, 1H), 8.68 (d, J = 2.2 Hz, 1H), 8.88 (d, J = 1.8 Hz, 1H). MS (ES) m/z 520.2 (M + 1). MP = 192-194° C. |
| Example 5.A-7 | 6-[Ethyl(methyl)amino]-N-[4-[[3-[[5-(trifluoromethyl)-2-pyridyl]oxy] phenyl]methylene]cyclohexyl]pyridine-3-carboxamide<br>$^1$H NMR (400 MHz, CDCl$_3$): δ 1.17 (t, J = 6.8 Hz, 3H), 1.26-1.37 (m, 1H), 1.44 (qd, J = 11.0, 5.6 Hz, 1H), 2.07-2.22 (m, 3H), 2.34-2.44 (m, 2H), 2.85-2.91 (m, 1H), 3.08 (s, 3H), 3.62 (q, J = 7.1 Hz, 2H), 4.15-4.24 (m, 1H), 5.77 (d, J = 7.8 Hz, 1H), 6.30 (s, 1H), 6.47 (d, J = 9.0 Hz, 1H), 6.98-7.03 (m, 3H), 7.10 (d, J = 7.8 Hz, 1H), 7.38 (t, J = 7.8 Hz, 1H), 7.85 (dd, J = 9.0, 2.7 Hz, 1H), 7.90 (dd, J = 8.6, 2.2 Hz, 1H), 8.45 (s, 1H), 8.52 (d, J = 2.2 Hz, 1H). MS (ES) m/z 511.3 (M + 1). M. P = 58-60° C. |
| Example 5.A-8 | 6-[(2-Hydroxy-1-methyl-ethyl)amino]-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.26 (d, J = 6.6 Hz, 3H), 1.26-1.36 (m, 1H), 1.42-1.50 (m, 1H), 1.88 (brs, 1H), 2.08-2.22 (m, 3H), 2.34-2.47 (m, 2H), 2.89 (d, J = 13.4 Hz, 1H), 3.60 (dd, J = 10.8, 6.9 Hz, 1H), 3.76 (dd, J = 11.0, 2.1 Hz, 1H), 4.0-4.12 (m, 1H), 4.13-4.23 (m, 1H), 4.88 (d, J = 6.1 Hz, 1H), 5.79 (d, J = 7.6 Hz, 1H), 6.31 (s, 1H), 6.44 (d, J = 8.8 Hz, 1H), 6.99-7.02 (m, 3H), 7.10 (d, J = 7.5 Hz, 1H), 7.38 (t, J = 7.6 Hz, 1H), 7.84 (d, J = 8.8 Hz, 1H), 7.90 (d, J = 8.8 Hz, 1H), 8.41 (s, 1H), 8.45 (s, 1H). MS (ES) m/z 527.2 (M + 1). M. P = 146-148° C. |
| Example 5.A-9 | 6-(2,2,2-Trifluoroethylamino)-N-[4-[[3-[[5-(trifluoromethyl)-2-pyridyl] oxy]phenyl]methylene]cyclohexyl]pyridine-3-carboxamide<br>$^1$H NMR (400 MHz, DMSO-d$_6$): δ 1.39 (qd, J = 11.9, 4.0 Hz, 1H), 1.50 (qd, J = 12.2, 3.9 Hz, 1H), 1.92-2.01 (m, 2H), 2.10 (t, J = 13.0 Hz, 1H), 2.31 (t, J = 13.6 Hz, 1H), 2.41 (d, J = 13.6 Hz, 1H), 2.84 (d, J = 13.6 Hz, 1H), 3.99- |

| | |
|---|---|
| | 4.09 (m, 1H), 5.06 (q, J = 9.1 Hz, 2H), 6.32 (s, 1H), 7.02 (s, 1H), 7.05-7.08 (m, 2H), 7.13 (d, J = 7.7 Hz, 1H), 7.25 (d, J = 8.8 Hz, 1H), 7.42 (t, J = 7.9 Hz, 1H), 8.20-8.26 (m, 2H), 8.34 (d, J = 7.5 Hz, 1H), 8.58 (s, 1H), 8.66 (d, J = 2.3 Hz, 1H). MS (ES) m/z 552.2 (M + 1). MP = 68-70° C. |
| Example 5.A-10 | 6-(Cyclopropylamino)-N-[4-[[3-[[5-(trifluoromethyl)-2-pyridyl]oxy]phenyl]methylene]cyclohexyl]pyridine-3-carboxamide<br>¹H NMR (400 MHz, CDCl₃): δ 0.48-0.68 (m, 2H), 0.76-0.89 (m, 2H), 1.25-1.38 (m, 1H), 1.40-1.50 (m, 1H), 2.00-2.22 (m, 4H), 2.35-2.42 (m, 1H), 2.48-2.59 (m, 1H), 2.86-2.93 (m, 1H), 4.16-4.25 (m, 1H), 5.41 (brs, 1H), 5.78 (d, J = 7.6 Hz, 1H), 6.31 (s, 1H), 6.76 (d, J = 8.8 Hz, 1H), 6.99-7.03 (m, 3H), 7.10 (d, J = 7.1 Hz, 1H), 7.38 (t, J = 7.8 Hz, 1H), 7.88-7.94 (m, 2H), 8.42-8.45 (m, 2H). MS (ES) m/z 509.2 (M + 1). MP = 114-117° C. |
| Example 5.A-11 | 6-[(2-Hydroxy-2-methyl-propyl)amino]-N-[4-[[3-[[5-(trifluoromethyl)-2-pyridyl]oxy]phenyl]methylene]cyclohexyl]pyridine-3-carboxamide<br>¹H NMR (400 MHz, CDCl₃): δ 1.26 (s, 6H), 1.26-1.37 (m, 1H), 1.44 (qd, J = 11.5, 5.4 Hz, 1H), 2.08-2.19 (m, 3H), 2.35-2.44 (m, 2H), 2.89 (d, J = 13.7 Hz, 1H), 3.41 (d, J = 5.9 Hz, 2H), 4.14-4.23 (m, 1H), 5.12 (s, 1H), 5.74 (d, J = 7.8 Hz, 1H), 6.30 (s, 1H), 6.46 (d, J = 8.8 Hz, 1H), 6.98-7.02 (m, 3H), 7.09 (d, J = 7.8 Hz, 1H), 7.38 (t, J = 7.8 Hz, 1H), 7.82 (dd, J = 8.8, 2.2 Hz, 1H), 7.89 (d, J = 8.8 Hz, 1H), 8.40 (s, 1H), 8.45 (s, 1H). MS(ES) m/z 541.1 (M + 1). MP = 75-77° C. |

Example 6.1

6-Ethoxy-N-[4-[[3-[[5-(trifluoromethyl)-2-pyridyl]oxy]phenyl]-methylene]cyclohexyl]pyridine-3-carboxamide

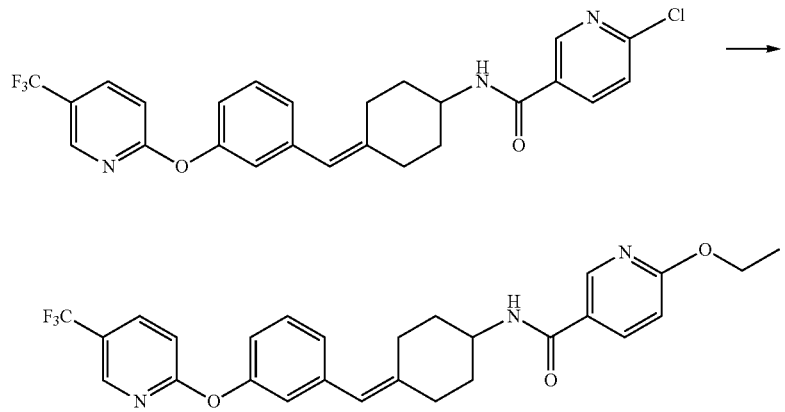

To a stirred solution of 6-chloro-N-[4-[[3-[[5-(trifluoromethyl)-2-pyridyl]oxy]phenyl]-methylene]cyclohexyl]pyridine-3-carboxamide (Example 2.A-22), 150 mg, 0.3 mmol) in Ethanol (5 mL) was added sodium ethoxide (42 mg, 0.6 mmol) and refluxed for 19 h. Volatiles were evaporated under reduced pressure. The resulting residue was taken in ethyl acetate (15 mL), washed with water (15 mL), brine (15 mL), dried over anhydrous sodium sulfate, filtered, concentrated and purified by preparative HPLC to give 30 mg (20%) of titled compound.

¹H NMR (400 MHz, CDCl₃): δ 1.28-1.51 (m, 2H), 1.40 (t, J=7.1 Hz, 3H), 2.10-2.21 (m, 3H), 2.37-2.43 (m, 2H), 2.87-2.92 (m, 1H), 4.18-4.23 (m, 1H), 4.39 (q, J=6.8 Hz, 2H), 5.85 (d, J=7.6 Hz, 1H), 6.31 (s, 1H), 6.75 (d, J=8.5 Hz, 1H), 6.99-7.02 (m, 3H), 7.10 (d, J=7.6 Hz, 1H), 7.38 (t, J=7.6 Hz, 1H), 7.90 (dd, J=8.6, 2.0 Hz, 1H), 7.96 (dd, J=8.6, 2.2 Hz, 1H), 8.45 (s, 1H), 8.52 (d, J=2.0 Hz, 1H). MS (ES) m/z 498.3 (M+1). MP=130-133° C.

Following example were prepared from the appropriate starting materials using the procedure described for Example 6.1.

| | |
|---|---|
| Example 6.A-1 | 6-(2,2,2-Trifluoroethoxy)-N-[4-[[3-[[5-(trifluoromethyl)-2-pyridyl]oxy]phenyl]methylene]cyclohexyl]pyridine-3-carboxamide<br>¹H NMR (400 MHz, CDCl₃): δ 1.28-1.39 (m, 1H), 1.46 (qd, J = 11.3, 5.4 Hz, 1H), 2.18-2.22 (m, 3H), 2.35-2.46 (m, 2H), 2.87-2.94 (m, 1H), 4.16-4.25 (m, 1H), 4.79 (q, J = 8.5 Hz, 2H), 5.92 (d, J = 7.8 Hz, 1H), 6.31 (s, 1H), 6.90 (d, J = 8.5 Hz, 1H), 6.98-7.02 (m, 3H), 7.09 (d, J = 7.8 Hz, 1H), 7.38 (t, J = 7.8 Hz, 1H), 7.90 (dd, J = 8.8, 2.5 Hz, 1H), 8.04 (dd, J = 8.8, 2.5 Hz, 1H), 8.45 (s, 1H), 8.52 (d, J = 2.2 Hz, 1H). MS (ES) m/z 552.2 (M + 1). MP = 67-68° C. |

Example 7.1

Ethyl 2-[3-(trifluoromethyl)-4-[[4-[[3-[[5-(trifluoromethyl)-2-pyridyl]oxy]phenyl]methylene]cyclohexyl]carbamoyl]pyrazol-1-yl]acetate

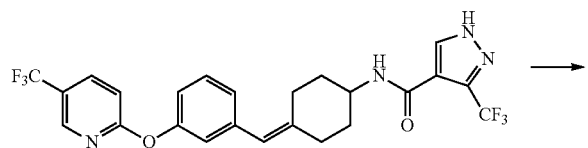

anhydrous sodium sulfate, filtered, concentrated and triturated with hexane to give 50 mg of ethyl 2-[3-(trifluoromethyl)-4-[[4-[[3-[[5-(trifluoromethyl)-2-pyridyl]oxy]phenyl]methylene]-cyclohexyl]carbamoyl]pyrazol-1-yl]acetate.

$^1$H NMR (400 MHz, CDCl$_3$): δ 1.31 (t, J=7.1 Hz, 3H), 1.34-1.56 (m, 2H), 2.05-2.22 (m, 3H), 2.33-2.44 (m, 2H), 2.80-2.86 (m, 1H), 4.13-4.22 (m, 1H), 4.25 (q, J=7.1 Hz, 2H), 4.94 (s, 2H), 5.95 (d, J=6.1 Hz, 1H), 6.31 (s, 1H), 6.98-7.02 (m, 3H), 7.09 (d, J=7.8 Hz, 1H), 7.38 (t, J=7.6 Hz, 1H), 7.91 (dd, J=8.7, 2.2 Hz, 1H), 8.03 (s, 1H), 8.45 (s, 1H). MS (ES) m/z 597.3 (M+1).

Following examples were prepared from appropriate starting materials in analogous manner of Example 7.1

| Example | |
|---|---|
| 7.A-1 | Ethyl-2-[4-[5-[[4-[[3-[[5-(trifluoromethyl)-2-pyridyl]oxy]phenyl]methylene]cyclohexyl]carbamoyl]-2-pyridyl]pyrazol-1-yl]acetate<br>$^1$H NMR (400 MHz, CDCl$_3$): δ 1.30 (t, J = 7.1 Hz, 3H), 1.37 (qd, J = 10.8, 3.9 Hz, 1H), 1.46 (qd, J = 12.0, 5.4 Hz, 1H), 2.12-2.25 (m, 3H), 2.37-2.46 (m, 2H), 2.88-2.94 (m, 1H), 4.20-4.29 (m, 3H), 4.95 (s, 2H), 5.93 (d, J = 7.8 Hz, 1H), 6.32 (s, 1H), 6.98-7.02 (m, 3H), 7.10 (d, J = 7.8 Hz, 1H), 7.38 (t, J = 7.9 Hz, 1H), 7.52 (d, J = 8.3 Hz, 1H), 7.90 (dd, J = 8.8, 2.4 Hz, 1H), 8.04-8.07 (m, 2H), 8.08 (s, 1H), 8.44 (s, 1H), 8.87 (d, J = 1.9 Hz, 1H). MS (ES) m/z 606.3 (M + 1). |
| 7.A-2 | Ethyl-2-[4-[[4-[[3-[[5-(trifluoromethyl)-2-pyridyl]oxy]phenyl]methylene]cyclohexyl]carbamoyl]pyrazol-1-yl]acetate<br>$^1$H NMR (400 MHz, DMSO-d$_6$): δ 1.20 (t, J = 7.1 Hz, 3H), 1.28-1.37 (m, 1H), 1.39-1.49 (qd, J = 11.7, 2.9 Hz, 1H), 1.89-1.97 (m, 2H), 2.07 (t, J = 12.7 Hz, 1H), 2.29 (t, J = 13.2 Hz, 1H), 2.39 (d, J = 13.2 Hz, 1H), 2.82 (d, J = 14.0 Hz, 1H), 3.93-4.03 (m, 1H), 4.15 (q, J = 6.8 Hz, 2H), 5.09 (s, 2H), 6.31 (s, 1H), 7.00 (s, 1H), 7.05 (d, J = 8.1 Hz, 1H), 7.12 (d, J = 7.5 Hz, 1H), 7.25 (d, J = 8.8 Hz, 1H), 7.42 (t, J = 7.8 Hz, 1H), 7.87 (s, 1H), 7.90 (d, J = 7.8 Hz, 1H), 8.17 (s, 1H), 8.24 (dd, J = 8.6, 2.0 Hz, 1H), 8.58 (s, 1H). MS (ES) m/z 529.3 (M + 1). |
| 7.A-3 | Ethyl-2-[3-[5-[[4-[[3-[[5-(trifluoromethyl)-2-pyridyl]oxy]phenyl]methylene]cyclohexyl]carbamoyl]-2-pyridyl]pyrazol-1-yl]acetate<br>$^1$H NMR (400 MHz, CDCl$_3$): δ 1.29 (t, J = 7.3 Hz, 3H), 1.32-1.56 (m, 2H), 2.12-2.27 (m, 3H), 2.37-2.45 (m, 2H), 2.88-2.29 (m, 1H), 4.21-4.30 (m, 3H), 5.00 (s, 2H), 6.12 (d, J = 6.4 Hz, 1H), 6.31 (s, 1H), 6.99-7.03 (m, 4H), 7.10 (d, J = 7.5 Hz, 1H), 7.38 (t, J = 7.8 Hz, 1H), 7.56 (d, J = 2.4 Hz, 1H), 7.90 (dd, J = 8.6, 2.5 Hz, 1H), 7.98 (d, J = 8.3 Hz, 1H), 8.11 (dd, J = 8.3, 2.2 Hz, 1H), 8.45 (s, 1H), 8.95 (s, 1H). MS (ES) m/z 606.3 (M + 1). |

-continued

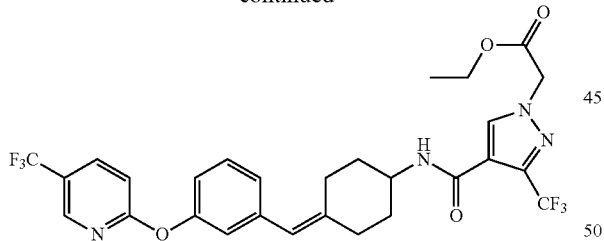

To a mixture of 3-(Trifluoromethyl)-N-[4-[[3-[[5-(trifluoromethyl)-2-pyridyl]oxy]-phenyl]methylene]cyclohexyl]-1H-pyrazole-4-carboxamide (Example 2.A-29) (50 mg, 0.1 mmol) in DMF (0.5 mL) was added ethyl bromoacetate (0.016 mL, 0.14 mmol) followed by potassium carbonate (26.8 mg, 0.2 mmol) at room temperature. After stirring for 2 h, reaction was quenched by the addition of water (5 mL). This was extracted with ethyl acetate (2×5 mL). Combined organic layer was washed with brine (10 mL), dried over

Example 8.1

2-[3-(Trifluoromethyl)-4-[[4-[[3-[[5-(trifluoromethyl)-2-pyridyl]oxy]-phenyl]methylene]cyclohexyl]carbamoyl]pyrazol-1-yl]acetic acid

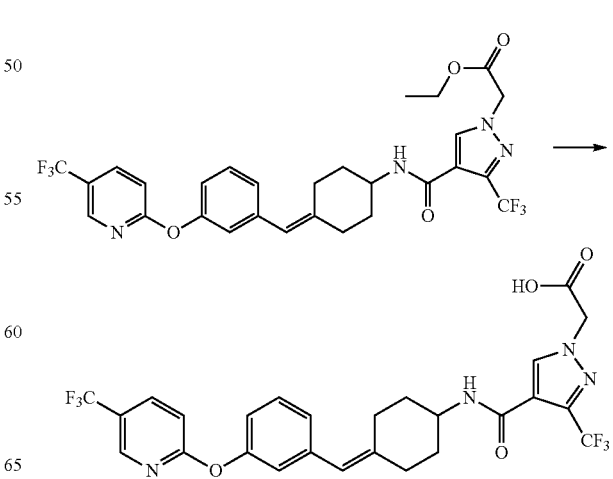

To a stirred solution of ethyl 2-[3-(trifluoromethyl)-4-[[4-[[3-[[5-(trifluoromethyl)-2-pyridyl]oxy]phenyl]methylene]cyclohexyl]carbamoyl]pyrazol-1-yl]acetate (Example 7.1) (50 mg, 0.1 mmol) in THF:MeOH (3:1 mixture, 4.0 mL) was added a solution of lithium hydroxide monohydrate (11 mg, 0.2 mmol) in water (0.5 mL) at room temperature. After stirring for 2 h, volatiles were evaporated under reduced pressure. Resulting residue was triturated with diethylether. Solid obtained was taken in water, acidified to pH 2. Obtained solid was filtered, dried under vacuum to give 35 mg (63%) of 2-[3-(trifluoromethyl)-4-[[4-[[3-[[5-(trifluoromethyl)-2-pyridyl]oxy]phenyl]-methylene]cyclohexyl]carbamoyl]pyrazol-1-yl]acetic acid as a solid.

$^1$H NMR (400 MHz, CDCl$_3$): δ 1.26-1.36 (m, 1H), 1.38-1.47 (m, 1H), 1.88-1.98 (m, 2H), 2.08 (t, J=13.2 Hz, 1H), 2.26-2.42 (m, 2H), 2.81 (d, J=13.1 Hz, 1H), 3.91-4.00 (m, 1H), 4.94 (brs, 2H), 6.31 (s, 1H), 7.01 (s, 1H), 7.06 (d, J=8.5 Hz, 1H), 7.12 (d, J=7.5 Hz, 1H), 7.25 (d, J=8.7 Hz, 1H), 7.42 (t, J=7.4 Hz, 1H), 8.14 (d, J=7.3 Hz, 1H), 8.24 (d, J=8.8 Hz, 1H), 8.34 (s, 1H), 8.58 (s, 1H), 13.50 (brs, 1H). MS (ES) m/z 569.2 (M+1). MP=176-178° C.

Following examples were prepared from the appropriate starting materials using the procedure described for Example 8.1.

| Example 8.A-1 | 2-[4-[5-[[4-[[3-[[5-(Trifluoromethyl)-2-pyridyl]oxy]phenyl]methylene]cyclohexyl]carbamoyl]-2-pyridyl]pyrazol-1-yl]acetic acid<br>$^1$H NMR (400 MHz, DMSO-d$_6$): δ 1.35-1.44 (m, 1H), 1.47-1.57 (m, 1H), 1.94-2.02 (m, 2H), 2.11 (t, J = 8.5 Hz, 1H), 2.33 (t, J = 8.8 Hz, 1H), 2.43 (d, J = 14.4 Hz, 1H), 2.84 (d, J = 14.0 Hz, 1H), 4.01-4.10 (m, 1H), 5.03 (s, 2H), 6.33 (s, 1H), 7.02 (s, 1H), 7.06 (d, J = 8.1 Hz, 1H), 7.13 (d, J = 7.8 Hz, 1H), 7.26 (d, J = 8.6 Hz, 1H), 7.43 (t, J = 8.1 Hz, 1H), 7.77 (d, J = 8.4 Hz, 1H), 8.12 (s, 1H), 8.16 (dd, J = 8.3, 2.0 Hz, 1H), 8.24 (dd, J = 8.5, 2.2 Hz, 1H), 8.38-8.41 (m, 2H), 8.59 (s, 1H), 8.93 (s, 1H), 13.17 (brs, 1H). MS (ES) m/z 578.3 (M + 1). MP = 280-285° C. |
|---|---|
| Example 8.A-2 | 2-[4-[[4-[[3-[[5-(Trifluoromethyl)-2-pyridyl]oxy]phenyl]methylene]cyclohexyl]carbamoyl]pyrazol-1-yl]acetic acid<br>$^1$H NMR (400 MHz, DMSO-d$_6$): δ 1.35 (qd, J = 11.5, 3.4 Hz, 1H), 1.47 (qd, J = 11.4, 3.4 Hz, 1H), 1.87-1.95 (m, 2H), 2.06 (t, J = 12.7 Hz, 1H), 2.28 (t, J = 12.3 Hz, 1H), 2.39 (d, J = 13.2 Hz, 1H), 2.82 (d, J = 14.0 Hz, 1H), 3.93-4.03 (m, 1H), 4.71 (s, 2H), 6.31 (s, 1H), 7.01 (s, 1H), 7.05 (d, J = 8.0 Hz, 1H), 7.12 (d, J = 7.5 Hz, 1H), 7.25 (d, J = 8.5 Hz, 1H), 7.42 (t, J = 7.8 Hz, 1H), 7.82 (s, 1H), 7.95 (d, J = 8.0 Hz, 1H), 8.16 (s, 1H), 8.24 (dd, J = 8.8, 2.2 Hz, 1H), 8.58 (s, 1H), 13.42 (brs, 1H). MS (ES) m/z 501.2 (M + 1). MP = 180-185° C. |
| Example 8.A-3 | 2-[3-[5-[[4-[[3-[[5-(Trifluoromethyl)-2-pyridyl]oxy]phenyl]methylene]cyclohexyl]carbamoyl]-2-pyridyl]pyrazol-1-yl]acetic acid<br>$^1$H NMR (400 MHz, DMSO-d$_6$): δ 1.36-1.45 (m, 1H), 1.47-1.58 (m, 1H), 1.94-2.04 (m, 2H), 2.11 (t, J = 10.7 Hz, 1H), 2.33 (t, J = 9.8 Hz, 1H), 2.42 (d, J = 13.2 Hz, 1H), 2.84 (d, J = 14.0 Hz, 1H), 4.02-4.10 (m, 1H), 4.52 (s, 2H), 6.32 (s, 1H), 6.80 (s, 1H), 7.02 (s, 1H), 7.05 (d, J = 8.3 Hz, 1H), 7.13 (d, J = 7.6 Hz, 1H), 7.24 (d, J = 8.8 Hz, 1H), 7.42 (t, J = 7.8 Hz, 1H), 7.68 (s, 1H), 7.94 (d, J = 8.3 Hz, 1H), 8.18 (d, J = 8.3 Hz, 1H), 8.23 (dd, J = 6.3, 2.5 Hz, 1H), 8.40 (d, J = 7.5 Hz, 1H), 8.58 (s, 1H), 8.95 (s, 1H). MS (ES) m/z 578.2 (M + 1). MP = 203-206° C. |
| Example 8.A-4 | 1-[5-[[4-[[3-[[5-(Trifluoromethyl)-2-pyridyl]oxy]phenyl]methylene]cyclohexyl]carbamoyl]-2-pyridyl]pyrazole-4-carboxylic acid<br>$^1$H NMR (400 MHz, DMSO-d$_6$): δ 1.35-1.45 (m, 1H), 1.48-1.58 (m, 1H), 1.94-2.04 (m, 2H), 2.08-2.16 (m, 1H), 2.29-2.42 (m, 2H), 2.85 (d, J = 13.7 Hz, 1H), 4.03-4.12 (m, 1H), 6.33 (s, 1H), 7.02 (s, 1H), 7.06 (d, J = 8.1 Hz, 1H), 7.13 (d, J = 7.9 Hz, 1H), 7.26 (d, J = 8.6 Hz, 1H), 7.43 (t, J = 8.1 Hz, 1H), 8.04 (d, J = 8.6 Hz, 1H), 8.21 (s, 1H), 8.24 (dd, J = 8.8, 2.4 Hz, 1H), 8.43 (dd, J = 8.6, 2.0 Hz, 1H), 8.54 (d, J = 7.8 Hz, 1H), 8.59 (s, 1H), 8.93 (d, J = 1.9 Hz, 1H), 9.98 (s, 1H), 12.86 (brs, 1H). MS (ES) m/z 564.2 (M + 1). MP = 239-241° C. |
| Example 8.A-5 | 1-[5-[[4-[[3-[[5-(Trifluoromethyl)-2-pyridyl]oxy]phenyl]methylene]cyclohexyl]carbamoyl]-2-pyridyl]pyrazole-3-carboxylic acid<br>$^1$H NMR (400 MHz, DMSO-d$_6$): δ 1.36-1.46 (m, 1H), 1.48-1.58 (m, 1H), 1.95-2.16 (m, 2H), 2.12 (t, J = 13.0 Hz, 1H), 2.33 (t, J = 12.2 Hz, 1H), 2.43 (d, J = 14.0 Hz, 1H), 2.85 (d, J = 13.9 Hz, 1H), 4.03-4.12 (m, 1H), 6.33 (s, 1H), 6.98 (d, J = 2.5 Hz, 1H), 7.02 (s, 1H), 7.06 (d, J = 8.0 Hz, 1H), 7.14 (d, J = 7.9 Hz, 1H), 7.26 (d, J = 8.6 Hz, 1H), 7.43 (t, J = 7.6 Hz, 1H), 8.06 (d, J = 8.6 Hz, 1H), 8.24 (dd, J = 8.6, 2.2 Hz, 1H), 8.45 (dd, J = 8.6, 1.7 Hz, 1H), 8.55 (d, J = 10.1 Hz, 1H), 8.56 (s, 1H), 8.75 (d, J = 2.5 Hz, 1H), 8.92 (d, J = 1.7 Hz, 1H), 13.25 (brs, 1H). MS (ES) m/z 564.2 (M + 1). MP = 179-181° C. |

Example 9.1

6-(1-Methylpyrazol-4-yl)-N-[4-[[3-[[5-(trifluoromethyl)-2-pyridyl]oxy]phenyl]methylene]cyclohexyl]pyridine-3-carboxamide

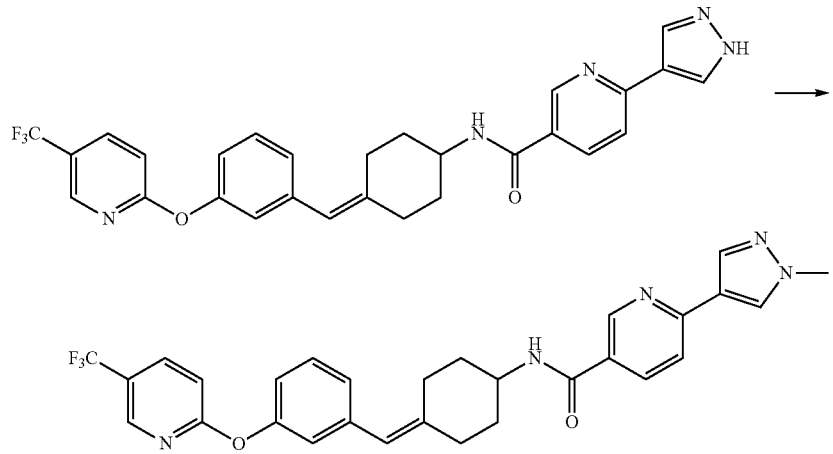

To a stirred solution of 6-(1H-pyrazol-4-yl)-N-[4-[[3-[[5-(trifluoromethyl)-2-pyridyl]oxy]phenyl]methylene]cyclohexyl]pyridine-3-carboxamide (Example 2.B-5) (60 mg, 0.1 mmol) in DMF (1 mL) was added methyl iodide (1 μL, 0.15 mmol) followed by potassium carbonate (55 mg, 0.4 mmol) at room temperature. After stirring for 19 h, reaction was quenched by the addition of water (10 mL). This was extracted with ethyl acetate (2×5 mL). Combined organic layer was washed with brine (10 mL), dried over anhydrous sodium sulfate, filtered, concentrated and purified by preparative TLC to give 7 mg (11%) of titled compound.

$^1$H NMR (400 MHz, CDCl$_3$): δ 1.36 (qd, J=12.0, 5.4 Hz, 1H), 1.48 (qd, J=11.2, 5.1 Hz, 1H), 2.12-2.23 (m, 3H), 2.36-2.47 (m, 2H), 2.88-2.94 (m, 1H), 3.97 (s, 3H), 4.19-4.27 (m, 1H), 5.96 (d, J=7.8 Hz, 1H), 6.32 (s, 1H), 6.99-7.03 (m, 3H), 7.10 (d, J=7.6, 1H), 7.38 (t, J=7.6 Hz, 1H), 7.49 (d, J=8.3 Hz, 1H), 7.90 (dd, J=8.6, 2.2 Hz, 1H), 7.97 (d, J=2.4 Hz, 2H), 8.05 (dd, J=8.3, 2.2 Hz, 1H), 8.45 (s, 1H), 8.86 (d, J=2.2 Hz, 1H). MS (ES) m/z 534.2 (M+1). MP=147-148° C.

Following examples were prepared from either 2-methyloxirane or 2-bromoethyl-tert-butyl-dimethyl-silane using procedure described for Example 9.1.

| Example | |
|---|---|
| Example 9.A-1 | 1-(2-Hydroxypropyl)-3-(trifluoromethyl)-N-[4-[[3-[[5-(trifluoromethyl)-2-pyridyl]oxy]phenyl]methylene]cyclohexyl]pyrazole-4-carboxamide<br>$^1$H NMR (400 MHz, CDCl$_3$): δ 1.27 (d, J = 6.3 Hz, 3H), 1.29-1.40 (m, 1H), 1.43-1.53 (m, 1H), 2.04-2.22 (m, 3H), 2.33-2.43 (m, 2H), 2.83 (d, J = 14.1 Hz, 1H), 4.04 (dd, J = 13.7, 8.2 Hz, 1H), 4.13-4.30 (m, 3H), 5.93 (d, J = 7.6 Hz, 1H), 6.31 (s, 1H), 6.98-7.03 (m, 3H), 7.09 (d, J = 7.2, 1H), 7.39 (t, J = 7.7 Hz, 1H), 7.90 (d, J = 8.2 Hz, 1H), 8.03 (s, 1H), 8.45 (s, 1H). MS (ES) m/z 569.3 (M + 1). MP = 87-89° C. |
| Example 9.A-2 | 6-[1-(2-Hydroxypropyl)pyrazol-3-yl]-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.27 (d, J = 6.3 Hz, 3H), 1.38 (qd, J = 11.4, 5.8 Hz, 1H), 1.50 (qd, J = 12.0, 6.2 Hz, 1H), 2.12-2.18 (m, 2H), 2.20-2.26 (m, 1H), 2.37-2.48 (m, 2H), 2.89-2.96 (m, 1H), 3.28 (brs, 1H), 4.07 (dd, J = 13.6, 8.0 Hz, 1H), 4.21-4.32 (m, 3H), 5.97 (d, J = 7.8 Hz, 1H), 6.32 (s, 1H), 6.96 (d, J = 2.2 Hz, 1H), 6.99-7.03 (m, 3H), 7.10 (d, J = 7.6 Hz, 1H), 7.39 (t, J = 7.8 Hz, 1H), 7.51 (d, J = 2.2 Hz, 1H), 7.90 (dd, J = 8.8, 2.2 Hz, 1H), 7.99 (d, J = 8.3 Hz, 1H), 8.10 (dd, J = 8.3, 2.2 Hz, 1H), 8.45 (s, 1H), 8.94 (s, 1H). MS (ES) m/z 578.1 (M + 1). MP = 74-75° C. |
| Example 9.A-3 | 6-[1-(2-Hydroxyethyl)pyrazol-3-yl]-N-[4-[[3-[[5-(trifluoromethyl)-2-pyridyl]oxy]phenyl]methylene]cyclohexyl]pyridine-3-carboxamide<br>$^1$H NMR (400 MHz, CDCl$_3$): δ 1.38 (qd, J = 11.0, 5.4 Hz, 1H), 1.50 (qd, J = 11.7, 5.6 1H), 2.12-2.27 (m, 3H), 2.37-2.46 (m, 2H), 2.88-2.95 (m, 2H), 4.08 (brs, 2H), 4.20-4.28 (m, 1H), 4.38 (t, J = 4.4 Hz, 2H), 5.98 (d, J = 7.3 Hz, 1H), 6.32 (s, 1H), 6.95 (d, J = 2.2 Hz, 1H), 6.99-7.03 (m, 3H), 7.10 (d, J = 7.6 Hz, 1H), 7.39 (t, J = 7.6 Hz, 1H), 7.53 (d, J = 2.0 Hz, 1H), 7.90 (dd, J = 8.5, 2.2 Hz, 1H), 7.98 (d, J = 8.0 Hz, 1H), 8.10 (dd, J = 8.4, 1.9 Hz, 1H), 8.45 (s, 1H), 8.94 (s, 1H). MS (ES) m/z 564.1 (M + 1). MP = 170-171° C. |

Example 10.1

5-Amino-6-chloro-N-[4-[[3-[[5-(trifluoromethyl)-2-pyridyl]oxy]-phenyl]methylene]cyclohexyl]pyridine-3-carboxamide

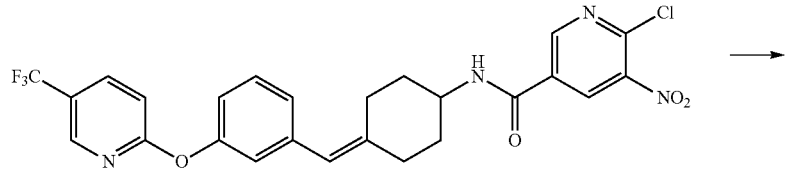

To a stirred solution of 6-chloro-5-nitro-N-[4-[[3-[[5-(trifluoromethyl)-2-pyridyl]oxy]phenyl]methylene]cyclohexyl]pyridine-3-carboxamide (Example 2.A-48), (120 mg, 0.2 mmol) in acetic acid (3 mL) was added iron powder (20 mg, 0.8 mmol) and heated to 70° C. for 2 h. Volatiles were evaporated under reduced pressure. Resulting residue was taken in water, pH adjusted to 6 using potassium phosphate tribasic. Aqueous layer was extracted with ethyl acetate (15 mL), washed with brine (15 mL), dried over anhydrous sodium sulfate, filtered, concentrated and purified by preparative HPLC to give 20 mg (18%) of titled compound.

$^1$H NMR (400 MHz, CDCl$_3$): δ 1.34 (qd, J=11.6, 3.4 Hz, 1H), 1.46 (qd, J=12.4, 4.8 Hz, 1H), 2.09-2.21 (m, 3H), 2.34-2.45 (m, 2H), 2.88-2.93 (m, 1H), 4.13-4.22 (m, 1H), 4.26 (s, 2H), 5.95 (d, J=8.3 Hz, 1H), 6.31 (s, 1H), 6.98-7.02 (m, 3H), 7.09 (d, J=7.6 Hz, 1H), 7.38 (t, J=7.6 Hz, 1H), 7.48 (d, J=2.0 Hz, 1H), 7.89 (d, J=8.6 Hz, 1H), 8.02 (d, J=1.7 Hz, 1H), 8.44 (s, 1H). MS (ES) m/z 503.2 (M+1), 504.1 (M+2). MP=155-156° C.

Example 11.1

6-(1H-Tetrazol-5-yl)-N-[4-[[3-[[5-(trifluoromethyl)-2-pyridyl]oxy]-phenyl]methylene]cyclohexyl]pyridine-3-carboxamide A mixture of 6-cyano-N-[4-[[3-[[5-(trifluoromethyl)-2-pyridyl]oxy]phenyl]-methylene]-cyclohexyl]pyridine-3-carboxamide (Example 2.A-27) (40 mg, 0.08 mmol), sodium azide (14 mg, 0.2 mmol), ammonium chloride (6 mg, 0.1 mmol) and lithium chloride (3 mg, 0.06 mmol) in DMF (2 mL) was heated to 110° C. for 11 h. Reaction mixture was cooled to room temperature, filtered through celite bed, filtrate was evaporated under reduced pressure. To this was added water (2 mL), neutralized with acid, precipitated solid was filtered through Buchner funnel, dried and purified by column chromatography to give 15 mg (34%) of titled compound.

$^1$H NMR (400 MHz, DMSO-d$_6$): δ 1.36-1.46 (m, 1H), 1.50-1.58 (m, 1H), 1.95-2.04 (m, 2H), 2.12 (t, J=12.3 Hz, 1H), 2.33 (t, J=12.1 Hz, 1H), 2.43 (d, J=13.8 Hz, 1H), 2.86 (d, J=12.0 Hz, 1H), 4.03-4.12 (m, 1H), 6.33 (s, 1H), 7.02 (s, 1H), 7.06 (d, J=7.7 Hz, 1H), 7.14 (d, J=7.7 Hz, 1H), 7.26 (d, J=8.8 Hz, 1H), 7.43 (t, J=7.9 Hz, 1H), 8.13 (d, J=8.2 Hz, 1H), 8.23-8.27 (m, 2H), 8.50 (d, J=7.7 Hz, 1H), 8.59 (s, 1H), 9.03 (s, 1H). MS (ES) m/z 522.2 (M+1). MP=197-198° C.

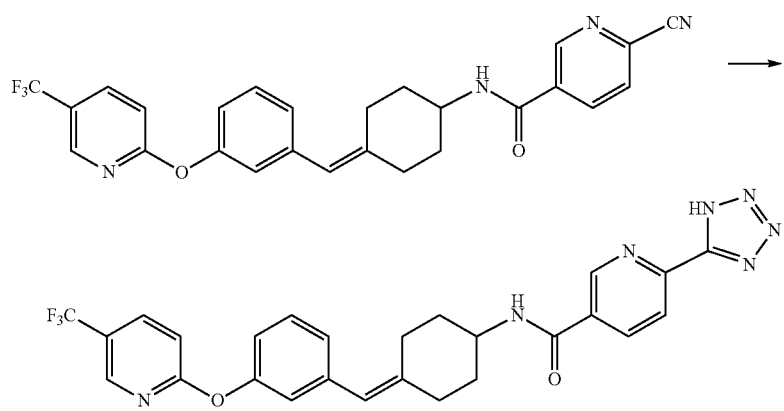

Example 12.1

6-(2-Oxopyrrolidin-1-yl)-N-[4-[[3-[[5-(trifluoromethyl)-2-pyridyl]-oxy]phenyl]methylene]cyclohexyl]pyridine-3-carboxamide

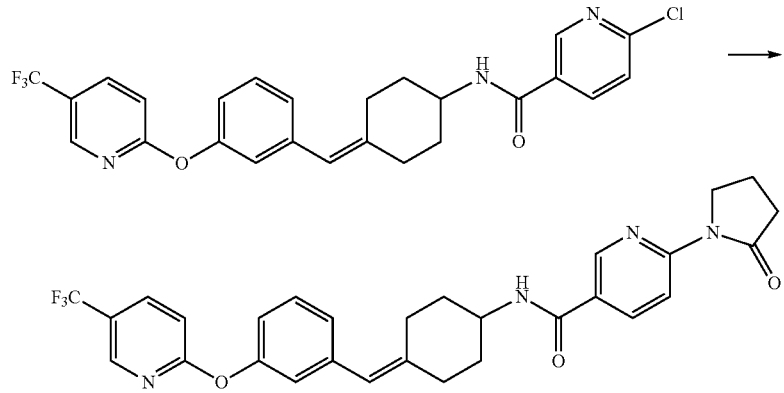

To a suspension of copper iodide (4 mg, 0.02 mmol), potassium carbonate (79 mg, 0.5 mmol) and trans-1,2-diaminocyclohexane (4 mg, 0.02 mmol) in dioxane (3 mL) was added 6-chloro-N-[4-[[3-[[5-(trifluoromethyl)-2-pyridyl]oxy]phenyl]methylene]-cyclohexyl]pyridine-3-carboxamide (Example 2.A-22) (140 mg, 0.3 mmol) and pyrrolidin-2-one (26 mg, 0.3 mmol) and heated at 100° C. for 24 h. Reaction mixture was cooled to room temperature and filtered. Filtrate was diluted with ethyl acetate (10 mL) washed with brine (10 mL), dried over anhydrous sodium sulfate, filtered, concentrated and purified by column chromatography to give 30 mg (19%) of titled compound.

$^1$H NMR (400 MHz, CDCl$_3$): δ 1.36-1.56 (m, 2H), 2.12-2.21 (m, 5H), 2.36-2.44 (m, 2H), 2.69 (t, J=8.1 Hz, 2H), 2.88-2.94 (m, 1H), 4.13 (t, J=7.1 Hz, 2H), 4.38-4.48 (m, 1H), 5.90 (d, J=78 Hz, 1H), 6.32 (s, 1H), 6.99-7.03 (m, 3H), 7.10 (d, J=7.6 Hz, 1H), 7.38 (t, J=7.6 Hz, 1H), 7.90 (dd, J=8.8, 2.0 Hz, 1H), 8.03 (dd, J=8.8, 1.9 Hz, 1H), 8.45 (s, 1H), 8.49 (d, J=8.8 Hz, 1H), 8.75 (s, 1H). MS (ES) m/z 537.3 (M+1). MP=80-83° C.

Example 13.1

3-(Trifluoromethyl)-N-[4-[1-[3-[[5-(trifluoromethyl)-2-pyridyl]oxy]-phenyl]ethylidene]cyclohexyl]-1H-pyrazole-4-carboxamide

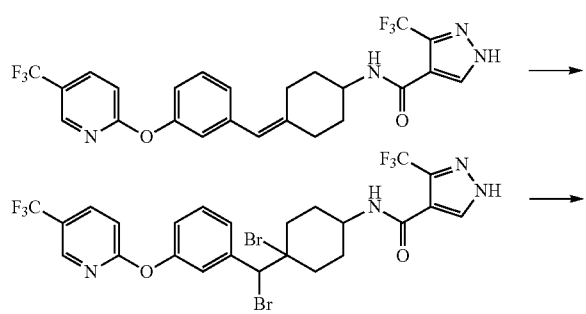

-continued

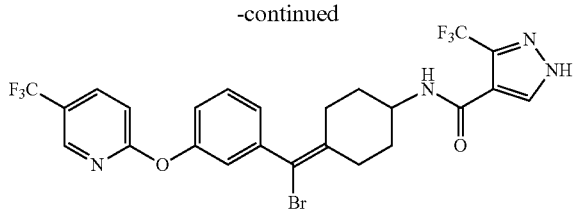

Step-I: N-[4-Bromo-4-[bromo-[3-[[5-(trifluoromethyl)-2-pyridyl]oxy]phenyl]-methyl]cyclohexyl]-3-(trifluoromethyl)-1H-pyrazole-4-carboxamide To a stirred suspension of 3-(trifluoromethyl)-N-[4-[[3-[[5-(trifluoromethyl)-2-pyridyl]oxy]phenyl]methylene]cyclohexyl]-1H-pyrazole-4-carboxamide (Example 2.A-29) (100 mg, 0.2 mmol), potassium carbonate (13 mg, 0.1 mmol) in DCM (2.5 mL) was added a solution of bromine (0.06 mL, 0.1 mmol) in DCM (2.5 mL) at ambient temperature. After stirring for 1.5 h, reaction was quenched with the addition of water and extracted with DCM (2×10 mL). Combined organic layer was washed with brine (10 mL), dried over anhydrous sodium sulfate, filtered, concentrated to give 120 mg (92%) of N-[4-bromo-4-[bromo-[3-[[5-(trifluoromethyl)-2-pyridyl]oxy]phenyl]methyl]cyclohexyl]-3-(trifluoromethyl)-1H-pyrazole-4-carboxamide. MS (ES) m/z 671.0 (M+1).

Step-II: N-[4-[Bromo-[3-[[5-(trifluoromethyl)-2-pyridyl]oxy]phenyl]methylene]-cyclohexyl]-3-(trifluoromethyl)-1H-pyrazole-4-carboxamide To a mixture of N-[4-Bromo-4-[bromo-[3-[[5-(trifluoromethyl)-2-pyridyl]oxy]phenyl]-methyl]cyclohexyl]-3-(trifluoromethyl)-1H-pyrazole-4-carboxamide (110 mg, 0.2 mmol) and 2N sodium hydroxide solution (0.4 mL) in MeOH (2 mL) was stirred at ambient temperature. After 4 h, volatiles were evaporated under reduced pressure. Resulting residue was taken in ethyl acetate (10 mL) and washed with water (10 mL), brine (10 mL), dried over anhydrous sodium sulfate, concentrated to give 80 mg (87%) of N-[4-[bromo-

[3-[[5-(trifluoromethyl)-2-pyridyl]oxy]phenyl]methylene]cyclohexyl]-3-(trifluoromethyl)-1H-pyrazole-4-carboxamide.

MS (ES) m/z 589.2 (M+), 591.2 (M+2).

Example 14.1

3-(Trifluoromethyl)-N-[4-[1-[3-[[5-(trifluoromethyl)-2-pyridyl]oxy]-phenyl]ethylidene]cyclohexyl]-1H-pyrazole-4-carboxamide

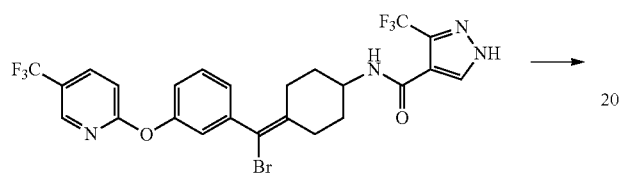

-continued

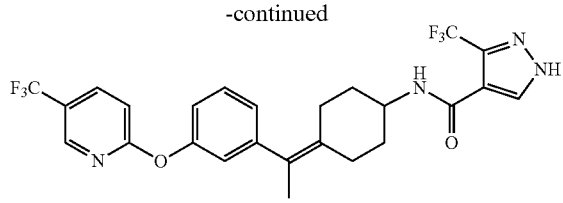

A solution of N-[4-[bromo-[3-[[5-(trifluoromethyl)-2-pyridyl]oxy]-phenyl]methylene]-cyclohexyl]-3-(trifluoromethyl)-1H-pyrazole-4-carboxamide (Example 13.1) (80 mg, 0.1 mmol), methyl boronic acid (9 mg, 0.1 mmol), silver oxide (62 mg, 0.3 mmol), passium carbonate (40 mg, 0.3 mmol) in toluene (5 mL) was degassed for 10 min with argon. To this was added 1,1'-bis(diphenylphosphine)ferrocene dichloropalladium (II) (11 mg, 0.01 mmol) and heated at 85° C. for 19 h. Reaction mixture was filtered through celite bed. Filtrate was diluted with ethyl acetate (10 mL), washed with water (10 mL), brine (10 mL), dried over anhydrous sodium sulfate, filtered, concentrated and purified by preparative HPLC to give 50 mg (70%) of titled compound.

$^1$H NMR (400 MHz, CDCl$_3$): δ 1.25-1.46 (m, 2H), 1.93-2.05 (m, 6H), 2.11-2.17 (m, 2H), 2.35-2.41 (m, 1H), 2.70 (d, J=13.2 Hz, 1H), 4.11-4.21 (m, 1H), 6.90 (brs, 1H), 6.99-7.13 (m, 3H), 7.38 (t, J=8.1 Hz, 1H), 7.89-7.92 (m, 1H), 8.11 (s, 1H), 8.45 (s, 1H), 11.11 (brs, 1H). MS (ES) m/z 525.2 (M+1). MP=80-82° C.

Example 15.1

6-(Methanesulfonamido)-N-[4-[[3-[[5-(trifluoromethyl)-2-pyridyl]-oxy]phenyl]methylene]cyclohexyl]pyridine-3-carboxamide

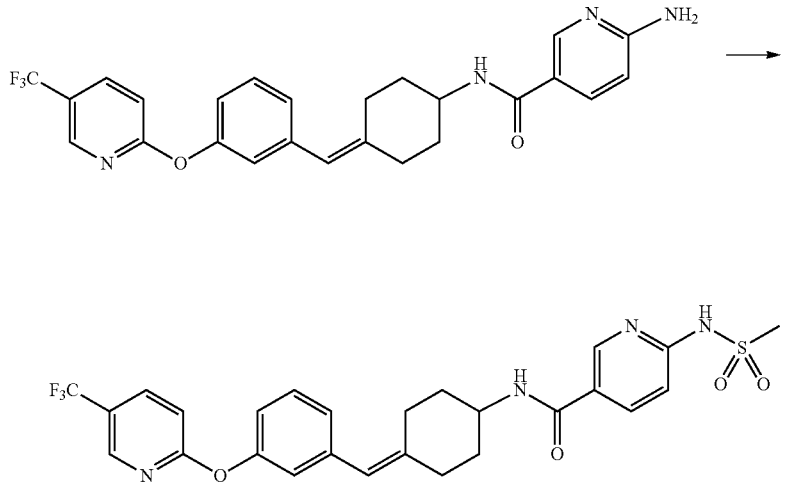

To a cooled solution of 6-amino-N-[4-[[3-[[5-(trifluoromethyl)-2-pyridyl]oxy]-phenyl]methylene]cyclohexyl]pyridine-3-carboxamide (Example 2.C-1) (150 mg, 0.3 mmol) in DCM (2 mL) was added methanesulfonyl chloride (0.03 mL, 0.3 mmol) followed by triethylamine (0.1 mL, 0.7 mmol) at 0° C. After 2 h, reaction was quenched by the addition of water (10 mL). Organic layer was diluted with DCM (10 mL), separated, washed with brine (10 mL), dried over anhydrous sodium sulfate, filtered, concentrated and purified by column chromatography to give 12 mg (7%) of titled compound as a white solid.

$^1$H NMR (400 MHz, CDCl$_3$): δ 1.29-1.40 (m, 1H), 1.42-1.58 (m, 1H), 2.08-2.22 (m, 3H), 2.35-2.48 (m, 2H), 2.35-2.48 (m, 2H), 2.87-2.93 (m, 1H), 3.21 (s, 3H), 4.16-4.36 (m, 1H), 5.95 (d, J=6.9 Hz, 1H), 6.32 (s, 1H), 6.98-7.03 (m, 3H), 7.09 (d, J=7.4, 1H), 7.39 (t, J=7.8 Hz, 1H), 7.90 (d, J=6.9 Hz, 1H), 8.11 (d, J=7.6 Hz, 1H), 8.45 (s, 1H), 8.60 (s, 1H). MS (ES) m/z 547.1 (M+1). MP=162-163° C.

Example 16.1 and 16.2

6-Amino-2-fluoro-N-[4-[[3-[[5-(trifluoromethyl)-2-pyridyl]oxy]phenyl]methylene]cyclohexyl]pyridine-3-carboxamide and 2-amino-6-fluoro-N-[4-[[3-[[5-(trifluoromethyl)-2-pyridyl]oxy]phenyl]-methylene]cyclohexyl]pyridine-3-carboxamide

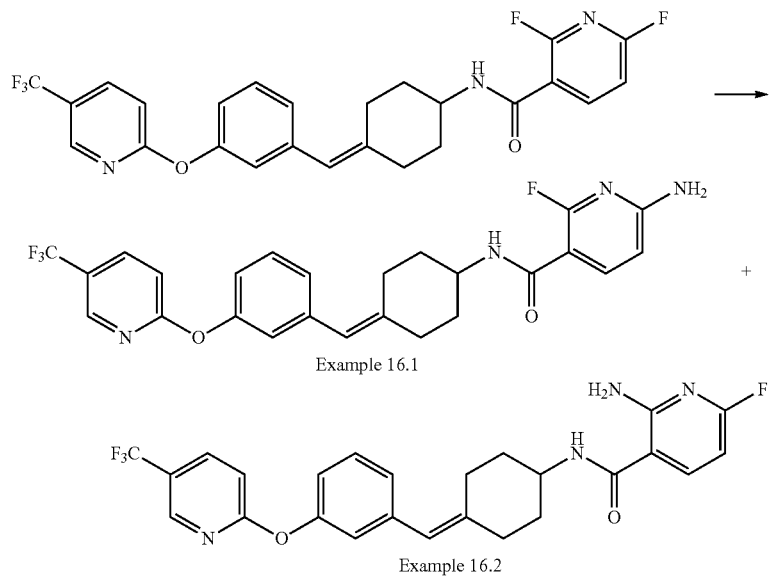

Example 16.1

Example 16.2

A mixture of 2,6-difluoro-N-[4-[[3-[[5-(trifluoromethyl)-2-pyridyl]oxy]phenyl]-methylene]cyclohexyl]pyridine-3-carboxamide (Example 2.A-49) (200 mg, 0.4 mmol), aqueous ammonia (1 mL) and isopropanol (2 mL) was heated at 100° C. for 3 h in sealed tube. Solvent was evaporated under reduced pressure. The products were separated by preparative HPLC to give 32 mg of Example 16.1 and 17 mg of Example 16.2

6-Amino-2-fluoro-N-[4-[[3-[[5-(trifluoromethyl)-2-pyridyl]oxy]phenyl]methylene]-cyclohexyl]pyridine-3-carboxamide (Example 16.1)

$^1$H NMR (400 MHz, CDCl$_3$): δ 1.39 (qd, J=12.0, 3.9 Hz, 1H), 1.49 (qd, J=11.0, 5.1 Hz, 1H), 2.05-2.21 (m, 3H), 2.34-2.45 (m, 2H), 2.85 (dt, J=14.0, 3.9 Hz, 1H), 4.16-4.27 (m, 1H), 4.84 (brs, 2H), 6.30 (s, 1H), 6.41 (dd, J=8.3, 2.5 Hz, 1H), 6.54 (dd, J=13.2, 8.1 Hz, 1H), 6.98-7.02 (m, 3H), 7.10 (d, J=7.9 Hz, 1H), 7.38 (t, J=8.1 Hz, 1H), 7.90 (dd, J=8.8, 2.5 Hz, 1H), 8.28 (dd, 10.3, 8.3 Hz, 1H), 8.45 (s, 1H). MS (ES) m/z 487.0 (M+1). MP=115-117° C.

2-Amino-6-fluoro-N-[4-[[3-[[5-(trifluoromethyl)-2-pyridyl]oxy]phenyl]methylene]-cyclohexyl]pyridine-3-carboxamide (Example 16.2)

$^1$H NMR (400 MHz, CDCl$_3$): δ 1.32 (qd, J=12.2, 4.6 Hz, 1H), 1.44 (qd, J=11.8, 5.4 Hz, 1H), 2.07-2.19 (m, 3H), 2.35-2.43 (m, 2H), 2.91 (d, J=14.2 Hz, 1H), 4.10-4.19 (m, 1H), 5.76 (d, J=7.6 Hz, 1H), 6.16 (dd, J=8.4, 2.5 Hz, 1H), 6.31 (s, 1H), 6.56 (brs, 2H), 6.98-7.03 (m, 3H), 7.10 (d, J=7.6 Hz, 1H), 7.38 (t, J=7.8 Hz, 1H), 7.65 (t, J=8.1 Hz, 1H), 7.91 (dd, J=8.5, 2.4 Hz, 1H), 8.45 (s, 1H). MS (ES) m/z 487.0 (M+1). MP=146-148° C.

Example 17.1

N-[4-[[3-[(5-Cyano-2-pyridyl)oxy]phenyl]methylene]-cyclohexyl]-pyridine-3-carboxamide

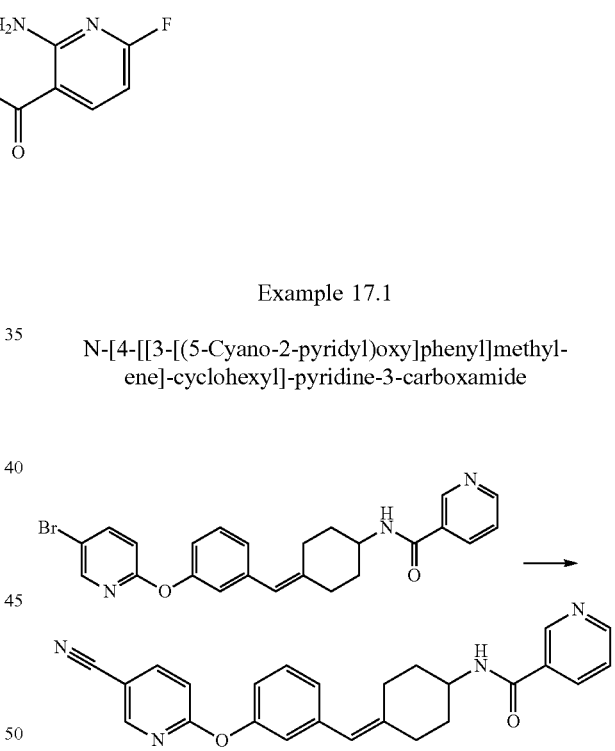

The solution of N-[4-[[3-[(5-bromo-2-pyridyl)oxy]phenyl]methylene]cyclohexyl]-pyridine-3-carboxamide (Example 2.E-4) (200 mg, 0.4 mmol) in DMF (3 mL) was degassed with argon for 5 min. at room temperature and added zinc cyanide (100 mg, 0.8 mmol) followed by tetrakis-(triphenylphosphine) palladium (0) (49 mg, 0.04 mmol). After stirring at 100° C. for 18 h, reaction mixture was cooled to room temperature, quenched by the addition of water (10 mL), This was extracted with ethyl acetate (2×10 mL), combined organic layer was washed with water (20 mL), brine (20 mL), dried over anhydrous sodium sulfate, filtered, concentrated and purified by preparative TLC to give 10 mg (6%) of the title compound.

$^1$H NMR (400 MHz, CDCl$_3$): δ 1.25-1.54 (m, 2H), 2.09-2.23 (m, 3H), 2.38-2.49 (m, 2H), 2.91 (d, J=14.2

1H), 4.21-4.26 (m, 1H), 6.05 (d, J=7.6 Hz, 1H), 6.32 (s, 1H), 6.98-7.04 (m, 3H), 7.12 (d, J=7.6 Hz, 1H), 7.40 (t, J=7.3 Hz, 2H), 7.92 (dd, J=8.5, 1.9 Hz, 1H), 8.11 (d, J=7.8 Hz, 1H), 8.47 (s, 1H), 8.72 (d, J=4.4 Hz, 1H), 8.94 (s, 1H). MS (ES) m/z 411.2 (M+1). MP=139-140° C.

Example 18.1

Disodium [5-[[4-[[3-[[5-(trifluoromethyl)-2-pyridyl]oxy]phenyl]-methylene]cyclohexyl]carbamoyl]pyrrolo[2,3-b]pyridin-1-yl]methyl phosphate

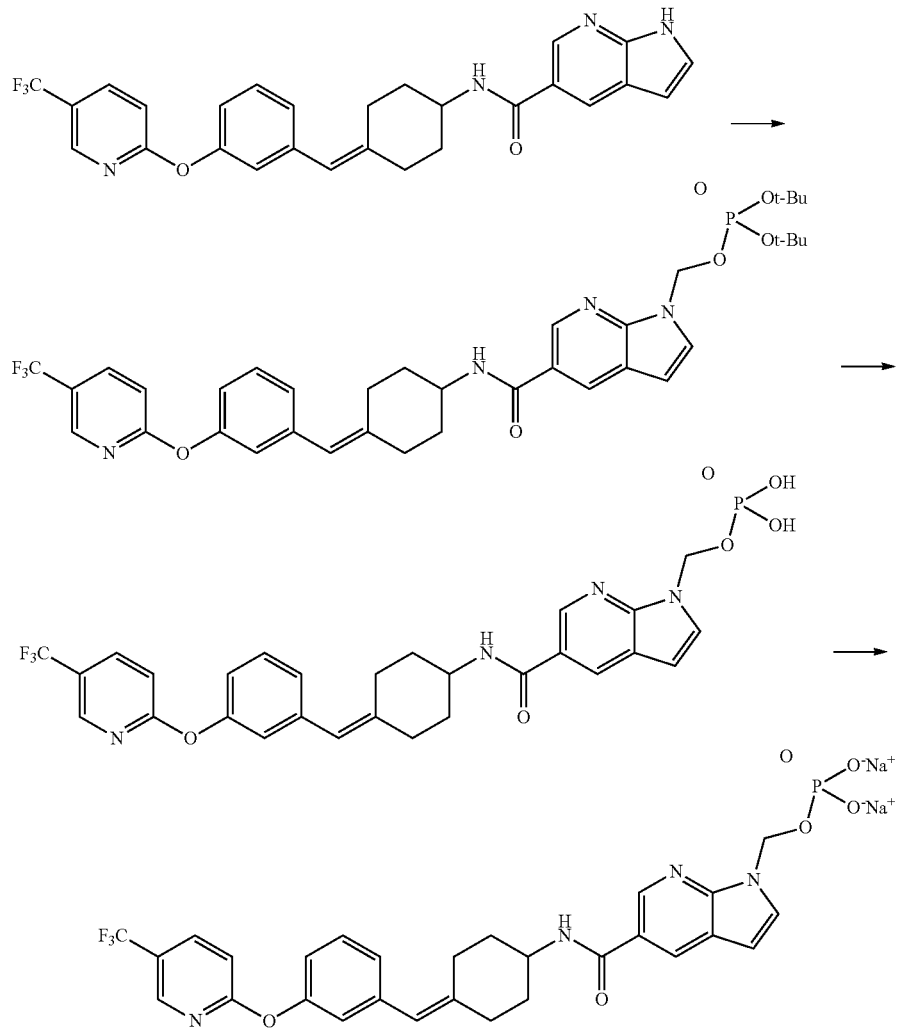

Step-I: di-tert-Butyl [5-[[4-[[3-[[5-(trifluoromethyl)-2-pyridyl]oxy]phenyl]-methylene]cyclohexyl]carbamoyl]pyrrolo[2,3-b]pyridin-1-yl]methyl phosphate To a suspension of sodium hydride (60% in mineral oil, 200 mg, 4.9 mmol) in DMF (10 mL) was added a solution of N-[4-[[3-[[5-(trifluoromethyl)-2-pyridyl]oxy]phenyl]-methylene]cyclohexyl]-1H-pyrrolo[2,3-b]pyridine-5-carboxamide (Example 2.D-5) (1.1 g, 2.2 mmol) in DMF (10 mL) at ambient temperature and stirred for 20 min. To this was added a solution of di tert-butyl chloromethyl phosphate (2.0 g, 7.8 mmol) in DMF (10 mL). After stirring for 1 h, reaction was quenched by the addition of water (90 mL). This was extracted with ethyl acetate (2×50 mL), combined organic layer was washed with brine (100 mL), dried over anhydrous sodium sulfate, filtered, concentrated and purified by column chromatography to give 1.0 g (63%) of ditert-butyl [5-[[4-[[3-[[5-(trifluoromethyl)-2-pyridyl]oxy]phenyl]methylene]cyclohexyl]carbamoyl]pyrrolo[2,3-b]pyridin-1-yl]methyl phosphate.

$^1$H NMR (400 MHz, CDCl$_3$): δ 1.22-1.28 (m, 2H), 1.38 (s, 18H), 2.14-2.25 (m, 3H), 2.41-2.48 (m, 2H), 2.09-2.94 (m, 1H), 4.20-4.30 (m, 1H), 6.02 (d, J=7.8 Hz, 1H), 6.12 (s, 1H), 6.15 (s, 1H), 6.32 (s, 1H), 6.58 (d, J=3.4 Hz, 1H), 6.99-7.03 (m, 3H), 7.11 (d, J=7.6 Hz, 1H), 7.39 (t, J=7.8 Hz, 1H), 7.55 (d, J=3.7 Hz, 1H), 7.90 (dd, J=8.8, 2.2 Hz, 1H), 8.32 (d, J=1.7 Hz, 1H), 8.45 (s, 1H), 8.73 (d, J=1.5 Hz, 1H). MS (ES) m/z 715.1 (M+1).

Step-II: [5-[[4-[[3-[[5-(Trifluoromethyl)-2-pyridyl]oxy]phenyl]methylene]-cyclohexyl]carbamoyl]pyrrolo[2,3-b]pyridin-1-yl]methyl dihydrogen phosphate To a stirred solution of ditert-butyl [5-[[4-[[3-[[5-(trifluoromethyl)-2-pyridyl]oxy]phenyl]methylene]cyclohexyl]carbamoyl]pyrrolo[2,3-b]pyridin-1-yl]methyl phosphate (1.0 g, 1.4 mmol) in DCM (10 mL) was added trifluoroacetic acid (0.8 mL, 11.2 mmol) at 0° C. After stirring for 1 h at room temperature, volatiles were evaporated under reduced pressure. The resulting residue was washed with diethyl ether to give 200 mg (24%) of [5-[[4-[[3-[[5-(trifluoromethyl)-2-pyridyl]oxy]phenyl]methylene]-cyclohexyl]carbamoyl]pyrrolo[2,3-b]pyridin-1-yl]methyl dihydrogen phosphate.

$^1$H NMR (400 MHz, DMSO-d$_6$): δ 1.37-1.45 (m, 1H), 1.50-1.58 (m, 1H), 1.94-2.04 (m, 2H), 2.11 (t, J=12.5 Hz, 1H), 2.33 (t, J=11.0 Hz, 1H), 2.41-2.43 (m, 1H), 2.85 (d, J=13.2 Hz, 1H), 4.02-4.11 (m, 1H), 6.03 (d, J=8.8 Hz, 2H), 6.32 (s, 1H), 6.67 (d, J=2.9 Hz, 1H), 7.02 (s, 1H), 7.06 (d, J=7.8 Hz, 1H), 7.13 (d, J=7.4 Hz, 1H), 7.25 (d, J=8.5 Hz, 1H), 7.42 (t, J=7.5 Hz, 1H), 7.78 (s, 1H), 8.24 (d, J=7.8 Hz, 1H), 8.32 (d, J=6.6 Hz, 1H), 8.42 (s, 1H), 8.58 (s, 1H), 8.73 (s, 1H). MS (ES) m/z 603.0 (M+1).

Step-III: Disodium [5-[[4-[[3-[[5-(trifluoromethyl)-2-pyridyl]oxy]phenyl]methylene]-cyclohexyl]carbamoyl]pyrrolo[2,3-b]pyridin-1-yl]methyl phosphate To a stirred solution of [5-[[4-[[3-[[5-(trifluoromethyl)-2-pyridyl]oxy]phenyl]methylene]-cyclohexyl]carbamoyl]pyrrolo[2,3-b]pyridin-1-yl]methyl dihydrogen phosphate (200 mg, 0.3 mmol) in acetone (3 mL) was added a solution of sodium carbonate (35 mg, 0.3 mmol) in water (1 mL) at room temperature and stirred for 4 h. Volatiles were evaporated under reduced pressure, resulting residue was triturated with n-pentane followed by DCM separately. The solid was dried under vacuum to give 150 mg (70%) of the titled compound. MS (ES) m/z 603.0 (M+1).

Example 19.1

N-[4-[[3-[[5-(Trifluoromethyl)-2-pyridyl]amino]phenyl]methylene]-cyclohexyl]pyridine-3-carboxamide

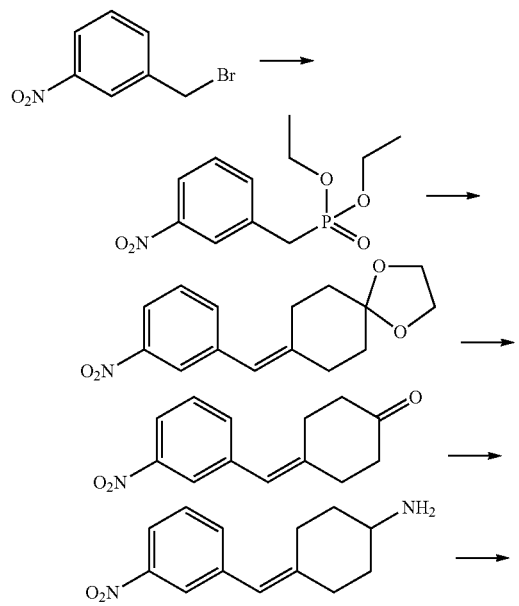

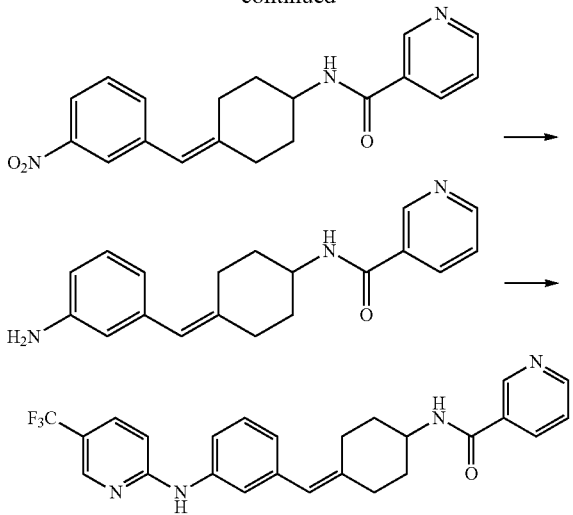

Step-I:
1-(Diethoxyphosphorylmethyl)-3-nitro-benzene

A stirred solution of 1-(Bromomethyl)-3-nitro-benzene (4.0 g, 18.5 mmol) and triethyl phosphite (5.3 mL, 31.5 mmol) was heated to 150° C. for 16 h. The reaction mixture was cooled to 0° C. and added n-pentane (100 mL). Solid formed was filtered through Buckner funnel and dried under reduced pressure to get 4.6 g (91%) of titled compound as a solid.

MS (ES) m/z 274.2 (M+1).

Step-II: 8-[(3-Nitrophenyl)methylene]-1,4-dioxaspiro[4.5]decane

To a stirred suspension of sodium hydride (1.1 g, 28.17 mmol) in THF (10 mL) was added a solution of 1-(diethoxyphosphorylmethyl)-3-nitrobenzene (4.6 g, 16.9 mmol) in THF (30 mL) at 0° C. and stirred for 4 h at room temperature. This was again cooled to 0° C., added a solution of 1,4-dioxaspiro[4.5]decan-8-one (2.2 g, 14.1 mmol) in THF (10 mL) and stirring continued for 16 h at room temperature. Reaction mixture was poured onto the ice cold water (150 mL) and extracted with ethyl acetate (2×100 mL). Combined organic layer was washed with brine (25 mL), dried over anhydrous sodium sulfate, filtered, concentrated and purified by column chromatography to give 3.5 g (90%) of titled compound.

$^1$H NMR (400 MHz, CDCl$_3$): δ 1.68 (t, J=6.3 Hz, 2H), 1.81 (t, J=6.3 Hz, 2H), 2.45-2.52 (m, 4H), 3.99 (s, 4H), 6.33 (s, 1H), 7.45-7.51 (m, 2H), 8.04-8.06 (m, 2H). MS (ES) m/z 276.3 (M+1).

Step-III:
4-[(3-Nitrophenyl)methylene]cyclohexanone

To a stirred solution of 8-[(3-nitrophenyl)methylene]-1,4-dioxaspiro[4.5]decane (2.0 g, 7.26 mmol) in acetone (50 mL) was added 1 N HCl (20 mL) and refluxed for 1 h. After cooling to room temperature solvent was evaporated under reduced pressure and aqueous layer extracted with ethyl acetate (2×20 mL). Combined organic layer was washed with saturated sodium bicarbonate solution (20 mL), brine (25 mL), dried over anhydrous sodium sulfate, filtered and evaporated under reduced pressure to furnish 1.50 g (89%) of titled compound.

$^1$H NMR (400 MHz, CDCl$_3$): δ 2.47 (t, J=7.1 Hz, 2H), 2.55 (t, J=7.4 Hz, 2H), 2.71-2.79 (m, 4H), 6.52 (s, 1H), 7.50-7.56 (m, 2H), 8.10-8.1 (m, 2H). MS (ES) m/z 232.2 (M+1).

Step-IV—[(3-Nitrophenyl)methylene]cyclohexanamine

A solution of 4-[(3-nitrophenyl)methylene]cyclohexanone (1.4 g, 6.05 mmol), 2 N methanolic ammonia (15 mL, 30.3 mmol) and titanium tetraisopropoxide (3.5 mL, 12.1 mmol) was stirred at room temperature for 6 h. To this was added sodium borohydride (0.35 g, 9.1 mmol) in portions and stirred for 16 h. Reaction mixture was quenched with the addition of aqueous ammonia (~30% in water, 10 mL) and stirred for 30 minutes. Solid formed was filtered through celite bed and residue was washed with methanol (20 mL). Solvent was evaporated under reduced pressure; the residue was partitioned between ethyl acetate and water (50 mL). Aqueous layer was separated, extracted with ethyl acetate (50 mL). Combined organic layer was washed with brine (25 mL), dried over anhydrous sodium sulfate, filtered and concentrated under reduced pressure to furnish 900 mg (42%) of titled compound.

MS (ES) m/z 233.1 (M+1).

Step-V: N-[4-[(3-Nitrophenyl)methylene]cyclohexyl]pyridine-3-carboxamide

To a stirred solution of 4-[(3-nitrophenyl)methylene]cyclohexanamine (900 mg, 3.9 mmol) in DCM (10 mL) was added triethylamine (1.1 mL, 7.8 mmol) and nicotinoyl chloride hydrochloride (Intermediate 4A) (1.0 g, 5.8 mmol). After stirring for 2 h, reaction mixture was diluted with DCM (25 mL) and washed with water (20 mL), brine (10 mL), dried over anhydrous sodium sulfate, filtered and concentrated under reduced pressure to give 900 mg (69%) of titled compound.

MS (ES) m/z 338.3 (M+1).

Step-VI: N-[4-[(3-Aminophenyl)methylene]cyclohexyl]pyridine-3-carboxamide

To a stirred solution of N-[4-[(3-nitrophenyl)methylene]cyclohexyl]pyridine-3-carboxamide (900 mg, 2.7 mmol) in acetic acid (10 mL) was added iron powder (600 mg, 10.7 mmol) and heated at 70° C. for 2 h. Filtered through celite bed, volatiles were evaporated under reduced pressure. Resulting residue was taken in water, pH was adjusted to 6 using potassium phosphate tribasic. Aqueous layer was extracted with ethyl acetate (2×10 mL), combined ethyl acetate layer washed with brine (15 mL), dried over anhydrous sodium sulfate, filtered and concentrated to give 400 mg (49%) of N-[4-[(3-aminophenyl)methylene]cyclohexyl]pyridine-3-carboxamide.

MS (ES) m/z 308.3 (M+1).

Step-VII: N-[4-[[3-[[5-(Trifluoromethyl)-2-pyridyl]amino]phenyl]methylene]-cyclohexyl]pyridine-3-carboxamide A suspension of N-[4-[(3-aminophenyl)methylene]cyclohexyl]pyridine-3-carboxamide (200 mg, 0.6 mmol), 2-chloro-5-trifluoromethylpyridine (130 mg, 0.7 mmol), X-phos (23 mg, 0.04 mmol), cesium carbonate (550 mg, 1.7 mmol) and toluene (5 mL) was degassed using argon for 30 min. To this was added tris-(dibenzylideneacetone)dipalladium (0) (40 mg, 0.07 mmol) and heated at 50° C. for 1 h. Reaction was quenched by the addition of water (10 mL), filtered through celite bed. Filtrate was extracted with ethyl acetate (2×25 mL). Combined organic layer was washed with brine (20 mL), dried over anhydrous sodium sulfate, filtered and concentrated under reduced pressure. The crude compound was purified by preparative HPLC to afford 10 mg (3%) of N-[4-[[3-[[5-(trifluoromethyl)-2-pyridyl]amino]phenyl]methylene]-cyclohexyl]pyridine-3-carboxamide as a white solid.

$^1$H NMR (400 MHz, CDCl$_3$): δ 1.33-1.42 (m, 2H), 2.15-2.22 (m, 3H), 2.41-2.45 (m, 2H), 2.90-2.93 (m, 1H), 4.24-4.26 (m, 1H), 5.98 (d, J=6.8 Hz, 1H), 6.32 (s, 1H), 6.86 (d, J=9.2 Hz, 1H), 6.91 (s, 1H), 6.99 (d, J=7.6 Hz, 1H), 7.19-7.20 (m, 2H), 7.33 (t, J=8.0, Hz, 1H), 7.40 (dd, J=7.8, 4.9 Hz, 1H), 7.65 (dd, J=8.0, 2.4 Hz, 1H), 8.11 (d, J=8.0 Hz, 1H), 8.43 (s, 1H), 8.73 (s, 1H), 8.95 (s, 1H). MS (ES) m/z 454.3 (M+1). MP=218-220° C.

Example 20

Chirally Pure Compounds

Analytical Methods Used for Chiral Separation:
Method A: Column-Chiralpak IA-3 (150×4.6) mm, 3 μm; Flow: 0.5 ml min-1; Mobile phase: Ethanol; Column Temp.: 40° C., Detection wavelength: 220/242 nm; Resolution-2.9
Method B: Column-Chiralpak IA-3 (150×4.6) mm, 3 μm; Flow: 0.6 ml min-1; Mobile phase: IPA: 0.1% TFA in Hexane (20:80); Column Temp.: 40° C., Detection wavelength: 220/242 nm; Resolution-4.1
Method C: Column-Chiralpak IA-3 (150×4.6) mm, 3 μm; Flow: 0.5 ml min-1; Mobile phase: Ethanol; Column Temp.: 40° C., Detection wavelength: 264 nm; Resolution-4.7
Method D: Column-Chiralcel OJ-RH (150×4.6) mm, 5 μm; Flow: 0.5 ml min-1; Mobile phase: Methanol:Water (90:10); Column Temp.: 25° C., Detection wavelength: 220 nm; Resolution-2.5
Method E: Column-Chiralpak IA-3 (150×4.6) mm, 3 μm; Flow: 0.5 ml min-1; Mobile phase: Ethanol; Column Temp.: 40° C., Detection wavelength: 256 nm; Resolution-2.5
Method F: Column-Chiralcel OJ-RH (150×4.6) mm, 5 μm; Flow: 0.5 ml min-1; Mobile phase: Methanol; Column Temp.: 25° C., Detection wavelength: 254 nm; Resolution-3.2
Method G: Column-Chiralpak IA-3 (150×4.6) mm, 3 μm; Flow: 0.5 ml min-1; Mobile phase: Ethanol; Column Temp.: 40° C., Detection wavelength: 262 nm; Resolution-4.2
Method H: Column-Chiralpak IA-3 (150×4.6) mm, 3 μm; Flow: 0.5 ml min-1; Mobile phase: Ethanol:Water (70:30); Column Temp.: 40° C., Detection wavelength: 220 nm; Resolution-3.8
Method I: Column-Chiralcel OJ-RH (150×4.6) mm, 5 μm; Flow: 0.5 ml min-1; Mobile phase: ACN:Water (50:50); Column Temp.: 25° C., Detection wavelength: 220 nm; Resolution-3.29
Method J: Column-Chiralcel OJ-RH (150×4.6) mm, 5 μm; Flow: 0.5 ml min-1; Mobile phase: ACN:Water (50:50); Column Temp.: 25° C., Detection wavelength: 220 nm; Resolution-1.93

Method K: Column-Chiralpak IA-3 (150×4.6) mm, 3 μm; Flow: 0.5 ml min-1; Mobile phase: Ethanol; Column Temp.: 25° C., Detection wavelength: 254 nm; Resolution-2.94

Method L: Column-Chiralpak IA-3 (150×4.6) mm, 3 μm; Flow: 0.5 ml min-1; Mobile phase: ACN:Water (90:10); Column Temp.: 40° C., Detection wavelength: 254 nm; Resolution-3.43

Method M: Column-Chiralpak IA-3 (150×4.6) mm, 3 μm; Flow: 0.5 ml min-1; Mobile phase: Ethanol:Water (70:30); Column Temp.: 40° C., Detection wavelength: 264 nm; Resolution-3.54

Method N: Column-Chiralpak IA-3 (150×4.6) mm, 3 μm; Flow: 0.5 ml min-1; Mobile phase: Ethanol:Water (80:20); Column Temp.: 25° C., Detection wavelength: 254 nm; Resolution-4.49

Method O: Column-Chiralcel OJ-RH (150×4.6) mm, 5 μm; Flow: 0.5 ml min-1; Mobile phase: Methanol (100%); Column Temp.: 40° C., Detection wavelength: 220 nm; Resolution-2.93

Method P: Column-Chiralcel OJ-RH (150×4.6) mm, 5 μm; Flow: 0.5 ml min-1; Mobile phase: Methanol:Water (90:10); Column Temp.: 40° C., Detection wavelength: 220 nm; Resolution-2.98

Method Q: Column-Chiralpak IA-3 (150×4.6) mm, 3 μm; Flow: 1.0 ml min-1; Mobile phase: 0.05% butylamine in Ethanol (100%); Column Temp.: 40° C., Detection wavelength: 236 nm; Resolution-7.16

Method R: Column-Chiralpak IA-3 (150×4.6) mm, 3 μm; Flow: 0.5 ml min-1; Mobile phase: 0.05% butylamine in Ethanol:water (90:10); Column Temp.: 25° C., Detection wavelength: 216 nm; Resolution-6.19

Method S: Column-Chiralpak IA-3 (150×4.6) mm, 3 μm; Flow: 1.0 ml min-1; Mobile phase: 0.05% butylamine in Ethanol (100%); Column Temp.: 40° C., Detection wavelength: 214 nm; Resolution-13.42

Following enantiomers were obtained by using either of Method A-Method S.

| | |
|---|---|
| Example 20.A-1 | (+)-N-[4-[[3-[[5-(Trifluoromethyl)-2-pyridyl]oxy]phenyl]methylene]cyclohexyl]pyridine-3-carboxamide MS (ES) m/z 454.1 (M + 1). MP = 135-136° C. $[\alpha]^{20}_D$ +21.2 (c 0.2, CHCl$_3$) |
| Example 20.A-2 | (−)-N-[4-[[3-[[5-(Trifluoromethyl)-2-pyridyl]oxy]phenyl]methylene]cyclohexyl]pyridine-3-carboxamide MS (ES) m/z 454.1 (M + 1). MP = 135-136° C. $[\alpha]^{20}_D$ − 22.8 (c 0.2, CHCl$_3$) |
| Example 20.A-3 | (+)-6-Amino-N-[4-[[3-[[5-(trifluoromethyl)-2-pyridyl]oxy]phenyl]methylene]cyclohexyl]pyridine-3-carboxamide MS (ES) m/z 469.2 (M + 1). MP = 145-147° C. $[\alpha]^{20}_D$ + 51.1 (c 0.2, CHCl$_3$) |
| Example 20.A-4 | (−)-6-Amino-N-[4-[[3-[[5-(trifluoromethyl)-2-pyridyl]oxy]phenyl]methylene]cyclohexyl]pyridine-3-carboxamide MS (ES) m/z 469.2 (M + 1). MP = 145-147° C. $[\alpha]^{20}_D$ − 56.3 (c 0.2, CHCl$_3$) |
| Example 20.A-5 | (+)-6-Amino-5-methyl-N-[4-[[3-[[5-(trifluoromethyl)-2-pyridyl]oxy]phenyl]methylene]cyclohexyl]pyridine-3-carboxamide MS (ES) m/z 483.1 (M + 1). MP = 142-144° C. $[\alpha]^{20}_D$ + 70.0 (c 0.2, CHCl$_3$) |
| Example 20.A-6 | (−)-6-Amino-5-methyl-N-[4-[[3-[[5-(trifluoromethyl)-2-pyridyl]oxy]phenyl]methylene]cyclohexyl]pyridine-3-carboxamide MS (ES) m/z 483.1 (M + 1). MP = 142-144° C. $[\alpha]^{20}_D$ − 60.4 (c 0.2, CHCl$_3$) |
| Example 20.A-7 | (+)-3-(Trifluoromethyl)-N-[4-[[3-[[5-(trifluoromethyl)-2-pyridyl]oxy]phenyl]methylene]cyclohexyl]-1H-pyrazole-4-carboxamide MS (ES) m/z 511.1 (M + 1). MP = 93-95° C. $[\alpha]^{20}_D$ + 30.7 (c 1.0, MeOH) |
| Example 20.A-8 | (−)-3-(Trifluoromethyl)-N-[4-[[3-[[5-(trifluoromethyl)-2-pyridyl]oxy]phenyl]methylene]cyclohexyl]-1H-pyrazole-4-carboxamide MS (ES) m/z 511.0 (M + 1). MP = 93-95° C. $[\alpha]^{20}_D$ − 30.7 (c 1.0, MeOH) |
| Example 20.A-9 | (+)-2-Amino-N-44-[[3-[[5-(trifluoromethyl)-2-pyridyl]oxy]phenyl]methylene]cyclohexyl]pyrimidine-5-carboxamide MS (ES) m/z 470.1 (M + 1). MP = 175-177° C. $[\alpha]^{20}_D$ + 76.0 (c 0.5, MeOH) |
| Example 20.A-10 | (−)-2-Amino-N-44-[[3-[[5-(trifluoromethyl)-2-pyridyl]oxy]phenyl]methylene]cyclohexyl]pyrimidine-5-carboxamide MS (ES) m/z 470.1 (M + 1). MP = 172-175° C. $[\alpha]^{20}_D$ − 66.0 (c 0.5, MeOH) |
| Example 20.A-11 | (+)-N-[4-[[3-[[5-(trifluoromethyl)-2-pyridyl]oxy]phenyl]methylene]cyclohexyl]-1H-pyrazole-4-carboxamide MS (ES) m/z 444.1 (M + 1). MP = 189-191° C. $[\alpha]^{20}_D$ + 15 (c 1.0, CHCl$_3$) |
| Example 20.A-12 | (−)-N-[4-[[3-[[5-(trifluoromethyl)-2-pyridyl]oxy]phenyl]methylene]cyclohexyl]-1H-pyrazole-4-carboxamide MS (ES) m/z 444.1 (M + 1). MP = 189-191° C. $[\alpha]^{20}_D$ − 15 (c 1.0, CHCl$_3$) |
| Example 20.A-13 | (+)-N-[4-[[3-[[5-(trifluoromethyl)-2-pyridyl]oxy]phenyl]methylene]cyclohexyl]-1H-pyrrolo[2,3-b]pyridine-5-carboxamide MS (ES) m/z 493.1 (M + 1). MP = 206-208° C. $[\alpha]^{20}_D$ + 58 (c 0.5, CHCl$_3$) |
| Example 20.A-14 | (−)-N-[4-[[3-[[5-(trifluoromethyl)-2-pyridyl]oxy]phenyl]methylene]cyclohexyl]-1H-pyrrolo[2,3-b]pyridine-5-carboxamide MS (ES) m/z 493.1 (M + 1). MP = 206-208° C. $[\alpha]^{20}_D$ + 54 (c 0.5, CHCl$_3$) |
| Example 20.A-15 | (+)-N-[4-[[3-[[5-(trifluoromethyl)-2-pyridyl]oxy]phenyl]methylene]cyclohexyl]pyridazine-3-carboxamide MS (ES) m/z 455.1 (M + 1). MP = 124-126° C. $[\alpha]^{20}_D$ + 23 (c 0.5, CHCl$_3$) |
| Example 20.A-16 | (−)-N-[4-[[3-[[5-(trifluoromethyl)-2-pyridyl]oxy]phenyl]methylene]cyclohexyl]pyridazine-3-carboxamide MS (ES) m/z 455.1 (M + 1). MP = 124-126° C. $[\alpha]^{20}_D$ − 21.6 (c 0.5, CHCl$_3$) |
| Example 20.A-17 | (+)-N-[4-[[3-[[5-(trifluoromethyl)-2-pyridyl]oxy]phenyl]methylene]cyclohexyl]-1H-indole-3-carboxamide MS (ES) m/z 492.1 (M + 1). MP = 86-88° C. $[\alpha]^{20}_D$ + 49.9 (c 0.5, CHCl$_3$) |
| Example 20.A-18 | (−)-N-[4-[[3-[[5-(trifluoromethyl)-2-pyridyl]oxy]phenyl]methylene]cyclohexyl]-1H-indole-3-carboxamide MS (ES) m/z 492.1 (M + 1). MP = 86-88° C. $[\alpha]^{20}_D$ − 43 (c 0.5, CHCl$_3$) |

-continued

| Example 20.A-19 | (+)-N-[4-[[3-[[5-(trifluoromethyl)-2-pyridyl]oxy]phenyl]methylene]cyclohexyl]pyrimidine-5-carboxamide MS (ES) m/z 455.1 (M + 1). MP = 163-165° C. $[\alpha]^{20}_D$ + 15.2 (c 0.5, CHCl$_3$) |
|---|---|
| Example 20.A-20 | (−)-N-[4-[[3-[[5-(Trifluoromethyl)-2-pyridyl]oxy]phenyl] methylene]cyclohexyl]pyrimidine-5-carboxamide MS (ES) m/z 455.1 (M + 1). MP = 167-167° C. $[\alpha]^{20}_D$ − 16.3 (c 0.5, CHCl$_3$) |
| Example 20.A-21 | (+)-2-Amino-N-[4-[[3-[(5-chloro-6-methyl-2-pyridyl)oxy]phenyl] methylene]cyclohexyl]pyrimidine-5-carboxamide MS (ES) m/z 450.1 (M + 1). MP = 148-151° C. $[\alpha]^{20}_D$ + 38.7 (c 0.5, CHCl$_3$) |
| Example 20.A-22 | (−)-2-Amino-N-[4-[[3-[(5-chloro-6-methyl-2-pyridyl)oxy]phenyl] methylene]cyclohexyl]pyrimidine-5-carboxamide MS (ES) m/z 450.1 (M + 1). MP = 140-142° C. $[\alpha]^{20}_D$ − 35 (c 0.5, CHCl$_3$) |

Following examples were synthesized from Intermediate 3R and appropriate carboxylic acid using the procedure for Example 2.2.

Example 20.A-2

(−)-N-[4-[[3-[[5-(Trifluoromethyl)-2-pyridyl]oxy] phenyl]-methylene]cyclohexyl]pyridine-3-carboxamide The titled compound was also synthesized from Intermediate 3R and carboxylic acid Intermediate 4AZ using the procedure described for Example 2.2

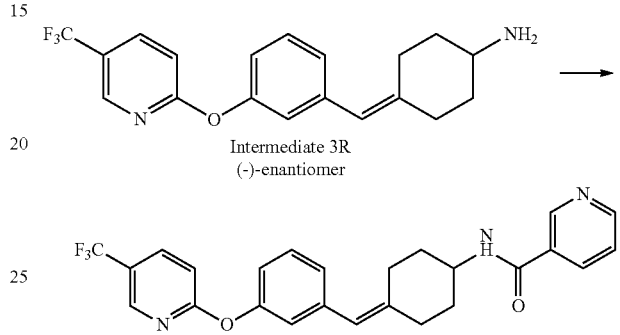

Intermediate 3R
(−)-enantiomer

Yield=61%, MS (ES) m/z 454.1 (M+1). MP=133-134° C. $[\alpha]^{20}_D$ −22.4 (c 0.5, CHCl$_3$)

Using above condition following exaples were prepared.

| Example No. | Amine | Carboxylic acid | Condition | Product |
|---|---|---|---|---|
| Example 20.A-4 | Intermediate 3R | (structure) | Example 20.A-1 | (structure) 58%, −56.3 (c 0.2, CHCl$_3$) |
| Example 20.A-6 | Intermediate 3R | (structure) | Example 20.A-1 | (structure) 43%, −60.4 (c 0.2, CHCl$_3$) |
| Example 20.A-8 | Intermediate 3R | (structure) | Example 20.A-1 | (structure) 54%, −30.7 (c 1.0, MeOH) |

| Example No. | Amine | Carboxylic acid | Condition | Product |
|---|---|---|---|---|
| Example 20.A-10 | Intermediate 3R | 2-aminopyrimidine-5-carboxylic acid | Example 20.A-1 | 54%, −72 (c 0.5, MeOH) |
| Example 20.A-18 | Intermediate 3R | 1H-indole-3-carboxylic acid | Example 20.A-1 | 57%, −43 (c 0.5, CHCl₃) |

The below list of examples, but not to be limited to these, are synthesized following the general synthesis described above:

N-(3-pyridyl)-2-[1-[3-[[5-(trifluoromethyl)-2-pyridyl]oxy]phenyl]ethylidene]bicyclo[2.2.2]octane-5-carboxamide and its (+) and (−) enantiomers;

N-[4-[[3-[[5-(trifluoromethyl)-2-pyridyl]methyl]phenyl]methylene]cyclohexyl]pyridine-3-carboxamide and its (+) and (−) enantiomers;

N-[4-[1-[3-[[5-(trifluoromethyl)-2-pyridyl]oxy]phenyl]ethylidene]cyclohexyl]pyridine-3-carboxamide and its (+) and (−) enantiomers;

N-[4-[phenyl-[3-[[5-(trifluoromethyl)-2-pyridyl]amino]phenyl]methylene]cyclohexyl]pyridine-3-carboxamide and its (+) and (−) enantiomers;

N-[4-[2-chloro-1-[3-[[5-(trifluoromethyl)-2-pyridyl]methyl]phenyl]ethylidene]cyclohexyl]pyridine-3-carboxamide and its (+) and (−) enantiomers;

N-[4-[[3-[1-[5-(trifluoromethyl)-2-pyridyl]cyclopropyl]phenyl]methylene]cyclohexyl]pyridine-3-carboxamide and its (+) and (−) enantiomers;

N-[(3E)-3-[[3-[1-[5-(trifluoromethyl)-2-pyridyl]cyclopropyl]phenyl]methylene]cyclohexyl]pyridine-3-carboxamide and its (+) and (−) enantiomers;

(3E)-N-(3-pyridyl)-3-[[3-[[5-(trifluoromethyl)-2-pyridyl]oxy]phenyl]methylene]cyclohexanecarboxamide and its (+) and (−) enantiomers;

N-[(3E)-3-[[3-[[5-(trifluoromethyl)-2-pyridyl]amino]phenyl]methylene]cyclohexyl]pyridine-3-carboxamide and its (+) and (−) enantiomers;

N-[(3E)-3-[[3-[[5-(trifluoromethyl)-2-pyridyl]methyl]phenyl]methylene]cyclohexyl]pyridine-3-carboxamide and its (+) and (−) enantiomers;

N-[(3E)-3-[[3-[1-[5-(trifluoromethyl)-2-pyridyl]cyclopropyl]phenyl]methylene]cyclohexyl]pyridine-3-carboxamide and its (+) and (−) enantiomers;

N-[(3E)-3-[1-[3-[[5-(trifluoromethyl)-2-pyridyl]amino]phenyl]ethylidene]cyclopentyl]pyridine-3-carboxamide and its (+) and (−) enantiomers;

N-[(3E)-3-[[3-[[5-(trifluoromethyl)-2-pyridyl]methyl]phenyl]methylene]cyclopentyl]pyridine-3-carboxamide and its (+) and (−) enantiomers;

N-[(3E)-3-[1-[3-[[5-(trifluoromethyl)-2-pyridyl]oxy]phenyl]ethylidene]cyclopentyl]pyridine-3-carboxamide and its (+) and (−) enantiomers;

(3E)-N-(3-pyridyl)-3-[1-[3-[[5-(trifluoromethyl)-2-pyridyl]oxy]phenyl]ethylidene]cyclopentanecarboxamide and its (+) and (−) enantiomers;

N-[(3E)-3-[1-[3-[1-[5-(trifluoromethyl)-2-pyridyl]cyclopropyl]phenyl]ethylidene]cyclopentyl]pyridine-3-carboxamide and its (+) and (−) enantiomers;

N-(3-pyridyl)-3-[1-[3-[[5-(trifluoromethyl)-2-pyridyl]amino]phenyl]propylidene]norpinane-6-carboxamide and its (+) and (−) enantiomers;

N-[(5E)-5-[[3-[[5-(trifluoromethyl)-2-pyridyl]oxy]phenyl]methylene]norbornan-2-yl]pyridine-3-carboxamide and its (+) and (−) enantiomers;

N-[(5E)-5-[[3-[[5-(trifluoromethyl)-2-pyridyl]oxy]phenyl]methylene]norbornan-2-yl]pyridine-3-carbothioamide and its (+) and (−) enantiomers;

N'-cyano-N-[(5E)-5-[[3-[[5-(trifluoromethyl)-2-pyridyl]oxy]phenyl]methylene]norbornan-2-yl]pyridine-3-carboxamidine and its (+) and (−) enantiomers;

N-[(5Z)-5-[1-[3-[[5-(trifluoromethyl)-2-pyridyl]oxy]phenyl]propylidene]norbornan-2-yl]pyridine-3-carboxamide and its (+) and (−) enantiomers;

N-(3-pyridyl)-6-[1-[3-[[5-(trifluoromethyl)-2-pyridyl]methyl]phenyl]ethylidene]norpinane-3-carboxamide and its (+) and (−) enantiomers;

(2E)-N-(3-pyridyl)-2-[[3-[[5-(trifluoromethyl)-2-pyridyl]amino]phenyl]methylene]bicyclo[2.2.2]octane-5-carboxamide and its (+) and (−) enantiomers;

(4E)-N-(3-pyridyl)-4-[[3-[[5-(trifluoromethyl)-2-pyridyl]oxy]phenyl]methylene]norpinane-1-carboxamide and its (+) and (−) enantiomers;

N-[(4Z)-3-methyl-4-[1-[3-[[5-(trifluoromethyl)-2-pyridyl]oxy]phenyl]ethylidene]cyclohexyl]pyridine-3-carboxamide and its (+) and (−) enantiomers;

N-[(2Z)-2-[1-[3-[[5-(trifluoromethyl)-2-pyridyl]amino]phenyl]ethylidene]-5-bicyclo[3.2.1]octanyl]pyridine-3-carboxamide and its (+) and (−) enantiomers;

(3E)-N-(3-pyridylmethyl)-3-[[3-[[5-(trifluoromethyl)-2-pyridyl]amino]phenyl]methylene]cyclopentanecarboxamide and its (+) and (−) enantiomers;

4-methyl-2-(3-pyridyl)-N-[4-[[3-[[5-(trifluoromethyl)-2-pyridyl]amino]phenyl]methylene]cyclohexyl]thiazole-5-carboxamide and its (+) and (−) enantiomers;

(2E)-N-(5-chlorothiazol-2-yl)-2-[[3-[[5-(trifluoromethyl)-2-pyridyl]methyl]phenyl]methylene]bicyclo[2.2.2]octane-5-carboxamide and its (+) and (−) enantiomers;

N-[4-[1-[3-[[5-(trifluoromethyl)-2-pyridyl]methyl]phenyl]ethylidene]cyclohexyl]pyrazine-2-carboxamide and its (+) and (−) enantiomers;

(3E)-N-pyrimidin-2-yl-3-[[3-[[5-(trifluoromethyl)-2-pyridyl]oxy]phenyl]methylene]cyclohexanecarboxamide and its (+) and (−) enantiomers;

2-Methyl-N-[(3E)-3-[[3-[[5-(trifluoromethyl)-2-pyridyl]oxy]phenyl]methylene]cyclopentyl]tetrazole-5-carboxamide and its (+) and (−) enantiomers;

N-[(2E)-2-[[3-[[5-(trifluoromethyl)-2-pyridyl]amino]phenyl]methylene]-5-bicyclo [2.2.2]octanyl]pyrimidine-5-carboxamide and its (+) and (−) enantiomers;

N-(1H-pyrazol-3-yl)-4-[[3-[[5-(trifluoromethyl)-2-pyridyl]methyl]phenyl]methylene]cyclohexanecarboxamide and its (+) and (−) enantiomers;

5-methyl-N-[(3E)-3-[1-[3-[[5-(trifluoromethyl)-2-pyridyl]methyl]phenyl]ethylidene]cyclohexyl]-1,3,4-oxadiazole-2-carboxamide and its (+) and (−) enantiomers;

5-methyl-N-[(3E)-3-[[3-[[5-(trifluoromethyl)-2-pyridyl]oxy]phenyl]methylene]cyclohexyl]-1,3,4-thiadiazole-2-carboxamide and its (+) and (−) enantiomers;

3-methyl-N-[(3E)-3-[[3-[[5-(trifluoromethyl)-2-pyridyl]amino]phenyl]methylene]cyclopentyl]-1,2,4-oxadiazole-5-carboxamide and its (+) and (−) enantiomers;

(2E)-N-thiazolo[5,4-b]pyridin-2-yl-2-[[3-[[5-(trifluoromethyl)-2-pyridyl]methyl]phenyl]methylene]bicyclo[2.2.2]octane-5-carboxamide and its (+) and (−) enantiomers;

3,5-Dimethyl-N-[(2E)-2-[[3-[[5-(trifluoromethyl)-2-pyridyl]amino]phenyl]methylene]-5-bicyclo[2.2.2]octanyl]isoxazole-4-carboxamide and its (+) and (−) enantiomers;

6-Amino-N-[4-[1-[3-[[5-(trifluoromethyl)-2-pyridyl]amino]phenyl]ethylidene]cyclohexyl]pyridine-3-carboxamide and its (+) and (−) enantiomers;

3-(Trifluoromethyl)-N-[(2E)-2-[[3-[4-(trifluoromethyl)phenoxy]phenyl]methylene]-5-bicyclo[2.2.2]octanyl]-1H-pyrazole-4-carboxamide and its (+) and (−) enantiomers;

2-Amino-N-[4-[1-[3-[[5-(trifluoromethyl)-2-pyridyl]amino]phenyl]propylidene]cyclohexyl]pyrimidine-5-carboxamide and its (+) and (−) enantiomers;

N-Pyrimidin-5-yl-4-[[3-[[5-(trifluoromethyl)-2-pyridyl]oxy]phenyl]methylene]cyclohexanecarboxamide and its (+) and (−) enantiomers;

2-Amino-N-[4-[[3-[[5-(trifluoromethyl)-2-pyridyl]methyl]phenyl]methylene]cyclohexyl]pyrimidine-5-carboxamide and its (+) and (−) enantiomers;

6-Amino-5-methyl-N-[(2E)-2-[1-[3-[4-(trifluoromethyl)phenoxy]phenyl]ethylidene]-5-bicyclo[2.2.2]octanyl]pyridine-3-carboxamide and its (+) and (−) enantiomers;

N-[(2E)-2-[[3-[4-(trifluoromethyl)phenoxy]phenyl]methylene]-5-bicyclo[2.2.2]octanyl]-1H-pyrrolo[2,3-b]pyridine-5-carboxamide and its (+) and (−) enantiomers;

N-Pyridazin-3-yl-4-[1-[3-[[5-(trifluoromethyl)-2-pyridyl]methyl]phenyl]ethylidene]cyclohexanecarboxamide and its (+) and (−) enantiomers;

6-Pyrrol-1-yl-N-[(2E)-2-[1-[3-[4-(trifluoromethyl)phenoxy]phenyl]ethylidene]-5-bicyclo [2.2.2]octanyl]pyridine-3-carboxamide and its (+) and (−) enantiomers;

(3E)-N-(6-cyclopropyl-3-pyridyl)-3-[1-[3-[[5-(trifluoromethyl)-2-pyridyl]oxy]phenyl]ethylidene]cyclohexanecarboxamide and its (+) and (−) enantiomers;

N-[4-[1-[3-[[5-(trifluoromethyl)-2-pyridyl]methyl]phenyl]ethylidene]cyclohexyl]-1H-indole-3-carboxamide and its (+) and (−) enantiomers;

6-(1H-pyrazol-4-yl)-N-[4-[1-[3-[[5-(trifluoromethyl)-2-pyridyl]amino]phenyl]ethylidene]cyclohexyl]pyridine-3-carboxamide and its (+) and (−) enantiomers;

6-(3,5-Dimethyl-1H-pyrazol-4-yl)-N-[4-[1-[3-[[5-(trifluoromethyl)-2-pyridyl]oxy]phenyl]propylidene]cyclohexyl]pyridine-3-carboxamide and its (+) and (−) enantiomers;

N-(3-pyridyl)-4-[1-[3-(2-quinolyloxy)phenyl]ethylidene]cyclohexanecarboxamide and its (+) and (−) enantiomers;

N-[4-[[3-(2-quinolyloxy)phenyl]methylene]cyclohexyl]pyridine-3-carboxamide and its (+) and (−) enantiomers;

N-[4-[[3-(2-pyridyloxy)phenyl]methylene]cyclohexyl]pyridine-3-carboxamide and its (+) and (−) enantiomers;

N-[4-[1-[3-[[5-(trifluoromethyl)-2-pyridyl]amino]phenyl]ethylidene]cyclohexyl]pyridine-3-carboxamide and its (+) and (−) enantiomers;

4-[1-[3-[(5-cyclopropyl-2-pyridyl)amino]phenyl]propylidene]-N-(3-pyridyl)cyclohexanecarboxamide and its (+) and (−) enantiomers;

N-[4-[[3-[5-(trifluoromethyl)pyrazin-2-yl]oxyphenyl]methylene]cyclohexyl]pyridine-3-carboxamide and its (+) and (−) enantiomers;

N-[4-[1-[3-[(5-fluoro-2-pyridyl)oxy]phenyl]propylidene]cyclohexyl]pyridine-3-carboxamide and its (+) and (−) enantiomers;

4-[1-[3-[(5-fluoro-2-pyridyl)methyl]phenyl]ethylidene]-N-(3-pyridyl)cyclohexanecarboxamide and its (+) and (−) enantiomers;

N-(3-pyridyl)-4-[[3-[[5-(trifluoromethyl)pyrimidin-2-yl]amino]phenyl]methylene]cyclohexanecarboxamide and its (+) and (−) enantiomers;

4-[[3-(5-ethylpyrimidin-2-yl)oxyphenyl]methylene]-N-(3-pyridyl)cyclohexanecarboxamide and its (+) and (−) enantiomers;

N-[4-[1-(3-phenoxyphenyl)ethylidene]cyclohexyl]pyridine-3-carboxamide and its (+) and (−) enantiomers;

N-[4-[1-[3-(furo[2,3-b]pyridin-2-ylamino)phenyl]ethylidene]cyclohexyl]pyridine-3-carboxamide and its (+) and (−) enantiomers;

N-(3-pyridyl)-4-[[3-(1H-pyrrolo[2,3-b]pyridin-2-yloxy)phenyl]methylene]cyclohexanecarboxamide and its (+) and (−) enantiomers;

N-[4-[1-(3-thieno[2,3-b]pyridin-2-yloxyphenyl)ethylidene]cyclohexyl]pyridine-3-carboxamide and its (+) and (−) enantiomers;

N-[4-[1-[3-(thieno[2,3-b]pyridin-6-ylamino)phenyl]ethylidene]cyclohexyl]pyridine-3-carboxamide and its (+) and (−) enantiomers;

N-[4-[(3-thieno[2,3-b]pyridin-6-yloxyphenyl)methylene]cyclohexyl]pyridine-3-carbothioamide and its (+) and (−) enantiomers;

N'-cyano-N-[4-[(3-thieno[2,3-b]pyridin-6-yloxyphenyl)methylene]cyclohexyl]pyridine-3-carboxamidine and its (+) and (−) enantiomers;

N-(3-pyridyl)-4-[1-[4-[[5-(trifluoromethyl)-2-pyridyl]oxy]-2-naphthyl]ethylidene]cyclohexanecarboxamide, N-[4-[[1-[[5-(trifluoromethyl)-2-pyridyl]oxy]-3-isoquinolyl]methylene]cyclohexyl]pyridine-3-carboxamide and its (+) and (−) enantiomers;

N-[4-[1-[4-[[5-(trifluoromethyl)-2-pyridyl]amino]pyrimidin-2-yl]ethylidene]cyclohexyl]pyridine-3-carboxamide and its (+) and (−) enantiomers;

N-(3-pyridyl)-4-[1-[5-[[5-(trifluoromethyl)-2-pyridyl]amino]pyridazin-3-yl]propylidene]cyclohexanecarboxamide and its (+) and (−) enantiomers;

N-[4-[[2-[[5-(trifluoromethyl)-2-pyridyl]oxy]pyrimidin-4-yl]methylene]cyclohexyl]pyridine-3-carboxamide and its (+) and (−) enantiomers;

N-[4-[1-[6-[[5-(trifluoromethyl)-2-pyridyl]oxy]pyrazin-2-yl]propylidene]cyclohexyl]pyridine-3-carboxamide and its (+) and (−) enantiomers;

N-(3-pyridyl)-4-[1-[6-[[5-(trifluoromethyl)-2-pyridyl]methyl]pyridazin-4-yl]ethylidene]cyclohexanecarboxamide and its (+) and (−) enantiomers;

N-(3-pyridyl)-4-[[2-[[5-(trifluoromethyl)-2-pyridyl]amino]-4-pyridyl]methylene]cyclohexanecarboxamide and its (+) and (−) enantiomers;

N-(3-pyridyl)-4-[[6-[[5-(trifluoromethyl)-2-pyridyl]oxy]-1H-indol-4-yl]methylene]cyclohexanecarboxamide and its (+) and (−) enantiomers;

N-[4-[1-[7-[[5-(trifluoromethyl)-2-pyridyl]oxy]-5-quinolyl]ethylidene]cyclohexyl]pyridine-3-carboxamide and its (+) and (−) enantiomers;

N-[4-[1-[5-[[5-(trifluoromethyl)-2-pyridyl]amino]-2-thienyl]ethylidene]cyclohexyl]pyridine-3-carboxamide and its (+) and (−) enantiomers;

N-[4-[[5-[[5-(trifluoromethyl)-2-pyridyl]oxy]-2-thienyl]methylene]cyclohexyl]pyridine-3-carbothioamide and its (+) and (−) enantiomers;

N'-cyano-N-[4-[[5-[[5-(trifluoromethyl)-2-pyridyl]oxy]-2-thienyl]methylene]cyclohexyl]pyridine-3-carboxamidine and its (+) and (−) enantiomers;

N-(4-pyridyl)-4-[[3-[[5-(trifluoromethyl)-2-pyridyl]oxy]phenyl]methylene]cyclohexanecarboxamide and its (+) and (−) enantiomers;

N-(4-pyridyl)-4-[[3-[1-[5-(trifluoromethyl)-2-pyridyl]cyclopropyl]phenyl]methylene]cyclohexanecarboxamide and its (+) and (−) enantiomers;

N-[4-[[3-[1-[5-(trifluoromethyl)-2-pyridyl]cyclopropyl]phenyl]methylene]cyclohexyl]pyridine-4-carboxamide and its (+) and (−) enantiomers;

N-[4-[[3-[[5-(trifluoromethyl)-2-pyridyl]methyl]phenyl]methylene]cyclohexyl]pyridine-4-carboxamide and its (+) and (−) enantiomers;

N-[4-[1-[3-[[5-(trifluoromethyl)-2-pyridyl]amino]phenyl]ethylidene]cyclohexyl]pyridine-4-carboxamide and its (+) and (−) enantiomers;

N-[4-[1-[3-[[5-(trifluoromethyl)-2-pyridyl]oxy]phenyl]ethylidene]cyclohexyl]pyridine-4-carboxamide and its (+) and (−) enantiomers;

N-[4-[[3-[[5-(trifluoromethyl)-2-pyridyl]methyl]phenyl]methylene]cyclohexyl]pyridine-3-carboxamide and its (+) and (−) enantiomers;

N-[4-[1-[3-[[5-(trifluoromethyl)-2-pyridyl]oxy]phenyl]ethylidene]cyclohexyl]pyridine-3-carboxamide and its (+) and (−) enantiomers;

5-chloro-N-[4-[[3-[[5-(trifluoromethyl)-2-pyridyl]amino]phenyl]methylene]cyclohexyl]thiazole-2-carboxamide and its (+) and (−) enantiomers;

N-(5-chlorothiazol-2-yl)-4-[1-[3-[[5-(trifluoromethyl)-2-pyridyl]amino]phenyl]ethylidene]cyclohexanecarboxamide and its (+) and (−) enantiomers;

N-[4-[1-[3-[[5-(trifluoromethyl)-2-pyridyl]oxy]phenyl]propylidene]cyclohexyl]pyrazine-2-carboxamide and its (+) and (−) enantiomers;

N-[4-[1-[3-[[5-(trifluoromethyl)-2-pyridyl]oxy]phenyl]propylidene]cyclohexyl]pyrimidine-2-carboxamide and its (+) and (−) enantiomers;

N-(1-Methyltetrazol-5-yl)-4-[1-[3-[[5-(trifluoromethyl)-2-pyridyl]methyl]phenyl]ethylidene]cyclohexanecarboxamide and its (+) and (−) enantiomers;

N-pyrimidin-5-yl-4-[[3-[[5-(trifluoromethyl)-2-pyridyl]amino]phenyl]methylene]cyclohexanecarboxamide and its (+) and (−) enantiomers;

N-(1H-pyrazol-3-yl)-4-[[3-[[5-(trifluoromethyl)-2-pyridyl]oxy]phenyl]methylene]cyclohexanecarboxamide and its (+) and (−) enantiomers;

N-[4-[[3-[1-[5-(trifluoromethyl)-2-pyridyl]cyclopropyl]phenyl]methylene]cyclohexyl]-1H-pyrazole-3-carboxamide and its (+) and (−) enantiomers;

N-[4-[[3-[[5-(trifluoromethyl)-2-pyridyl]methyl]phenyl]methylene]cyclohexyl]-1H-pyrazole-3-carboxamide and its (+) and (−) enantiomers;

N-[4-[[3-[[5-(trifluoromethyl)-2-pyridyl]amino]phenyl]methylene]cyclohexyl]-1H-pyrazole-3-carboxamide and its (+) and (−) enantiomers;

N-[4-[1-[3-[[5-(trifluoromethyl)-2-pyridyl]oxy]phenyl]ethylidene]cyclohexyl]-1H-pyrazole-3-carboxamide and its (+) and (−) enantiomers;

5-methyl-N-[4-[1-[3-[[5-(trifluoromethyl)-2-pyridyl]oxy]phenyl]ethylidene]cyclohexyl]-1,3,4-oxadiazole-2-carboxamide and its (+) and (−) enantiomers;

5-Methyl-N-[4-[1-[3-[[5-(trifluoromethyl)-2-pyridyl]amino]phenyl]ethylidene]cyclohexyl]-1,3,4-thiadiazole-2-carboxamide and its (+) and (−) enantiomers;

N-(3-methyl-1,2,4-oxadiazol-5-yl)-4-[1-[3-[[5-(trifluoromethyl)-2-pyridyl]oxy]phenyl]ethylidene]cyclohexanecarboxamide and its (+) and (−) enantiomers;

N-[4-[[3-[[5-(trifluoromethyl)-2-pyridyl]oxy]phenyl]methylene]cyclohexyl]thiazolo[5,4-b]pyridine-2-carboxamide and its (+) and (−) enantiomers;

N-[4-[1-[3-[[5-(trifluoromethyl)-2-pyridyl]amino]phenyl]ethylidene]cyclohexyl]-5,6,7,8-tetrahydroimidazo[1,2-a]pyridine-2-carboxamide and its (+) and (−) enantiomers;

N-[4-[[3-[1-[5-(trifluoromethyl)-2-pyridyl]cyclopropyl]phenyl]methylene]cyclohexyl]pyridazine-3-carboxamide and its (+) and (−) enantiomers;

N-pyridazin-3-yl-4-[[3-[[5-(trifluoromethyl)-2-pyridyl]amino]phenyl]methylene]cyclohexanecarboxamide and its (+) and (−) enantiomers;

N-[4-[1-[3-[[5-(trifluoromethyl)-2-pyridyl]amino]phenyl]ethylidene]cyclohexyl]pyridazine-3-carboxamide and its (+) and (−) enantiomers;

N-[4-[[3-[[5-(trifluoromethyl)-2-pyridyl]methyl]phenyl]methylene]cyclohexyl]pyridazine-3-carboxamide and its (+) and (−) enantiomers;

3,5-dimethyl-N-[4-[[3-[[5-(trifluoromethyl)-2-pyridyl]oxy]phenyl]methylene]cyclohexyl]isoxazole-4-carboxamide and its (+) and (−) enantiomers;

N-[4-[1-[3-[[5-(trifluoromethyl)-2-pyridyl]oxy]phenyl]propylidene]cyclohexyl]-1,5-naphthyridine-3-carboxamide and its (+) and (−) enantiomers;

N-(3-methylisothiazol-5-yl)-4-[1-[3-[[5-(trifluoromethyl)-2-pyridyl]methyl]phenyl]ethylidene]cyclohexanecarboxamide and its (+) and (−) enantiomers;

N-thieno[3,2-b]pyridin-2-yl-4-[[3-[[5-(trifluoromethyl)-2-pyridyl]amino]phenyl]methylene]cyclohexanecarboxamide and its (+) and (−) enantiomers;

N-thieno[2,3-b]pyridin-2-yl-4-[[3-[[5-(trifluoromethyl)-2-pyridyl]oxy]phenyl]methylene]cyclohexanecarboxamide and its (+) and (−) enantiomers;

N-[4-[1-[3-[[5-(trifluoromethyl)-2-pyridyl]oxy]phenyl]ethylidene]cyclohexyl]thiazolo[4,5-c]pyridine-2-carboxamide and its (+) and (−) enantiomers;

N-[4-[[3-[[5-(trifluoromethyl)-2-pyridyl]oxy]phenyl]methylene]cyclohexyl]thiazolo[4,5-c]pyridine-2-carbothioamide and its (+) and (−) enantiomers; and N'-cyano-N-[4-[[3-[[5-(trifluoromethyl)-2-pyridyl]oxy]phenyl]methylene]cyclohexyl]thiazolo[4,5-c]pyridine-2-carboxamidine and its (+) and (−) enantiomers.

FAAH Assay

Material and Reagents: All reagents were purchased from Sigma-Aldrich unless specified. Human and Rat Fatty Acid Amide Hydrolase (FAAH) genes used in assay have been described by Patricelli et al. (*Biochemistry*. 1998, 37(43), 15177-87). The transmembrane domain-deleted Fatty Acid Amide Hydrolase (FAAH) genes were cloned into pET15b (Novagen, #69661) (human FAAH)/pET 28a (Novagen, #69864-3) (rat FAAH gene) plasmids and expressed in *E coli* BL21 DE3. Chaperone protein groEL-groES in pGRO7 plasmid (Takara Bio Inc, Japan) was co-expressed with Fatty Acid Amide Hydrolase (FAAH) to improve solubility of the protein expressed in *E coli*. The protein was expressed and enriched as described in Mileni et al. (*Proc Natl Acad Sci USA*. 2008, 105(35),12820-4). Briefly, the bacterial cultures in Luria Broth (2 L) were induced with arabinose (2 mM) and Isopropyl (β-D-1-thiogalactopyranoside, IPTG (1 mM), for 20 h at room temperature. The cultures were centrifuged at 1200×g for 10 min and the cell pellet was resuspended in 100 mL buffer containing of 20 mM NaPi (pH 7.4), 100 mM NaCl, Benzonase (500u), Aprotinin (1 µg/mL) and Leupeptin (1 µg/mL). Cells were lyzed by sonication (Amp 20%, Pulse 15 s×15, on ice) and the cell debris removed by centrifugation at 5000×g for 20 min. The supernatant was enriched via ultracentrifugation at 100,000×g for 1 h and the cell pellet was resuspended in 16 mL buffer containing 20 mM NaPi (pH 7.8), 500 mM NaCl, 1% Triton X-100. The resuspended cell extract was subjected to ultra-centrifugation at 100,000×g for 1 h and the enriched supernatant was used in the in vitro assay. All protein extraction steps were carried out on ice or at 4° C.

In Vitro Assay: The biological activity of the compounds was evaluated using a fluorescence based assay to quantify the hydrolysis of arachidonyl 7-amino, 4 methyl coumarin amide (AAMCA), a fluorogenic substrate for Fatty Acid Amide Hydrolase (FAAH) (*Anal Biochem*. 2005, 343(1): 143-51). The assay was carried out in 200 µL volume in a 96-well black polystyrene plate (Greiner Bio-one, Germany). Each reaction consisted of human Fatty Acid Amide Hydrolase (FAAH) protein and 10 µM AAMCA in assay buffer containing 50 mM HEPES, 1 mM EDTA and 0.1% BSA, pH 7.4. The reaction was incubated with 2 µL of varying concentrations of inhibitor in DMSO (final concentration of DMSO 1%) with shaking for 1 min and monitored for increase in fluorescence in kinetic mode for 50 min. Increase in fluorescence was measured using a Flexstation III microplate reader (Molecular Devices, Sunnyvale, Calif.) at excitation wavelength of 355 nm and emission at 460 nm. Rate of reaction as a function of the concentration of the inhibitor was used to determine the $IC_{50}$ of the inhibitors. Data was analyzed using GraphPad Prism 5 (GraphPad Software Inc., San Diego, Calif.). The activity of the compounds for rat Fatty Acid Amide Hydrolase (FAAH) was evaluated as described above with rat Fatty Acid Amide Hydrolase (FAAH) protein and 10 µM AAMCA substrate.

Compounds of formula (I) were tested for its human and rat Fatty Acid Amide Hydrolase (FAAH) inhibitory activities using above mentioned assay method, and were found to be active with $IC_{50}$ value in the range of 100 µM to 0.01 nM.

Below table exemplifies Fatty Acid Amide Hydrolase (FAAH) inhibitory activity of some of the tested compounds from the present invention.

| Ex No./ADV No | hFAAH $IC_{50}$ (nM) | rFAAH $IC_{50}$ (nM) |
| --- | --- | --- |
| 1.1 | 16 | 60 |
| 1.A-1 | 17 | — |
| 1.A-3 | 9 | 44 |
| 1.2 | 17 | — |
| 2.1 | 2 | 24 |
| 2.A-5 | 9 | 27% inhibition at 100 nM |
| 2.A-11 | 11 | 194 |
| 2.A-17 | 10 | 14% inhibition at 100 nM |
| 2.A-4 | 508 | 70% inhibition at 30 uM |
| 2.D-5 | 2 | 16 |
| 2.A-24 | 9 | 31% inhibition at 100 nM |
| 2.A-34 | 18 | 50% inhibition at 1 µM |
| 2.A-1 | 10 | 418 |
| 2.A-9 | 2 | 53 |
| 2.A-12 | 3 | 100 |
| 2.A-16 | 15 | 38% inhibition at 100 nM (tier I) |
| 2.B-1 | 10 | 237 |
| 2.D-3 | 23 | 38% inhibition at 100 nM (tier I) |
| 2.A-20 | 334 | No inhibition at 100 nM |
| 2.A-19 | 6 | 145 |
| 2.A-8 | 14 | 14% inhibition at 100 nM (tier I) |
| 2.D-6 | 10 | 87 |
| 2.A-6 | 102 | 37% inhibition at 100 nM (tier I) |
| 2.A-14 | 10 | 25% inhibition at 100 nM (tier I) |
| 2.A-15 | 5 | 188 |
| 2.A-26 | 5 | 84 |
| 2.A-22 | 5 | 81 |
| 2.A-32 | 6 | 40% inh at 100 nM |
| 2.A-25 | 16 | No inh at 100 nM |
| 2.A-27 | 55 | 27% inh at 100 nM (tier I) |
| 10.1 | 1 | 6 |
| 2.2 | 5 | 28 |
| 2.A-30 | 5 | 14 |
| 2.A-28 | 31 | No inhibition at 100 nM |
| 2.A-37 | 57 | No inhibition at 100 nM |
| 2.A-42 | 13 | 14 |
| 2.A-43 | 4 | 18 |
| 2.C-1 | 5 | 31 |
| 4.A-3 | 3 | 16 |
| 2.C-5 | 37 | NI at 100 nM |
| 5.A-1 | 4 | 11 |
| 5.1 | 7 | 13 |
| 5.A-7 | 128 | 15 |
| 5.A-10 | 25 | 74 |
| 2.C-2 | 5 | 21 |
| 6.1 | 10 | 8 |
| 2.C-3 | 19 | NI at 100 nM |
| 2.C-4 | 4 | 21 |
| 5.A-8 | 16 | 32 |
| 5.A-2 | 54% inhn at 100 nM | 28 |
| 5.A-6 | 7 | 7 |
| 2.B-4 | 2 | 11 |
| 2.B-5 | 2 | 9 |
| 11.1 | 12 | 50% inhibition at 100 nM (Tier I) |
| 2.B-6 | 7 | 21 |
| 2.B-9 | 9 | 22 |
| 2.B-8 | 5 | 21 |
| 2.B-7 | 6 | 85 |
| 2.B-11 | 17 | 52 |
| 2.B-13 | 2 | 14 |
| 2.B-14 | 2 | 11 |
| 2.B-15 | 3 | 9 |
| 2.A-18 | 45% inh at 100 nM (tier I) | 38% inhibition at 100 nM (tier I) |
| 2.A-23 | 5 | 29 |
| 2.A-29 | 3 | 24 |

-continued

| Ex No./ADV No | hFAAH IC$_{50}$ (nM) | rFAAH IC$_{50}$ (nM) |
| --- | --- | --- |
| 2.A-35 | 29 | 38% inhibition at 100 nM (Tier-I) |
| 2.A-36 | 50% inhn at 100 nM (Tier I) | NI inhibition at 100 nM |
| 2.A-39 | 63 | 30 |
| 2.A-38 | 20% inhn at 100 nM (Tier I) | 54% inhibition at 100 nM (Tier I) |
| 2.C-6 | 1 | 16 |
| 2.E-17 | 3 | 27 |
| 2.E-20 | 3 | 71 |
| 2.E-24 | 34 | 47% inhibition at 100 nM (Tier I) |
| 2.E-19 | 40% inhn at 100 nM (Tier I) | 40% inhibition at 100 nM (Tier I) |
| 2.E-28 | 6 | 75 |
| 2.E-23 | 12 | 65 |
| 2.E-22 | 2 | 21 |
| 2.E-18 | 13 | 55% inhibition at 100 nM (Tier I) |
| 2.E-16 | 3 | 24 |
| 2.E-25 | 7 | 32 |
| 2.E-27 | 1 | 17 |
| 8.A-4 | 27 | 15% inhibition at 100 nM (tier I) |
| 8.A-2 | 40% inhn at 100 nM (tier I) | NI inhibition at 100 nM (tier I) |
| 8.A-5 | 34 | 55% inhibition at 100 nM (tier I) |
| 8.A-1 | 72% inhn at 100 nM (tier I) | 15% inhibition at 100 nM (tier I) |
| 20.A-1 | 429 | 60% inhibition at 10 uM |
| 20.A-2 | 0.7 | 13 |
| 20.A-3 | 361 | 70% inhibition at 10 uM |
| 20.A-4 | 1 | 11 |
| 20.A-5 | 247 | — |
| 20.A-6 | 1 | 10 |
| 20.A-8 | 1 | 30 |
| 20.A-7 | 67 | 85% inhibition at 10 uM |
| 20.A-9 | 40 | — |
| 20.A-10 | 0.6 | 7 |
| 20.A-11 | 78 | 86% inhibition at 10 uM |
| 20.A-12 | 1.7 | 35.5 |
| 20.A-13 | 55 | 407 |
| 20.A-14 | 1 | 8.6 |
| 20.A-15 | 431 | 408 |
| 20.A-16 | 4 | 115 |
| 20.A-19 | 14.3 | — |
| 20.A-20 | 0.8 | |
| 20.A-17 | 155 | 90% inhibition at 10 uM |
| 20.A-18 | 4 | 35 |
| 20.A-21 | 9 | |
| 20.A-22 | 1.1 | |

Although the subject matter has been described in considerable detail with reference to certain preferred embodiments thereof, other embodiments are possible. As such, the spirit and scope of the appended claims should not be limited to the description of the preferred embodiment contained therein.

We claim:
1. A compound of formula (I):

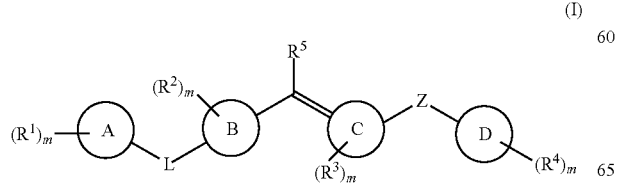

or its tautomer, polymorph, stereoisomer, prodrug, solvate, pharmaceutically acceptable salt or a pharmaceutical composition thereof, wherein, ring A is

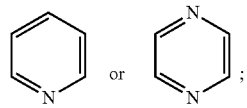 [SMILES: c1ccncc1 ; c1cnccn1]

ring B is phenyl;
ring C is selected from the group consisting of:

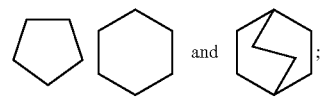

ring D is selected from the group consisting of:

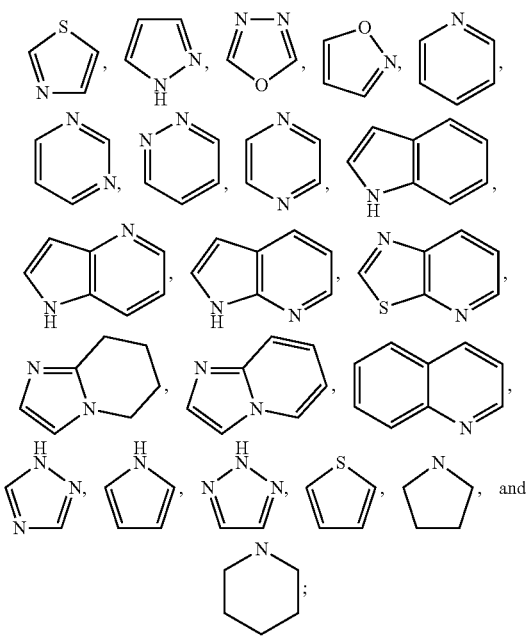

L is —O— or —N(R)—;
Z is selected from —C(Y)NR—(CR$^a$R$^b$)$_q$— or —NRC(Y)—C(R$^a$R$^b$)$_q$;
Y is O;
R is hydrogen;
R$^1$, R$^2$, R$^3$ and R$^4$ are independently selected from hydrogen, halo, cyano, nitro, —(CR$^a$R$^b$)$_n$OR$^6$, —(CR$^a$R$^b$)$_n$C(O)R$^6$, —(CR$^a$R$^b$)$_n$COOR$^6$, —(CR$^a$R$^b$)$_n$NR$^7$R$^8$, C$_{1-6}$alkyl, perhaloalkyl, cycloalkyl, heterocyclyl, or heteroaryl;
wherein each substituent is unsubstituted or substituted with 1 or 2 substituents independently selected from alkyl, halogen, perhaloalkyl, —(CR$^a$R$^b$)$_n$OR$^6$, —(CR$^a$R$^b$)$_n$COOR$^6$, cycloalkyl, or —CH$_2$OPO$_3^{2-}$;
R$^5$ is selected from hydrogen, halogen, or C$_{1-6}$ alkyl;
R$^6$ is selected from hydrogen, alkyl, or —(CR$^a$R$^b$)$_n$OR$^6$;
R$^7$ and R$^8$ are independently selected from the group consisting of hydrogen, alkyl, or —(CR$^a$R$^b$)$_n$C(O)R$^6$;

$R^a$ and $R^b$ are independently selected from the group consisting of hydrogen, halogen, and alkyl;

m is independently selected from 0, 1, and 2;

n is an integer and selected from 0, 1, and 2; and q is 0 or 1.

2. A pharmaceutical composition comprising a pharmaceutically acceptable carrier and a pharmaceutically effective amount of a compound of any of claim 1.

3. The compound of formula (I):

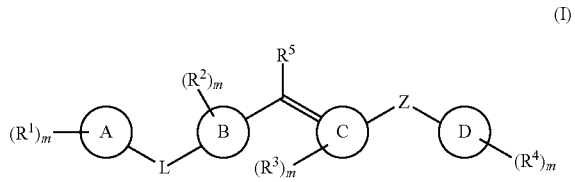

(I)

as claimed in claim 1 or its tautomer, polymorph, stereoisomer, prodrug, solvate, pharmaceutically acceptable salt or a pharmaceutical composition thereof, wherein, ring A is selected from pyridine or pyrazine;

ring B is phenyl;

ring C is selected from cyclopentyl, cyclohexyl, or bicyclo[2.2.2]octane;

ring D is selected from phenyl, pyrrole, thiazole, pyrazole, isoxazole, oxadiazole, triazole, pyridine, pyrimidine, pyridazine, pyrazine, indole, thiazolopyridine, or pyrrolopyridine;

L is —O— or —N(R)—;

Z is selected from —C(Y)NR—(CR$^a$R$^b$)$_q$— or —NRC(Y)—C(R$^a$R$^b$)$_q$;

Y is O;

R is hydrogen;

$R^1$, $R^2$, $R^3$ and $R^4$ are independently selected from hydrogen, halo, cyano, nitro, —(CR$^a$R$^b$)$_n$OR$^6$, —(CR$^a$R$^b$)$_n$C(O)R$^6$, —(CR$^a$R$^b$)$_n$COOR$^6$, —(CR$^a$R$^b$)$_n$NR$^7$R$^8$, $C_{1-6}$alkyl, perhaloalkyl, cycloalkyl, heterocyclyl, or heteroaryl;

wherein each substituent is unsubstituted or substituted with 1 or 2 substituents independently selected from alkyl, halogen, perhaloalkyl, —(CR$^a$R$^b$)$_n$OR$^6$, —(CR$^a$R$^b$)$_n$COOR$^6$, cycloalkyl or —CH$_2$OPO$_3^{2-}$;

$R^5$ is selected from hydrogen, or $C_{1-6}$ alkyl;

$R^6$ is selected from hydrogen or alkyl;

$R^7$ and $R^8$ are independently selected from the group consisting of hydrogen and alkyl;

$R^a$ and $R^b$ are independently selected from the group consisting of hydrogen and halogen;

m is independently selected from 0, 1 and 2;

n is an integer and selected from 0, 1 and 2; and q is 0 or 1.

4. A pharmaceutical composition comprising a pharmaceutically acceptable carrier and a pharmaceutically effective amount of a compound of any of claim 3.

5. A compound of formula (I):

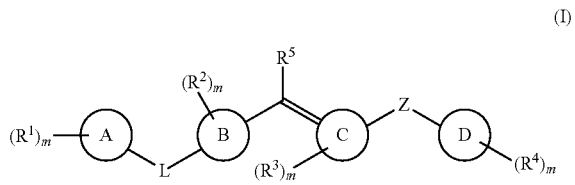

(I)

or its tautomer, polymorph, stereoisomer, prodrug, solvate, co-crystal or a pharmaceutically acceptable salt thereof, which is selected from a group consisting of:

N-(5-Chlorothiazol-2-yl)-4-[[3-[[5-(trifluoromethyl)-2-pyridyl]oxy]phenyl]methylene]cyclohexanecarboxamide and its (+) and (−) enantiomers;

N-Pyridazin-3-yl-4-[[3-[[5-(trifluoromethyl)-2-pyridyl]oxy]phenyl]methylene]cyclohexanecarboxamide and its (+) and (−) enantiomers;

N-(5-Fluorothiazol-2-yl)-4-[[3-[[5-(trifluoromethyl)-2-pyridyl]oxy]phenyl]methylene]cyclohexanecarboxamide and its (+) and (−) enantiomers;

N-Pyrazin-2-yl-4-[[3-[[5-(trifluoromethyl)-2-pyridyl]oxy]phenyl]methylene]cyclohexanecarboxamide and its (+) and (−) enantiomers;

N-(3-Pyridylmethyl)-4-[[3-[[5-(trifluoromethyl)-2-pyridyl]oxy]phenyl]methylene]cyclohexanecarboxamide and its (+) and (−) enantiomers;

N-(3-Pyridyl)-4-[[3-[[5-(trifluoromethyl)-2-pyridyl]oxy]phenyl]-methylene]cyclohexanecarboxamide hydrochloride and its (+) and (−) enantiomers;

N-[4-[[3-[[5-(Trifluoromethyl)-2-pyridyl]oxy]phenyl]methylene]cyclohexyl]pyridine-3-carboxamide and its (+) and (−) enantiomers;

6-Methyl-N-[4-[[3-[[5-(trifluoromethyl)-2-pyridyl]oxy]phenyl]-methylene]cyclohexyl]pyridine-3-carboxamide and its (+) and (−) enantiomers;

N-[(3E)-3-[[3-[[5-(Trifluoromethyl)-2-pyridyl]oxy]phenyl]methylene]-cyclohexyl]pyrazine-2-carboxamide and its (+) and (−) enantiomers;

N-[4-[[3-[[5-(Trifluoromethyl)-2-pyridyl]oxy]phenyl]methylene]cyclohexyl]-1H-pyrazole-3-carboxamide and its (+) and (−) enantiomers;

N-[4-[[3-[[5-(Trifluoromethyl)-2-pyridyl]oxy]phenyl]methylene]cyclohexyl]thiophene-2-carboxamide and its (+) and (−) enantiomers;

2,2-Difluoro-2-(2-pyridyl)-N-[4-[[3-[[5-(trifluoromethyl)-2-pyridyl]oxy]phenyl]methylene]cyclohexyl]acetamide and its (+) and (−) enantiomers;

N-[4-[[3-[[5-(Trifluoromethyl)-2-pyridyl]oxy]phenyl]methylene]cyclohexyl]pyridine-2-carboxamide and its (+) and (−) enantiomers;

N-[4-[[3-[[5-(Trifluoromethyl)-2-pyridyl]oxy]phenyl]methylene]cyclohexyl]pyrazine-2-carboxamide and its (+) and (−) enantiomers;

6-(Trifluoromethyl)-N-[4-[[3-[[5-(trifluoromethyl)-2-pyridyl]oxy]phenyl]methylene]cyclohexyl]pyridine-3-carboxamide and its (+) and (−) enantiomers;

5-Methyl-N-[4-[[3-[[5-(trifluoromethyl)-2-pyridyl]oxy]phenyl]methylene]cyclohexyl]isoxazole-3-carboxamide and its (+) and (−) enantiomers;

N-[4-[[3-[[5-(Trifluoromethyl)-2-pyridyl]oxy]phenyl]methylene]cyclohexyl]pyridine-4-carboxamide and its (+) and (−) enantiomers;

N-[4-[[3-[[5-(Trifluoromethyl)-2-pyridyl]oxy]phenyl]methylene]cyclohexyl]-1H-pyrazole-4-carboxamide and its (+) and (−) enantiomers;

tert-Butyl(2S)-2-[[4-[[3-[[5-(trifluoromethyl)-2-pyridyl]oxy]phenyl]methylene]cyclohexyl]carbamoyl]pyrrolidine-1-carboxylate and its (+) and (−) enantiomers;

N-[4-[[3-[[5-(Trifluoromethyl)-2-pyridyl]oxy]phenyl]methylene]cyclohexyl]pyridazine-3-carboxamide and its (+) and (−) enantiomers;

N-[4-[[3-[[5-(Trifluoromethyl)-2-pyridyl]oxy]phenyl]methylene]cyclohexyl]pyrimidine-5-carboxamide and its (+) and (−) enantiomers;

2-(3-Pyridyl)-N-[4-[[3-[[5-(trifluoromethyl)-2-pyridyl]oxy]phenyl]methylene]cyclohexyl]acetamide and its (+) and (−) enantiomers;
6-Fluoro-N-[4-[[3-[[5-(trifluoromethyl)-2-pyridyl]oxy]phenyl]methylene]cyclohexyl]pyridine-3-carboxamide and its (+) and (−) enantiomers;
5-Fluoro-N-[4-[[3-[[5-(trifluoromethyl)-2-pyridyl]oxy]phenyl]methylene]cyclohexyl]pyridine-3-carboxamide and its (+) and (−) enantiomers;
N-[4-[[3-[[5-(Trifluoromethyl)-2-pyridyl]oxy]phenyl]methylene]cyclohexyl]pyrimidine-2-carboxamide and its (+) and (−) enantiomers;
N-[4-[[3-[[5-(Trifluoromethyl)-2-pyridyl]oxy]phenyl]methylene]cyclohexyl]pyridazine-4-carboxamide and its (+) and (−) enantiomers;
1-Methyl-N-[4-[[3-[[5-(trifluoromethyl)-2-pyridyl]oxy]phenyl]methylene]cyclohexyl]pyrazole-4-carboxamide and its (+) and (−) enantiomers;
N-[4-[[3-[[5-(Trifluoromethyl)-2-pyridyl]oxy]phenyl]methylene]cyclohexyl]-2H-triazole-4-carboxamide and its (+) and (−) enantiomers;
5-Methyl-N-[4-[[3-[[5-(trifluoromethyl)-2-pyridyl]oxy]phenyl]methylene]cyclohexyl]-1,3,4-oxadiazole-2-carboxamide and its (+) and (−) enantiomers;
2-Ethyl-N-[4-[[3-[[5-(trifluoromethyl)-2-pyridyl]oxy]phenyl]methylene]cyclohexyl]pyrimidine-5-carboxamide and its (+) and (−) enantiomers;
6-Chloro-N-[4-[[3-[[5-(trifluoromethyl)-2-pyridyl]oxy]phenyl]methylene]cyclohexyl]pyridine-3-carboxamide and its (+) and (−) enantiomers;
5-Methyl-N-[4-[[3-[[5-(trifluoromethyl)-2-pyridyl]oxy]phenyl]methylene]cyclohexyl]-1H-pyrazole-4-carboxamide and its (+) and (−) enantiomers;
6-(Dimethylamino)-N-[4-[[3-[[5-(trifluoromethyl)-2-pyridyl]oxy]phenyl]methylene]cyclohexyl]pyridine-3-carboxamide and its (+) and (−) enantiomers;
2-Chloro-N-[4-[[3-[[5-(trifluoromethyl)-2-pyridyl]oxy]phenyl]methylene]cyclohexyl]pyridine-3-carboxamide and its (+) and (−) enantiomers;
2-Fluoro-N-[4-[[3-[[5-(trifluoromethyl)-2-pyridyl]oxy]phenyl]methylene]cyclohexyl]pyridine-3-carboxamide and its (+) and (−) enantiomers;
6-Cyano-N-[4-[[3-[[5-(trifluoromethyl)-2-pyridyl]oxy]phenyl]methylene]cyclohexyl]pyridine-3-carboxamide and its (+) and (−) enantiomers;
2-Methyl-N-[4-[[3-[[5-(trifluoromethyl)-2-pyridyl]oxy]phenyl]methylene]cyclohexyl]pyridine-3-carboxamide and its (+) and (−) enantiomers;
3-(Trifluoromethyl)-N-[4-[[3-[[5-(trifluoromethyl)-2-pyridyl]oxy]phenyl]methylene]cyclohexyl]-1H-pyrazole-4-carboxamide and its (+) and (−) enantiomers;
5-Methyl-N-[4-[[3-[[5-(trifluoromethyl)-2-pyridyl]oxy]phenyl]methylene]cyclohexyl]pyridine-3-carboxamide and its (+) and (−) enantiomers;
tert-Butyl N-[3-[[4-[[3-[[5-(trifluoromethyl)-2-pyridyl]oxy]phenyl]methylene]cyclohexyl]carbamoyl]-4-pyridyl]carbamates and its (+) and (−) enantiomers;
5-Chloro-N-[4-[[3-[[5-(trifluoromethyl)-2-pyridyl]oxy]phenyl]methylene]cyclohexyl]pyridine-3-carboxamide and its (+) and (−) enantiomers;
3-Methyl-N-[4-[[3-[[5-(trifluoromethyl)-2-pyridyl]oxy]phenyl]methylene]cyclohexyl]triazole-4-carboxamide and its (+) and (−) enantiomers;
N-[4-[[3-[[5-(Trifluoromethyl)-2-pyridyl]oxy]phenyl]methylene]cyclohexyl]benzamide and its (+) and (−) enantiomers;
3,5-Dimethyl-N-[4-[[3-[[5-(trifluoromethyl)-2-pyridyl]oxy]phenyl]methylene]cyclohexyl]-1H-pyrazole-4-carboxamide and its (+) and (−) enantiomers;
5-Methyl-3-(trifluoromethyl)-N-[4-[[3-[[5-(trifluoromethyl)-2-pyridyl]oxy]phenyl]methylene]cyclohexyl]-1H-pyrazole-4-carboxamide and its (+) and (−) enantiomers;
2,6-Dimethyl-N-[4-[[3-[[5-(trifluoromethyl)-2-pyridyl]oxy]phenyl]methylene]cyclohexyl]pyridine-3-carboxamide and its (+) and (−) enantiomers;
5-Isopropyl-3-methyl-N-[4-[[3-[[5-(trifluoromethyl)-2-pyridyl]oxy]phenyl]methylene]cyclohexyl]-1H-pyrazole-4-carboxamide and its (+) and (−) enantiomers;
5-Isopropyl-N-[4-[[3-[[5-(trifluoromethyl)-2-pyridyl]oxy]phenyl]methylene]cyclohexyl]-1H-pyrazole-4-carboxamide and its (+) and (−) enantiomers;
3-(Hydroxymethyl)-5-methyl-N-[4-[[3-[[5-(trifluoromethyl)-2-pyridyl]oxy]phenyl]methylene]cyclohexyl]-1H-pyrazole-4-carboxamide and its (+) and (−) enantiomers;
N-[4-[[3-[[5-(Trifluoromethyl)-2-pyridyl]oxy]phenyl]methylene]cyclohexyl]isoxazole-5-carboxamide and its (+) and (−) enantiomers;
6-Cyclopropyl-N-[4-[[3-[[5-(trifluoromethyl)-2-pyridyl]oxy]phenyl]methylene]cyclohexyl]pyridine-3-carboxamide and its (+) and (−) enantiomers;
6-Ethyl-N-[4-[[3-[[5-(trifluoromethyl)-2-pyridyl]oxy]phenyl]methylene]cyclohexyl]pyridine-3-carboxamide and its (+) and (−) enantiomers;
5-Ethyl-N-[4-[[3-[[5-(trifluoromethyl)-2-pyridyl]oxy]phenyl]methylene]cyclohexyl]-1H-pyrazole-4-carboxamide and its (+) and (−) enantiomers;
3-Methyl-N-[4-[[3-[[5-(trifluoromethyl)-2-pyridyl]oxy]phenyl]methylene]cyclohexyl]-1H-1,2,4-triazole-5-carboxamide and its (+) and (−) enantiomers;
N-[4-[[3-[[5-(Trifluoromethyl)-2-pyridyl]oxy]phenyl]methylene]cyclohexyl]-1H-1,2,4-triazole-3-carboxamide and its (+) and (−) enantiomers;
3-Methyl-N-[4-[[3-[[5-(trifluoromethyl)-2-pyridyl]oxy]phenyl]methylene]cyclohexyl]isoxazole-5-carboxamide and its (+) and (−) enantiomers;
6-Chloro-5-nitro-N-[4-[[3-[[5-(trifluoromethyl)-2-pyridyl]oxy]phenyl]methylene]cyclohexyl]pyridine-3-carboxamide and its (+) and (−) enantiomers;
2,6-Difluoro-N-[4-[[3-[[5-(trifluoromethyl)-2-pyridyl]oxy]phenyl]methylene]cyclohexyl]pyridine-3-carboxamide and its (+) and (−) enantiomers;
tert-Butyl4-[[4-[[3-[[5-(trifluoromethyl)-2-pyridyl]oxy]phenyl]methylene]cyclohexyl]carbamoyl]piperidine-1-carboxylate and its (+) and (−) enantiomers;
4-Methyl-5-(3-pyridyl)-N-[4-[[3-[4-(trifluoromethyl)phenoxy]phenyl]methylene]cyclohexyl]thiazole-2-carboxamide and its (+) and (−) enantiomers;
5-(2-Pyridyl)-N-[4-[[3-[[5-trifluoromethyl)-2-ridyl]oxy]phenyl]methylene]cyclohexyl]-1,3,4-oxadiazole-2-carboxamide and its (+) and (−) enantiomers;
6-(3,5-Dimethylpyrazol-1-yl)-N-[4-[[3-[[5-(trifluoromethyl)-2-pyridyl]oxy]phenyl]methylene]cyclohexyl]pyridine-3-carboxamide and its (+) and (−) enantiomers;
6-(1H-Pyrazol-3-yl)-N-[4-[[3-[[5-(trifluoromethyl)-2-pyridyl]oxy]phenyl]methylene]cyclohexyl]pyridine-3-carboxamide and its (+) and (−) enantiomers;
6-(1H-Pyrazol-4-yl)-N-[4-[[3-[[5-(trifluoromethyl)-2-pyridyl]oxy]phenyl]methylene]cyclohexyl]pyridine-3-carboxamide and its (+) and (−) enantiomers;

6-(4-Methylpyrazol-1-yl)-N-[4-[[3-[[5-(trifluoromethyl)-2-pyridyl]oxy]phenyl]methylene]cyclohexyl]pyridine-3-carboxamide and its (+) and (−) enantiomers;

5-Pyrazol-1-yl-N-[4-[[3-[[5-(trifluoromethyl)-2-pyridyl]oxy]phenyl]methylene]cyclohexyl]pyridine-3-carboxamide and its (+) and (−) enantiomers;

6-(4-Chloropyrazol-1-yl)-N-[4-[[3-[[5-(trifluoromethyl)-2-pyridyl]oxy]phenyl]methylene]cyclohexyl]pyridine-3-carboxamide and its (+) and (−) enantiomers;

6-(3-Methylpyrazol-1-yl)-N-[4-[[3-[[5-(trifluoromethyl)-2-pyridyl]oxy]phenyl]methylene]cyclohexyl]pyridine-3-carboxamide and its (+) and (−) enantiomers;

5-Methyl-6-pyrazol-1-yl-N-[4-[[3-[[5-(trifluoromethyl)-2-pyridyl]oxy]phenyl]methylene]cyclohexyl]pyridine-3-carboxamide and its (+) and (−) enantiomers;

6-(3,5-Dimethyl-1H-pyrazol-4-yl)-N-[4-[[3-[[5-(trifluoromethyl)-2-pyridyl]oxy]phenyl]methylene]cyclohexyl]pyridine-3-carboxamide and its (+) and (−) enantiomers;

Ethyl-1-[5-[[4-[[3-[[5-(trifluoromethyl)-2-pyridyl]oxy]phenyl]methylene]cyclohexyl]carbamoyl]-2-pyridyl]pyrazole-4-carboxylate and its (+) and (−) enantiomers;

6-(1,2,4-Triazol-4-yl)-N-[4-[[3-[[5-(trifluoromethyl)-2-pyridyl]oxy]phenyl]methylene]cyclohexyl]pyridine-3-carboxamide and its (+) and (−) enantiomers;

6-(Triazol-1-yl)-N-[4-[[3-[[5-(trifluoromethyl)-2-pyridyl]oxy]phenyl]methylene]cyclohexyl]pyridine-3-carboxamide and its (+) and (−) enantiomers;

6-(Triazol-2-yl)-N-[4-[[3-[[5-(trifluoromethyl)-2-pyridyl]oxy]phenyl]methylene]cyclohexyl]pyridine-3-carboxamide Ethyl-1-[5-[[4-[[3-[[5-(trifluoromethyl)-2-pyridyl]oxy]phenyl]methylene]cyclohexyl]carbamoyl]-2-pyridyl]pyrazole-3-carboxylate and its (+) and (−) enantiomers;

2-Pyrazol-1-yl-N-[4-[[3-[[5-(trifluoromethyl)-2-pyridyl]oxy]phenyl]methylene]cyclohexyl]pyrimidine-5-carboxamide and its (+) and (−) enantiomers;

6-(3-Methyl-1H-pyrazol-4-yl)-N-[4-[[3-[[5-(trifluoromethyl)-2-pyridyl]oxy]phenyl]methylene]cyclohexyl]pyridine-3-carboxamide and its (+) and (−) enantiomers;

6-(5-Isopropyl-1H-pyrazol-3-yl)-N-[4-[[3-[[5-(trifluoromethyl)-2-pyridyl]oxy]phenyl]methylene]cyclohexyl]pyridine-3-carboxamide and its (+) and (−) enantiomers;

6(5-Ethyl-1H-pyrazol-3-yl)-N-[4-[[3-[[5-(trifluoromethyl)-2-pyridyl]oxy]phenyl]methylene]cyclohexyl]pyridine-3-carboxamide and its (+) and (−) enantiomers;

6-(3-Cyclopropyl-1H-pyrazol-4-yl)-N-[4-[[3-[[5-(trifluoromethyl)-2-pyridyl]oxy]phenyl]methylene]cyclohexyl]pyridine-3-carboxamide and its (+) and (−) enantiomers;

6-(3-Isopropyl-1H-pyrazol-4-yl)-N-[4-[[3-[[5-(trifluoromethyl)-2-pyridyl]oxy]phenyl]methylene]cyclohexyl]pyridine-3-carboxamide and its (+) and (−) enantiomers;

6-(4-Hydroxy-4-methyl-1-piperidyl)-N-[4-[[3-[[5-(trifluoromethyl)-2-pyridyl]oxy]phenyl]methylene]cyclohexyl]pyridine-3-carboxamide and its (+) and (−) enantiomers;

6-[1-(2-Hydroxyethyl)pyrazol-4-yl]-N-[4-[[3-[[5-(trifluoromethyl)-2-pyridyl]oxy]phenyl]methylene]cyclohexyl]pyridine-3-carboxamide and its (+) and (−) enantiomers;

6-Amino-N-[4-[[3-[[5-(trifluoromethyl)-2-pyridyl]oxy]phenyl]methylene]cyclohexyl]pyridine-3-carboxamide and its (+) and (−) enantiomers;

6-Methoxy-N-[4-[[3-[[5-(trifluoromethyl)-2-pyridyl]oxy]phenyl]methylene]cyclohexyl]pyridine-3-carboxamide and its (+) and (−) enantiomers;

6-Hydroxy-N-[4-[[3-[[5-(trifluoromethyl)-2-pyridyl]oxy]phenyl]methylene]cyclohexyl]pyridine-3-carboxamide and its (+) and (−) enantiomers;

5-Hydroxy-N-[4-[[3-[[5-(trifluoromethyl)-2-pyridyl]oxy]phenyl]methylene]cyclohexyl]pyridine-3-carboxamide and its (+) and (−) enantiomers;

2-Amino-N-[4-[[3-[[5-(trifluoromethyl)-2-pyridyl]oxy]phenyl]methylene]cyclohexyl]pyridine-3-carboxamide and its (+) and (−) enantiomers;

2-Amino-N-[4-[[3-[[5-(trifluoromethyl)-2-pyridyl]oxy]phenyl]methylene]cyclohexyl]pyrimidine-5-carboxamide and its (+) and (−) enantiomers;

6-Amino-5-methyl-N-[4-[[3-[[5-(trifluoromethyl)-2-pyridyl]oxy]phenyl]methylene]cyclohexyl]pyridine-3-carboxamide and its (+) and (−) enantiomers;

6-(1-Hydroxy-1-methyl-ethyl)-N-[4-[[3-[[5-(trifluoromethyl)-2-pyridyl]oxy]phenyl]methylene]cyclohexyl]pyridine-3-carboxamide and its (+) and (−) enantiomers;

6-(Hydroxymethyl)-N-[4-[[3-[[5-(trifluoromethyl)-2-pyridyl]oxy]phenyl]methylene]cyclohexyl]pyridine-3-carboxamide and its (+) and (−) enantiomers;

5-Amino-N-[4-[[3-[[5-(trifluoromethyl)-2-pyridyl]oxy]phenyl]methylene]cyclohexyl]pyrazine-2-carboxamide and its (+) and (−) enantiomers;

6-Amino-N-[4-[[3-[[5-(trifluoromethyl)-2-pyridyl]oxy]phenyl]methylene]cyclohexyl]pyridazine-3-carboxamide and its (+) and (−) enantiomers;

N-[4-[[3-[[5-(Trifluoromethyl)-2-pyridyl]oxy]phenyl]methylene]cyclohexyl]imidazo[1,2-a]pyridine-2-carboxamide and its (+) and (−) enantiomers;

N-[4-[[3-[[5-(Trifluoromethyl)-2-pyridyl]oxy]phenyl]methylene]cyclohexyl]-5,6,7,8-tetrahydroimidazo[1,2-a]pyridine-2-carboxamide and its (+) and (−) enantiomers;

N-[4-[[3-[[5-(Trifluoromethyl)-2-pyridyl]oxy]phenyl]methylene]cyclohexyl]thiazolo[5,4-b]pyridine-2-carboxamide and its (+) and (−) enantiomers;

N-[4-[[3-[[5-(Trifluoromethyl)-2-pyridyl]oxy]phenyl]methylene]cyclohexyl]imidazo[1,2-b]pyridazine-3-carboxamide and its (+) and (−) enantiomers;

N-[4-[[3-[[5-(Trifluoromethyl)-2-pyridyl]oxy]phenyl]methylene]cyclohexyl]-1H-pyrrolo[2,3-b]pyridine-5-carboxamide and its (+) and (−) enantiomers;

N-[4-[[3-[[5-(Trifluoromethyl)-2-pyridyl]oxy]phenyl]methylene]cyclohexyl]-1H-indole-3-carboxamide and its (+) and (−) enantiomers;

N-[4-[[3-[[5-(Trifluoromethyl)-2-pyridyl]oxy]phenyl]methylene]cyclohexyl]-1H-indole-2-carboxamide and its (+) and (−) enantiomers;

N-[4-[[3-[[5-(Trifluoromethyl)-2-pyridyl]oxy]phenyl]methylene]cyclohexyl]-quinoline-3-carboxamide and its (+) and (−) enantiomers;

1-Methyl-N-[4-[[3-[[5-(trifluoromethyl)-2-pyridyl]oxy]phenyl]methylene]cyclohexyl]pyrrolo[2,3-b]pyridine-5-carboxamide and its (+) and (−) enantiomers;

1-Ethyl-N-[4-[[3-[[5-(trifluoromethyl)-2-pyridyl]oxy]phenyl]methylene]cyclohexyl]pyrrolo[2,3-b]pyridine-5-carboxamide and its (+) and (−) enantiomers;

2-Methyl-N-[4-[[3-[[5-(trifluoromethyl)-2-pyridyl]oxy]phenyl]methylene]cyclohexyl]-1H-pyrrolo[2,3-b]pyridine-5-carboxamide and its (+) and (−) enantiomers;

N-[4-[[3-[[5-(Trifluoromethyl)-2-pyridyl]oxy]phenyl]methylene]cyclohexyl]-1H-pyrrolo[3,2-b]pyridine-3-carboxamide and its (+) and (−) enantiomers;

N-[4-[[3-[[5-(Trifluoromethyl)-2-pyridyl]oxy]phenyl]methylene]cyclohexyl]-1H-pyrrolo[2,3-b]pyridine-3-carboxamide and its (+) and (−) enantiomers;

1-(2-Hydroxy-2-methyl-propyl)-N-[4-[[3-[[5-(trifluoromethyl)-2-pyridyl]oxy]phenyl]methylene]cyclohexyl]pyrrolo[2,3-b]pyridine-5-carboxamide and its (+) and (−) enantiomers;

N-[(3E)-3-[[3-[[5-(Trifluoromethyl)-2-pyridyl]oxy]phenyl]methylene]cyclohexyl]pyridine-3-carboxamide and its (+) and (−) enantiomers;

N-[(3E)-3-[[3-[[5-(Trifluoromethyl)-2-pyridyl]oxy]phenyl]methylene]cyclopentyl]pyridine-3-carboxamide and its (+) and (−) enantiomers;

N-[(3E)-3-[[3-[[5-(Trifluoromethyl)-2-pyridyl]oxy]phenyl]methylene]cyclohexyl]-1H-pyrazole-3-carboxamide and its (+) and (−) enantiomers;

N-[4-[[3-[(5-Bromo-2-pyridyl)oxy]phenyl]methylene]cyclohexyl]pyridine-3-carboxamide and its (+) and (−) enantiomers;

N-[4-[[3-[5-(Trifluoromethyl)pyrazin-2-yl]oxyphenyl]methylene]cyclohexyl]-1H-pyrazole-4-carboxamide and its (+) and (−) enantiomers;

N-[4-[[3-[(5-Chloro-2-pyridyl)oxy]phenyl]methylene]cyclohexyl]-1H-pyrazole-4-carboxamide and its (+) and (−) enantiomers;

N-[4-[[3-[(5-Bromo-2-pyridyl)oxy]phenyl]methylene]cyclohexyl]pyridazine-4-carboxamide and its (+) and (−) enantiomers;

N-[4-[[3-[(5-Bromo-2-pyridyl)oxy]phenyl]methylene]cyclohexyl]-6-fluoro-pyridine-3-carboxamide and its (+) and (−) enantiomers;

6-Amino-N-[4-[[3-[(5-bromo-2-pyridyl)oxy]phenyl]methylene]cyclohexyl]pyridine-3-carboxamide and its (+) and (−) enantiomers;

N-[4-[[3-[(5-Cyclopropyl-2-pyridyl)oxy]phenyl]methylene]cyclohexyl]-1H-pyrazole-4-carboxamide and its (+) and (−) enantiomers;

6-Chloro-N-[(2E)-2-[[3-[[5-(trifluoromethyl)-2-pyridyl]oxy]phenyl]methylene]-5-bicyclo[2.2.2]octanyl]pyridine-3-carboxamide and its (+) and (−) enantiomers;

N-[4-[[2-Fluoro-5-[[5-(trifluoromethyl)-2-pyridyl]oxy]phenyl]methylene]cyclohexyl]-3-(trifluoromethyl)-1H-pyrazole-4-carboxamide and its (+) and (−) enantiomers;

N-[4-[[2-Fluoro-5-[[5-(trifluoromethyl)-2-pyridyl]oxy]phenyl]methylene]cyclohexyl]-6-pyrazol-1-yl-pyridine-3-carboxamide and its (+) and (−) enantiomers;

N-[4-[[3-[[3-Chloro-5-(trifluoromethyl)-2-pyridyl]oxy]phenyl]methylene]cyclohexyl]-6-pyrazol-1-yl-pyridine-3-carboxamide and its (+) and (−) enantiomers;

N-[4-[[3-[[3-Chloro-5-(trifluoromethyl)-2-pyridyl]oxy]phenyl]methylene]cyclohexyl]-3-(trifluoromethyl)-1H-pyrazole-4-carboxamide and its (+) and (−) enantiomers;

6-Amino-N-[4-[[3-[(5-chloro-6-methyl-2-pyridyl)oxy]phenyl]methylene]cyclohexyl]pyridine-3-carboxamide and its (+) and (−) enantiomers;

6-Amino-N-[4-[[3-[[6-methyl-5-(trifluoromethyl)-2-pyridyl]oxy]phenyl]methylene]cyclohexyl]pyridine-3-carboxamide and its (+) and (−) enantiomers;

N-[4-[[3-[[6-Methyl-5-(trifluoromethyl)-2-pyridyl]oxy]phenyl]methylene]cyclohexyl]-3-(trifluoromethyl)-1H-pyrazole-4-carboxamide and its (+) and (−) enantiomers;

6-Amino-N-[4-[[3-[[6-cyclopropyl-5-(trifluoromethyl)-2-pyridyl]oxy]phenyl]methylene]cyclohexyl]pyridine-3-carboxamide and its (+) and (−) enantiomers;

6-Amino-N-[4-[[3-[[6-chloro-5-(trifluoromethyl)-2-pyridyl]oxy]phenyl]methylene]cyclohexyl]pyridine-3-carboxamide and its (+) and (−) enantiomers;

6-Amino-N-[4-[[3-methyl-5-[[5-(trifluoromethyl)-2-pyridyl]oxy]phenyl]methylene]cyclohexyl]pyridine-3-carboxamide and its (+) and (−) enantiomers;

2-Amino-N-[4-[[3-[[6-methyl-5-(trifluoromethyl)-2-pyridyl]oxy]phenyl]methylene]cyclohexyl]pyrimidine-5-carboxamide and its (+) and (−) enantiomers;

6-Amino-5-methyl-N-[4-[[3-[[6-methyl-5-(trifluoromethyl)-2-pyridyl]oxy]phenyl]methylene]cyclohexyl]pyridine-3-carboxamide and its (+) and (−) enantiomers;

6-Amino-N-[4-[[3-[[6-ethyl-5-(trifluoromethyl)-2-pyridyl]oxy]phenyl]methylene]cyclohexyl]pyridine-3-carboxamide and its (+) and (−) enantiomers;

6-Amino-N-[4-[[3-[(5-chloro-6-methyl-2-pyridyl)oxy]phenyl]methylene]cyclohexyl]-5-methyl-pyridine-3-carboxamide and its (+) and (−) enantiomers;

6-Amino-N-[4-[[2-methyl-5-[[5-(trifluoromethyl)-2-pyridyl]oxy]phenyl]methylene]cyclohexyl]pyridine-3-carboxamide and its (+) and (−) enantiomers;

2-Amino-N-[4-[[3-[(5-chloro-6-methyl-2-pyridyl)oxy]phenyl]methylene]cyclohexyl]pyrimidine-5-carboxamide and its (+) and (−) enantiomers;

6-Amino-N-[4-[[3-[[6-cyano-5-(trifluoromethyl)-2-pyridyl]oxy]phenyl]methylene]cyclohexyl]pyridine-3-carboxamide and its (+) and (−) enantiomers;

N-[(5E)-5-[[3-[[5-(Trifluoromethyl)-2-pyridyl]oxy]phenyl]methylene]norbornan-2-yl]-1H-pyrazole-4-carboxamide and its (+) and (−) enantiomers;

N-[4-[[3-[(5-chloro-6-methyl-2-pyridyl)oxy]phenyl]methylene]cyclohexyl]-3-(trifluoromethyl)-1H-pyrazole-4-carboxamide and its (+) and (−) enantiomers;

N-[4-[[3-[(5-chloro-6-methyl-2-pyridyl)oxy]phenyl]methylene]cyclohexyl]-6-(3,5-dimethyl-1H-pyrazol-4-yl)pyridine-3-carboxamide and its (+) and (−) enantiomers;

N-[4-[[3-[(5-Cyclopropyl-2-pyridyl)oxy]phenyl]methylene-cyclohexyl]pyridine-3-carboxamide and its (+) and (−) enantiomers;

N-[4-[[3-[(5-Cyclopropyl-2-pyridyl)oxy]phenyl]methylene]cyclohexyl]pyridazine-4-carboxamide and its (+) and (−) enantiomers;

N-[4-[[3-[(5-Cyclopropyl-2-pyridyl)oxy]phenyl]methylene]cyclohexyl]-6-fluoro-pyridine-3-carboxamide and its (+) and (−) enantiomers;

N-[4-[[3-[(5-Cyclopropyl-2-pyridyl)oxy]phenyl]methylene]cyclohexyl]pyridazine-3-carboxamide and its (+) and (−) enantiomers;

6-Amino-N-[4-[[3-[(5-cyclopropyl-2-pyridyl)oxy]phenyl]methylene]cyclohexyl]pyridine-3-carboxamide and its (+) and (−) enantiomers;

(2S)-N-[4-[[3-[[5-(Trifluoromethyl)-2-pyridyl]oxy]phenyl]methylene-cyclohexyl]pyrrolidine-2-carboxamide and its (+) and (−) enantiomers;

N-[4-[[3-[[5-(Trifluoromethyl)-2-pyridyl]oxy]phenyl]methylene]cyclohexyl]-piperidine-4-carboxamide and its (+) and (−) enantiomers;

4-Amino-N-[4-[[3-[[5-(trifluoromethyl)-2-pyridyl]oxy] phenyl]methylene]cyclohexyl]pyridine-3-carboxamide and its (+) and (−) enantiomers;
6-Amino-5-chloro-N-[4-[[3-[[5-(trifluoromethyl)-2-pyridyl]oxy]phenyl]methylene]cyclohexyl]pyridine-3-carboxamide and its (+) and (−) enantiomers;
6-Amino-N-[4-[[3-[(5-cyclopropyl-2-pyridyl)oxy]phenyl]methylene]cyclohexyl]pyridine-3-carboxamide and its (+) and (−) enantiomers;
6-(Dimethylamino)-N-[4-[[3-[[5-(trifluoromethyl)-2-pyridyl]oxy]-phenyl]methylene]cyclohexyl]pyridine-3-carboxamide and its (+) and (−) enantiomers;
6-(Methylamino)-N-[4-[[3-[[5-(trifluoromethyl)-2-pyridyl]oxy]phenyl]methylene]cyclohexyl]pyridine-3-carboxamide and its (+) and (−) enantiomers;
6-Pyrrolidin-1-yl-N-[4-[[3-[[5-(trifluoromethyl)-2-pyridyl]oxy]phenyl]methylene]cyclohexyl]pyridine-3-carboxamide and its (+) and (−) enantiomers;
6-[[(1R)-2-Hydroxy-1-methyl-ethyl]amino]-N-[4-[[3-[[5-(trifluoromethyl)-2-pyridyl]oxy]phenyl]methylene]cyclohexyl]pyridine-3-carboxamide and its (+) and (−) enantiomers;
6-Morpholino-N-[4-[[3-[[5-(trifluoromethyl)-2-pyridyl] oxy]phenyl]methylene]cyclohexyl]pyridine-3-carboxamide and its (+) and (−) enantiomers;
6-Piperazin-1-yl-N-[4-[[3-[[5-(trifluoromethyl)-2-pyridyl]oxy]phenyl]methylene]cyclohexyl]pyridine-3-carboxamide and its (+) and (−) enantiomers;
6-Pyrazol-1-yl-N-[4-[[3-[[5-(trifluoromethyl)-2-pyridyl] oxy]phenyl]methylene]cyclohexyl]pyridine-3-carboxamide and its (+) and (−) enantiomers;
6-[Ethyl(methyl)amino]-[4-[[3-[[5-(trifluoromethyl)-2-pyridyl]oxy]phenyl]methylene]cyclohexyl]pyridine-3-carboxamide and its (+) and (−) enantiomers;
6-[(2-Hydroxy-1-methyl-ethyl)amino]-N-[4-[[3-[[5-(trifluoromethyl)-2-pyridyl]oxy]phenyl]methylene]cyclohexyl]pyridine-3-carboxamide and its (+) and (−) enantiomers;
6-(2,2,2-Trifluoroethylamino)-N-[4-[[3-[[5-(trifluoromethyl)-2-pyridyl]oxy]phenyl]methylene]cyclohexyl] pyridine-3-carboxamide and its (+) and (−) enantiomers;
6-(Cyclopropylamino)-N-[4-[[3-[[5-(trifluoromethyl)-2-pyridyl]oxy]phenyl]methylene]cyclohexyl]pyridine-3-carboxamide and its (+) and (−) enantiomers;
6-[(2-Hydroxy-2-methyl-propyl)amino]-N-[4-[[3-[[5-(trifluoromethyl)-2-pyridyl]oxy]phenyl]methylene]cyclohexyl]pyridine-3-carboxamide and its (+) and (−) enantiomers;
6-Ethoxy-N-[4-[[3-[[5-(trifluoromethyl)-2-pyridyl]oxy] phenyl]-methylene]cyclohexyl]pyridine-3-carboxamide and its (+) and (−) enantiomers;
6-(2,2,2-Trifluoroethoxy)-N-[4-[[3-[[5-(trifluoromethyl)-2-pyridyl]oxy]phenyl]methylene]cyclohexyl]pyridine-3-carboxamide and its (+) and (−) enantiomers;
Ethyl-2-[3-(trifluoromethyl)-4-[[4-[[3-[[5-(trifluoromethyl)-2-pyridyl]oxy]phenyl]methylene]cyclohexyl] carbamoyl]pyrazol-1-yl]acetate and its (+) and (−) enantiomers;
Ethyl-2-[4-[5-[[4-[[3-[[5-(trifluoromethyl)-2-pyridyl] oxy]phenyl]methylene]cyclohexyl]carbamoyl]-2-pyridyl]pyrazol-1-yl]acetate and its (+) and (−) enantiomers;
Ethyl-2-[4-[[4-[[3-[[5-(trifluoromethyl)-2-pyridyl]oxy] phenyl]methylene]cyclohexyl]carbamoyl]pyrazol-1-yl]acetate and its (+) and (−) enantiomers;
Ethyl-2-[3-[5-[[4-[[3-[[5-(trifluoromethyl)-2-pyridyl] oxy]phenyl]methylene]cyclohexyl]carbamoyl]-2-pyridyl]pyrazol-1-yl]acetate and its (+) and (−) enantiomers;
2-[3-(Trifluoromethyl)-4-[[4-[[3-[[5-(trifluoromethyl)-2-pyridyl]oxy]-phenyl]methylene]cyclohexyl]carbamoyl]pyrazol-1-yl]acetic acid and its (+) and (−) enantiomers;
2-[4-[5-[[4-[[3-[[5-(Trifluoromethyl)-2-pyridyl]oxy]phenyl]methylene]cyclohexyl]carbamoyl]-2-pyridyl]pyrazol-1-yl]acetic acid and its (+) and (−) enantiomers;
2-[4-[[4-[[3-[[5-(Trifluoromethyl)-2-pyridyl]oxy]phenyl] methylene]cyclohexyl]carbamoyl]pyrazol-1-yl]acetic acid and its (+) and (−) enantiomers;
2-[3-[5-[[4-[[3-[[5-(Trifluoromethyl)-2-pyridyl]oxy]phenyl]methylene]cyclohexyl]carbamoyl]-2-pyridyl]pyrazol-1-yl]acetic acid and its (+) and (−) enantiomers;
1-[5-[[4-[[3-[[5-(Trifluoromethyl)-2-pyridyl]oxy]phenyl] methylene]cyclohexyl]carbamoyl]-2-pyridyl]pyrazole-4-carboxylic acid and its (+) and (−) enantiomers;
1-[5-[[4-[[3-[[5-(Trifluoromethyl)-2-pyridyl]oxy]phenyl] methylene]cyclohexyl]carbamoyl]-2-pyridyl]pyrazole-3-carboxylic acid and its (+) and (−) enantiomers;
6-(1-Methylpyrazol-4-yl)-[4-[[3-[[5-(trifluoromethyl)-2-pyridyl]oxy]phenyl]methylene]cyclohexyl]pyridine-3-carboxamide and its (+) and (−) enantiomers;
1-(2-Hydroxypropyl)-3-(trifluoromethyl)-N-[4-[[3-[[5-(trifluoromethyl)-2-pyridyl]oxy]phenyl]methylene]cyclohexyl]pyrazole-4-carboxamide and its (+) and (−) enantiomers;
6-[1-(2-Hydroxypropyl)pyrazol-3-yl]-N-[4-[[3-[[5-(trifluoromethyl)-2-pyridyl]oxy]phenyl]methylene]cyclohexyl]pyridine-3-carboxamide and its (+) and (−) enantiomers;
6-[1-(2-Hydroxyethyl)pyrazol-3-yl]-N-[4-[[3-[[5-(trifluoromethyl)-2-pyridyl]oxy]phenyl]methylene]cyclohexyl]pyridine-3-carboxamide and its (+) and (−) enantiomers;
5-Amino-6-chloro-N-[4-[[3-[[5-(trifluoromethyl)-2-pyridyl]oxy]-phenyl]methylene]cyclohexyl]pyridine-3-carboxamide and its (+) and (−) enantiomers;
6-(1H-Tetrazol-5-yl)-N-[4-[[3-[[5-(trifluoromethyl)-2-pyridyl]oxy]-phenyl]methylene]cyclohexyl]pyridine-3-carboxamide and its (+) and (−) enantiomers;
6-(2-Oxopyrrolidin-1-yl)-N-[4-[[3-[[5-(trifluoromethyl)-2-pyridyl]-oxy]phenyl]methylene]cyclohexyl]pyridine-3-carboxamide and its (+) and (−) enantiomers;
3-(Trifluoromethyl)-N-[4-[1-[3-[[5-(trifluoromethyl)-2-pyridyl]oxy]-phenyl]ethylidene]cyclohexyl]-1H-pyrazole-4-carboxamide and its (+) and (−) enantiomers;
3-(Trifluoromethyl)-N-[4-[1-[3-[[5-(trifluoromethyl)-2-pyridyl]oxy]-phenyl]ethylidene]cyclohexyl]-1H-pyrazole-4-carboxamide and its (+) and (−) enantiomers;
6-(Methanesulfonamido)-N-[4-[[3-[[5-(trifluoromethyl)-2-pyridyl]-oxy]phenyl]methylene]cyclohexyl]pyridine-3-carboxamide and its (+) and (−) enantiomers;
6-Amino-2-fluoro-N-[4-[[3-[[5-(trifluoromethyl)-2-pyridyl]oxy]phenyl]methylene]cyclohexyl]pyridine-3-carboxamide and its (+) and (−) enantiomers;
2-amino-6-fluoro-N-[4-[[3-[[5-(trifluoromethyl)-2-pyridyl]oxy]phenyl]-methylene]cyclohexyl]pyridine-3-carboxamide and its (+) and (−) enantiomers;
N-[4-[[3-[(5-Cyano-2-pyridyl)oxy]phenyl]methylene]-cyclohexyl]-pyridine-3-carboxamide and its (+) and (−) enantiomers;

Disodium [5-[[4-[[3-[[5-(trifluoromethyl)-2-pyridyl]oxy]phenyl]-methylene]cyclohexyl]carbamoyl]pyrrolo[2,3-b]pyridin-1-yl]methyl phosphate and its (+) and (−) enantiomers;

N-[4-[[3-[[5-(Trifluoromethyl)-2-pyridyl]amino]phenyl]methylene]-cyclohexyl]pyridine-3-carboxamide and its (+) and (−) enantiomers;

N-(3-pyridyl)-2-[1-[3-[[5-(trifluoromethyl)-2-pyridyl]oxy]phenyl]ethylidene]bicyclo[2.2.2]octane-5-carboxamide and its (+) and (−) enantiomers;

N-[4-[[3-[[5-(trifluoromethyl)-2-pyridyl]methyl]phenyl]methylene]cyclohexyl]pyridine-3-carboxamide and its (+) and (−) enantiomers;

N-[4-[1-[3-[[5-(trifluoromethyl)-2-pyridyl]oxy]phenyl]ethylidene]cyclohexyl]pyridine-3-carboxamide and its (+) and (−) enantiomers;

N-[4-[phenyl-[3-[[5-(trifluoromethyl)-2-pyridyl]amino]phenyl]methylene]cyclohexyl]pyridine-3-carboxamide and its (+) and (−) enantiomers;

N-[4-[2-chloro-1-[3-[[5-(trifluoromethyl)-2-pyridyl]methyl]phenyl]ethylidene]cyclohexyl]pyridine-3-carboxamide and its (+) and (−) enantiomers;

N-[4-[[3-[1-[5-(trifluoromethyl)-2-pyridyl]cyclopropyl]phenyl]methylene]cyclohexyl]pyridine-3-carboxamide and its (+) and (−) enantiomers;

N-[(3E)-3-[[3-[1-[5-(trifluoromethyl)-2-pyridyl]cyclopropyl]phenyl]methylene]cyclohexyl]pyridine-3-carboxamide and its (+) and (−) enantiomers;

(3E)-N-(3-pyridyl)-3-[[3-[[5-(trifluoromethyl)-2-pyridyl]oxy]phenyl]methylene]cyclohexanecarboxamide and its (+) and (−) enantiomers;

N-[(3E)-3-[[3-[[5-(trifluoromethyl)-2-pyridyl]amino]phenyl]methylene]cyclohexyl]pyridine-3-carboxamide and its (+) and (−) enantiomers;

N-[(3E)-3-[[3-[[5-(trifluoromethyl)-2-pyridyl]methyl]phenyl]methylene]cyclohexyl]pyridine-3-carboxamide and its (+) and (−) enantiomers;

N-[(3E)-3-[[3-[1-[5-(trifluoromethyl)-2-pyridyl]cyclopropyl]phenyl]methylene]cyclohexyl]pyridine-3-carboxamide and its (+) and (−) enantiomers;

N-[(3E)-3-[1-[3-[[5-(trifluoromethyl)-2-pyridyl]amino]phenyl]ethylidene]cyclopentyl]pyridine-3-carboxamide and its (+) and (−) enantiomers;

N-[(3E)-3-[[3-[[5-(trifluoromethyl)-2-pyridyl]methyl]phenyl]methylene]cyclopentyl]pyridine-3-carboxamide and its (+) and (−) enantiomers;

N-[(3E)-3-[1-[3-[[5-(trifluoromethyl)-2-pyridyl]oxy]phenyl]ethylidene]cyclopentyl]pyridine-3-carboxamide and its (+) and (−) enantiomers;

(3E)-N-(3-pyridyl)-3-[1-[3-[[5-(trifluoromethyl)-2-pyridyl]oxy]phenyl]ethylidene]cyclopentanecarboxamide and its (+) and (−) enantiomers;

N-[(3E)-3-[1-[3-[1-[5-(trifluoromethyl)-2-pyridyl]cyclopropyl]phenyl]ethylidene]cyclopentyl]pyridine-3-carboxamide and its (+) and (−) enantiomers;

N-(3-pyridyl)-3-[1-[3-[[5-(trifluoromethyl)-2-pyridyl]amino]phenyl]propylidene]norpinane-6-carboxamide and its (+) and (−) enantiomers;

N-[(5E)-5-[[3-[[5-(trifluoromethyl)-2-pyridyl]oxy]phenyl]methylene]norbornan-2-yl]pyridine-3-carboxamide and its (+) and (−) enantiomers;

N-[(5E)-5-[[3-[[5-(trifluoromethyl)-2-pyridyl]oxy]phenyl]methylene]norbornan-2-yl]pyridine-3-carbothioamide and its (+) and (−) enantiomers;

N'-cyano-N-[(5E)-5-[3-[[5-(trifluoromethyl)-2-pyridyl]oxy]phenyl]methylene]norbornan-2-yl]pyridine-3-carboxamidine and its (+) and (−) enantiomers;

N-[(5Z)-5-[1-[3-[[5-(trifluoromethyl)-2-pyridyl]oxy]phenyl]propylidene]norbornan-2-yl]pyridine-3-carboxamide and its (+) and (−) enantiomers;

N-(3-pyridyl)-6-[1-[3-[[5-(trifluoromethyl)-2-pyridyl]methyl]phenyl]ethylidene]norpinane-3-carboxamide and its (+) and (−) enantiomers;

(2E)-N-(3-pyridyl)-2-[[3-[[5-(trifluoromethyl)-2-pyridyl]amino]phenyl]methylene]bicyclo[2.2.2]octane-5-carboxamide and its (+) and (−) enantiomers;

(4E)-N-(3-pyridyl)-4-[[3-[[5-(trifluoromethyl)-2-pyridyl]oxy]phenyl]methylene]norpinane-1-carboxamide and its (+) and (−) enantiomers;

N-[(4Z)-3-methyl-4-[1-[3-[[5-(trifluoromethyl)-2-pyridyl]oxy]phenyl]ethylidene]cyclohexyl]pyridine-3-carboxamide and its (+) and (−) enantiomers;

N-[(2Z)-2-[1-[3-[[5-(trifluoromethyl)-2-pyridyl]amino]phenyl]ethylidene]-5-bicyclo[3.2.1]octanyl]pyridine-3-carboxamide and its (+) and (−) enantiomers;

(3E)-N-(3-pyridylmethyl)-3-[[3-[[5-(trifluoromethyl)-2-pyridyl]amino]phenyl]methylene]cyclopentanecarboxamide and its (+) and (−) enantiomers;

4-methyl-2-(3-pyridyl)-N-[4-[[3-[[5-(trifluoromethyl)-2-pyridyl]amino]phenyl]methylene]cyclohexyl]thiazole-5-carboxamide and its (+) and (−) enantiomers;

(2E)-N-(5-chlorothiazol-2-yl)-2-[[3-[[5-(trifluoromethyl)-2-pyridyl]methyl]phenyl]methylene]bicyclo[2.2.2]octane-5-carboxamide and its (+) and (−) enantiomers;

N-[4-[1-[3-[[5-(trifluoromethyl)-2-pyridyl]methyl]phenyl]ethylidene]cyclohexyl]pyrazine-2-carboxamide and its (+) and (−) enantiomers;

(3E)-N-pyrimidin-2-yl-3-[[3-[[5-(trifluoromethyl)-2-pyridyl]oxy]phenyl]methylene]cyclohexanecarboxamide and its (+) and (−) enantiomers;

2-Methyl-N-[(3E)-3-[[3-[[5-(trifluoromethyl)-2-pyridyl]oxy]phenyl]methylene]cyclopentyl]tetrazole-5-carboxamide and its (+) and (−) enantiomers;

N-[(2E)-2-[[3-[[5-(trifluoromethyl)-2-pyridyl]amino]phenyl]methylene]-5-bicyclo[2.2.2]octanyl]pyrimidine-5-carboxamide and its (+) and (−) enantiomers;

N-(1H-pyrazol-3-yl)-4-[[3-[[5-(trifluoromethyl)-2-pyridyl]methyl]phenyl]methylene]cyclohexanecarboxamide and its (+) and (−) enantiomers;

5-methyl-N-[(3E)-3-[1-[3-[[5-(trifluoromethyl)-2-pyridyl]methyl]phenyl]ethylidene]cyclohexyl]-1,3,4-oxadiazole-2-carboxamide and its (+) and (−) enantiomers;

5-methyl-N-[(3E)-3-[[3-[[5-(trifluoromethyl)-2-pyridyl]oxy]phenyl]methylene]cyclohexyl]-1,3,4-thiadiazole-2-carboxamide and its (+) and (−) enantiomers;

3-methyl-N-[(3E)-3-[[3-[[5-(trifluoromethyl)-2-pyridyl]amino]phenyl]methylene]cyclopentyl]-1,2,4-oxadiazole-5-carboxamide and its (+) and (−) enantiomers;

(2E)-N-thiazolo[5,4-b]pyridin-2-yl-2-[[3-[[5-(trifluoromethyl)-2-pyridyl]methyl]phenyl]methylene]bicyclo[2.2.2]octane-5-carboxamide and its (+) and (−) enantiomers;

3,5-Dimethyl-N-[(2E)-2-[[3-[[5-(trifluoromethyl)-2-pyridyl]amino]phenyl]methylene]-5-bicyclo[2.2.2]octanyl]isoxazole-4-carboxamide and its (+) and (−) enantiomers;

6-Amino-N-[4-[1-[3-[[5-(trifluoromethyl)-2-pyridyl]amino]phenyfl]ethylidene]cyclohexyl]pyridine-3-carboxamide and its (+) and (−) enantiomers;

3-(Ttrifluoromethyl)-N-[(2E)-2-[[3-[4-(trifluoromethyl)phenoxy]phenyl]methylene]-5-bicyclo[2.2.2]octanyl]-1H-pyrazole-4-carboxamide and its (+) and (−) enantiomers;

2-Amino-N-[4-[1-[3-[[5-(trifluoromethyl)-2-pyridyl]amino]phenyl]propylidene]cyclohexyl]pyrimidine-5-carboxamide and its (+) and (−) enantiomers;

N-Pyrimidin-5-yl-4-[[3-[[5-(trifluoromethyl)-2-pyridyl]oxy]phenyl]methylene]cyclohexanecarboxamide and its (+) and (−) enantiomers;

2-Amino-N-[4-[[3-[[5-(trifluoromethyl)-2-pyridyl]methyl]phenyl]methylene]cyclohexyl]pyrimidine-5-carboxamide and its (+) and (−) enantiomers;

6-Amino-5-methyl-N-[(2E)-2-[1-[3-[4-(trifluoromethyl)phenoxy]phenyl]ethylidene]-5-bicyclo[2.2.2]octanyl]pyridine-3-carboxamide and its (+) and (−) enantiomers;

N-[(2E)-2-[[3-[4-(trifluoromethyl)phenoxy]phenyl]methylene]-5-bicyclo[2.2.2]octanyl]-1H-pyrrolo[2,3-b]pyridine-5-carboxamide and its (+) and (−) enantiomers;

N-Pyridazin-3-yl-4-[1-[3-[[5-(trifluoromethyl)-2-pyridyl]methyl]phenyl]ethylidene]cyclohexanecarboxamide and its (+) and (−) enantiomers;

6-Pyrrol-1-yl-N-[(2E)-2-[1-[3-[4-(trifluoromethyl)phenoxy]phenyl]ethylidene]-5-bicyclo[2.2.2]octanyl]pyridine-3-carboxamide and its (+) and (−) enantiomers;

(3E)-N-(6-cyclopropyl-3-pyridyl)-3-[1-[3-[[5-(trifluoromethyl)-2-pyridyl]oxy]phenyl]ethylidene]cyclohexanecarboxamide and its (+) and (−) enantiomers;

N-[4-[1-[3-[[5-(trifluoromethyl)-2-pyridyl]methyl]phenyl]ethylidene]cyclohexyl]-1H-indole-3-carboxamide and its (+) and (−) enantiomers;

6-(1H-pyrazol-4-yl)-N-[4-[1-[3-[[5-(trifluoromethyl)-2-pyridyl]amino]phenyl]ethylidene]cyclohexyl]pyridine-3-carboxamide and its (+) and (−) enantiomers;

6-(3,5-Dimethyl-1H-pyrazol-4-yl)-N-[4-[1-[3-[[5-(trifluoromethyl)-2-pyridyl]oxy]phenyl]propylidene]cyclohexyl]pyridine-3-carboxamide and its (+) and (−) enantiomers;

N-(3-pyridyl)-4-[1-[3-(2-quinolyloxy)phenyl]ethylidene]cyclohexanecarboxamide and its (+) and (−) enantiomers;

N-[4-[[3-(2-quinolyloxy)phenyl]methylene]cyclohexyl]pyridine-3-carboxamide and its (+) and (−) enantiomers;

N-[4-[[3-(2-pyridyloxy)phenyl]methylene]cyclohexyl]pyridine-3-carboxamide and its (+) and (−) enantiomers;

N-[4-[1-[3-[[5-(trifluoromethyl)-2-pyridyl]amino]phenyl]ethylidene]cyclohexyl]pyridine-3-carboxamide and its (+) and (−) enantiomers;

4-[1-[3-[(5-cyclopropyl-2-pyridyl)amino]phenyl]propylidene]-N-(3-pyridyl)cyclohexanecarboxamide and its (+) and (−) enantiomers;

N-[4-[[3-[5-(trifluoromethyl)pyrazin-2-yl]oxyphenyl]methylene]cyclohexyl]pyridine-3-carboxamide and its (+) and (−) enantiomers;

N-[4-[1-[3[(5-fluoro-2-pyridyl)oxy]phenyl]propylidene]cyclohexyl]pyridine-3-carboxamide and its (+) and (−) enantiomers;

4-[1-[3-[(5-fluoro-2-pyridyl)methyl]phenyl]ethylidene]-N-(3-pyridyl)cyclohexanecarboxamide and its (+) and (−) enantiomers;

N-(3-pyridyl)-4-[[3-[[5-(trifluoromethyl)pyrimidin-2-yl]amino]phenyl]methylene]cyclohexanecarboxamide and its (+) and (−) enantiomers;

4-[[3-(5-ethylpyrimidin-2-yl)oxyphenyl]methylene]-N-(3-pyridyl)cyclohexanecarboxamide and its (+) and (−) enantiomers;

N-[4-[1-(3-phenoxyphenyl)ethylidene]cyclohexyl]pyridine-3-carboxamide and its (+) and (−) enantiomers;

N-[4-[1-[3-(furo[2,3-b]pyridin-2-ylamino)phenyl]ethylidene]cyclohexyl]pyridine-3-carboxamide and its (+) and (−) enantiomers;

N-(3-pyridyl)-4-[[3-(1H-pyrrolo[2,3-b]pyridin-2-yloxy)phenyl]methylene]cyclohexanecarboxamide and its (+) and (−) enantiomers;

N-[4-[1-(3-thieno[2,3-b]pyridin-2-yloxyphenyl)ethylidene]cyclohexyl]pyridine-3-carboxamide and its (+) and (−) enantiomers;

N-[4-[1-[3-(thieno[2,3-b]pyridin-6-ylamino)phenyl]ethylidene]cyclohexyl]pyridine-3-carboxamide and its (+) and (−) enantiomers;

N-[4-[(3-thieno[2,3-b]pyridin-6-yloxyphenyl)methylene]cyclohexyl]pyridine-3-carbothioamide and its (+) and (−) enantiomers;

N'-cyano-N-[4-[(3-thieno[2,3-b]pyridin-6-yloxyphenyl)methylene]cyclohexyl]pyridine-3-carboxamidine and its (+) and (−) enantiomers;

N-(3-pyridyl)-4-[1-[4-[[5-(trifluoromethyl)-2-pyridyl]oxy]-2-naphthyl]ethylidene]cyclohexanecarboxamide, N-[4-[[1-[[5-(trifluoromethyl)-2-pyridyl]oxy]-3-isoquinolyl]methylene]cyclohexyl]pyridine-3-carboxamide and its (+) and (−) enantiomers;

N-[4-[1-[4-[[5-(trifluoromethyl)-2-pyridyl]amino]pyrimidin-2-yl]ethylidene]cyclohexyl]pyridine-3-carboxamide and its (+) and (−) enantiomers;

N-(3-pyridyl)-4-[1-[5-[[5-(trifluoromethyl)-2-pyridyl]amino]pyridazin-3-yl]propylidene]cyclohexanecarboxamide and its (+) and (−) enantiomers;

N-[4-[[2-[[5-(trifluoromethyl)-2-pyridyl]oxy]pyrimidin-4-yl]methylene]cyclohexyl]pyridine-3-carboxamide and its (+) and (−) enantiomers;

N-[4-[1-[6-[[5-(trifluoromethyl)-2-pyridyl]oxy]pyrazin-2-yl]propylidene]cyclohexyl]pyridine-3-carboxamide and its (+) and (−) enantiomers;

N-(3-pyridyl)-4-[1-[6-[[5-(trifluoromethyl)-2-pyridyl]methyl]pyridazin-4-yl]ethylidene]cyclohexanecarboxamide and its (+) and (−) enantiomers;

N-(3-pyridyl)-4-[[2-[[5-(trifluoromethyl)-2-pyridyl]amino]-4-pyridyl]methylene]cyclohexanecarboxamide and its (+) and (−) enantiomers;

N-(3-pyridyl)-4-[[6-[[5-(trifluoromethyl)-2-pyridyl]oxy]-1H-indol-4-yl]methylene]cyclohexanecarboxamide and its (+) and (−) enantiomers;

N-[4-[1-[7-[[5-(trifluoromethyl)-2-pyridyl]oxy]-5-quinolyl]ethylidene]cyclohexyl]pyridine-3-carboxamide and its (+) and (−) enantiomers;

N-[4-[1-[5-[[5-(trifluoromethyl)-2-pyridyl]amino]-2-thienyl]ethylidene]cyclohexyl]pyridine-3-carboxamide and its (+) and (−) enantiomers;

N-[4-[[5-[[5-(trifluoromethyl)-2-pyridyl]oxy]-2-thienyl]methylene]cyclohexyl]pyridine-3-carbothioamide and its (+) and (−) enantiomers;

N'-cyano-N-[4-[[5-[[5-(trifluoromethyl)-2-pyridyl]oxy]-2-thienyl]methylene]cyclohexyl]pyridine-3-carboxamidine and its (+) and (−) enantiomers;

N-(4-pyridyl)-4-[[3-[[5-(trifluoromethyl)-2-pyridyl]oxy]phenyl]methylene]cyclohexanecarboxamide and its (+) and (−) enantiomers;

N-(4-pyridyl)-4-[[3-[1-[5-(trifluoromethyl)-2-pyridyl]cyclopropyl]phenyl]methylene]cyclohexanecarboxamide and its (+) and (−) enantiomers;

N-[4-[[3-[1-[5-(trifluoromethyl)-2-pyridyl]cyclopropyl]phenyl]methylene]cyclohexyl]pyridine-4-carboxamide and its (+) and (−) enantiomers;
N-[4-[[3-[[5-(trifluoromethyl)-2-pyridyl]methyl]phenyl]methylene]cyclohexyl]pyridine-4-carboxamide and its (+) and (−) enantiomers;
N-[4-[1-[3-[[5-(trifluoromethyl)-2-pyridyl]amino]phenyl]ethylidene]cyclohexyl]pyridine-4-carboxamide and its (+) and (−) enantiomers;
N-[4-[1-[3-[[5-(trifluoromethyl)-2-pyridyl]oxy]phenyl]ethylidene]cyclohexyl]pyridine-4-carboxamide and its (+) and (−) enantiomers;
N-[4-[[3-[[5-(trifluoromethyl)-2-pyridyl]methyl]phenyl]methylene]cyclohexyl]pyridine-3-carboxamide and its (+) and (−) enantiomers;
N-[4-[1-[3-[[5-(trifluoromethyl)-2-pyridyl]oxy]phenyl]ethylidene]cyclohexyl]pyridine-3-carboxamide and its (+) and (−) enantiomers;
5-chloro-N-[4-[[3-[[5-(trifluoromethyl)-2-pyridyl]amino]phenyl]methylene]cyclohexyl]thiazole-2-carboxamide and its (+) and (−) enantiomers;
N-(5-chlorothiazol-2-yl)-4-[1-[3-[[5-(trifluoromethyl)-2-pyridyl]amino]phenyl]ethylidene]cyclohexanecarboxamide and its (+) and (−) enantiomers;
N-[4-[1-[3-[[5-(trifluoromethyl)-2-pyridyl]oxy]phenyl]propylidene]cyclohexyl]pyrazine-2-carboxamide and its (+) and (−) enantiomers;
N-[4-[1-[3-[[5-(trifluoromethyl)-2-pyridyl]oxy]phenyl]propylidene]cyclohexyl]pyrimidine-2-carboxamide and its (+) and (−) enantiomers;
N-(1-Methyltetrazol-5-yl)-4-[1-[3-[[5-(trifluoromethyl)-2-pyridyl]methyl]phenyl]ethylidene]cyclohexanecarboxamide and its (+) and (−) enantiomers;
N-pyrimidin-5-yl-4-[[3-[[5-(trifluoromethyl)-2-pyridyl]amino]phenyl]methylene]cyclohexanecarboxamide and its (+) and (−) enantiomers;
N-(1H-pyrazol-3-yl)-4-[[3-[[5-(trifluoromethyl)-2-pyridyl]oxy]phenyl]methylene]cyclohexanecarboxamide and its (+) and (−) enantiomers;
N-[4-[[3-[1-[5-(trifluoromethyl)-2-pyridyl]cyclopropyl]phenyl]methylene]cyclohexyl]-1H-pyrazole-3-carboxamide and its (+) and (−) enantiomers;
N-[4-[[3-[[5-(trifluoromethyl)-2-pyridyl]methyl]phenyl]methylene]cyclohexyl]-1H-pyrazole-3-carboxamide and its (+) and (−) enantiomers;
N-[4-[[3-[[5-(trifluoromethyl)-2-pyridyl]amino]phenyl]methylene]cyclohexyl]-1H-pyrazole-3-carboxamide and its (+) and (−) enantiomers;
N-[4-[1-[3-[[5-(trifluoromethyl)-2-pyridyl]oxy]phenyl]ethylidene]cyclohexyl]-1H-pyrazole-3-carboxamide and its (+) and (−) enantiomers;
5-methyl-N-[4-[1-[3-[[5-(trifluoromethyl)-2-pyridyl]oxy]phenyl]ethylidene]cyclohexyl]-1,3,4-oxadiazole-2-carboxamide and its (+) and (−) enantiomers;
5-Methyl-N-[4-[1-[3-[[5-(trifluoromethyl)-2-pyridyl]amino]phenyl]ethylidene]cyclohexyl]-1,3,4-thiadiazole-2-carboxamide and its (+) and (−) enantiomers;
N-(3-methyl-1,2,4-oxadiazol-5-yl)-4-[1-[3-[[5-(trifluoromethyl)-2-pyridyl]oxy]phenyl]ethylidene]cyclohexanecarboxamide and its (+) and (−) enantiomers;
N-[4-[[3-[[5-(trifluoromethyl)-2-pyridyl]oxy]phenyl]methylene]cyclohexyl]thiazolo[5,4-b]pyridine-2-carboxamide and its (+) and (−) enantiomers;
N-[4-[1-[3-[[5-(trifluoromethyl)-2-pyridyl]amino]phenyl]ethylidene]cyclohexyl]-5,6,7,8-tetrahydroimidazo[1,2-a]pyridine-2-carboxamide and its (+) and (−) enantiomers;
N-[4-[[3-[1-[5-(trifluoromethyl)-2-pyridyl]cyclopropyl]phenyl]methylene]cyclohexyl]pyridazine-3-carboxamide and its (+) and (−) enantiomers;
N-pyridazin-3-yl-4-[[3-[[5-(trifluoromethyl)-2-pyridyl]amino]phenyl]methylene]cyclohexanecarboxamide and its (+) and (−) enantiomers;
N-[4-[1-[3-[[5-(trifluoromethyl)-2-pyridyl]amino]phenyl]ethylidene]cyclohexyl]pyridazine-3-carboxamide and its (+) and (−) enantiomers;
N-[4-[[3-[[5-(trifluoromethyl)-2-pyridyl]methyl]phenyl]methylene]cyclohexyl]pyridazine-3-carboxamide and its (+) and (−) enantiomers;
3,5-dimethyl-N-[4-[[3-[[5-(trifluoromethyl)-2-pyridyl]oxy]phenyl]methylene]cyclohexyl]isoxazole-4-carboxamide and its (+) and (−) enantiomers;
N-[4-[1-[3-[[5-(trifluoromethyl)-2-pyridyl]oxy]phenyl]propylidene]cyclohexyl]-1,5-naphthyridine-3-carboxamide and its (+) and (−) enantiomers;
N-(3-methylisothiazol-5-yl)-4-[1-[3-[[5-(trifluoromethyl)-2-pyridyl]methyl]phenyl]ethylidene]cyclohexanecarboxamide and its (+) and (−) enantiomers;
N-thieno[3,2-b]pyridin-2-yl-4-[[3-[[5-(trifluoromethyl)-2-pyridyl]amino]phenyl]methylene]cyclohexanecarboxamide and its (+) and (−) enantiomers;
N-thieno[2,3-b]pyridin-2-yl-4-[[3-[[5-(trifluoromethyl)-2-pyridyl]oxy]phenyl]methylene]cyclohexanecarboxamide and its (+) and (−) enantiomers;
N-[4-[1-[3-[[5-(trifluoromethyl)-2-pyridyl]oxy]phenyl]ethylidene]cyclohexyl]thiazolo[4,5-c]pyridine-2-carboxamide and its (+) and (−) enantiomers;
N-[4-[[3-[[5-(trifluoromethyl)-2-pyridyl]oxy]phenyl]methylene]cyclohexyl]thiazolo[4,5-c]pyridine-2-carbothioamide and its (+) and (−) enantiomers; and
N'-cyano-N-[4-[[3-[[5-(trifluoromethyl)-2-pyridyl]oxy]phenyl]methylene]cyclohexyl]thiazolo[4,5-c]pyridine-2-carboxamidine and its (+) and (−) enantiomers.

6. A pharmaceutical composition comprising a pharmaceutically acceptable carrier and a pharmaceutically effective amount of a compound of any of claim 5.

7. A method for treating, or adjunct treatment, in a mammal a disease or condition mediated by modulating FAAH activity, which comprises administering to the mammal an effective amount of a compound according to claim 1.

8. A method for treating, or adjunct treatment, in a mammal a disease or condition mediated by modulating FAAH activity, which comprises administering to the mammal an effective amount of a compound according to claim 3.

9. A method for treating, or adjunct treatment, in a mammal a disease or condition mediated by modulating FAAH activity, which comprises administering to the mammal an effective amount of a compound according to claim 5.

10. A process for preparing a compound of formula (I),

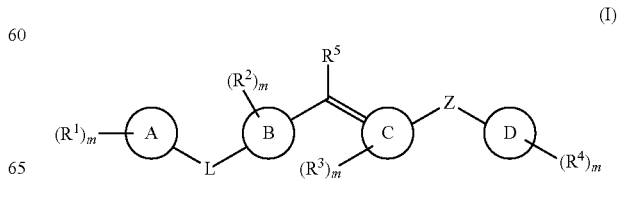

or its tautomer, polymorph, stereoisomer, prodrug, solvate, pharmaceutically acceptable salt, pharmaceutical composition thereof wherein:

ring A is heteroaryl;

L is —O— or —N(R)—;

ring B is aryl;

ring C is cycloalkyl;

Z is selected from —C(Y)NR—(CR$^a$R$^b$)$_q$— or —NRC(Y)—C(R$^a$R$^{ab}$)$_q$;

Y is O;

R is hydrogen;

ring D is heteroaryl or heterocyclyl;

R$^1$, R$^2$, R$^3$ and R$^4$ are independently selected from hydrogen, halo, cyano, nitro, —(CR$^a$R$^b$)$_n$OR$^6$, —(CR$^a$R$^b$)$_n$C(O)R$^6$, —(CR$^a$R$^b$)$_n$COOR$^6$, —(CR$^a$R$^b$)$_n$NR$^7$R$^8$, C$_{1-6}$alkyl, perhaloalkyl, cycloalkyl, heterocyclyl, or heteroaryl;

wherein each substituent is unsubstituted or substituted with 1 or 2 substituents independently selected from alkyl, halogen, perhaloalkyl, —(CR$^a$R$^b$)$_n$OR$^6$, —(CR$^a$R$^b$)$_n$COOR$^6$, cycloalkyl or —CH$_2$OPO$_3^{2-}$;

R$^5$ is selected from hydrogen, halogen, or C$_{1-6}$ alkyl;

R$^6$ is selected from hydrogen, alkyl, —(CR$^a$R$^b$)$_n$OR$^6$;

R$^7$ and R$^8$ are independently selected from the group consisting of hydrogen, alkyl, —(CR$^a$R$^b$)$_n$C(O)R$^6$;

R$^a$ and R$^b$ are independently selected from the group consisting of hydrogen, halogen, and alkyl;

m is independently selected from 0, 1, and 2;

n is an integer and selected from 0, 1, and 2;

and q is 0 or 1;

said process comprising:

coupling a compound of formula (II):

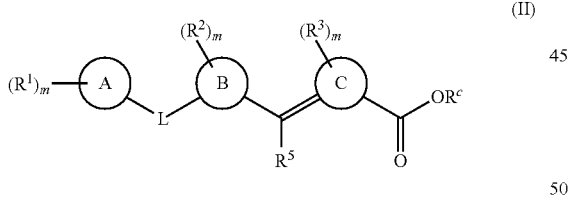

(II)

wherein R$^c$ is selected from hydrogen, alkyl, arylalkyl and all other symbols are defined herein with a compound of formula (III):

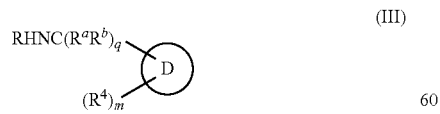

(III)

under amide coupling reaction conditions to obtain a compound of formula (I) or its tautomer, polymorph, stereoisomer, prodrug, solvate, pharmaceutically acceptable salt, pharmaceutical composition thereof.

11. A process for preparing a compound of formula (I),

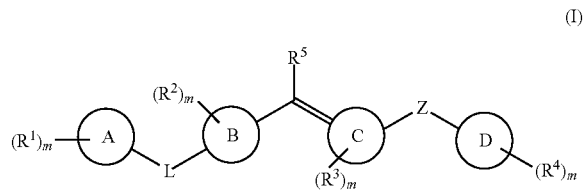

(I)

or its tautomer, polymorph, stereoisomer, prodrug, solvate, pharmaceutically acceptable salt, pharmaceutical composition thereof wherein:

ring A is heteroaryl;

L is —O— or —N(R)—;

ring B is aryl;

ring C is cycloalkyl;

Z is selected from —C(Y)NR—(CR$^a$R$^b$)$_q$— or —NRC(Y)—C(R$^a$R$^b$)$_q$;

Y is O;

R is hydrogen;

ring D is heteroaryl or heterocyclyl;

R$^1$, R$^2$, R$^3$ and R$^4$ are independently selected from hydrogen, halo, cyano, nitro, —(CR$^a$R$^b$)$_n$OR$^6$, —(CR$^a$R$^b$)$_n$C(O)R$^6$, —(CR$^a$R$^b$)$_n$COOR$^6$, —(CR$^a$R$^b$)$_n$NR$^7$R$^8$, C$_{1-6}$alkyl, perhaloalkyl, cycloalkyl, heterocyclyl, or heteroaryl;

wherein each substituent is unsubstituted or substituted with 1 or 2 substituents independently selected from alkyl, halogen, perhaloalkyl, —(CR$^a$R$^b$)$_n$OR$^6$, —(CR$^a$R$^b$)$_n$COOR$^6$, cycloalkyl or —CH$_2$OPO$_3^{2-}$;

R$^5$ is selected from hydrogen, halogen, or C$_{1-6}$ alkyl;

R$^6$ is selected from hydrogen, alkyl, —(CR$^a$R$^b$)$_n$OR$^6$;

R$^7$ and R$^8$ are independently selected from the group consisting of hydrogen, alkyl, —(CR$^a$R$^b$)$_n$C(O)R$^6$;

R$^a$ and R$^b$ are independently selected from the group consisting of hydrogen, halogen, and alkyl;

m is independently selected from 0, 1, and 2;

n is an integer and selected from 0, 1, and 2;

and q is 0 or 1;

said process comprising:

coupling a compound of formula (IV):

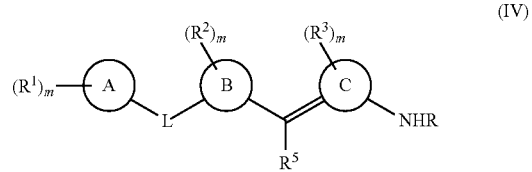

(IV)

with a compound of formula (V):

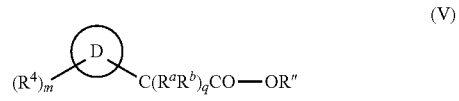

(V)

wherein R″ is selected from hydrogen, alkyl, arylalkyl under amide coupling reaction conditions to obtain a compound of formula (I) or its tautomer, polymorph, stereoisomer, prodrug, solvate, pharmaceutically acceptable salt, pharmaceutical composition thereof.

* * * * *